United States Patent
Patel et al.

(10) Patent No.: US 11,154,622 B2
(45) Date of Patent: Oct. 26, 2021

(54) COMPOSITIONS AND METHODS FOR EXPRESSION OF MULTIPLE BIOLOGICALLY ACTIVE POLYPEPTIDES FROM A SINGLE VECTOR FOR TREATMENT OF CARDIAC CONDITIONS AND OTHER PATHOLOGIES

(71) Applicant: Precigen, Inc., Blacksburg, VA (US)

(72) Inventors: Dimki S. Patel, Blacksburg, VA (US); Amit N. Patel, Salt Lake City, UT (US)

(73) Assignee: PRECIGEN, INC., Blacksburg, VA (US)

(*) Notice: Subject to any disclaimer, the term of this patent is extended or adjusted under 35 U.S.C. 154(b) by 0 days.

(21) Appl. No.: 15/978,036

(22) Filed: May 11, 2018

(65) Prior Publication Data

US 2018/0360992 A1 Dec. 20, 2018

Related U.S. Application Data

(63) Continuation of application No. PCT/US2016/061668, filed on Nov. 11, 2016.

(60) Provisional application No. 62/254,139, filed on Nov. 11, 2015.

(51) Int. Cl.
| | |
|---|---|
| *A61K 48/00* | (2006.01) |
| *C07K 14/52* | (2006.01) |
| *A61K 38/18* | (2006.01) |
| *A61K 38/19* | (2006.01) |
| *C12N 15/62* | (2006.01) |
| *A61K 38/17* | (2006.01) |
| *C07K 14/47* | (2006.01) |
| *C07K 14/475* | (2006.01) |
| *A61K 41/00* | (2020.01) |
| *A61P 9/00* | (2006.01) |

(52) U.S. Cl.
CPC ...... *A61K 48/0058* (2013.01); *A61K 38/1738* (2013.01); *A61K 38/1866* (2013.01); *A61K 38/195* (2013.01); *A61K 41/0028* (2013.01); *A61K 48/00* (2013.01); *A61P 9/00* (2018.01); *C07K 14/475* (2013.01); *C07K 14/4728* (2013.01); *C07K 14/52* (2013.01); *C07K 14/521* (2013.01); *C12N 15/62* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,985,461 A | 1/1991 | Hsu et al. |
| 5,117,057 A | 5/1992 | Hsu et al. |
| 5,225,443 A | 7/1993 | Murphy et al. |
| 5,378,726 A | 1/1995 | Yanagi et al. |
| 5,530,028 A | 6/1996 | Lidert et al. |
| 6,013,836 A | 1/2000 | Hsu et al. |
| 7,091,038 B2 | 8/2006 | Palli et al. |
| 7,531,326 B2 | 5/2009 | Kapitskaya et al. |
| 7,563,879 B2 | 7/2009 | Palli |
| 7,601,508 B2 | 10/2009 | Palli et al. |
| 7,776,587 B2 | 8/2010 | Palli et al. |
| 7,807,417 B2 | 10/2010 | Palli et al. |
| 7,829,676 B2 | 11/2010 | Zhang et al. |
| 7,919,269 B2 | 4/2011 | Zhang et al. |
| 7,935,510 B2 | 5/2011 | Palli et al. |
| 8,021,878 B2 | 9/2011 | Palli |
| 8,030,067 B2 | 10/2011 | Zhang et al. |
| 8,076,454 B2 | 12/2011 | Palli et al. |
| 8,076,517 B2 | 12/2011 | Hormann et al. |
| 8,105,825 B2 | 1/2012 | Dhadialla et al. |
| 8,168,426 B2 | 5/2012 | Dhadialla et al. |
| 8,202,718 B2 | 6/2012 | Palli et al. |
| 8,236,527 B2 * | 8/2012 | Chen ............... C07K 14/4716 435/320.1 |
| 8,236,556 B2 | 8/2012 | Kapitskaya et al. |
| 8,497,093 B2 | 7/2013 | Palli |
| 8,513,007 B2 | 8/2013 | Penn et al. |

(Continued)

FOREIGN PATENT DOCUMENTS

| | | |
|---|---|---|
| EP | 2968608 A2 | 10/2016 |
| WO | WO-2001070816 A2 | 9/2001 |

(Continued)

OTHER PUBLICATIONS

Perin, E, et al., "Comparison of intracoronary and transendocardial delivery of allogeneic mesenchymal cells in a canine model of acute myocardial infarction," J Mol Cell Cardiol, vol. 44, No. 3, pp. 486-95, 2008.
Suzuki, K., et al., "Development of a novel method for cell transplantation through the coronary artery," Circulation, vol. 102, No. 19 Suppl 3, pp. 111359-11364, 2000.
Noyez, L., et al., "Retrograde versus antegrade delivery of cardioplegic solution in myocardial revascularization. A clinical trial in patients with three-vessel coronary artery disease who underwent myocardial revascularization with extensive use of the internal mammary art," J Thorac Cardiovasc Surg, vol. 105, No. 5, pp. 854-863, 1993.
Anderson, S., et al., "ICAM-1 expression and leukocyte behavior in the microcirculation of chronically ischemic rat skeletal muscles," Microvasc Res, vol. 71, No. 3, pp. 205-11, 2006.

(Continued)

*Primary Examiner* — Marianne P Allen
(74) *Attorney, Agent, or Firm* — Wilson Sonsini Goodrich & Rosati

(57) ABSTRACT

The present invention provides compositions and methods useful for treating disorders amenable to therapy via introduction of multigenic expression vectors. More particularly, the invention provides vectors and polynucleotides encoding polypeptides for treatment of cardiac disorders wherein said polypeptides may comprise a cytokine, a chemokine, and/or an angiogenic polypeptide, or functional derivatives thereof. Also provided, as compositions of the invention, are linkers useful for connecting and expressing functional (biologically active) polypeptides from single, multigenic-expression constructs.

14 Claims, 38 Drawing Sheets

Specification includes a Sequence Listing.

(56) References Cited

U.S. PATENT DOCUMENTS

| | | | |
|---|---|---|---|
| 8,513,213 | B2 | 8/2013 | Penn et al. |
| 8,598,409 | B2 | 12/2013 | Kapitskaya et al. |
| 8,715,959 | B2 | 5/2014 | Palli et al. |
| 8,883,756 | B2 | 11/2014 | Penn et al. |
| 9,034,650 | B2 | 5/2015 | Padidam |
| 2004/0049037 | A1 | 3/2004 | Tice et al. |
| 2004/0171651 | A1 | 9/2004 | Hormann et al. |
| 2005/0209283 | A1 | 9/2005 | Hormann et al. |
| 2006/0020146 | A1 | 1/2006 | Hormann et al. |
| 2009/0123441 | A1 | 5/2009 | Braughler et al. |
| 2009/0136465 | A1 | 5/2009 | Merenick et al. |
| 2011/0212528 | A1 | 9/2011 | Palli et al. |
| 2011/0268766 | A1 | 11/2011 | Beech et al. |
| 2012/0167239 | A1 | 6/2012 | Palli et al. |
| 2013/0195800 | A1 | 8/2013 | Roeth et al. |
| 2014/0308247 | A1 | 10/2014 | Roeth et al. |

FOREIGN PATENT DOCUMENTS

| | | | |
|---|---|---|---|
| WO | WO-2002029075 | A2 | 4/2002 |
| WO | WO-2002066612 | A2 | 8/2002 |
| WO | WO-2002066613 | A2 | 8/2002 |
| WO | WO-2002066614 | A2 | 8/2002 |
| WO | WO-2002066615 | A2 | 8/2002 |
| WO | WO-02083851 | | 10/2002 |
| WO | WO-2003027266 | A2 | 4/2003 |
| WO | WO-2003027289 | A1 | 4/2003 |
| WO | WO-2005108617 | A2 | 11/2005 |
| WO | WO-2005108617 | A3 | 2/2006 |
| WO | WO-2008073154 | A2 | 6/2008 |
| WO | WO-2008073154 | A3 | 6/2008 |
| WO | WO-2008088870 | A1 | 7/2008 |
| WO | WO-2009045370 | A2 | 4/2009 |
| WO | WO-2009048560 | A1 | 4/2009 |
| WO | WO-2009045370 | A3 | 4/2010 |
| WO | WO-2010042189 | A2 | 4/2010 |
| WO | WO-2011119773 | A1 | 9/2011 |
| WO | WO-2012122025 | A2 | 9/2012 |
| WO | WO-2012122025 | A3 | 4/2013 |
| WO | WO-2014089121 | A2 | 6/2014 |
| WO | WO-2014145199 | A2 | 9/2014 |
| WO | WO-2014145199 | | 11/2014 |
| WO | WO-2010042189 | A3 | 3/2016 |
| WO | WO-2016187585 | | 11/2016 |

OTHER PUBLICATIONS

Boekstegers, P., et al., "Selective suction and pressure-regulated retroinfusion: an effective and safe approach to retrograde protection against myocardial ischemia in patients undergoing normal and high risk percutaneous transluminal coronary angioplasty," J Am Coll Cardiol, vol. 31, No. 7, pp. 1525-1533, 1998.

Pohl, T., et al., "Retroinfusion-supported stenting in high-risk patients for percutaneous intervention and bypass surgery: results of the prospective randomized myoprotect I study," Cath Cardiovasc Intervent, vol. 62, No. 3, pp. 323-330, 2004.

Incorvati, R., et al., "Clinical applications of coronary sinus retroperfusion during high risk percutaneous transluminal coronary angioplasty," J Am Coll Cardiol, vol. 22, No. 1, pp. 127-134, 1993.

Lokmic, Z. a. G. M., "Visualisation and stereological assessment of blood and lymphatic vessels," Histolog Histopathol, vol. 26, No. 6, pp. 781-796, 2011.

Lesley, J., et la. "TSG-6 modulates the interaction between hyaluronan and cell surface CD44," J Biol Chem, vol. 279, No. 24, pp. 25745-25754, 2004.

Patel, A. N., et al., "Revive Trial: Retrograde Delivery of Autologous Bone Marrow in Patients With Heart Failure," Stem Cells Transl Med, vol. 4, pp. 1021-1027, 2015.

Ramppon, C., et al., "Molecular mechanism of systemic delivery of neural precursor cells to the brain: assembly of brain endothelial apical cups and control of transmigration by CD44," Stem Cells, vol. 26, No. 7, pp. 1673-1682, 2008.

Henschler, R. E., et al. "Homing of Mesenchymal Stem Cells," Infusionsther Transfusionsmed, vol. 35, No. 4, pp. 306-312, 2008.

Ruster, B., et al., "Mesenchymal stem cells display coordinated rolling and adhesion behavior on endothelial cells," Blood, vol. 108, No. 12, pp. 3938-3944, 2006.

Hart, C., et al. "Expression and function of homing-essential molecules and enhanced in vivo homing ability of human peripheral blood-derived hematopoietic progenitor cells after stimulation with stem cell factor," Stem Cells, vol. 22, No. 4, pp. 580-589, 2004.

Bachrach, E., et al., "Muscle engraftment of myogenic progenitor cells following intraarterial transplantation," Muscle Nerve, vol. 34, No. 1, pp. 44-52, 2006.

Boeksteger, P., et al. "Myocardial gene transfer by selective pressure-regulated retroinfusion of coronary veins," Gene Ther, vol. 7, No. 3, pp. 232-240, 2000.

Alino, S. Alino, et al. "Naked DNA delivery to whole pig cardiac tissue by coronary sinus retrograde injection employing non-invasive catheterization," J Gene Med, vol. 12, No. 11, pp. 920-926, 2010.

Youssef, E. Youssef, et al., "Enhancing myocardial plasmid expression by retrograde coronary venous delivery," Cath Cardiovasc Intervent, vol. 65, No. 4, pp. 528-534, 2005.

Raake, P.W., et al., "Myocardial gene transfer by selective pressure-regulated retroinfusion of coronary veins: comparison with surgical and percutaneous intramyocardial gene delivery," J Am Coll Cardiol, vol. 44, No. 5, pp. 1124-1129, 2004.

Von Degenfeld, G., et al., "Selective pressure- regulated retroinfusion of fibroblast growth factor-2 into the coronary vein enhances regional myocardial blood flow and function in pigs with chronic myocardial ischemia," J Am Coll Cardiol, vol. 42, No. 6, pp. 1120-1128, 2003.

Suzuki, K., et al., "Targeted cell delivery into infarcted rat hearts by retrograde intracoronary infusion: distribution, dynamics, and influence on cardiac function," Circulation, vol. 110, No. 11 Suppl 1, pp. 11225-11230, 2004.

George, J., et al. "Transvenous intramyocardial cellular delivery increases retention in comparison to intracoronary delivery in a porcine model of acute myocardial infarction," J Intery Cardiol, vol. 21, No. 5, pp. 424-431, 2008.

Thompson, C., et al. "Percutaneous transvenous cellular cardiomyoplasty: A novel nonsurgical approach for myocardial cell transplantation," J Am Coll Cardiol, vol. 41, No. 11, pp. 1964-1971, 2003.

Raake, P. W., et al., "Cardio-specific long-term gene expression in a porcine model after selective pressure-regulated retroinfusion of adeno-associated viral (AAV) vectors," Gene Ther, vol. 15, No. 1, pp. 12-17, 2008.

Tuma, J., et al., "Safety and feasibility of percutaneous retrograde coronary sinus delivery of autologous bone marrow mononuclear cell transplantation in patients with chronic refractory angina," J Transl Med, vol. 9, p. 183, 2011.

Wright, N. T., et al., "The three-dimensional solution structure of Ca(2+)-bound S100A1 as determined by NMR spectroscopy," J Mol Biol, vol. 353, No. 2, pp. 410-426, 2005.

Donato, R., "Functional roles of S100 proteins, calcium-binding proteins of the EF-hand type," Biochim Biophys Acta, vol. 1450, No. 3, pp. 191-231, 1999.

Zimmer, D. B., et al., "Molecular mechanisms of S100-target protein interactions," Microsc Res Tech, vol. 60, No. 6, pp. 552-559, 2003.

Hove-Madsen, L., et al. "Sarcoplasmic reticulum Ca2+ uptake and thapsigargin sensitivity in permeabilized rabbit and rat ventricular myocytes," Circ Res, vol. 73, No. 5, pp. 820-828, 1993.

Lopez, J. J., et al., "VeEGFadministration in chronic myocardial ischemia in pigs," Cardiovasc Res, pp. 272-281, 1998.

James, J., et al., "Transgenic rabbits expressing mutant essential light chain do not develop hypertrophic cardiomyopathy.," J Mol Cell Cardiol, vol. 34, No. 7, pp. 872-882, 2002.

Patel. J., et al., "Coronary Sinus Delivery of SDF-1 Plasmid for the Treatment of Heart Failure," American Society of Gene and Cell Therapy, p. poster presentation, 2014.

Hedman, M., et al., "Safety and Feasibility of Catheter-Based Local Intracoronary Vascular Endothelial Growth Factor Gene Transfer in

(56) References Cited

OTHER PUBLICATIONS the Prevention of Postangioplasty and In-Stent Restenosis and in the Treatment of Chronic Myocardial Ischemia. Phase II Results of the Kuopio," Circulation, vol. 107, pp. 2677-2683, 2003.
Katz, M. G., et al. "Gene Therapy in Cardiac Surgery: Clinical Trials, Challenges and Perspectives," Ann Thorac Surg, vol. 101, pp. 2407-2416, 2016.
Kolsut, P., et al. "Gene therapy of coronary artery disease with phvegf165—early outcome," Kardiol Pol, vol. 59, pp. 373-384, 2003.
Ruel, M., et al., "Concomitant treatment with oral L-arginine improves the efficacy of surgical angiogenesis in patients with severe diffuse coronary artery disease: the Endothelial Modulation in Angiogenic Therapy randomized controlled trial," J Thorac Cardiovasc Surg, vol. 135, pp. 762-770, 2008.
Pleger, S. T. Pleger,et al., "Cardiac AAV9-S100A1 gene therapy rescues post-ischemic heart failure in a preclinical large animal model," Sci Transl Med, vol. 3, No. 92, pp. 92ra64-92ra64, 2011.
Lee, R. J., et al. "VEGF Gene Delivery to Myocardium: Deleterious Effects of Unregulated Expression," Circulation, vol. 102, pp. 898-901, 2000.
Katz, M. Katz, A. Fargnoli, R. Williams and C. Bridges, "Gene Therapy Delivery Systems for Enhancing Viral and Nonviral Vectors for Cardiac Diseases:and Nonviral Vectors for Cardiac Diseases: Current Concepts and Future Applications," Human Gene Ther, vol. 24, pp. 914-927, 2013.
Brinks, Brinks, et al., "S100A1 genetically targeted therapy reverses dysfunction of human failing cardiomyocytes," J Am Coll Cardiol, vol. 58, No. 9, pp. 966-973, 2011.
Giordano, F. J., "Retrograde coronary perfusion: a superior route to deliver therapeutics to the heart?," J Am Coll Cardiol, vol. 42, No. 6, pp. 1129-1131, 2003.
Wang, Y., et la., "2A self-cleaving peptide-based multi-gene expression system in the silkworm Bombyx mori," Sci Rep, vol. 5, No. 16273, pp. 1-10, 2015.
Scimia, M. C., et al., "Cardiovascular gene therapy for myocardial infarction," Expert Opin Biol Ther, vol. 14, No. 2, pp. 183-195, 2014.
Marenholz, I., et al., "S100 proteins in mouse and man: from evolution to function and pathology (including an update of the nomenclature)," Biochem Biophys Res Commun. vol. 322, No. 4, pp. 1111-1122, 2004.
Nagasawa, T., "CXCL12/SDF-1 and CXCR4," Front. Immunol, vol. 6, pp. 301, 2015.
Holmes, David, et al. "The Vascular Endothelial Growth Factor (VEGF) Family: Angiogenic Factors in Health and Disease." Genome Biol. vol. 6, No. 2, pp. 209, (2005).
Chen, S, et al. "Myocardial regeneration in adriamycin cardiomyopathy by nuclear expression of GLP1 using ultrasound targeted microbubble destruction." Biochem Biophys Res Commun. vol. 458, No. 4, pp. 823-829, 2015.
Mayer, C.R., et al. "Ultrasound targeted microbubble destruction for drug and gene delivery." Expert Opin Drug Deliv., vol. 5, No. 10, pp. 1121-1138, 2008.
Musialek, P., et al., "Randomized transcoronary delivery of CD34(+) cells with perfusion versus stop-flow method in patients with recent myocardial infarction: Early cardiac retention of (m)Tc-labeled cells activity," J Nuclear Cardiol, vol. 18, No. 1, pp. 104-116, 2011.
Robinson, S., et al., "Arterial delivery of genetically labelled skeletal myoblasts to the murine heart: long-term survival and phenotypic modification of implanted myoblasts," Cell Transplant, vol. 5, No. 1, pp. 77-91, 1996.
Chung, E. S., et al., "Changes in ventricular remodelling and clinical status during the year following a single administration of stromal cell-derived factor-1 non-viral gene therapy in chronic ischaemic heart failure patients: the STOP-HF randomized Phase II trial," Eur Heart J, vol. 36, pp. 2228-2238, 2015.

Remppis, A. Remppis, T. Greten, B. Schafer and P. Hunziker, "Altered expression of the Ca 2+-binding protein S100A1 in human cardiomyopathy," Biochim Biophys Acta, vol. 1313, No. 3, pp. 253-257, 1996.
Webber, C., et al. "Therapeutic safety of high myocardial expression levels of the molecular inotrope S100A1 in a preclinical heart failure model," Gene Ther, vol. 21, pp. 131-138, 2014.
Rhode, D., et la., "S100A1: a multifaceted therapeutic target in cardiovascular disease," J Cardiovasc Transl Res, vol. 3, No. 5, pp. 525-537, 2010.
Rhode, D., et la., "Infiltration of both T cells and neutrophils in the skin is accompanied by the expression of endothelial leukocyte adhesion molecule-1 (ELAM-1): an immunohistochemical and ultrastructural study," J Invest Dermatol, vol. 98, No. 5, pp. 794-799, 1992.
European Search Report dated Apr. 30, 2019 for EP Appl. No. 16810130.1.
Habazettl, H., et al., "Selectins and beta 2-integrins mediate post-ischaemic venular adhesion of polymorphonuclear leukocytes, but not capillary plugging, in isolated hearts," Pflugers Arch, vol. 438, No. 4, pp. 479-485, 1999.
Hiasa, K.I., Gene Transfer of Stromal Cell-Derived Factor-1 Enhances Ischemic Vasculogenesis and Angiogenesis via Vascular Endothelial Growth Factor/Endothelial Nitric Oxide Synthase-related Pathway: Next-Generation Chemokine Therapy for Therapeutic Neovascularization, Circulation, vol. 109, No. 20, May 25, 2004.
International Search Report and Written Opinion dated Apr. 7, 2017 for PCT/US2016/061668.
Hellawell, J. L. Hellawell, et al., "Myocardial reverse remodeling," Cardiovasc Ther, vol. 30, No. 3, pp. 172-181, 2012.
Suzuki, K., et al., "Intracoronary infusion of skeletal myoblasts improves cardiac function in doxorubicin-induced heart failure," Circulation, vol. 104, No. 12 Suppl 1, pp. 1213-1217, 2001.
Kriz, A., et al., A plasmid-based multigene expression system for mammalian cells, Nature Communications, Nov. 16, 2010, vol. 1, pp. 120:1-6.
Penn, M. S., et al., "An open-label dose escalation study to evaluate the safety of administration of nonviral stromal cell-derived factor-1 plasmid to treat symptomatic ischemic heart failure," Circ Res, vol. 112, No. 5, pp. 816-825, 2013.
Penn, M. S. Penn, et al., "SDF-1 in myocardial repair," Gene Ther, vol. 19, No. 6, pp. 583-587, 2012.
Malecki, et al., Construction of a bicistonic proangiogenic expression vector and its application in experimental angiogenesis in vivo, ACTA Biochimica Polonica, Polskie Towarzystwo Biochemiczne, PL. Jan. 2003; 50(3):875-882.
Yu, J. X., et al., "Combination of stromal-derived factor-la and vascular endothelial growth factor gene-modified endothelial progenitor cells is more effective for ischemic neovascularization," J Vasc Surg, vol. 50, No. 3, pp. 608-616, 2009.
Musialek, P. W., et al., "Transcoronary stem cell delivery using physiological endothelium-targeting perfusion technique: the rationale and a pilot study involving a comparison with conventional over-the-wire balloon coronary occlusions in patients after recent myocardial infarcti," Kardiol Pol, vol. 64, No. 5, pp. 489-498, 2006.
Pan, et al., Cloning and prokaryotic expression of VEGF-SLC fusion gene, Database Accession No. PREV201100484946; Chinese Journal of Biologicals, May 2011;24(5):566-570.
Rincon M.Y. et al., Gene therapy for cardiovascular disease: advances invector development, targeting, and delivery for clinical translation. Cardiovasc Res., Aug. 3, 2015, vol. 108, No. 1, pp. 4-20, p. 5, 14.
Rohde, et al., S100A1 gene therapy for heart failure: A novel strategy on the verge of clinical trials, Journal of Molecular and cellular cardiology, academic press GB, Aug. 2010; 50(5):777-784.
Pleger, S. T., et al. "Stable myocardial-specific AAV6-S100A1 gene therapy results in chronic functional heart failure rescue," Circulation, vol. 115, No. 19, pp. 2506-2515, 2007.
Tian, Xiao-bin et al., Construction and expression of bicistronic vector containing human bone morphogenetic protein 2 and vascular endothelial growth factor-1645 genes in vitro, Chinese Medical Journal, vol. 122, No. 4, Jan. 1, 2009, pp. 471-473, XP055338963, China.

(56) References Cited

OTHER PUBLICATIONS

Winters, Amalia A. et al., Evaluation of Multiple Biological Therapies for Ischemic Cardiac Disease, Cell Transplantation, vol. 25, pp. 1591-1607, 2016.
Wolfram, J.A. et al., Gene Therapy to Treat Cardiovascular Disease, Journal of American Heart Association, vol. 2, No. 4, Aug. 20, 2013, pp. 1-11.
Xiao-Bin, et al., Construction and expression of a bicistronic vector containing human bone morphogenetic protein 2 and vascular endothelial growth factor-165 genes in vitro, Chinese medical journal, Jan. 2009; 4:471-473.
Yu, et al., Combination of stromal-derived factor-1[alpha] and vascular endothelial growth factor gene-modified endothelial progenitor cells is more effective for ischemic neovascularization, Journal of Vascular Surgery. Sep. 2009; 50(3):608-616, XP-055014974.
Taimeh, Z., et al., "Vascular endothelial growth factor in heart failure," Nat Rev Cardiol, vol. 10, No. 9, pp. 519-530, 2013.
Yu, J., et al., "Combination of stromal-derived factor-1a and vascular endothelial growth factor gene-modified endothelial progenitor cells is more effective for ischemic neovascularization," J Vasc Surg, vol. 50, No. 3, pp. 608-616, 2009.
Williams, et al., "Plasmid-mediated gene therapy for cardiovascular disease", Cardiovascular Research (2011) 91, 565-576.
Klein et al., 1998 Exp Neurol. Apr. 1998;150(2):183-94.

\* cited by examiner

| | Kozak | Linker | GOI | [SDF1] (ng/ml) |
|---|---|---|---|---|
| 1 | No | Furin-(AP)-F2A | S100A1-SDF1 | 10.84 |
| 3 | | | SDF1-S100A1 | 19.17 |
| 4 | | | SDF1-VEGF191 | 5.56 |
| 5 | | | VEGF191-SDF1 | 10.77 |
| 7 | | (GSG)-P2A | S100A1-SDF1 | 26.90 |
| 9 | | | SDF1-S100A1 | 2.09 |
| 10 | | | SDF1-VEGF191 | 0 |
| 11 | | | VEGF191-SDF1 | 9.77 |
| 13 | | Furin-(APVKQGSG)-P2A | S100A1-SDF1 | 16.88 |
| 15 | | | SDF1-S100A1 | 12.27 |
| 16 | | | SDF1-VEGF191 | 4.99 |
| 17 | | | VEGF191-SDF1 | 10.36 |
| 19 | Yes | Furin-(AP)-F2A | SDF1-VEGF191 | 0.43 |
| 20 | | | VEGF191-SDF1 | 0 |
| 21 | | (GSG)-P2A | S100A1-SDF1 | 5.33 |
| 22 | | | SDF1-S100A1 | 10.94 |
| 23 | | | SDF1-VEGF191 | 0 |
| 24 | | | VEGF191-SDF1 | 3.74 |
| 25 | | Furin-(APVKQGSG)-P2A | S100A1-SDF1 | 16.95 |
| 26 | | | SDF1-S100A1 | 18.45 |
| 27 | | | SDF1-VEGF191 | 5.42 |
| 28 | | | VEGF191-SDF1 | 4.96 |
| 30/36 | No | N/A | VEGF191 | 0 |
| 31/37 | | | S100A1 | 0 |
| 32/38 | | | SDF1 | 26.22 |
| 35 | | | Mock | 0 |
| 41/42 | | | Untransfected | 0 |

| | Kozak | Linker | GOI | [VEGF] (µg/ml) |
|---|---|---|---|---|
| 2 | No | Furin-(AP)-F2A | S100A1-VEGF191 | 6.95 |
| 4 | | | SDF1-VEGF191 | 4.43 |
| 5 | | | VEGF191-SDF1 | 6.72 |
| 6 | | | VEGF191-S100A1 | 13.60 |
| 8 | | (GSG)-P2A | S100A1-VEGF191 | 9.64 |
| 10 | | | SDF1-VEGF191 | 10.95 |
| 11 | | | VEGF191-SDF1 | 12.57 |
| 12 | | | VEGF191-S100A1 | 13.94 |
| 14 | | Furin-(APVKQGSG)-P2A | S100A1-VEGF191 | 8.49 |
| 16 | | | SDF1-VEGF191 | 3.97 |
| 17 | | | VEGF191-SDF1 | 7.58 |
| 18 | | | VEGF191-S100A1 | 15.49 |
| 19 | Yes | Furin-(AP)-F2A | SDF1-VEGF191 | 3.86 |
| 20 | | | VEGF191-SDF1 | 2.65 |
| 23 | | (GSG)-P2A | SDF1-VEGF191 | 5.53 |
| 24 | | | VEGF191-SDF1 | 5.69 |
| 27 | | Furin-(APVKQGSG)-P2A | SDF1-VEGF191 | 5.53 |
| 28 | | | VEGF191-SDF1 | 6.96 |
| 29 | | | VEGF191-S100A1 | 10.78 |
| 30/36* | No | N/A | VEGF191 | 0.18 |
| 31/37 | | | S100A1 | 0 |
| 32/38 | | | SDF1 | 0 |
| 35 | | | Mock | 0 |
| 41/42 | | | Untransfected | 0 |

| | Kozak | Linker | GOI | [S100A1] (µg/ml) |
|---|---|---|---|---|
| 1 | No | Furin-(AP)-F2A | S100A1-SDF1 | 25.4 |
| 2 | | | S100A1-VEGF191 | 27.6 |
| 3 | | | SDF1-S100A1 | 70.7 |
| 6 | | | VEGF191-S100A1 | 14.5 |
| 7 | | (GSG)-P2A | S100A1-SDF1 | 38.0 |
| 8 | | | S100A1-VEGF191 | 22.2 |
| 9 | | | SDF1-S100A1 | 65.4 |
| 12 | | | VEGF191-S100A1 | 13.4 |
| 13 | | Furin-(APVKQGSG)-P2A | S100A1-SDF1 | 51.1 |
| 14 | | | S100A1-VEGF191 | 59.3 |
| 15 | | | SDF1-S100A1 | 36.0 |
| 18 | | | VEGF191-S100A1 | 13.0 |
| 21 | Yes | (GSG)-P2A | S100A1-SDF1 | 13.1 |
| 22 | | | SDF1-S100A1 | 27.0 |
| 25 | | Furin-(APVKQGSG)-P2A | S100A1-SDF1 | 37.4 |
| 26 | | | SDF1-S100A1 | 35.5 |
| 29 | | | VEGF191-S100A1 | 10.9 |
| 30/36* | No | N/A | VEGF191 | 0 |
| 31/37 | | | S100A1 | 53.2 |
| 32/38 | | | SDF1 | 0 |
| 35 | | | Mock | 0 |
| 41/42 | | | Untransfected | 0 |

COMPOSITIONS AND METHODS FOR EXPRESSION OF MULTIPLE BIOLOGICALLY ACTIVE POLYPEPTIDES FROM A SINGLE VECTOR FOR TREATMENT OF CARDIAC CONDITIONS AND OTHER PATHOLOGIES

CROSS-REFERENCE TO RELATED APPLICATION

The present application is a continuation of PCT International Application No. PCT/US2016/061668 filed on Nov. 11, 2016, which claims the benefit of U.S. provisional Patent Application No. 62/254,139, filed Nov. 11, 2015, each of which is hereby incorporated by reference in its entirety for all purposes.

REFERENCE TO SEQUENCE LISTING

The present application contains a Sequence Listing which has been filed electronically in ASCII format and is hereby incorporated by reference in its entirety. Said ASCII copy, created on Jan. 28, 2020, is named 50471-701.301_SL.text and is 271,839 bytes in size.

FIELD OF THE INVENTION

The present invention provides novel nucleic acids and vectors, and polypeptides encoded by same, for multigenic therapeutic treatment of diseases, disorders and pathologic conditions. More particularly, the present invention provides novel nucleic acids, vectors, polypeptides and methods for multigenic treatment and prevention of cardiac diseases and disorders. Moreover, the present invention provides novel nucleic acids and polypeptide linkers, which provide advantageous protein expression from nucleic acids and vectors, useful for multigenic therapeutic treatment of diseases, disorders and pathologic conditions.

BACKGROUND OF THE INVENTION

Cardiac disease represents a significant unmet medical need; with some estimates indicating at least 25 million patients worldwide. Moreover, according to the United States of America (U.S.) government's Centers for Disease Control and Prevention (CDC) "Heart Failure Fact Sheet" as of 2013, over 5 million people in the U.S. have heart failure conditions.

Heart failure has been estimated to cause 1 in 9 deaths with as many as 825,000 new cases each year. The average survival rate 5 years after diagnosis is at about 40% and represents the highest hospital readmission rate among any diagnosis-related group. The cost in the U.S. has been estimated to be as high as $32 billion per year. Heart failure treatment options include medications, invasive devices, and heart transplant.

Congestive heart failure (CHF) describes the inability of the heart to provide sufficient cardiac output to supply the metabolic demand of the body. There are more than 22 million people worldwide currently diagnosed with CHF and over 5 million patients in the US. Because the incidence and severity of heart disease increases with age, the overall incidence is expected to rise in the future due to the aging population. The prognosis for patients with CHF remains poor, with a five year mortality rate of 50%. According to the American Heart Association (AHA), cardiovascular disease claimed 810,000 lives in the United States in 2013, which accounts for ~1 in every 3 reported deaths. Pharmacological management of end stage heart failure focus on three goals as follows: 1) improvement of morbidity and mortality (ACE inhibitors, angiotensin II type I receptor antagonists, selected β-blockers, and aldosterone antagonists); 2) control of symptoms (diuretics (eventually thiazide plus loop diuretic), digitalis (low dose); temporary inotropes, and selected anti-arrhythmics); and 3) palliation (opioids, anti-depressants, anxiolytics, oxygen and continuous inotropes). However, as disease progresses, therapeutic options become limited to cardiac resynchronization therapy (CRT); considering implantable cardioverter-defibrillator (ICD); heart transplantation and ventricular assist devices (VAD), which are used both as a bridge to transplantation and increasingly as destination therapy due to the lack of donor hearts. Although the overall 5-year survival is 70-80% in heart transplantation patients receiving triple immunosuppressive therapy, heart transplantation as a treatment option is limited by the continuing shortage of donor hearts, the increasing number of transplant candidates and the very high yearly cost over $100,000 per year. Data collected by the Interagency Registry for Mechanically Assisted Circulatory Support (INTERMACS), showed that between Jun. 23, 2006 and Jun. 30 2013, 12,335 patients received an FDA approved durable mechanical circulatory support (MCS) device, with a rate of accrual that has continued at a pace of 2,000 patients per year.

There is an increasing study of cell and gene therapies for the treatment of CHF, but with limited results due to issues with biologic effect, cell retention, timing of delivery, and lack of mechanism or limited single gene effect. Even so, many clinical gene therapy trials have demonstrated modest effects at one year. Although gene therapy has a defined mechanism of action, single genes used to improve angiogenesis, stem cell homing, or inotropy have not been sufficient to treat CHF. Because CHF is multifactorial in terms of scarring, decreased contractile function and cell loss, a multigenic approach may better address these individual factors while keeping these extremely sick patients safe.

Traditionally, vectors for gene therapy are single gene. An increasing demand for more complex multigene vectors has arisen in recent years. In particular, this demand is stimulated by the need of combination therapies for cancer and antiviral treatment. Combination gene therapy is medicine's best attempt to prevent mutation and resistance in cancer. By combining two or three agents a more complete and effective response may be obtained.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a disclosure herein and a disclosure in an incorporated reference, the disclosure herein controls.

SUMMARY OF THE DISCLOSURE

An increasing number of patients with congestive heart failure (CHF) continue to have limited therapeutic options. For example, a common CHF treatment results in placement of a destination left ventricular assist device (LVAD)). Accordingly, a different approach involving biologic options to promote recovery from CHF are needed.

A single gene-based approach to treating cardiac disorders is reasonable in patients with unique genetic mutations, i.e. Troponin I or Heavy chain myosin. However, in most patients with cardiac pathology, the end-stage disease is due to multiple factors. Therefore, in such cases a single gene approach is unlikely to work. Cardiac patients usually have scar tissue requiring positive remodeling via cell recruitment and/or angiogenesis. They usually also require an increase in inotropic function via calcium or other pathways. Hence, a combination of genes which effect calcium handling, cell recruitment and angiogenesis together provides a more appropriate path to treat and recover these end-stage CHF patients. Moreover, when considering a gene based approach to treating cardiac disorders (such as, but not limited to, CHF), the use of a viral vectors may antagonize the human immune system, or patients may already have preformed anti-viral antibodies (e.g., anti-AAV1/AAV2 antibodies), which could cause safety and efficacy issues. Thus, the use of plasmid DNA, which has low to no adverse immune response in humans and can be re-dosed as needed, provides an advantageous mode of therapeutic gene delivery.

As such, one embodiment of the present invention provides a triple effector non-viral plasmid-based DNA for therapeutic treatment of cardiac diseases and disorders (for example, but not limited to, CHF). In one embodiment, the present invention provides a triple effector non-viral plasmid-based DNA vector (construct). In a particular embodiment of the present invention, an expression plasmid referred to as pXoX encodes and expresses biologically active SDF1α, S100A1, and VEGF, wherein these three effector genes of interest (GOI) are separated by selectively designed linker sequences described herein.

A multigenic plasmid DNA approach to treat cardiac diseases and disorders (for example, but not limited to, CHF) is based on positive in vitro, pre-clinical and clinical data from other studies in which single genes have been utilized. Each gene of interest described below has a specific function for inotropy (e.g., S100A1), cell homing (e.g., SDF-1 α), and angiogenesis (e.g., VEGF165). The rationale for a single plasmid construct comprising all three genes, instead of each individual gene on separately delivered plasmids, is that if single genes (on individual, separate vectors) are delivered to cells, there is no means by which the amount of transfection of each gene to a cell can be controlled. This variability in gene delivery would make the therapy unsafe and non-reproducible even though it would provide a simpler approach than single, multigenic constructs of the present invention. Hence, in one embodiment, vectors such as pXoX constitutively express S100A1 (an intracellular protein), SDF-1α (a secreted protein), and VEGF165 (a secreted protein). With pXoX, the pDNA construct is transcribed as a single mRNA which is translated as three individual functional proteins via cleavage by the combined activity of furin and P2A (fp2a). The 2A self-cleaving peptide encodes a sequence (P2A) that mediates a translational effect known as "ribosome skipping", "stop-go" and "stop-carry on" translation that results in co-expression of multiple proteins from a single transcript mRNA under the control of a single promoter. Constitutive expression is driven by promoters, such as, but not limited to, a CAG promoter (a hybrid promoter containing the chicken beta-actin (CBA) promoter with a CMV enhancer and hybrid CBA exon 1/rabbit beta-globin intron B). Further description of three effectors and their rationale for inclusion in constructs of the invention are described below.

S100A1

S100A1 is a member of the Ca2+-binding EF-hand protein superfamily (Rohde et al, *J Cardiovasc Transl Res*, vol. 3, no. 5, pp. 525-537, 2010). S100A1 is a 10.4 kDa protein that functions as a homodimer primarily in cardiomyocytes to regulate Ca2+-controlled networks and fluxes to control contractile function, excitability, metabolism, maintenance, and survival. Animal and human studies have demonstrated decreased expression of S100A1 in heart failure (Pleger et al., *Circulation*, vol. 115, no. 19, pp. 2506-2515, 2007; and, Remppis et al., *Biochim Biophys Acta*, vol. 1313, no. 3, pp. 253-257, 1996). Viral delivery of S100A1 has been successfully used in large animal models of heart failure. Specifically, AAV9-S100A1 gene therapy evaluated in a pig model demonstrated protection from hemodynamic deterioration, improvement of cardiac function, and heart rate normalization (Rohde et al, *J Mol Cell Cardiol*, vol. 50, no. 5, pp. 777-784, 2011). Another study using AAV6-S100A1 in a pig model of heart failure demonstrated the safety of over-expression of S100A1 demonstrating no increase in arrhythmias or right ventricular dysfunction; however, there was a significant increase in left ventricular ejection fraction and cardiac remodeling (Weber et al, *Gene Ther*, vol. 21, pp. 131-138, 2014). Studies such as these support the potential for S100A1 therapy in humans with end-stage heart failure.

SDF-1α

Stromal cell-derived factor-la (SDF-1α) is an 8 kDa chemokine that plays an important role in recruitment of cardiac stem cells, inhibition of cardiac myocyte death, and improvement in cardiac function by binding to receptor CXCR4 on mesenchymal stem cells (Penn et al, *Gene Ther*, vol. 19, no. 6, pp. 583-587, 2012). A non-viral DNA plasmid encoding human SDF-1α was tested in several clinical trials (Penn et al., *Circ Res*, vol. 112, no. 5, pp. 816-825, 2013; and, Chung et al, *Eur Heart J*, vol. 36, pp. 2228-2238, 2015). Findings from these trials demonstrated that over-expression of SDF-1α is relatively safe with no incidence of serious unanticipated related adverse events including arrhythmias or progression to further heart failure episodes. Such study also demonstrated that SDF-1α over-expression could improve function in patients with CHF injected intramyocardially at doses of 15 mg or 30 mg. Moreover, plasmid DNA delivered retrograde via the coronary sinus at a dose of 45 mg was found to be safe.

VEGF

The vascular endothelial growth factor (VEGF) family of proteins is involved in new vessel formation, endothelial cell migration and activation, stem cell recruitment, and tissue regeneration (Taimeh et al, *Nat Rev Cardiol*, vol. 10, no. 9, pp. 519-530, 2013). Dysfunctional vascular regulation is an important component of the pathophysiology of heart failure, and reduced levels of VEGF have been observed in models of advanced heart failure. There are many isoforms of VEGF. However, VEGF165 has been used in both pre-clinical and clinical models. The utility of targeting VEGF as a treatment option for heart failure has been demonstrated using gene transfer with vectors such as naked plasmid DNA and adenovirus in animal models showing improved collateral perfusion and overall cardiac function. Clinical use of VEGF165 has been studied both as a directly injected pDNA and via a viral vector with positive but limited results. In certain embodiments, VEGF 165 has a sequence comprising amino acids 27-191 of a VEGF191 sequence disclosed herein. In certain embodiments, VEGF 165 has a sequence comprising amino acids 27, 28, 29, 30, 31, 32, 33, or 34 to 180, 181, 182, 183, 184, 185, 186, 187, 188, 189, 190, or 191 of a VEGF191 sequence disclosed herein. In certain embodiments, VEGF 165 has a sequence comprising amino acids 30-185 of a VEGF191 sequence disclosed herein.

The CAG promoter utilized in conjunction with each individual gene (i.e., S100A1, SDF1α, and VEGF165) has demonstrated the individual effects on scar tissue, cardiac function and remodeling. The effect of each gene is unique on cardiac tissue. The potential enhanced effect of all three genes has been tested only in vitro. However, local administration of the combination of VEGF with SDF-1α has been demonstrated to be enhanced in a murine model of hind limb ischemia by promoting endothelial progenitor cell-induced neovascularization (Yu et al, *J Vasc Surg*, vol. 50, no. 3, pp. 608-616, 2009).

Accordingly, provided herein are polynucleotide constructs (such as, but not limited to, non-viral plasmid vectors) encoding a polypeptide comprising a first functional (i.e., biologically active) polypeptide, a second functional polypeptide and, optionally, a third functional polypeptide.

Provided herein are polynucleotide constructs encoding a polypeptide comprising an S100 polypeptide, a second functional polypeptide and, optionally, a third functional polypeptide, wherein the second and, optional, third functional polypeptides comprise any one of a cytokine, a chemokine, or an angiogenic polypeptide.

Provided herein are polynucleotide constructs comprising polynucleotide sequences encoding polypeptide linker sequences for separation of the first and second and, optionally, separation of the second and third functional polypeptides.

Provided are polypeptides encoded by a polynucleotide described herein. Also provided are cells comprising at least one polynucleotide or vector described herein.

Provided herein are methods of treating a cardiac condition comprising contacting a cell with a therapeutically effective amount of a polynucleotide described herein. In some cases, the cell is a myocardial cell.

Provided herein are methods of treating cardiac diseases and disorders, for example, but not limited to, congestive heart failure (CHF), in a subject comprising providing to a subject a therapeutically effective amount of a composition comprising a polynucleotide or vector described herein. In some cases, the subject is a mammal or human subject. In some cases, the subject is administered at least one additional therapy.

Provided herein are pharmaceutical compositions comprising a polynucleotide described herein, or a polypeptide encoded by a polynucleotide described herein and a pharmaceutically acceptable excipient.

Provided are compositions comprising: at least one plasmid microbubble complex, wherein the microbubble comprises a lipid, a gas and a plasmid comprising a polynucleotide described herein. In some embodiments, the lipid forms a shell enclosing said gas and plasmid. In some cases, the gas is a perfluorocarbon gas, such as perfluoropropane. In some embodiments, the microbubble complex comprises at least one of 1,2-dipalmitoyl-sn-glycero-3 -phosphatidylcholine and 1,2-dipalmitoyl-sn-glycero-3-phosphatidylethanolamine glycerol.

Provided are methods comprising administering to a subject a plasmid microbubble complex composition described herein; and contacting the subject with an ultrasonic energy sufficient to result in ultrasound disruption of the at least one microbubble at a predetermined tissue or organ. In some cases, disruption of the at least one microbubble at said predetermined tissue or organ delivers said plasmid into said tissue or organ. In some instances the tissue or organ is an organ, which can be the heart, liver, or kidney.

Provided is a method of treating a cardiac disease or disorder (for example, but not limited to, congestive heart failure, cardiomyopathy, arrhythmia, pericardial disease, aorta disease, marfan syndrome and coronary artery disease.) in a subject comprising: administering to the subject an amount of plasmid microbubble complex composition described herein; contacting the subject with an ultrasonic energy sufficient to result in ultrasound disruption of the at least one microbubble and delivering the plasmid to the heart of the subject.

BRIEF DESCRIPTION OF THE DRAWINGS

Unique and preferred features of the invention are set forth with particularity in the appended claims. Understanding of the features and advantages of the present invention may also be obtained by reference to the following detailed description that sets forth illustrative embodiments, in which the principles of the invention are utilized, and the accompanying drawings of which:

FIG. 5A. HUVEC proliferation following recombinant VEGF treatment FIG. 5B. shows HUVEC proliferation following treatment with VEGF-transfected induced pluripotent stem cells (iPSC) cell supernatant. iPSC cells were transfected and incubated for 96 hours. Supernatant was collected and used to culture HUVECS. HUVEC proliferation was measured by CellTiter-Glo.

FIG. 14A. shows that transfected cardiomyocytes from a DCM subject with double gene and triple-gene constructs produce functional VEGF protein able to induce HUVEC proliferation. (Note: Sample 8 was not tested in Run1, Run2.) FIG. 14B shows that transfected cardiomyocytes from a healthy subject with double gene and triple-gene constructs produce functional VEGF protein which is able to induce HUVEC proliferation.

FIG. 15A. ELISA assay standard curve showing absorbance of SDF1. FIG. 15B. SDF1 concentration in the 293T supernatant. The data demonstrates successful expression of functional (i.e., biologically active) polypeptides encoded by polynucleotides described herein, comprising linkers disclosed herein.

FIG. 16A. ELISA assay standard curve showing absorbance of VEGF. FIG. 16B. VEGF concentration in the 293T supernatant. This data demonstrates successful expression of functional (i.e., biologically active) polypeptides encoded by polynucleotides described herein, comprising linkers disclosed herein.

FIG. 17A. ELISA assay standard curve showing absorbance of S100A1. FIG. 17B. S100A1 concentration in the 293T lysate. This data demonstrates successful expression of functional (i.e., biologically active) polypeptides encoded by polynucleotides described herein, comprising linkers disclosed herein.

FIG. 25B. contractile duration of beating rate of iPSC cells transfected with pStuffer, a vector encoding for pS100A1, or a vector encoding for S100A1 comprising a 2A tail. The data indicates that the presence of a 2A tail at the 3' end of a vector encoding for S100A1 does not affect the function of S100A1. (pStuffer is a plasmid with the same backbone configuration as pXoX, with the open reading frame (ORF) replaced with a non-expressing, similar-sized stuffer sequence.)

FIG. 26B. contractile rate of iPSC cells transfected with DNA1, DNA2, DNA3, DNA4, DNA5, or an untransfected control. FIG. 26C. contractile duration of DNA1, DNA2, DNA3, DNA4, DNA5, or an untransfected control. Data shows the restoration of DCM contractile properties to healthy control levels.

FIG. 27A shows a schematic depiction of the pXoX triple gene vector encoding biologically active SDF1α, S100A1, and VEGF. FIG. 27B identifies individual gene elements in the triple-gene vector.

FIGS. 31 A-C show in vivo therapeutic results via echocardiographic measurement of cardiac structure and as function of fractional shortening.

DETAILED DESCRIPTION OF THE DISCLOSURE

Figure 1:
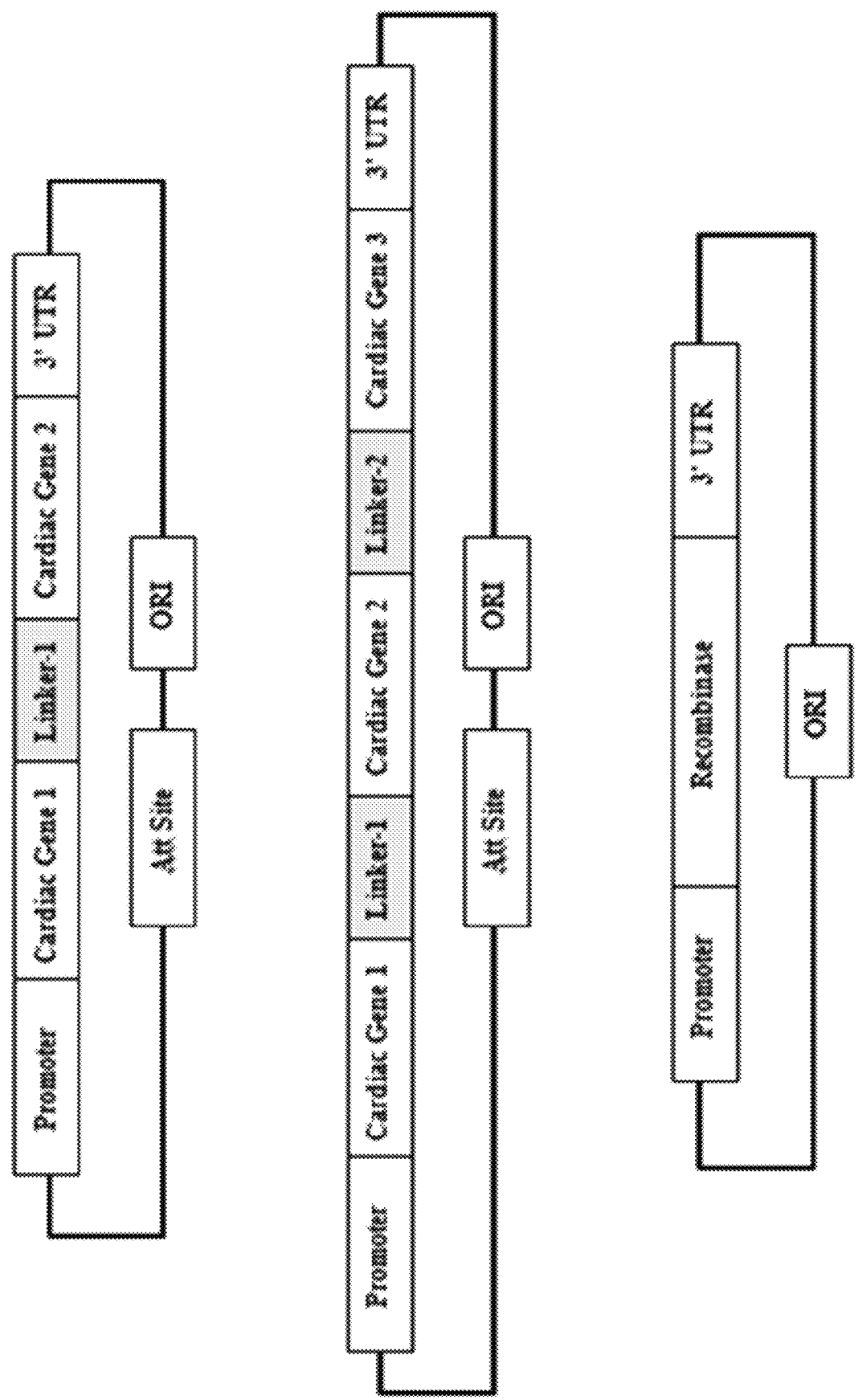
FIG. 1 displays ways in which non-viral delivery of cardiac effector genes is accomplished via alternate configurations of novel vector constructs comprising linker sequences described herein.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

The S100 family of proteins includes, for instance, S100A1, S100A2, S100A3, S100A4, S100A5, S100A6, S100A7, S100A8, S100A9, S100A10, S100A11, S100A12, S100A13, S100A14, S100A15, and S100A16. In some cases are proteins similar to a S100A protein for instance S100A7L (S100 calcium binding protein A7-like). Other S100 proteins include S100B, S100G, S100P and S100Z and variants and fragments thereof which may be included in embodiments described herein. Also included in embodiments described herein are S100 proteins which are the result of pseudogene products that may be expressed by vectors described herein.[61]

The SDF family of proteins include for instance, a protein encoded by an antimicrobial gene that can encode a stromal cell-derived alpha chemokine member of an intercrine family. [62] Embodiments described herein can comprise encoded proteins which may function as ligands for a G-protein coupled receptor, chemokine (C-X-C motif) receptor 4, and may play a role in many diverse cellular functions, including embryogenesis, immune surveillance, inflammation response, tissue homeostasis, and tumor growth and metastasis. Also included are transcript variants encoding different isoforms, and said isoforms and transcript variants may be expressed by vectors described herein. In some embodiments described herein, are SDF family proteins wherein the first two cysteine residues are separated by one amino acid (C-X-C chemokine). The following protein isoforms have been identified in humans and may be expressed by vectors described herein and included in methods and compositions described herein: SDF-1 Alpha, SDF-1 Beta, SDF-1 Gamma, SDF-1 Delta, SDF-1 Epsilon and SDF-1 Theta, and fragments and variants thereof.

The VEGF family of proteins described herein includes members of the PDGF/VEGF growth factor family. For instance included in methods and compositions described herein, can be splice variants and isoforms and fragments and derivatives of VEGF121, VEGF121b, VEGF145, VEGF165, VEGF165b, VEGF189, VEGF191, VEGF206. [63].

In some cases, the 5100 polypeptide can be a S100A1, and any functional derivative thereof. In some embodiments, the second functional polypeptide can be an angiogenic polypeptide. An angiogenic polypeptide can be a vascular endothelial growth factor (VEGF) polypeptide. In a few embodiments, a VEGF polypeptide is selected from a group consisting of VEGF121, VEGF121b, VEGF145, VEGF165, VEGF165b, VEGF189, VEGF191, VEGF206, fragments and variants thereof. In certain embodiments, VEGF 165 has a sequence comprising amino acids 27-191 of a VEGF191 sequence disclosed herein. In certain embodiments, VEGF 165 has a sequence comprising amino acids 27, 28, 29, 30, 31, 32, 33, or 34 to 180, 181, 182, 183, 184, 185, 186, 187, 188, 189, 190, or 191 of a VEGF191 sequence disclosed herein. In certain embodiments, VEGF 165 has a sequence comprising amino acids 30-185 of a VEGF191 sequence disclosed herein. In some cases, a VEGF polypeptide described herein can comprise a sequence with at least 45%, 50%, 55%, 60%, 65%, 70%, 75%, 80%, 85%, 90%, 95%, or 99% identity to the sequence of VEGF 191 or VEGF165 disclosed herein. In some cases, a VEGF polypeptide can comprise a sequence with at least 45%, 50%, 55%, 60%, 65%, 70%, 75%, 80%, 85%, 90%, 95%, or 99% identity to the sequence of VEGF191 polypeptide disclosed herein.

In other embodiments, the third functional polypeptide can be a chemokine. The chemokine can be a stromal cell derived factor 1 (SDF) polypeptide. An SDF polypeptide can be selected from the group consisting of SDF1, SDF-1α, SDF-1β, fragments and variants thereof [62]. An SDF polypeptide can comprise a sequence with at least 45%, 50%, 55%, 60%, 65%, 70%, 75%, 80%, 85%, 90%, 95%, or 99% identity to the sequence of SDF1 polypeptide disclosed herein.

In some embodiments described herein, an S100 polypeptide can be connected to the second polypeptide by a first polypeptide linker. In some cases, the polypeptide linker can be a cleavable linker or an uncleavable linker.

Provided herein are embodiments wherein a polypeptide construct encoded by a polynucleotide described herein can comprise a calcium-binding protein (S100) polypeptide, a second functional polypeptide, and further comprise a third functional polypeptide. In some cases, the third functional polypeptide can be any one of a cytokine, a chemokine, an angiogenic polypeptide, and any functional derivative thereof.

In certain embodiments, the third functional polypeptide can be an angiogenic polypeptide. In some embodiments, the angiogenic polypeptide can be a VEGF polypeptide. A VEGF polypeptide can be selected from a group consisting of VEGF121, VEGF121b, VEGF145, VEGF165, VEGF165b, VEGF189, VEGF191, VEGF206, fragments and variants thereof. A VEGF polypeptide can comprise a sequence with at least 45%, 50%, 55%, 60%, 65%, 70%, 75%, 80%, 85%, 90%, 95%, or 99% identity to the sequence of the VEGF165 polypeptide. In some cases, a VEGF polypeptide can comprise a sequence with at least 45%, 50%, 55%, 60%, 65%, 70%, 75%, 80%, 85%, 90%, 95%, or 99% identity to the sequence of VEGF191 polypeptide.

In some embodiments, the third functional polypeptide can be a chemokine. In certain embodiments, the chemokine can be a SDF polypeptide. In some embodiments, the SDF polypeptide is selected from a group consisting of SDF1, SDF-1α, SDF-1β, fragments and variants thereof. In some cases, the SDF polypeptide can comprise a sequence with at least 45%, 50%, 55%, 60%, 65%, 70%, 75%, 80%, 85%, 90%, 95%, or 99% identity to the sequence of SDF1 polypeptide described herein.

In some embodiments, the third functional polypeptide can be connected to at least one of said S100 polypeptide and said second functional polypeptide by a second polypeptide linker which can be optionally cleavable. Polypeptide linkers can be independently selected from the linkers described herein.

Provided herein are polynucleotides encoding at least one polypeptide construct comprising at least a first polypeptide and a second polypeptide, wherein a first polypeptide can be an angiogenic polypeptide and a second polypeptide can be a chemokine or variant or fragment thereof. In some cases, an angiogenic polypeptide can be a VEGF polypeptide selected from a group consisting of VEGF121, VEGF121b, VEGF145, VEGF165, VEGF165b, VEGF189, VEGF191, VEGF206, fragments and variants thereof. A polypeptide can comprise a sequence with at least 45%, 50%, 55%, 60%, 65%, 70%, 75%, 80%, 85%, 90%, 95%, or 99% identity to the sequence of a VEGF polypeptide.

Provided are VEGF polypeptides comprising a sequence with at least 45%, 50%, 55%, 60%, 65%, 70%, 75%, 80%, 85%, 90%, 95%, or 99% identity to the sequence of VEGF191. In some cases, a second polypeptide can be an SDF polypeptide. An SDF polypeptide can be selected from the group consisting of SDF1, SDF-1α, SDF-1β, fragments and variants thereof. In some cases, an SDF polypeptide can comprise a sequence with at least 45%, 50%, 55%, 60%, 65%, 70%, 75%, 80%, 85%, 90%, 95%, or 99% identity to the sequence of SDF1.

Provided herein are methods of improving vasculogenesis in a subject comprising providing to said subject a therapeutically effective amount of a composition comprising a polynucleotide described herein or a polypeptide encoded by a polynucleotide described herein.

Provided herein are expression vectors, comprising at least one promoter operably linked to at least two polypeptides selected from a SDF1 polypeptide, a S100A1 polypeptide, a VEGF polypeptide and fragments and variants thereof. In some cases, at least two polypeptides are connected by a linker. In some cases, at least one promoter can be selected from the group consisting of CAG promoter, CMV promoter, SV40 promoter, adenovirus promoter, Beta actin promoter, metallothionin promoter, EFla promoter, myosin light chain promoter, myosin heavy chain promoter, NCX1 promoter and other suitable cardiac promoters. An expression vector can be a cardiac expression vector.

Provided herein are polypeptide constructs comprising at least a first polypeptide, and a second polypeptide, wherein the first polypeptide can be a calcium binding protein, or variant or fragment thereof and the second polypeptide can be an angiogenic polypeptide, a chemokine, or variant or fragment thereof. Also disclosed are polypeptide constructs comprising at least a first polypeptide, a second polypeptide, and a third polypeptide wherein a first polypeptide can be an angiogenic polypeptide or variant or fragment thereof, a second polypeptide can be a chemokine, or variant or fragment thereof; and a third polypeptide can be a calcium binding protein, or variant or fragment thereof. In some cases, a polypeptide construct described herein can comprise S100A1, a variant or a fragment thereof. In some cases, a polypeptide construct can comprise SDF1, a variant or a fragment thereof. In further cases, a polypeptide construct described herein can comprise VEGF, a variant or a fragment thereof.

Provided are pharmaceutical compositions comprising a polynucleotide described herein, or a polypeptide construct provided herein, or a polypeptide construct encoded by a polynucleotide described herein, and a pharmaceutically acceptable excipient. Provided herein are methods of treating a cardiac diseases and disorders in a subject comprising providing to the subject a therapeutically effective amount of a composition comprising a polynucleotide described herein, or a polypeptide construct provided herein, or a polypeptide construct encoded by a polynucleotide described herein.

In some embodiments, a polynucleotide construct encoding a polypeptide construct described herein further comprises a third functional polypeptide connected by a second linker polypeptide to the second functional polypeptide. In some cases, the third functional polypeptide can be selected from a list consisting of VEGF, SDF1, S100A1, variants and derivatives thereof. In some cases, the second linker can be the same or different from the first linker described herein. In some cases, the linkers and functional polypeptides can be expressed in-frame.

Provided herein are cells comprising a polynucleotide described herein.

Provided herein is a method comprising: contacting at least one cardiac cell with a polynucleotide encoding a polypeptide construct comprising at least a first polypeptide and a second polypeptide, wherein a first polypeptide is an angiogenic polypeptide variant or fragment thereof; and a second polypeptide is at least one of a chemokine, a calcium binding protein, or variant or fragment thereof. In some embodiments, an angiogenic polypeptide variant or fragment thereof can be a VEGF polypeptide selected from a group consisting of VEGF121, VEGF121b, VEGF145, VEGF165, VEGF165b, VEGF189, VEGF191, VEGF206, fragments and variants thereof. A VEGF polypeptide can comprise a sequence with at least 45%, 50%, 55%, 60%, 65%, 70%, 75%, 80%, 85%, 90%, 95%, or 99% identity to the sequence of VEGF165. In certain embodiments, VEGF 165 has a sequence comprising amino acids 27-191 of a VEGF191 sequence disclosed herein. In certain embodiments, VEGF 165 has a sequence comprising amino acids 27, 28, 29, 30, 31, 32, 33, or 34 to 180, 181, 182, 183, 184, 185, 186, 187, 188, 189, 190, or 191 of a VEGF191 sequence disclosed herein. In certain embodiments, VEGF 165 has a sequence comprising amino acids 30-185 of a VEGF191 sequence disclosed herein. In some cases, a VEGF polypeptide described herein can comprise a sequence with at least 45%, 50%, 55%, 60%, 65%, 70%, 75%, 80%, 85%, 90%, 95%, or 99% identity to the sequence of VEGF 191 or VEGF165 disclosed herein. A VEGF polypeptide can comprise a sequence with at least 45%, 50%, 55%, 60%, 65%, 70%, 75%, 80%, 85%, 90%, 95%, or 99% identity to the sequence of VEGF191. In some cases, a second polypeptide can be a chemokine. A chemokine can be a stromal cell-derived factor 1 (SDF) polypeptide. In some cases, an SDF polypeptide useful in compositions and methods provided herein can be selected from the group consisting of SDF1, SDF-1α, SDF-1β, fragments and variants thereof. An SDF polypeptide can comprise a sequence with at least 45%, 50%, 55%, 60%, 65%, 70%, 75%, 80%, 85%, 90%, 95%, or 99% identity to SDF1-α.

In some cases, a polynucleotide encoding a polypeptide construct can be introduced ex vivo. In certain embodiments, a polynucleotide encoding a polypeptide construct can be introduced in vivo. An introduction in vivo can be selected from a group consisting of percutaneous coronary artery catheterization, coronary venous blockade, cardiac recirculation, antegrade coronary artery infusion, retrograde perfusion, direct injection, and any combination thereof.

Provided herein are methods of treating a cardiac disease or disorder in a subject (for example, but not limited to, by improving vasculogenesis, cardiac function or cardiac remodeling) in a subject comprising administering to said subject an amount of a polynucleotide encoding a construct comprising a VEGF polypeptide, and at least one of a SDF polypeptide and a S100 polypeptide. A VEGF polypeptide in an embodiment described herein can be selected from a group consisting of VEGF121, VEGF121b, VEGF145, VEGF165, VEGF165b, VEGF189, VEGF191, VEGF206, fragments and variants thereof. A VEGF polypeptide can comprise a sequence with at least 45%, 50%, 55%, 60%, 65%, 70%, 75%, 80%, 85%, 90%, 95%, or 99% identity to the sequence of VEGF165. In certain embodiments, VEGF 165 has a sequence comprising amino acids 27-191 of a VEGF191 sequence disclosed herein. A VEGF polypeptide can comprise a sequence with at least 45%, 50%, 55%, 60%, 65%, 70%, 75%, 80%, 85%, 90%, 95%, or 99% identity to the sequence of VEGF191. An SDF polypeptide can be selected from the group consisting of SDF1, SDF-1α, SDF-1β, fragments and variants thereof. An S100 polypeptide can be S100A1, fragment or variant thereof.

In certain embodiments, a subject treated with methods and compositions of the invention can have a congestive heart failure (CHF). A subject can have a left ventricular assist device (LVAD) in place. A subject can have a cardiomyopathy. A cardiomyopathy can be selected from the group consisting of dilated cardiomyopathy (DCM), hypertrophic cardiomyopathy (HCM), restrictive cardiomyopathy (RCM), arrhythmogenic right ventricular cardiomyopathy (ARVC), and any combination thereof.

In further embodiments, a subject treated with methods and compositions of the invention can have any one or more of: aneurysm, atherosclerosis, congenital heart defect, pericardial disorder, acute decompensated heart failure, angina, arteriosclerotic heart disease, athletic heart syndrome, atrioventricular fistula, autoimmune heart disease, brown atrophy of the heart, cardiac amyloidosis, cardiac arrhythmia, cardiac asthma, cardiac contractility modulation, cardiac syndrome x, cardiogenic shock, cardiomegaly, cardiomyopathy, cardiophobia, cardiorenal syndrome, cardiotoxicity, cardiovascular disease, carditis, chronic rheumatic heart diseases, coeur en sabot, coronary artery aneurysm, coronary artery anomaly, coronary artery disease, coronary artery dissection, coronary artery ectasia, coronary occlusion, coronary steal, coronary thrombosis, coronary vasospasm, coxsackievirus-induced cardiomyopathy, diastolic heart failure, dressler syndrome, duroziez's disease, eisenmenger's syndrome, embryocardia, embryonic recall, endocardial fibroelastosis, heart failure with preserved ejection fraction, heart neoplasia, high-output heart failure, hyperdynamic precordium, hypertensive heart disease, idiopathic giant-cell myocarditis, inflammatory heart disease, interventricular dyssynchrony, intraventricular dyssynchrony, ischemic heart disease, isolated atrial amyloidosis, keshan disease, kounis syndrome, mydicar, myocardial bridge, myocardial disarray, myocardial rupture, myocardial scarring, myocardial stunning, myocarditis, nonbacterial thrombotic endocarditis, ostial disease, peripheral arterial disease, phosphorus and non-atherosclerotic heart disease, postpericardiotomy syndrome, pressure-controlled intermittent coronary sinus occlusion (picso), recovery from cardiopulmonary resuscitation, recovery from traumatic cardiac arrest, right axis deviation, rheumatic heart disease, roemheld syndrome, saturated fat and cardiovascular disease controversy, scar-fc, shone's syndrome, subacute bacterial endocarditis, valvular heart disease, ventricular aneurysm, and viral cardiomyopathy.

Provided herein are methods of treating or preventing a cardiovascular condition in a subject comprising: administering to a subject an amount of a construct comprising a S100A polypeptide, and a second functional polypeptide, wherein said second functional polypeptide is at least one of a cytokine, a chemokine and an angiogenic polypeptide. In some cases, an administration to a subject can be performed preventively. In some cases, an administration to a subject can be performed therapeutically. In some cases, a subject can be administered at least one additional treatment to said subject. In some cases, a second functional polypeptide can be VEGF, SDF, or a combination thereof Provided herein are methods comprising administering to a subject at least one non-viral vector comprising a polynucleotide encoding a polypeptide sequence described herein comprising at least two functional proteins or portions thereof; at least one promotor; and at least one engineered recombination site; wherein said at least one promoter drives expression of said at least two functional proteins. In some cases, at least one promotor can be constitutive. In some cases, at least one promoter can be tissue-specific. In some cases, at least one promoter can be inducible. In some cases, at least one tissue-specific promotor is a myosin light chain (MLC) promoter. In some cases, an inducible promoter is a small molecule ligand-inducible two polypeptide ecdysone receptor-based gene switch.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, arnidoketones, 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5 -Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5 -Dimethyl-benzoic acid N-(1- tert-butyl-butyl)-N'-(2-ethy 1 -3-methoxy-benzoyl)-hydrazide), and any combination thereof. A linker can be a cleavable linker.

In some embodiments, a first functional polypeptide and a second functional polypeptide connected by a first linker polypeptide, wherein the first linker polypeptide comprises a sequence with at least 40%, 50%, 60%, 80% or 100% identity to the sequence APVKQ (SEQ ID NO: 42). In some cases, the linker polypeptide comprises a sequence selected from the group consisting of APVKQ (SEQ ID NO: 42), GPVKQ (SEQ ID NO: 43), VPVKQ (SEQ ID NO: 44), IPVKQ (SEQ ID NO: 45), MPVKQ (SEQ ID NO: 46), APIKQ (SEQ ID NO: 47), GPIKQ (SEQ ID NO: 48), VPIKQ (SEQ ID NO: 49), IPIKQ (SEQ ID NO: 50), MPIKQ (SEQ ID NO: 51), APAKQ (SEQ ID NO: 52), GPAKQ (SEQ ID NO: 53), VPAKQ (SEQ ID NO: 54), IPAKQ (SEQ ID NO: 55), MPAKQ (SEQ ID NO: 56), APVRQ (SEQ ID NO: 57), GPVRQ (SEQ ID NO: 58), VPVRQ (SEQ ID NO: 59), IPVRQ (SEQ ID NO: 60), MPVRQ (SEQ ID NO: 61), APIRQ (SEQ ID NO: 62), GPIRQ (SEQ ID NO: 63), VPIRQ (SEQ ID NO: 64), IPIRQ (SEQ ID NO: 65), MPIRQ (SEQ ID NO: 66), APARQ (SEQ ID NO: 67), GPARQ (SEQ ID NO: 68), VPARQ (SEQ ID NO: 69), IPARQ (SEQ ID NO: 70), MPARQ (SEQ ID NO: 71), APVKN (SEQ ID NO: 72), GPVKN (SEQ ID NO: 73), VPVKN (SEQ ID NO: 74), IPVKN (SEQ ID NO: 75), MPVKN (SEQ ID NO: 76), APIKN (SEQ ID NO: 77), GPIKN (SEQ ID NO: 78), VPIKN (SEQ ID NO: 79), IPIKN (SEQ ID NO: 80), MPIKN (SEQ ID NO: 81), APAKN (SEQ ID NO: 82), GPAKN (SEQ ID NO: 83), VPAKN (SEQ ID NO: 84), IPAKN (SEQ ID NO: 85), MPAKN (SEQ ID NO: 86), APVRN (SEQ ID NO: 87), GPVRN (SEQ ID NO: 88), VPVRN (SEQ ID NO: 89), IPVRN (SEQ ID NO: 90), MPVRN (SEQ ID NO: 91), APIRN (SEQ ID NO: 92), GPIRN (SEQ ID NO: 93), VPIRN (SEQ ID NO: 94), IPIRN (SEQ ID NO: 95), MPIRN (SEQ ID NO: 96), APARN (SEQ ID NO: 97), GPARN (SEQ ID NO: 98), VPARN (SEQ ID NO: 99), IPARN (SEQ ID NO: 100) and MPARN (SEQ ID NO: 101). In some cases, a polypeptide linker may also include one or more GS linker sequences, for instance (GS)n (SEQ ID NO: 109), (SG)n (SEQ ID NO: 110), (GSG)n (SEQ ID NO: 111) and (SGS)n (SEQ ID NO: 112) wherein n can be any number from zero to fifteen. In some embodiments, the first functional polypeptide can be different from the second functional polypeptide.

In some embodiments, a method can further comprise administering to a subject at least one secondary vector. At least one secondary vector can be an mRNA. At least one secondary vector can be a plasmid. In some embodiments, at least one secondary vector can comprise at least one recombinase. A recombinase can be selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase. In some embodiments, at least two genes can be integrated into a genome of a subject by a recombinase. In some embodiments, at least one recombination site can be a phage genomic recombination attachment site (attP) or a bacterial genomic recombination attachment site (attB). In some embodiments, a recombinase used as described in the invention herein comprises a site-specific serine recombinase; such as, but not limited to, SpBC2 recombinase (see, for example, U.S. Pat. No. 9,034,650 issued May 19, 2015 (U.S. Pub. No. 2006/0172377) which is hereby incorporated by reference herein in its entirety).

A vector can be good manufacturing practices (GMP) compatible.

Provided are polypeptides comprising a sequence with at least 40%, 50% 60%, 80%, or 100% identity to a sequence selected from the group consisting of SEQ ID NO: 32, SEQ ID NO: 34, SEQ ID NO: 36, SEQ ID NO: 38, and SEQ ID NO: 40. In some embodiments, the polypeptide comprises a sequence with at least 40%, 50%, 60%, 70%, 75%, 80%, 85%, 90%, 95%, or 99% identity to a sequence selected from the group consisting of SEQ ID NO: 32, SEQ ID NO: 34, SEQ ID NO: 36, SEQ ID NO: 38, and SEQ ID NO: 40.

Provided are polypeptides comprising a sequence with at least 40%, 50%, 60%, 80%, or 100% identity to a sequence selected from the group consisting of SEQ ID NO: 102, SEQ ID NO: 104 and SEQ ID NO: 106. In some embodiments is a polypeptide comprising a sequence with at least 45%, 50%, 55%, 60%, 65%, 70%, 75%, 80%, 85%, 90%, 95%, or 99% identity to a sequence selected from the group consisting of SEQ ID NO: 102, SEQ ID NO: 104 and SEQ ID NO: 106.

Provided is a polypeptide comprising a sequence with at least 45%, 50%, 55%, 60%, 65%, 70%, 75%, 80%, 85%, 90%, 95%, or 99% identity to a polypeptide sequence encoded by the nucleic acid sequence of SEQ ID NO. 108.

Provided herein are polynucleotides encoding a polypeptide construct comprising a first functional polypeptide and a second functional polypeptide connected by a first linker polypeptide, wherein the first linker polypeptide comprises a sequence with at least 40%, 50%, 60%, 80%, or 100% identity to the sequence APVKQ. In some cases, the linker polypeptide comprises a sequence selected from the group consisting of APVKQ (SEQ ID NO: 42). In some cases, the linker polypeptide comprises a sequence selected from the group consisting of APVKQ (SEQ ID NO: 42), GPVKQ (SEQ ID NO: 43), VPVKQ (SEQ ID NO: 44), IPVKQ (SEQ ID NO: 45), MPVKQ (SEQ ID NO: 46), APIKQ (SEQ ID NO: 47), GPIKQ (SEQ ID NO: 48), VPIKQ (SEQ ID NO: 49), IPIKQ (SEQ ID NO: 50), MPIKQ (SEQ ID NO: 51), APAKQ (SEQ ID NO: 52), GPAKQ (SEQ ID NO: 53), VPAKQ (SEQ ID NO: 54), IPAKQ (SEQ ID NO: 55), MPAKQ (SEQ ID NO: 56), APVRQ (SEQ ID NO: 57), GPVRQ (SEQ ID NO: 58), VPVRQ (SEQ ID NO: 59), IPVRQ (SEQ ID NO: 60), MPVRQ (SEQ ID NO: 61), APIRQ (SEQ ID NO: 62), GPIRQ (SEQ ID NO: 63), VPIRQ (SEQ ID NO: 64), IPIRQ (SEQ ID NO: 65), MPIRQ (SEQ ID NO: 66), APARQ (SEQ ID NO: 67), GPARQ (SEQ ID NO: 68), VPARQ (SEQ ID NO: 69), IPARQ (SEQ ID NO: 70), MPARQ (SEQ ID NO: 71), APVKN (SEQ ID NO: 72), GPVKN (SEQ ID NO: 73), VPVKN (SEQ ID NO: 74), IPVKN (SEQ ID NO: 75), MPVKN (SEQ ID NO: 76), APIKN (SEQ ID NO: 77), GPIKN (SEQ ID NO: 78), VPIKN (SEQ ID NO: 79), IPIKN (SEQ ID NO: 80), MPIKN (SEQ ID NO: 81), APAKN (SEQ ID NO: 82), GPAKN (SEQ ID NO: 83), VPAKN (SEQ ID NO: 84), IPAKN (SEQ ID NO: 85), MPAKN (SEQ ID NO: 86), APVRN (SEQ ID NO: 87), GPVRN (SEQ ID NO: 88), VPVRN (SEQ ID NO: 89), IPVRN (SEQ ID NO: 90), MPVRN (SEQ ID NO: 91), APIRN (SEQ ID NO: 92), GPIRN (SEQ ID NO: 93), VPIRN (SEQ ID NO: 94), IPIRN (SEQ ID NO: 95), MPIRN (SEQ ID NO: 96), APARN (SEQ ID NO: 97), GPARN (SEQ ID NO: 98), VPARN (SEQ ID NO: 99), IPARN (SEQ ID NO: 100) and MPARN (SEQ ID NO: 101). In some cases, a polypeptide linker may also include one or more GS linker sequences, for instance (GS)n (SEQ ID NO: 113), (SG)n (SEQ ID NO: 114), (GSG)n (SEQ ID NO: 115) and (SGS)n (SEQ ID NO: 116) wherein n can be any number from one to fifteen. In some embodiments, the first functional polypeptide can be different from the second functional polypeptide. In other cases, at least one of said first and second functional polypeptides can be a protein, hormone, antibody, glycoprotein or derivative or fragment thereof.

Provided herein are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W).

Provided are polypeptides encoded by polynucleotides described herein, and compositions comprising these polypeptides. Also provided are therapeutic, and/or diagnostic methods comprising contacting an individual with a polynucleotide disclosed herein or a polypeptide expressed therefrom or derivative, or conjugate thereof.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ (SEQ ID NO: 42); and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ (SEQ ID NO: 42).

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The term "cardiovascular disease" and "circulatory disorder" are used interchangeably, and are used herein to describe a disease or disorder which is caused by damage to the circulatory system and which damage can be reduced and/or alleviated by providing a therapeutically effective amount of a polynucleotide described herein or a polypeptide construct encoded by a polynucleotide disclosed herein, to damaged areas of the heart and/or circulatory system of the subj ect. As used herein, the term "circulatory damage" is used to refer to injury to the circulatory system that may be caused be any of a number of diseases or disorders. Exemplary cardiovascular diseases which may be treated using a polynucleotide described herein or a polypeptide construct encoded by a polynucleotide disclosed herein and methods according to the present invention include for example, myocardial infarct, cardiomyopathy, peripheral vascular disease, congenital heart disease, other genetic diseases, and injury or trauma caused by ischemia, accidents, environmental insult. In addition, a therapeutically effective amount polynucleotide described herein or a polypeptide construct encoded by a polynucleotide disclosed herein may be used to reduce and/or eliminate the effects on the central nervous system of a heart attack in a subject, which is otherwise caused by lack of blood flow or ischemia to a site in the brain of said subject or which has occurred from physical injury to the brain and/or spinal cord.

The term "vector" or grammatical equivalents as used herein can refer any polynucleotide construct capable of directing the expression of a polypeptide construct of interest and which is useful in transferring the polypeptide construct of interest into target cells. Thus, the term includes cloning and expression vehicles, as well as integrating vectors.

Based on an increasing number of patients with congestive heart failure (CHF) with limited options (for example, commonly resulting in the requirement for destination left ventricular assist devices (LVAD) therapy), biologic options to promote recovery from CHF are needed. Thus, one embodiment of the present invention provides a triple effector plasmid-based DNA - pXoX (SDF1α, S100A1, and VEGF) to improve cardiac performance (for, example, but not limited to, as assessed by measuring the number and duration of temporary weans from LVAD support in patients who have been implanted with destination LVADS at least thirty days post-surgery). Implantation of LVADs alone can result in improved cardiac function, most of which occurs within the first 30 days or so following implantation. Also, inflammatory processes which are normally associated with surgery recover to a new baseline by 30 days post-surgery, which may result in decreased risk of treatment with pXoX to this high risk patient population.

Figure 27A:
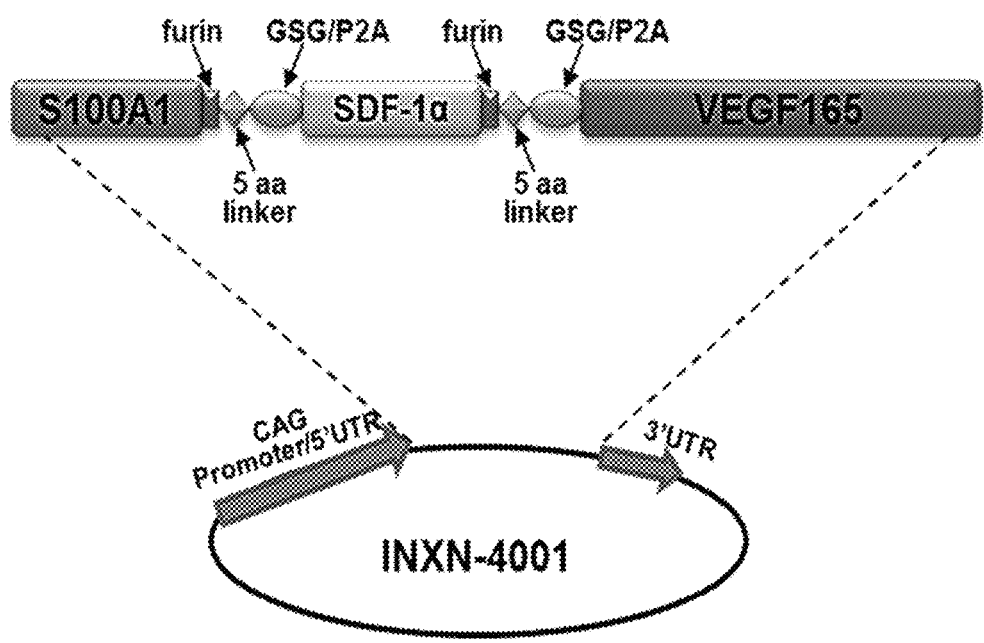
FIG. 27A and FIG. 27B show a triple-gene vector encoding for S100A1, SDF-1 alpha, and VEGF165.
Figure 27B:
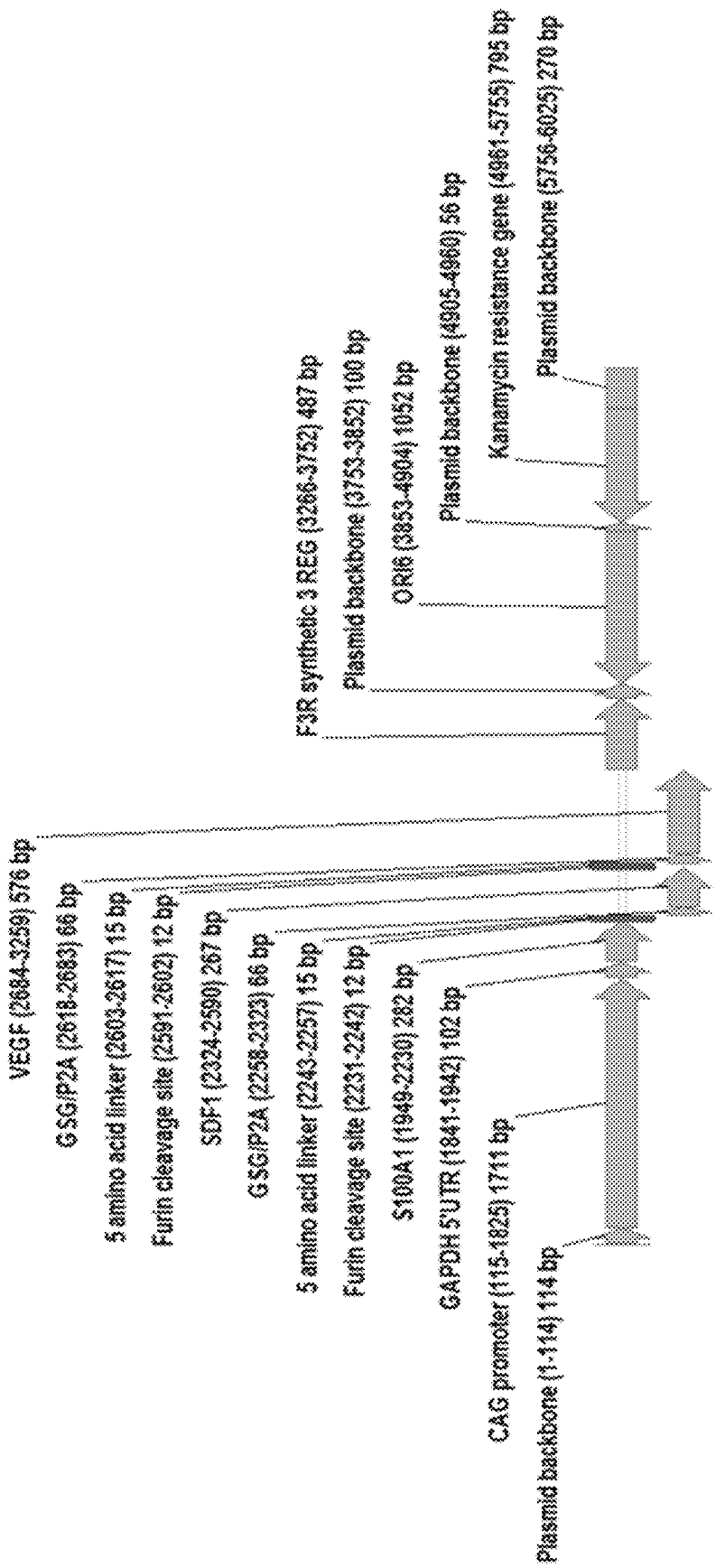

The pXoX plasmid constitutively expresses three proteins (S100A1, SDF-1α, and VEGF165) under the control of a CAG promoter, as a single mRNA that is processed into the individual effector proteins during translation via cleavage by the combined activity of furin and 2A self-cleaving peptides (fp2a). The plasmid backbone contains a kanamycin selection marker and an origin of replication derived from pBR322. An illustration of the pXoX plasmid is provided below in FIG. 27A and FIG. 27B.

The present invention also provides linkers for use, for instance, in compositions and methods useful for treatment of cardiac pathologies, conditions, and disorders (e.g., heart failure, cardiomyopathy, arrhythmia, pericardial disease, aorta disease, marfan syndrome and coronary artery disease.) using novel multigenic vectors, combinations of genetic sequences, proteins (polypeptides), and techniques described and provided for herein. As used herein, the term "linker" can mean any polynucleotide or polypeptide sequence that is used to connect any one polynucleotide or polypeptide sequence with another polynucleotide or polypeptide sequence, respectively (e.g., First GOI-Linker-Second GOI-Linker-Third GOI-Linker-etc . . . ). For example, in some instances a linker may be a polynucleotide open-reading frame encoding a fusion protein such that a first polypeptide sequence is covalently linked ("fused") by an intervening amino acid sequence to a second polypeptide sequence (and so on for third, fourth, fifth, etc . . . subsequent polypeptides in the same open-reading frame). As used herein a "linker" may also be a non-coding, linking polynucleotide sequence such as a promoter (e.g., CAG promoter or CMV promoter) or an IRES (Internal Ribosome Entry Site) which function to couple a first polynucleotide coding region (ORF) to a second polynucleotide coding region (ORF) (and so on for third, fourth, fifth, etc . . . subsequent polynucleotide open-reading frames).

Gene therapy as used herein refers to the transfer of polynucleotide described herein (e.g., DNA or RNA) of interest into a subject to treat or prevent a genetic or acquired disease or condition. Polynucleotide of interest can encode a product (e.g., a polypeptide construct) whose in vivo production is desired. In some embodiments, the polynucleotide of interest also encodes a suicide gene. In some cases, gene therapy can be used to treat a cardiovascular condition described herein.

Vectors

Provided herein can be vectors for gene therapy of a disorder comprising using a polynucleotide described herein. A vector can be utilized for introducing exogenous nucleic acids such as DNA, mRNA, small interfering RNA (siRNA), microRNA (miRNA) or antisense oligonucleotides. Given the large size and the negative charge of these macromolecules, their delivery can be mediated by carriers or vectors. Vectors of interest include, in particular, any episomal vector, e.g. viral vectors, plasmid vectors, artificial chromosomes, mini-circles and the like.

Gene delivery systems can be classified into two categories, non-viral systems and recombinant viral systems, each of which can have unique profiles in gene transfer expression. Non-viral vectors can include naked plasmid DNA, liposomal DNA complexes, polymer-carried DNA, and oligonucleotides. Plasmids can be double-stranded circular DNA-containing transgenes encoding proteins of interest, and also have enhancer and promoter sequences. A vector can be a non-viral vector.

Figure 20:
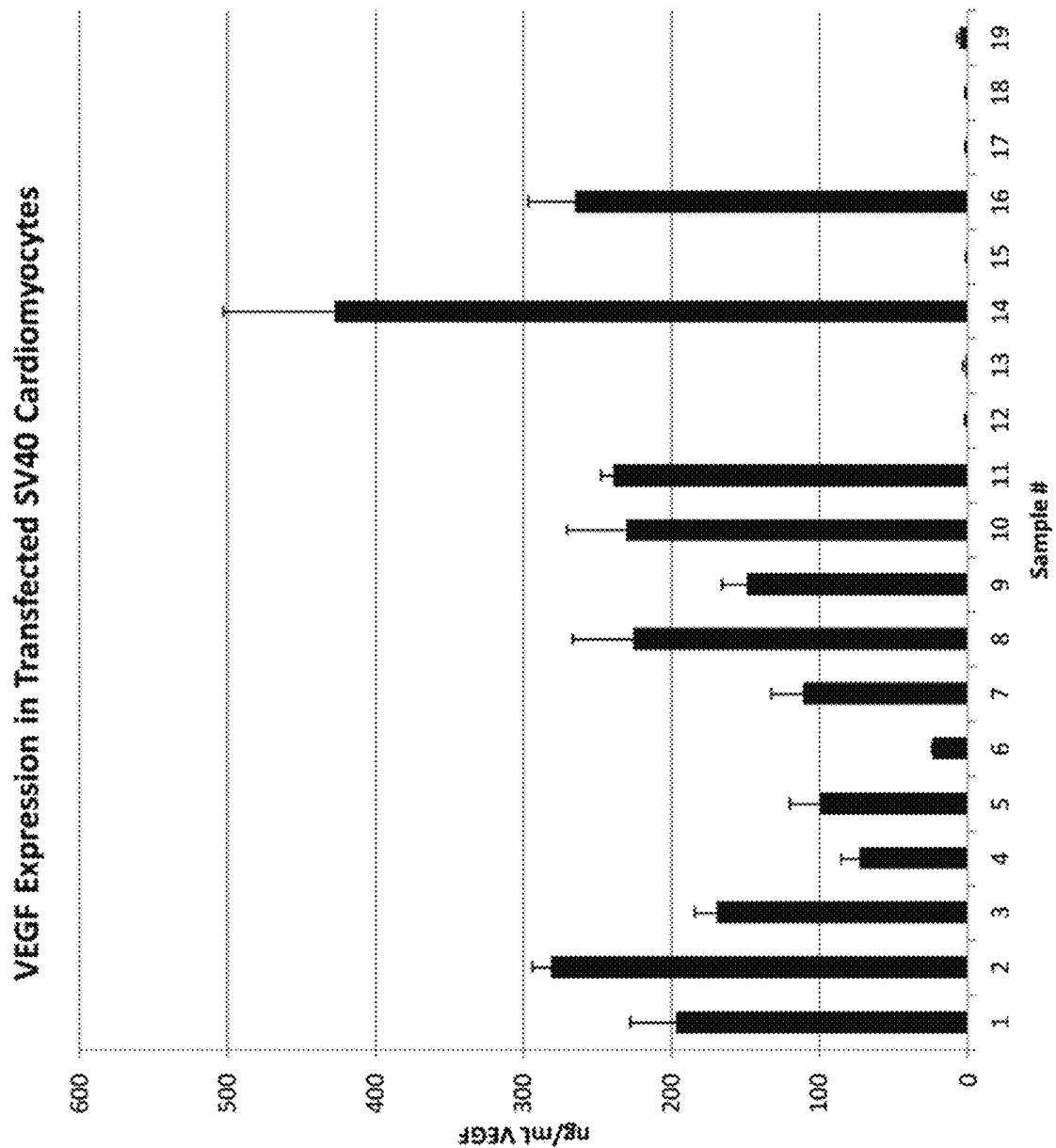
FIG. 20 shows a bar graph of VEGF concentrations as produced by cardiomyocytes transfected with single-gene, double-gene and triple-gene constructs.

A vector can comprise genes or fragments or variants thereof, wherein at least one gene, fragment or variant thereof is connected to another gene, fragment or variant thereof by a linker disclosed herein. A vector can comprise a single-gene or multiple genes, or fragments or variants thereof. A vector can comprise genes, or fragments or variants thereof, wherein at least one gene, fragment or variant thereof can be connected to another gene, fragment or variant thereof by a linker disclosed herein. For example, a vector can be singe gene, double gene (see, e.g. Table 1), or triple-gene, wherein at least one gene, fragment or variant thereof is connected to another gene, fragment or variant thereof by a linker disclosed herein. A vector can comprise a number of genes from 1 to 10, or fragments or variants thereof. A vector can comprise 1, 2, 3, 4, 5, 6, 7, 8, 9, or 10 genes, fragments or variants thereof An exemplary triple-gene vector is shown in FIG. 20A and FIG. 20B An exemplary vector sequence is shown in Table 5. In some cases, a vector can allow the simultaneous expression of two, three, or more polypeptides separately but from the same RNA transcript. A vector can also comprise a reporter polypeptide. For example, a vector can express one, two, three or more polypeptides and a reporter polypeptide.

In some cases, a vector can be constructed with at least one gene or fragment thereof. In other cases, a vector may contain up to 10 genes or fragments thereof. Genes or fragments thereof that can be expressed may be described by SEQ ID No. 102 to 107. Any homologs, isoforms, precursors, or modified portions thereof of SEQ ID No. 102 to 107 may also be expressed by vectors described herein. Genes or any fragment thereof can be separated by a linker described herein. Various linkers that may be utilized in a vector can comprise sequences shown in for instance SEQ ID No.32 to SEQ ID No. 41. In other cases, relevant linkers that can be utilized in a vector can comprise for instance a sequence shown in any of SEQ ID No. 42 to 101. For example, a portion of a gene can be at least one of a SDF gene (encoded by SEQ ID NO: 103 or 60%, 70%, 80%, 90%, or 95% identity thereto), a VEGF gene (encoded by SEQ ID NO: 107 or 60%, 70%, 80%, 90%, or 95% identity thereto) and a S100A gene (encoded by SEQ ID NO: 105 or 60%, 70%, 80%, 90%, or 95% identity thereto), which can be followed by a first linker sequence, a second gene or portion thereof which is selected from a SDF gene (encoded by SEQ ID NO: 103 or 60%, 70%, 80%, 90%, or 95% identity thereto), a VEGF gene (encoded by SEQ ID NO: 107 or 60%, 70%, 80%, 90%, or 95% identity thereto) and a S100A gene (encoded by SEQ ID NO: 105 or 60%, 70%, 80%, 90%, or 95% identity thereto), optionally followed by a second linker sequence, and subsequently a third gene or portion thereof selected from a SDF gene (encoded by SEQ ID NO: 103 or 60%, 70%, 80%, 90%, or 95% identity thereto), a VEGF gene (encoded by SEQ ID NO: 107 or 60%, 70%, 80%, 90%, or 95% identity thereto) and a S100A gene (encoded by SEQ ID NO: 105 or 60%, 70%, 80%, 90%, or 95% identity thereto). Different combinations of these constructs for instance, as described by SEQ ID No. 1 to SEQ ID No. 31 and can be utilized for therapeutic purposes.

A vector can be modular. A modular vector can allow for the replacement of one gene or nucleic acid segment for a different gene or nucleic acid segment, for example, using restriction enzyme digestion.

Multigenic expression of genes and proteins of interest can be mediated by a vector. Any vector system can be used including, but not limited to, plasmid vectors, retroviral vectors, lentiviral vectors, adenovirus vectors, poxvirus vectors, herpesvirus vectors, adeno-associated virus vectors, etc. Plasmid vectors are advantageous in avoiding host anti-viral immune responses. Plasmids can be episomal and non-integrating, which can reduce the risk of insertional mutagenesis compared with viral vectors. In some cases, an enhancer may be used in polynucleotide constructs of the invention. An enhancer can refer to a sequence that can function at no fixed distance from a transcription start site and can be either 5' or 3' to the transcription unit. Furthermore, enhancers can be within an intron as well as within the coding sequence itself. Enhancers are usually between 10 and 300 base pairs in length, and they function in cis. An enhancer can be from 10 bp to 50 bp, 50 bp to 100 bp, 100 bp to 150 bp, 150 bp to 200 bp, 200 bp to 250 bp, 250 bp to 300 bp. Enhancers can function to increase transcription from nearby promoters. Enhancers can also contain response elements that mediate the regulation of transcription. While many enhancer sequences are now known from mammalian genes (globin, elastase, albumin, fetoprotein and insulin), one may also use an enhancer from a eukaryotic cell virus for general expression. The choice of enhancer—promoter combination has a great impact on both the level and the duration of transgene expression. An enhancer can be a simian virus 40 (SV40) enhancer, a human immunodeficiency virus I (HIV-I) enhancer, ground squirrel hepatitis virus (GHV) enhancer, adenovirus enhancer, human prothrombin (hTHGB) enhancer, or human C2 complement gene (hC2) enhancer to name a few.

In some embodiments, an enhancer sequence can be used to increase expression of a gene. For example, a CMV enhancer can increase transgene expression under different cell-specific promoters and different cell types making it a broadly applicable tool to increase transgene expression levels.

In some cases, a mini-circle vector can be used. Mini-circle vectors can differ from bacterial plasmid vectors in that they may lack an origin of replication, and may lack drug selection markers commonly found in bacterial plasmids, e.g. β-lactamase, tet, and the like. A minicircle may be substantially free of vector sequences other than the recombinase hybrid product sequence, and the sequence of interest, i.e. a transcribed sequence and regulatory sequences required for expression. In some cases, a dog bone vector may be utilized. A dog bone vector may be generated without the use of bacteria and may have reduced bacterial elements when compared to a plasmid. Reduced bacterial elements may reduce toxicity of vector introduction into a cell, into a subject, or a combination of both.

Some embodiments described herein comprise polynucleotides (and polypeptides encoded by said polynucleotides) which may be incorporated into vectors (including non-viral and viral vectors (including DNA and RNA/mRNA vectors, which may be linear or circular vectors)) wherein said polynucleotides comprise a construct configuration selected from the group consisting of:

a) 5'-(promoter)-S100-(linker)-SDF-(linker)-VEGF-3';
b) 5'-(promoter)-S100-(linker)-VEGF-(linker)-SDF-3';
c) 5'-(promoter)-S100A1-(linker)-SDF1-(linker)-VEGF-3';
d) 5'-(promoter)-S100A1-(linker)-VEGF-(linker)-SDF1-3';
e) 5'-(promoter)-S100A1-(linker)-SDF1-(linker)-VEGF165-3';
f) 5'-(promoter)-S100A1-(linker)-VEGF165-(linker)-SDF1-3';
g) 5'-(promoter)-S100A1-(linker)-SDF1α-(linker)-VEGF165-3';
h) 5'-(promoter)-S100A1-(linker)-VEGF165-(linker)-SDF1α-3';
i) 5'-(promoter)-S100A1-(linker)-SDF1-(linker)-VEGF191-3';
j) 5'-(promoter)-S100A1-(linker)-VEGF191-(linker)-SDF1-3';
k) 5'-(promoter)-S100A1-(linker)-SDF1α-(linker)-VEGF191-3';
l) 5'-(promoter)-S100A1-(linker)-VEGF191-(linker)-SDF1α-3';
m) 5'-(promoter)-S100-(fp2a)-SDF-(linker)-VEGF-3';
n) 5'-(promoter)-S100-(fp2a)-VEGF-(linker)-SDF-3';
o) 5'-(promoter)-S100A1-(fp2a)-SDF1-(linker)-VEGF-3';
p) 5'-(promoter)-S100A1-(fp2a)-VEGF-(linker)-SDF1-3';
q) 5'-(promoter)-S100A1-(fp2a)-SDF1-(linker)-VEGF165-3';
r) 5'-(promoter)-S100A1-(fp2a)-VEGF165-(linker)-SDF1-3';
s) 5'-(promoter)-S100A1-(fp2a)-SDF1α-(linker)-VEGF165-3';
t) 5'-(promoter)-S100A1-(fp2a)-VEGF165-(linker)-SDF1α-3';
u) 5'-(promoter)-S100A1-(fp2a)-SDF1-(linker)-VEGF191-3';
v) 5'-(promoter)-S100A1-(fp2a)-VEGF191-(linker)-SDF1-3';
w) 5'-(promoter)-S100A1-(fp2a)-SDF1α-(linker)-VEGF191-3';
x) 5'-(promoter)-S100A1-(fp2a)-VEGF191-(linker)-SDF1α-3';
y) 5'-(promoter)-S100-(fp2a)-SDF-(fp2a)-VEGF-3';
z) 5'-(promoter)-S100-(fp2a)-VEGF-(fp2a)-SDF-3';
aa) 5'-(promoter)-S100A1-(fp2a)-SDF1-(fp2a)-VEGF-3';
ab) 5'-(promoter)-S100A1-(fp2a)-VEGF-(fp2a)-SDF1-3';
ac) 5'-(promoter)-S100A1-(fp2a)-SDF1-(fp2a)-VEGF165-3';
ad) 5'-(promoter)-S100A1-(fp2a)-VEGF165-(fp2a)-SDF1-3';
ae) 5'-(promoter)-S100A1-(fp2a)-SDF1α-(fp2a)-VEGF165-3';
af) 5'-(promoter)-S100A1-(fp2a)-VEGF165-(fp2a)-SDF1α-3';
ag) 5'-(promoter)-S100A1-(fp2a)-SDF1-(fp2a)-VEGF191-3';
ah) 5'-(promoter)-S100A1-(fp2a)-VEGF191-(fp2a)-SDF1-3';
ai) 5'-(promoter)-S100A1-(fp2a)-SDF1a-(fp2a)-VEGF191-3';
aj) 5'-(promoter)-S100A1-(fp2a)-VEGF191-(fp2a)-SDF1α-3';
ak) 5'-(promoter)-S100-(fp2a)-SDF-(fmdv)-VEGF-3';
al) 5'-(promoter)-S100-(fp2a)-VEGF-(fmdv)-SDF-3';
am) 5'-(promoter)-S100A1-(fp2a)-SDF1-(fmdv)-VEGF-3';
an) 5'-(promoter)-S100A1-(fp2a)-VEGF-(fmdv)-SDF1-3';
ao) 5'-(promoter)-S100A1-(fp2a)-SDF1-(fmdv)-VEGF165-3';
ap) 5'-(promoter)-S100A1-(fp2a)-VEGF165-(fmdv)-SDF1-3';
aq) 5'-(promoter)-S100A1-(fp2a)-SDF1α-(fmdv)-VEGF165-3';
ar) 5'-(promoter)-S100A1-(fp2a)-VEGF165-(fmdv)-SDF1α-3';
as) 5'-(promoter)-S100A1-(fp2a)-SDF1-(fmdv)-VEGF191-3';
at) 5'-(promoter)-S100A1-(fp2a)-VEGF191-(fmdv)-SDF1-3';
au) 5'-(promoter)-S100A1-(fp2a)-SDF1α-(fmdv)-VEGF191-3';
av) 5'-(promoter)-S100A1-(fp2a)-VEGF191-(fmdv)-SDF1α-3';
aw) 5'-(promoter)-S100-(fp2a)-SDF-(p2a)-VEGF-3';
ax) 5'-(promoter)-S100-(fp2a)-VEGF-(p2a)-SDF-3';
ay) 5'-(promoter)-S100A1-(fp2a)-SDF1-(p2a)-VEGF-3';
az) 5'-(promoter)-S100A1-(fp2a)-VEGF-(p2a)-SDF1-3';
ba) 5'-(promoter)-S100A1-(fp2a)-SDF1-(p2a)-VEGF165-3';
bb) 5'-(promoter)-S100A1-(fp2a)-VEGF165-(p2a)-SDF1-3';
bc) 5'-(promoter)-S100A1-(fp2a)-SDF1α-(p2a)-VEGF165-3';
db) 5'-(promoter)-S100A1-(fp2a)-VEGF165-(p2a)-SDF1α-3';
be) 5'-(promoter)-S100A1-(fp2a)-SDF1-(p2a)-VEGF191-3';
bf) 5'-(promoter)-S100A1-(fp2a)-VEGF191-(p2a)-SDF1-3';
bg) 5'-(promoter)-S100A1-(fp2a)-SDF1α-(p2a)-VEGF191-3';
bh) 5'-(promoter)-S100A1-(fp2a)-VEGF191-(p2a)-SDF1α-3',
bi) 5'-(promoter)-S100-(fp2a)-SDF-(GSG-p2a)-VEGF-3';
bk) 5'-(promoter)-S100-(fp2a)-VEGF-(GSG-p2a)-SDF-3';
bl) 5'-(promoter)-S100A1-(fp2a)-SDF1-(GSG-p2a)-VEGF-3';
bm) 5'-(promoter)-S100A1-(fp2a)-VEGF-(GSG-p2a)-SDF1-3';
bn) 5'-(promoter)-S100A1-(fp2a)-SDF1-(GSG-p2a)-VEGF165-3';
bo) 5'-(promoter)-S100A1-(fp2a)-VEGF165-(GSG-p2a)-SDF1-3';
bp) 5'-(promoter)-S100A1-(fp2a)-SDF1α-(GSG-p2a)-VEGF165-3';
bq) 5'-(promoter)-S100A1-(fp2a)-VEGF165-(GSG-p2a)-SDF1α-3';
br) 5'-(promoter)-S100A1-(fp2a)-SDF1 -(GS G-p2a)-VEGF191 -3';

bs) 5'-(promoter)-S100A1-(fp2a)-VEGF191 -(GSG-p2a)-SDF1 -3';
bt) 5'-(promoter)-S100A1-(fp2a)-SDF1α-(GSG-p2a)-VEGF191-3'; and,
bu) 5'-(promoter)-S100A1-(fp2a)-VEGF191 -(GSG-p2a)-SDF1α-3';
wherein "promoter" is any transcriptional promoter sequence;
wherein "S100" encodes any polypeptide, isoform, or fragment thereof in the S100 family of proteins;
wherein "SDF" encodes any polypeptide, isoform, or fragment thereof in the SDF family of proteins;
wherein "VEGF" encodes any polypeptide, isoform, or fragment thereof in the VEGF family of proteins;
wherein the parenthetical symbols " (" and ") " indicate any number of additional nucleotides (nts) (from 0 to 1000 nts) whether coding sequences or non-coding sequences;
wherein "linker" indicates any linker useful for expression of adjacent biologically active polypeptides;
wherein "S100A1" is at least 65%, 70%, 75%, 80%, 85%, 90%, 95%, 99% identical or is 100% identical to the nucleotide sequence of SEQ ID NO: 105 or to the amino acid sequence of SEQ ID NO: 104, in the, respective, context of polynucleotide or polypeptide sequences;
wherein "SDF-1α" is at least 65%, 70%, 75%, 80%, 85%, 90%, 95%, 99% identical or is 100% identical to the nucleotide sequence of SEQ ID NO: 103 or to the amino acid sequence of SEQ ID NO: 102, in the, respective, context of polynucleotide or polypeptide sequences;
wherein "VEGF165" is at least 65%, 70%, 75%, 80%, 85%, 90%, 95%, 99% identical or is 100% identical to the nucleotide sequence of SEQ ID NO: 127 or to the amino acid sequence of SEQ ID NO: 126, in the, respective, context of polynucleotide or polypeptide sequences;
wherein "VEGF191" is at least 65%, 70%, 75%, 80%, 85%, 90%, 95%, 99% identical or is 100% identical to the nucleotide sequence of SEQ ID NO: 107 or to the amino acid sequence of SEQ ID NO: 106, in the, respective, context of polynucleotide or polypeptide sequences;
wherein "fp2a" is at least 40%, 45%, 50%, 55%, 65%, 70%, 75%, 80%, 85%, 90%, 95% identical or is 100% identical to the nucleotide sequence of SEQ ID NO: 41 or to the amino acid sequence of SEQ ID NO: 40, in the, respective, context of polynucleotide or polypeptide sequences;
wherein "fmdv" is at least 40%, 45%, 50%, 55%, 65%, 70%, 75%, 80%, 85%, 90%, 95% identical or is 100% identical to the nucleotide sequence of SEQ ID NO: 35 or to the amino acid sequence of SEQ ID NO: 34, in the, respective, context of polynucleotide or polypeptide sequences;
wherein "p2a" is at least 40%, 45%, 50%, 55%, 65%, 70%, 75%, 80%, 85%, 90%, 95% identical or is 100% identical to the nucleotide sequence of SEQ ID NO: 37 or to the amino acid sequence of SEQ ID NO: 36, in the, respective, context of polynucleotide or polypeptide sequences; and,
wherein "GSG-p2a" is at least 40%, 45%, 50%, 55%, 65%, 70%, 75%, 80%, 85%, 90%, 95% identical or is 100% identical to the nucleotide sequence of SEQ ID NO: 39 or to the amino acid sequence of SEQ ID NO: 40, in the, respective, context of polynucleotide or polypeptide sequences.

In some embodiments, lead candidate therapeutic polynucleotides of the invention comprise polynucleotides (and polypeptides encoded by said polynucleotides) which may be incorporated into vectors (including non-viral and viral vectors (including DNA and RNA/mRNA vectors, which may be linear or circular vectors)) wherein said polynucleotides comprise a construct configuration selected from the group consisting of:
a) 5'-(promoter)-S100A1-(linker)-SDF1α-(linker)-VEGF191-3';
b) 5'-(promoter)-S100A1-(linker)-VEGF191-(linker)-SDF1α-3';
c) 5'-(promoter)-S100A1-(linker)-SDF1α-(linker)-VEGF165-3';
d) 5'-(promoter)-S100A1-(linker)-VEGF165-(linker)-SDF1α-3';
e) 5'-(promoter)-S100A1-(fp2a)-SDF1α-(linker)-VEGF191-3';
f) 5'-(promoter)-S100A1-(fp2a)-VEGF191-(linker)-SDF1α-3';
g) 5'-(promoter)-S100A1-(fp2a)-SDF1α-(linker)-VEGF165-3';
h) 5'-(promoter)-S100A1-(fp2a)-VEGF165-(linker)-SDF1α-3';
i) 5'-(promoter)-S100A1-(fp2a)-SDF1α-(fp2a)-VEGF191-3';
j) 5'-(promoter)-S100A1-(fp2a)-VEGF191-(fp2a)-SDF1α-3';
k) 5'-(promoter)-S100A1-(fp2a)-SDF1α-(fp2a)-VEGF165-3';
l) 5'-(promoter)-S100A1-(fp2a)-VEGF165-(fp2a)-SDF1α-3';
m) 5'-(promoter)-S100A1-(fp2a)-SDF1α-(fmdv)-VEGF191-3';
n) 5'-(promoter)-S100A1-(fp2a)-VEGF191-(fmdv)-SDF1α-3';
o) 5'-(promoter)-S100A1-(fp2a)-SDF1α-(fmdv)-VEGF165-3';
p) 5'-(promoter)-S100A1-(fp2a)-VEGF165-(fmdv)-SDF1α-3';
q) 5'-(promoter)-S100A1-(fp2a)-SDF1 ci-(p2a)-VEGF191 -3';
r) 5'-(promoter)-S100A1-(fp2a)-VEGF191-(p2a)-SDF1α-3';
s) 5'-(promoter)-S100A1-(fp2a)-SDF1α-(p2a)-VEGF165-3';
t) 5'-(promoter)-S100A1-(fp2a)-VEGF165-(p2a)-SDF1α-3';
u) 5'-(promoter)-S100A1-(fp2a)-SDF1α-(GSG-p2a)-VEGF191 -3';
v) 5'-(promoter)-S100A1-(fp2a)-VEGF191 -(GSG-p2a)-SDF1α-3';
w) 5'-(promoter)-S100A1-(fp2a)-SDF1α-(GSG-p2a)-VEGF165-3'; and,
x) 5'-(promoter)-S100A1-(fp2a)-VEGF165-(GSG-p2a)-SDF1α-3';
wherein "promoter" is any transcriptional promoter sequence;
wherein "S100" encodes any polypeptide, isoform, or fragment thereof in the S100 family or proteins;
wherein "SDF" encodes any polypeptide, isoform, or fragment thereof in the SDF family of proteins;
wherein "VEGF" encodes any polypeptide, isoform, or fragment thereof in the VEGF family of proteins;
wherein the parenthetical symbols " (" and ") " indicate any number of additional nucleotides (nts) (from 0 to 1000 nts) whether coding sequences or non-coding sequences;
wherein "linker" indicates any linker useful for expression of adjacent biologically active polypeptides;
wherein "S100A1" is at least 65%, 70%, 75%, 80%, 85%, 90%, 95%, 99% identical or is 100% identical to the nucleotide sequence of SEQ ID NO: 105 or to the amino acid sequence of SEQ ID NO: 104, in the, respective, context of polynucleotide or polypeptide sequences;

wherein "SDF-1α" is at least 65%, 70%, 75%, 80%, 85%, 90%, 95%, 99% identical or is 100% identical to the nucleotide sequence of SEQ ID NO: 103 or to the amino acid sequence of SEQ ID NO: 102, in the, respective, context of polynucleotide or polypeptide sequences;

wherein "VEGF165" is at least 65%, 70%, 75%, 80%, 85%, 90%, 95%, 99% identical or is 100% identical to the nucleotide sequence of SEQ ID NO: 127 or to the amino acid sequence of SEQ ID NO: 126, in the, respective, context of polynucleotide or polypeptide sequences;

wherein "VEGF191" is at least 65%, 70%, 75%, 80%, 85%, 90%, 95%, 99% identical or is 100% identical to the nucleotide sequence of SEQ ID NO: 107 or to the amino acid sequence of SEQ ID NO: 106, in the, respective, context of polynucleotide or polypeptide sequences;

wherein "fp2a" is at least 40%, 45%, 50%, 55%, 65%, 70%, 75%, 80%, 85%, 90%, 95% identical or is 100% identical to the nucleotide sequence of SEQ ID NO: 41 or to the amino acid sequence of SEQ ID NO: 40, in the, respective, context of polynucleotide or polypeptide sequences;

wherein "fmdv" is at least 40%, 45%, 50%, 55%, 65%, 70%, 75%, 80%, 85%, 90%, 95% identical or is 100% identical to the nucleotide sequence of SEQ ID NO: 35 or to the amino acid sequence of SEQ ID NO: 34, in the, respective, context of polynucleotide or polypeptide sequences;

wherein "p2a" is at least 40%, 45%, 50%, 55%, 65%, 70%, 75%, 80%, 85%, 90%, 95% identical or is 100% identical to the nucleotide sequence of SEQ ID NO: 37 or to the amino acid sequence of SEQ ID NO: 36, in the, respective, context of polynucleotide or polypeptide sequences; and, wherein "GSG-p2a" is at least 40%, 45%, 50%, 55%, 65%, 70%, 75%, 80%, 85%, 90%, 95% identical or is 100% identical to the nucleotide sequence of SEQ ID NO: 39 or to the amino acid sequence of SEQ ID NO: 40, in the, respective, context of polynucleotide or polypeptide sequences.

In a preferred embodiment, compositions of the present invention may be used to treat congestive heart failure (e.g., compositions of the present invention may be used to treat congestive heart failure in patients with implanted destination left ventricular assist devices (LVAD)).

In a preferred embodiment, compositions of the present invention are administered to patients through retrograde coronary sinus infusion (RCSI).

In one embodiment, compositions of the present invention are administered to animal models (for example, but not limited to, pigs (porcine model)) wherein retrograde coronary sinus infusion (RCSI) is used to study an animal model of myocardial ischemia.

In certain embodiments, the functionality of each effector in pXoX was verified in transfected healthy and diseased patient-induced pluripotent stem cell (iPSC)-derived cardiomyocytes using effector-specific assays. In particular, S100A1 demonstrated an improvement in contractile properties. SDF-1α was shown to induce the CXCR4 dependent migration of Jurkat cells and peripheral blood lymphocytes (PBLs). VEGF165 demonstrated an increase in proliferation of human umbilical endothelial cells (HUVECs).

In another embodiment, transfection of pXoX in vitro safety testing in healthy and diseased patient-induced pluripotent stem cell (iPSC)-derived cardiomyocytes did not demonstrate risks for adverse effects on cardiac conduction, based on assessments of changes in Field Potential Duration (MEA), which correlate closely with effects on QT intervals of the electrocardiogram (ECG).

In another embodiment, transfection of pXoX restored beat rate, contraction duration and contraction rate in dilated cardiomyopathy patient iPSC-CMs to levels comparable to those seen in iPSC-CM from a healthy phenotype. In a preferred embodiment, the best improvements in contractile properties were observed for the pXoX triple effector plasmid, relative to single or dual effector plasmids.

In certain embodiments, vectors and polynucleotide constructs of the invention comprise dual-gene (double-gene) sequences (and polypeptides encoded by same) such as those described in Table 1.

TABLE 1

Vector Features - Dual-Gene (Double-Gene) Constructs

| SEQ ID No. | Name* | Orientation (N to C terminus) | Linker |
|---|---|---|---|
| 1 | CAG-S100A1-fmdv-SDF1-NXB-V2 | S100A1-SDF1 | fmdv |
| 2 | CAG-SDF1-fmdv-S100A1-NXB-V2 | SDF1-S100A1 | fmdv |
| 3 | CAG-SDFl-fmdv-VEGF191-NXB-V2 | SDF-VEGF191 | fmdv |
| 4 | CAG-VEGF191-fmdv-SDF1-NXB-V2 | VEGF191-SDF1 | fmdv |
| 5 | CAG-S100A1-p2a-SDF1-NXB-V2 | S100A1-SDF1 | p2a |
| 6 | CAG-SDF1-p2a-S100A1-NXB-V2 | SDF1-S100A1 | p2a |
| 7 | CAG-SDF1-p2a-VEGF191-NXB-V2 | SDF1-VEGF191 | p2a |
| 8 | CAG-VEGF-191-p2a-SDF1-NXB-V2 | VEGF191-SDF1 | p2a |
| 9 | CAG-S100A1-fp2a-SDF1-NXB-V2 | S100A1-SDF1 | fp2a |
| 10 | CAG-SDF1-fp2a-S100A1-NXB-V2 | SDF1-S100A1 | fp2a |
| 11 | CAG-SDF1-fp2a-VEGF191-NXB-V2 | SDF1-VEGF191 | fp2a |
| 12 | CAG-VEGF191-fp2a-SDF-1NXB-V2 | VEGF191-SDF1 | fp2a |
| 13 | CAG-VEGF191-fp2a-S100A1NXB-V2 | VEGF191-S100A1 | fp2a |
| 14 | CAG-S100A1-fmdv-VEGF191-NXB-V2 | S100A1-VEGF191 | fmdv |
| 15 | CAG-VEGF191-fmdv-S100A1-NXB-V2 | VEGF191-S100A1 | fmdv |
| 16 | CAG-S100A1-p2a-VEGF191-NXB-V2 | S100A1-VEGF191 | p2a |
| 17 | CAG-VEGF191-p2a-S100A1-NXB-V2 | VEGF191-S100A1 | p2a |
| 18 | CAG-S100A1-fp2a-VEGF191-NXB-V2 | S100A1-VEGF191 | fp2a |
| 19 | IGE-641pCAGCAG(1660043)GAPDH(5883)Kozak1744359F3R(26319) | S100A1-SDF1 | fmdv |
| 20 | IGE-642 pCAG CAG(1660043)GAPDH(5883)Kozak1744365F3R(26319) | SDF1-S100A1 | fmdv |
| 21 | IGE-643 pCAG CAG(1660043)GAPDH(5883)Kozak+1744369F3R(26319) | SDF1-VEGF191 | fmdv |

TABLE 1-continued

| | | | |
|---|---|---|---|
| 22 | IGE-644 pCAG CAG(1660043)GAPDH(5883) Kozak 1744395F3R(26319) | VEGF191-SDF1 | fmdv |
| 23 | IG E-645 pcag CAG(1660043)_GAPDH(5883)_Kozak+1744405_F3R(26319) | S100A1-SDF1 | p2a |
| 24 | IGE-646_pCAG_CAG(1660043)_GAPDH(5883)_Kozak+1744407_F3R(26319) | SDF1-S100A1 | p2a |
| 25 | IGE-647_pCAG_CAG(1660043)_GAPDH(5883)_Kozak+1744420_F3R(26319) | SDF1-VEGF191 | p2a |
| 26 | IGE-648_pCAG_CAG(1660043)_GAPDH(5883)_Kozak+1744423_F3R(26319) | VEGF191-SDF1 | p2a |
| 27 | IGE-649_pCAG_CAG(1660043)_GAPDH(5883)_Kozak+1744427_F3R(26319) | S100A1-SDF1 | fp2a |
| 28 | IGE-650pCAG CAG(1660043)GAPDH(5883) Kozak1744430F3R(26319) | SDF1-S100A1 | fp2a |
| 29 | IGE-651 pCAG CAG(1660043)GAPDH(5883) Kozak1744431F3R(26319) | SDF1-VEGF191 | fp2a |
| 30 | IGE-652 pCAG CAG(1660043)GAPDH(5883) Kozak1744432F3R(26319) | VEGF191-SDF1 | fp2a |
| 31 | IGE-653 pCAG CAG(1660043)GAPDH(5883) Kozak1744433F3R(26319) | VEGF-S100A1 | fp2a |

*"CAG" and "NXB-V2" represent the CAG promoter plus 5' and 3' elements and the new X vector backbone version-2 as found in constructs of the invention (such as in pXoX as indicated below):

Sequence of "CAG" and "NXB-V2" vector elements

| CAG_NXB-V2 | Nucleotide Positions in SEQ ID NO: 108 |
|---|---|
| NXB-V2 = Plasmid Backbone components: | 1-114 (114 bp); 3753-3852 (100 bp); 3853-4904 (1052 bp); 4905-4960 (56 bp); 4961-5755 (795 bp); and, 5756-6025 (270 bp) |
| CAG = CAG Promoter + 5' and 3' elements: | 115-1825 (1711 bp); 1841-1942 (102 bp); and 3266-3752 (487 bp) |

Promoters

Promoters are a major cis-acting element within the vector genome design that can dictate the overall strength of expression as well as cell-specificity. A promotor can be a ubiquitous promotor, a cell-specific promotor, or a combination thereof. A ubiquitous or constitutive promoter can be a CMV, CBA (CAG and CBh), EF-1alpha, PKG, UBC, GUSB (hGBp), UCOE, to name a few. A promotor can be a promotor that has activity within a target cell of interest, e.g., cardiac promotor. In some cases a promotor is a CAG. In other cases a promoter is a constitutive promoter such as Ef1a. A promoter can be a human promotor, such as human Ef1a (hEf1a). A bidirectional promoter can also be used. For example, a constitutive bidirectional promoter can be a human cytomegalovirus promoter.

In some embodiments, such as those where a gene product polypeptide is secreted, ubiquitous expression in all or select cell types can desired. Constitutive promoters such as the human elongation factor 1α-subunit (EF1α), immediate-early cytomegalovirus (CMV), chicken β-actin (CBA) and its derivative CAG, the β glucuronidase (GUSB), or ubiquitin C (UBC) can be used to promote expression in most tissues (Husain et al., 2009; Qin et al., 2010; Norrman et al., 2010). Generally, CBA and CAG promote the larger expression among the constitutive promoters (Xu et al., 2001; Yin et al., 2011); however, their size of ~1.7 kbs in comparison to CMV (~0.8 kbs) or EF1α(~1.2 kbs) can limit its use in vectors with packaging constraints. In some cases, a GUSB or UBC promoter can provide ubiquitous gene expression with a smaller size of 378 bps and 403 bps, respectively, but they can be considerably weaker than a CMV or CBA promoter (Husain et al., 2009; Qin et al., 2010). Thus, modifications to constitutive promoters in order to reduce the size without affecting its expression have been pursued and examples such as the CBh (~800 bps) and the miniCBA (~800 bps) can promote expression comparable and even higher in selected tissues (Gray et al., 2011). In some cases "ubiquitous" promoters can be prone to silencing or promote differential expression strength in selected cell types (McCown et al., 1996; Klein et al., 1998; Gray et al., 2011).

Viral enhancers and promoters derived from cytomegalovirus (CMV), respiratory syncytial virus (RSV) and simian virus 40 (SV40) can be used to achieve high levels of expression in a range of mammalian cell and tissue types, such as in cardiomyocytes. Constitutive mammalian promoters, such as the human ubiquitin C (UBC) and the eukaryotic translation elongation factor 1 alpha 1 (EEF1A1) promoters can have more persistent expression. Tissue-specific promoters can be utilized to reduce off-target transgene expression. Numerous cis-acting sequences, including polyadenylation signals, introns and scaffold/matrix attachment regions (S/MARs) 52, can increase the level and persistence of transgene expression in some cases.

Compact DNA vectors that lack a bacterial backbone (e.g., minicircles) can maintain superior levels and duration of gene expression relative to full-length DNA plasmids. A dog bone vector may also be utilized. A dog bone vector can be generated without the use of bacteria. In some cases, a lipid-based DNA vectors can also be used in some cases, a transposon system can be utilized. For example, a transposition system can be or can be based on the recombinases phiC31, PiggyBac57, Sleeping Beauty, or combinations thereof.

Figure 2:
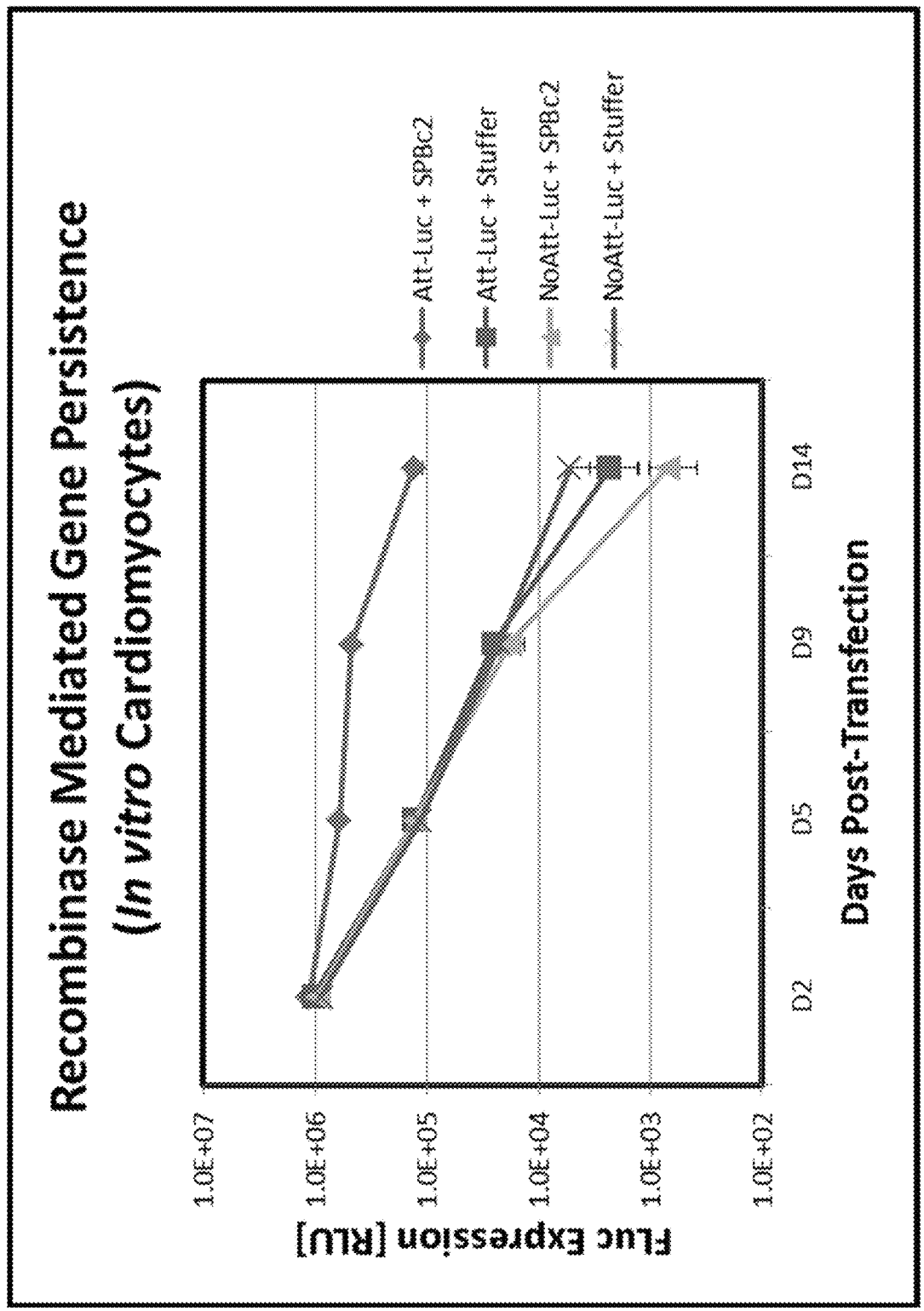
FIG. 2 shows persistent expression of Luciferase in cardiomyocytes from constructs comprising linkers described herein, in primary cells (in vitro) via introduction of vectors comprising att-site-luciferase with SPBc2 (recombinase) transfection. Cells lacking either att-site or recombinase rapidly returned to baseline expression levels. Day 2 (D2), Day 5 (D5), Day 9 (D9), Day 14 (D14).
Figure 3:
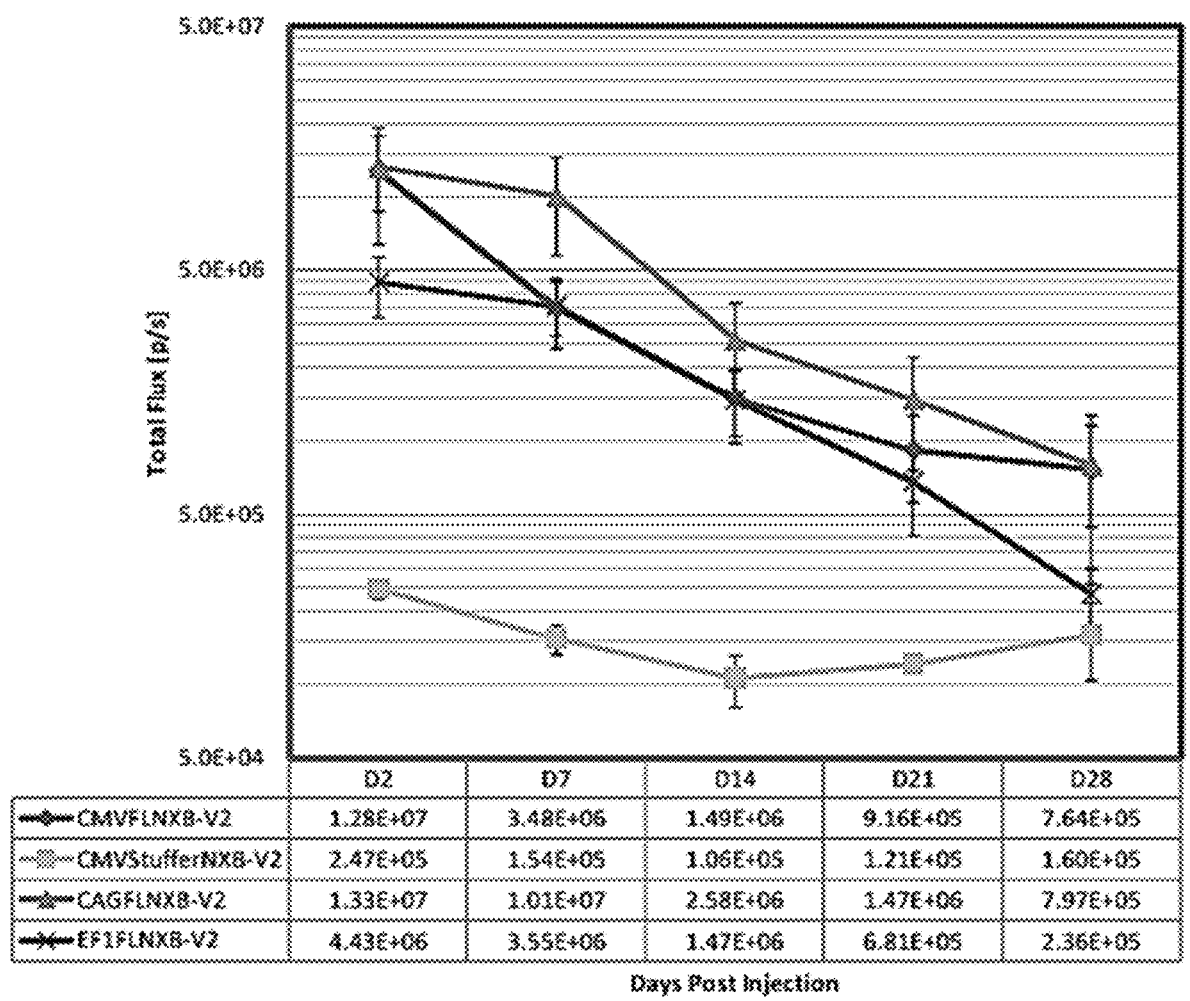
FIG. 3 shows data for luciferase expression achieved in a rodent model from a plasmid vector backbone from which cardiac effector genes (pXoX encoding biologically active SDF1α, S100A1, and VEGF) may be expressed, via separation by linkers described herein.
Figure 4:
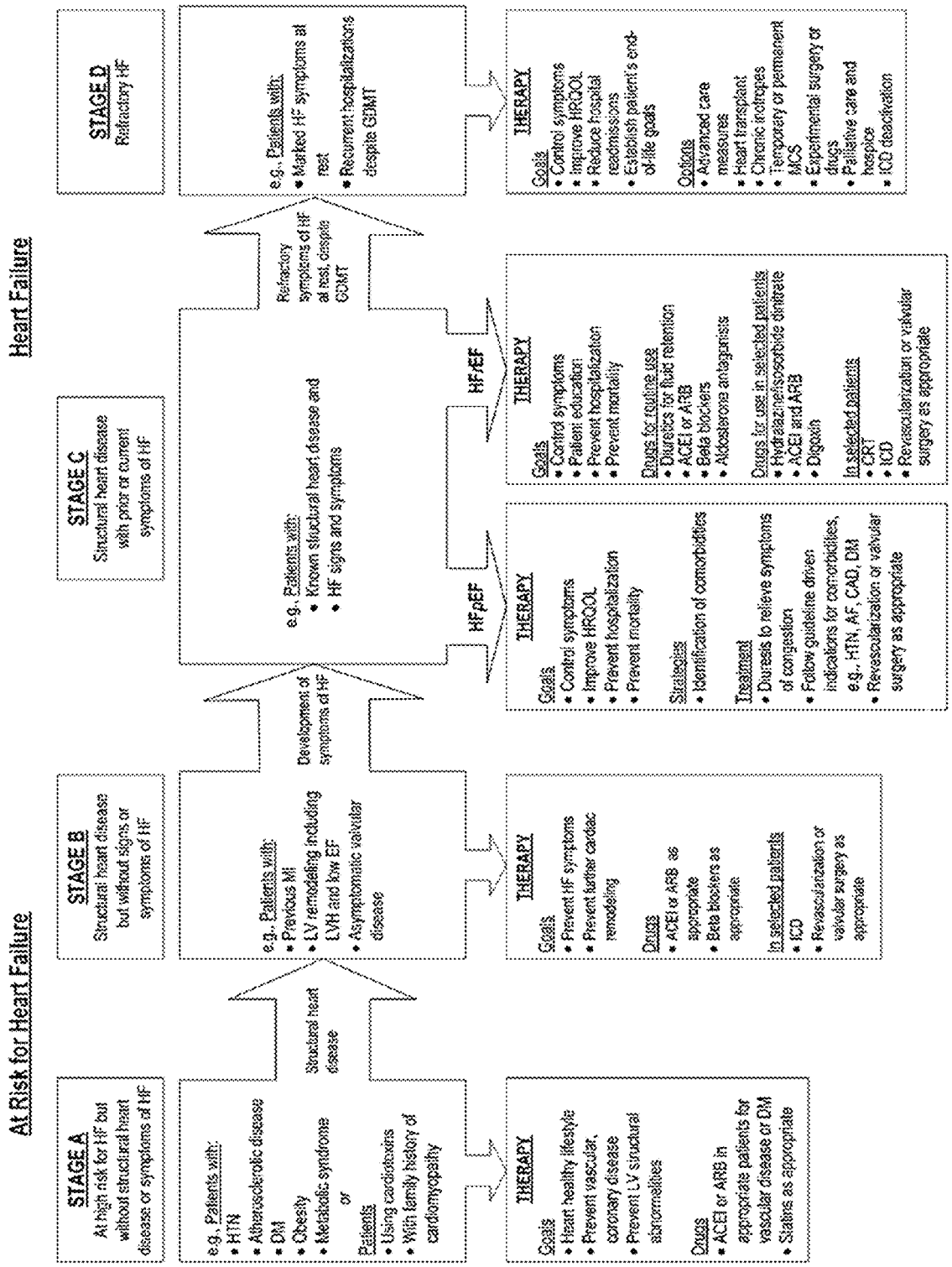
FIG. 4 shows various stages of progress through heart failure conditions and the corresponding standard-of-care modes and methods for intervention and treatment.

In some cases, cardiac gene effector vectors described herein can be integrated into a cell genome via use of recombinase, FIG. 2. A recombinase can be an att-site recombinase. In some cases, a recombinase can be selected from recombinases as described in: U.S. Pat. No. 9,034,650;

US Pub. No. 2015/0275232; and, WO2008/073154, each of which is incorporated by reference herein in its entirety.

A recombinase can be introduced into a cell via an mRNA encoding a recombinase. In certain embodiments, integration of a recombinase into a cell genome can be prevented by introduction and expression of a recombinase via use of an mRNA encoding a recombinase. In some cases, an mRNA encoding a recombinase can be a synthetic or a cGMP-grade mRNA, FIG. 1.

In some cases, a recombinase can be introduced into a cell via an expression plasmid comprising a "suicide gene" and a gene encoding a recombinase. In certain embodiments a suicide gene and recombinase gene can be separated by an intervening internal ribosome entry site (IRES).

In some cases, a cell in which vectors can be introduced or genomically integrated (e.g., via recombinase) can be a primary cell (e.g., such as, but not limited to, a cardiomyocyte, FIG. 2). In some cases, a gene encoded within a vector can be genomically inserted at a targeted genomic location in a cell.

Internal ribosome entry site (IRES) elements can allow expression of multiple genes from one transcript (Mountford and Smith 1995). The term "IRES" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner.

An IRES sequence can allow eukaryotic ribosomes to bind and begin translation without binding to a 5' capped end. In certain cases, an IRES region can be derived from a virus, such as picornavirus, encephalomyocarditis virus, hepatitis C virus IRES sequence. In other cases, can IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

An IRES sequence of viral, cellular or a combination thereof can be utilized in a vector. An IRES can be from encephalomyocarditis (EMCV) or poliovirus (PV).

In some cases, an IRES element is selected from a group consisting of Poliovirus (PV), Encephalomyelitis virus (EMCV), Foot-and-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), Rhopalosiphum padi virus (RhPV), Cricket paralysis virus (CrPV), Ectropis obliqua picorna-like virus (EoPV), Plautia stali intestine virus (PSIV), Triatoma virus (TrV), Bee paralysis dicistrovirus (IAPV, KBV), Black currant reversion virus (BRV), Pelargonium flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), Leishmania RNA virus-1 (LRV-1), and combinations or modifications thereof.

In some cases, an IRES is selected from a group consisting of Apaf-1, XIAP, HIAP2/c-IAP1, DAP5, Bcl-2, c-myc, CAT-1, INR, Differentiation LEF-1, PDGF2, HIF-1a, VEGF, FGF2, BiP, BAG-1, CIRP, p53, SHMT1, PITSLREp58, CDK1, Rpr, hid, hsp70, grim, skl, Antennapedia, dFoxO, dInR, Adh-Adhr, HSP101, ADH, URE-2,GPR1, NCE102, YMR181a, MSN1, BOI1, FLO8, GIC1, and any combination or modification thereof.

When an IRES element is included between two open reading frames (ORFs), initiation of translation can occur by a canonical 5'- m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosomes can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

In some cases, a viral 2A sequence can be used. A 2A sequence can be derived from a picornaviral 2A sequence. A picornaviral 2A sequence can be selected from the group consisting of the Enteroviral 2A sequences, Rhinoviral 2A sequences, Cardioviral 2A sequences, Aphthoviral 2A sequences, Hepatoviral 2A sequences, Erboviral 2A sequences, Kobuviral 2A sequences, Teschoviral 2A sequences, and the Parechoviral 2A sequences.

2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 base pairs in length. 2A linked genes can be expressed in one single open reading frame and "self-cleavage" can occur co-translationally between the last two amino acids, GP, at the C-terminus of the 2A polypeptide, giving rise to equal amounts of co-expressed proteins. In some cases, a polypeptide comprising a 2A sequence may not give rise to equal amounts of protein post cleavage. In some cases, a first protein may be 10%, 20%, 30%, 40%, 50%, 60%, 70%, 80%, 90%, or up to 100% greater in concentration when compared to a second protein. In some cases, a second protein may be 10%, 20%, 30%, 40%, 50%, 60%, 70%, 80%, 90%, or up to 100% greater in concentration when compared to a second protein.

A viral 2A sequence can be about 20 amino acids. In some cases, a viral 2A sequence can contain a consensus motif Asp-Val/Ile-Glu-X-Asn-Pro-Gly-Pro (SEQ ID NO: 117). A consensus motif sequence can act co-translationally. For example, formation of a normal peptide bond between a glycine and proline residue can be prevented, which can result in ribosomal skipping and, thereby, "cleavage" of a nascent polypeptide. This effect can produce multiple genes at equimolar levels.

A 2A peptide can allow translation of multiple proteins in a single open reading frame into a polypeptide that can be subsequently "cleaved" into individual polypeptide through a ribosome-skipping mechanism (Funston, Kallioinen et al. 2008). In some embodiments, a "2A" sequence can include: p2a, GSG-p2a, T2A, E2A, F2A, and BmCPV2A, BmIFV2A, and any combination thereof.

A vector can also include additional a 2A/furin sequence located between polycistronic genes to permit production of expression products originating from e.g., a second gene by enzymatic cleavage of a polypeptide product. In some cases additional linkers may be utilized to facilitate cleavage between multiple genes in a multigene vector.

In some cases, a vector can comprise an IRES sequence and a 2A sequence. In other cases, expression of multiple genes linked with 2A peptides can be facilitated by a spacer sequence (GSG) ahead of the 2A peptides. In some cases, constructs can combine a spacers, linkers, adaptors, promotors, or combinations thereof. For example, a construct can have a spacer (SGSG (SEQ ID NO: 118) or GSG) and furin linker (RAKR (SEQ ID NO: 32)) cleavage site with different 2A peptides. A spacer can be an I-Ceui (intron encoding endonuclease). In certain embodiments two or more of the cardiac effector genes are separated by an intervening internal ribosome entry site (IRES).

Polynucleotide Linkers

In embodiments described herein, a polynucleotide linker can be utilized in a polynucleotide described herein. A polynucleotide linker can be a double-stranded segment of DNA containing desired restriction sites that may be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications (e.g., SDF1 polypeptide, a S100A1 polypeptide, a VEGF polypeptide and fragments and variants thereof).

A polynucleotide linker can be an oligomer. For example, a linker can be from about 5 to 20 nucleotides in length. A polynucleotide linker can be or can be about from 5, 6, 7, 8, 9, 10, 11, 12, 13, 14, 15, 16, 17, 18, 19, or 20 nucleotides in length. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

Polypeptide Linkers

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described below. In some cases, a linker is APVKQGSG (SEQ ID NO: 119).

In certain cases, a linker polypeptide can comprise an amino acid sequence "RAKR" (SEQ ID NO: 32). In certain cases, a Furin linker polypeptide can be encoded by a polynucleotide sequence polynucleotide sequence comprising "CGTGCAAAGCGT." (SEQ ID NO: 33).

In certain cases, a linker polypeptide can be a linker comprising a sequence disclosed in the table below:

TABLE 2

Linker amino acid sequences and polynucleotide sequences

| SEQ ID No. | Linker Name | Sequence (N- to C- terminus or 5' to 3' as applicable) |
|---|---|---|
| 32 | Furinlink1 | RAKR |
| 33 | Furinlink1 | CGTGCAAAGCGT |
| 34 | fmdv | RAKRAPVKQTLNFDLLKLAGDVESNPGP |
| 35 | fmdv | AGAGCCAAGAGGGCACCGGTGAAACAGAC TTTGAATTTTGACCTTCTGAAGTTGGCAG GAGACGTTGAGTCCAACCCTGGGCCC |
| 36 | p2a | ATNFSLLKQAGDVEENPGP |
| 37 | p2a | GCTACTAACTTCAGCCTGCTGAAGCAGGC TGGAGACGTGGAGGAGAACCCTGGACCT |
| 38 | GSG-p2a | GSGATNFSLLKQAGDVEENPGP |
| 39 | GSG-p2a | GGAAGCGGAGCTACTAACTTCAGCCTGCT GAAGCAGGCTGGAGACGTGGAGGAGAACC CTGGACCT |
| 40 | fp2a | RAKRAPVKQGSGATNFSLLKQAGDVEENP GP |
| 41 | fp2a | CGTGCAAAGCGTGCACCGGTGAAACAGGG AAGCGGAGCTACTAACTTCAGCCTGCTGA AGCAGGCTGGAGACGTGGAGGAGAACCCT GGACCT |

In some embodiments, a linker can be utilized in a polynucleotide described herein. A linker can be a flexible linker, a rigid linker, an in vivo cleavable linker, or any combination thereof. In some cases, a linker may link a functional domains together (as in flexible and rigid linkers) or releasing free functional domain in vivo as in in vivo cleavable linkers.

Linkers may improve biological activity, increase expression yield, and achieving desirable pharmacokinetic profiles. A linker can also comprise hydrazone, peptide, disulfide, or thioester.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 120). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers may not have rigid structures, they can serve as a passive linker to keep a distance between functional domains. The length of a flexible linkers can be adjusted to allow for proper folding or to achieve optimal biological activity of the fusion proteins.

A linker described herein can further include a rigid linker in some cases. A rigid linker may be utilized to maintain a fixed distance between domains of a polypeptide. Examples of rigid linkers can be: Alpha helix-forming linkers, Pro-rich sequence, (XP)n (SEQ ID NO: 121), X-Pro backbone, A(EAAAK)nA (n=2-5)(SEQ ID NO: 122), to name a few. Rigid linkers can exhibit relatively stiff structures by adopting a-helical structures or by containing multiple Pro residues in some cases.

A linker described herein can be cleavable in some cases. In other cases a linker is not cleavable. Linkers that are not cleavable may covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond may be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein may also be carried out by proteases that can be expressed in vivo under pathological conditions (e.g. cancer or inflammation), in specific cells or tissues, or constrained within certain cellular compartments. In some cases, a cleavable linker may allow for targeted cleavage. For example, the specificity of many proteases can offer slower cleavage of a linker in constrained compartments. A cleavable linker can also comprise hydrazone, peptides, disulfide, or thioester. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO. 34. In certain embodiments, an fmdv linker polypeptide is one or more of the linkers encoded in a single vector linking two or more fusion proteins. In certain cases, an fmdv linker polypeptide can be encoded by a polynucleotide open-reading frame (ORF) nucleic acid sequence. In some cases, an ORF encoding fmdv comprises or consists of a sequence of SEQ ID NO. 35. In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO. 35.

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 36. In certain embodiments, the p2a linker polypeptide can be one or more of the linkers encoded in a single vector linking two or more fusion proteins. In some cases, a p2a linker polypeptide can be encoded by a polynucleotide open-reading frame (ORF) nucleic acid sequence. In certain embodiments, an ORF encoding p2a comprises or consists of the sequence of SEQ ID NO.37.In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 37.

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 38. In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG-p2a can comprises the sequence of SEQ ID NO.39. In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 39.

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 40. In certain cases, an fp2a linker polypeptide can be one or more of the linkers encoded in a single vector linking two or more fusion proteins. In some cases, a fp2a linker polypeptide can be encoded by a polynucleotide open-reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 41.

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99% , or 100% identical to a sequence of SEQ ID NO: 42 to SEQ ID NO:101. In other cases, multiple linkers can be used in a vector. For example, genes of interest (e.g., S100A1, SDF-1α, and VEGF165) can be separated by at least two linkers, as shown in FIG. 20A and FIG. 20B. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

TABLE 3

Linker polypeptide Sequences:

| SEQ ID No. | Sequence |
|---|---|
| 42 | APVKQ |
| 43 | GPVKQ |
| 44 | VPVKQ |
| 45 | IPVKQ |
| 46 | MPVKQ |
| 47 | APIKQ |
| 48 | GPIKQ |
| 49 | VPIKQ |
| 50 | IPIKQ |
| 51 | MPIKQ |
| 52 | APAKQ |
| 53 | GPAKQ |
| 54 | VPAKQ |
| 55 | IPAKQ |
| 56 | MPAKQ |
| 57 | APVRQ |
| 58 | GPVRQ |
| 59 | VPVRQ |
| 60 | IPVRQ |
| 61 | MPVRQ |
| 62 | APIRQ |
| 63 | GPIRQ |
| 64 | VPIRQ |
| 65 | IPIRQ |
| 66 | MPIRQ |
| 67 | APARQ |
| 68 | GPARQ |
| 69 | VPARQ |
| 70 | IPARQ |
| 71 | MPARQ |
| 72 | APVKN |
| 73 | GPVKN |
| 74 | VPVKN |
| 75 | IPVKN |
| 76 | MPVKN |
| 77 | APIKN |

TABLE 3-continued

Linker polypeptide Sequences:

| SEQ ID No. | Sequence |
|---|---|
| 78 | GPIKN |
| 79 | VPIKN |
| 80 | IPIKN |
| 81 | MPIKN |
| 82 | APAKN |
| 83 | GPAKN |
| 84 | VPAKN |
| 85 | IPAKN |
| 86 | MPAKN |
| 87 | APVRN |
| 88 | GPVRN |
| 89 | VPVRN |
| 90 | IPVRN |
| 91 | MPVRN |
| 92 | APIRN |
| 93 | GPIRN |
| 94 | VPIRN |
| 95 | IPIRN |
| 96 | MPIRN |
| 97 | APARN |
| 98 | GPARN |
| 99 | VPARN |
| 100 | IPARN |
| 101 | MPARN |

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, the linker comprises a sequence provided in Table 3 disclosed herein. In some cases, a polypeptide linker may also include one or more GS linker sequences, for instance (GS)n (SEQ ID NO: 109), (SG)n (SEQ ID NO: 110), (GSG)n (SEQ ID NO: 111) and (SGS)n (SEQ ID NO: 112) wherein n can be any number from zero to fifteen. Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ (SEQ ID NO: 42); and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ (SEQ ID NO: 42). In some cases, the linker comprises a sequence provided in Table 3 disclosed herein. In some cases, a polypeptide linker may also include one or more GS linker sequences, for instance (GS)n (SEQ ID NO: 109), (SG)n (SEQ ID NO: 110), (GSG)n (SEQ ID NO: 111) and (SGS)n (SEQ ID NO: 112) wherein n can be any number from zero to fifteen. In some cases, the improved expression is at least about 10%, 15%, 20%, 25%, 30%, 35%, 40%, 45%, 50%, 55%, 60%, 65%, 70%, 75%, 80%, 85%, 90%, 95% or 100% higher as compared to a corresponding polypeptide construct that does not have a linker polypeptide comprising a sequence with at least 60% identity to the sequence APVKQ (SEQ ID NO: 42).

In preferred embodiments, a unique aspect of the present invention is provided and enabled by the specific sequential order of polypeptides encoded by constructs of the invention. Thus, in one aspect of the invention, specifically placing S100A1 protein first achieves and allows functional expression of biologically active S100A1 molecules because the remaining 2A tail on S100A1 was, surprisingly, discovered not to interfere with S100A1 biological activity. In contrast, it was discovered that placing S100A1 as the second gene resulted in incomplete cleavage of genes expressed via the construct.

Accordingly, analysis of pXoX expression using mass spectrometry, as indicated below in Table 13 showed that S100A1 was the only effector that did not exhibit furin cleavage resulting in removal of the C-terminal 2A peptide. Hence, there is no 2A C-terminal tail left on SDF1a or VEGF. Only S100A1 has a 2A linker-tail present. The exact ending amino acid sequence is PG. It cleaves between G and P of ending PGP sequence. Hence, the C-terminal linker tail on S100A1 as expressed from pXoX comprises the sequence (from N- to C-terminus) S101A1 polypeptide fused to (N-terminus)-RAKRAPVKQGSGATNFSLLKQAGD-VEENPG-(C-terminus) (SEQ ID NO: 123) which may be referred to herein as the "2A tail". For example, in one embodiment, from the initial methionine of S100A1 to the C-terminal end of the fp2a cleaved linker tail a first GOI of the invention comprises the sequence:
MGSELETAMETLINVFHAHSGKEGDKYKL-SKKELKELLQTELSGFLDAQKDVDAVDKV MKELDENGD GEVD F QEYVV LVAALTVACNNFF-WEN S RAKRAPVKQ GS GATNF S LLKQ AGD-VEENPG (SEQ ID NO: 124), which may be encoded by a polynucleotide sequence:
ATGGGCAGCGAACTGGAAACCGCCATGGA-GACTTTGATAAATGTTTTCCACGCGCAT AGCGGCAAAGAAGGGGACAAGTACAAGCTGT-CAAAAAAGGAGCTGAAAGAACTGC TGCA-GACCGAATT-GAGCGGCTTCCTGGACGCTCAGAAAGATGTC-GATGCCGTCGACA AAGTGAT-GAAAGAGCTTGACGAGAACGGTGACGGT-GAAGTCGATTTTCAGGAATAT GTGGTGCTGGTGGCCGCCCTTACTGTAG-CATGCAACAATTTCTTTTGGGAAAATTCA CGTGCAAAGCGTGCACCGGTGAAACAGG-GAAGCGGAGCTACTAACTTCAGCCTGCT GAAGCAGGCTGGAGACGTGGAG-GAGAACCCTGGA (SEQ ID NO: 125); or degenerate polynucleotides encoding the same amino acid sequence, or amino acid or nucleic acid sequences at least 45%, 50%, 55%, 60%, 65%, 70%, 75%, 80%, 90%, 95%, 97%, 98% or 99% identical to the above referenced 2A tail.

However, as provided by data presented herein, it has been demonstrated that this S100A1 tail is 'inert'—i.e. does not affect S100A1 function (biological activity).

Vector Modifications

A polynucleotide vector useful for the methods and compositions described herein can be a good manufacturing practices (GMP) compatible vector. For example, a GMP vector may be purer than a non-GMP vector. In some cases, purity can be measured by bioburden. For example, bioburden can be the presence or absence of aerobes, anaerobes, sporeformers, fungi, or combinations thereof in a vector composition. In some cases, a pure vector can be endotoxin low or endotoxin free. Purity can also be measured by double-stranded primer-walking sequencing. Plasmid identity can be a source of determining purity of a vector. A GMP vector of the invention can be from 10% to 99% more pure than a non-GMP vector. A GMP vector can be from 10%, 15%, 20%, 25%, 30%, 35%, 40%, 45%, 50%, 55%, 60%, 65%, 70%, 75%, 80%, 85%, 90%, 95%, 96%, 97%, 98%, or 99% more pure than a non-GMP vector as measured by the presence of bioburden, endotoxin, sequencing, or combinations thereof.

In some cases, a terminator sequence at the end of the first gene program is used. A terminator sequence can ensure that a transcript is terminating prior to initiating a second gene program. For example, an expression vectors may contain sequences necessary for the termination of transcription and for stabilizing an mRNA. Such sequences are commonly available from the 5' and, occasionally 3', untranslated regions of eukaryotic or viral DNAs or cDNAs. These regions can contain nucleotide segments transcribed as polyadenylated fragments in the untranslated portion of the mRNA. Cells comprising the expression vector are grown under conditions that provide for expression of the desired polypeptide, either in vivo or in vitro.

In some cases, a spacer sequence can be used at the end of a first polypeptide encoded by a polynucleotide in a vector. In other cases, a spacer sequence can be used at the end of a second gene in a vector. A spacer sequence can also be used following a first gene and a second gene in a vector.

These vectors can be used to express a polypeptide encoded by a gene, or portion of a gene of interest. A gene of portion or a gene can be inserted by using any method, viral or non-viral. For example; a method can be a non-viral based technique.

In some cases, vector modifications can be made. For example, a modification can include the addition of an inducible gene switch for controlled gene expression, changes in order and/or selection of cardiac effector genes to be combined, promoter replacement (e.g., strong, left ventricle specific expression), and combinations thereof.

In certain embodiments, translation initiation sequences preceding a cardiac effector polypeptide coding sequence in vectors of the invention comprise a Kozak consensus sequence. This may be indicated in descriptions provided herein as "Kozak"="Yes".

In certain embodiments, translation initiation sequences preceding a cardiac effector polypeptide coding sequence in vectors of the invention lack a Kozak consensus sequence. This may be indicated in descriptions provided herein as "Kozak"="No".

In certain embodiments, expression of any one, two, or three cardiac effector polypeptides (such as SDF1, S100A1 and VEGF191) may be driven via a constitutive or inducible promoter. In certain cases, expression of at least two genes is equal. In other cases, expression of at least two genes is not equal. In some cases, an upstream gene may be expressed at a higher concentration than a downstream gene. In other cases, a downstream gene may be expressed at a higher concentration than an upstream gene. A linker may be involved in controlling levels of expression. For example, a cleavable linker may be engineered such that cleavage is more efficient or less efficient.

In some cases, an inducible promoter can be a small molecule ligand-inducible two polypeptide ecdysone receptor-based gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/U52002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/U52002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. No. 7,935,510; 8,076,454; PCT/U52008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. application Ser. No. 14/001,943 (U.S. Pub. No. 20140308247) each of which is incorporated by reference in its entirety.

In some cases, a ligand used for dose-regulated control of ecdysone receptor-based inducible gene switch regulation can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxy-cholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present invention include RG-115819 (3,5 -Dimethyl-benzoic acid N-(1-ethyl-2,2-dimethyl-propyl)-N'-(2-methyl-3-methoxy-benzoyl)-hydrazide-), RG-115932 ((R)-3,5-Di-methyl-benzoic acid N-(1-tert-butyl-butyl)-N'-(2-ethyl-3-methoxy-benzoyl)-hydrazide), and RG-115830 (3,5-Dimethyl-b enzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

In some embodiments, two or three genes of interest (for example, but not limited to, cardiac effector genes) that express polypeptides of interest, can be incorporated into and/or expressed from a single vector under control of a single promoter. In certain embodiments the single promoter is a constitutive promoter. In certain embodiments the single promoter is a constitutive tissue-specific promoter. In certain embodiments the single promoter is a small molecule ligand-inducible ecdysone receptor-based promoter.

In certain embodiments, expression of the gene switch polypeptides is under control of a myosin light chain (MLC) promoter.

Vectors can be delivered in vivo by administration to a subject, typically by systemic administration (e.g., intravenous, intraperitoneal, intramuscular, subdermal, or intracranial infusion) or topical application, as described below. Alternatively, vectors can be delivered to cells ex vivo, such as cells explanted from a subject (e.g., cardiomyocytes, cardiac tissue biopsy), followed by reimplantation of the cells into a subject, usually after selection for cells which have incorporated the vector. Prior to or after selection, the cells can be expanded.

The transfection efficiency of cells with any of the nucleic acid delivery platforms described herein, for example, nucleofection or electroporation, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%.

The efficiency of integration of a gene into a cell (e.g., but not limited to, a cardiomyocyte), can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%.

Certain aspects disclosed herein can utilize vectors. For example, vectors that can be used include, but not limited to, Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR54O, pRIT5 (Pharmacia). Eukaryotic: pWL-neo, pSv2cat, pOG44, pXT1, pSG (Stratagene) pSVK3, pBPv, pMSG, pSVL (Pharmiacia). Also, any other plasmids and vectors can be used as long as they are replicable and viable in a selected host. Any vector and those commercially available (and variants or derivatives thereof) can be engineered to include one or more recombination sites for use in the methods. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3 pREP4, pCEP4, and pEBVHis (Invitrogen, Corp.), and variants or derivatives thereof. Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSYSPORT1 (Invitrogen) and variants or derivatives thereof. Additional vectors of interest can also include pTrxFus, pThioHis, pLEX, pTrcHis, pTrcHis2, pRSET, pBlueBa-cHis2, pcDNA3.1/His, pcDNA3.1(-)/Myc-His, pSecTag, pEBVHis, pPIC9K, pPIC3.5K, pA081S, pPICZ, pPICZA, pPICZB, pPICZC, pGAPZA, pGAPZB, pGAPZC, pBlue-Bac4.5, pBlueBacHis2, pMelBac, pSinRep5, pSinHis, pIND, pIND(SP1), pVgRXR, pcDNA2.1, pYES2, pZEr01.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; X ExCell, X gt11, pTrc99A, pKK223-3, pGEX-1X T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32L1C, pET-30LIC, pBAC-2 cp LIC, pBACgus-2 cp LIC, pT7Blue-2 LIC, pT7Blue-2, X SCREEN-1, X BlueSTAR, pET-3abcd, pET-7abc, pET9abcd, pET11 abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd (+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFPN, pEGFP-C, pEBFP, pGFPuv, pGFP, p6xHis-GFP, pSEAP2-Basic, pSEAP2-Contral, pSEAP2-Promoter, pSEAP2-Enhancer, p I3gal -Basic, p13gal-Control, p I3gal -Promoter, p I3gal -Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, 2Xgt10, Xgt11, pWE15, and X TriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-llabcd, pSPUTK, pESP-1, pCMVLacI, pOP-RSVI/MCS, pOPI3 CAT, pXT1, pSG5, pPbac, pMbac, pMClneo, pMClneo Poly A, pOG44, p0G45, pFRTI3GAL, pNE0I3GAL, pRS403, pRS404, pRS405, pRS406, pRS413, pRS414, pRS415, and pRS416 from Stratagene, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp, and variants or derivatives thereof.

Therapy Indications

Provided herein are methods and compositions for improving vasculogenesis in a subject. Also provided are methods and compositions for treatment for cardiovascular disease. In some cases, a cardiovascular disease can be cardiomyopathy. Cardiomyopathy can be defined by a pathologically abnormal myocardium. There can be four major classifications of cardiomyopathy: dilated (DCM), hypertrophic (HCM), restrictive (RCM), and arrhythmogenic RV (ARVC). Vectors comprising polynucleotides described herein can be used to treat cardiomyopathy using gene therapy. In some cases, at least one additional therapy is also administered before, during, after, or any combination thereof of a gene therapy treatment.

In some cases, a polypeptide can be incorporated in a polynucleotide sequence described herein and introduced to a subject with a disorder, or in need of improved vasculogenesis. For example, a subject can have a cardiomyopathy disorder and can be treated by administration of a polynucleotide described herein to treat the disorder. In some cases, a polynucleotide encoding a gene or a polypeptide described herein can be introduced by gene therapy. Genes and polypeptides that can be introduced to a subject with a cardiomyopathy can include for instance: ATP-binding cassette, sub-family C, member 9 (ABCC9), Actin, a, cardiac muscle 1 (ACTC1), Actinin, α2 (ACTN2), Ankyrin repeat domain 1 (cardiac muscle) (ANKRD1), BCL2-associated athanogene 3 (BAG3), Calsequestrin 2 (cardiac muscle) (CASQ2), Caveolin 3 (CAV3), COX15 homolog, cytochrome c oxidase assembly protein (COX15), Crystallin α B Cysteine and glycine-rich protein 3 (CRYAB), Cysteine and glycine-rich protein 3 (CSRP3), Cardiotrophin 1 (CTF1), Desmin (DES), Dystrophin (DMD), DnaJ (Hsp40) homolog, subfamily C, member 19 (DNAJC19), Desmocollin 2 (DSC2), Desmoglein 2 (DSG2), Desmoplakin (DSP), Dystrobrevin, α (DTNA), Emerin (EMD), Eyes absent homolog 4 (EYA4), Four and a half LIM domains 2 (FHL2), Fukutin (FKTN), Forkhead box D4 (FOXD4), Galactosidase, α (GLA), Junction plakoglobin (JUP), Laminin, α4 (LAMA4), Lysosomal-associated membrane protein 2 (LAMP2), LIM domain binding 3 (LDB3), Lamin A/C (LMNA), Myosin binding protein C, cardiac (MYBPC3), Myosin, heavy chain 6, cardiac muscle, a (MYH6), Myosin, heavy chain 7, cardiac muscle, α (MYH7), Myosin, light chain 2, regulatory, cardiac, slow (MYH12), Myosin, light chain 3, alkali; ventricular, skeletal, slow (MYL3), Myosin light chain kinase 2 (MYLK2), Myozenin 2 (MYOZ2), Nexilin (F actin binding protein) (NEXN), Plakophilin 2 (PKP2), Phospholamban (PLN), Protein kinase, AMP-activated, γ 2, non-catalytic subunit (PRKAG2), Presenilin 1 (PSEN1), Presenilin 2 (PSEN2), RNA binding motif protein 20 (RBM20), Ryanodine receptor 2 (cardiac) (RYR2), Sodium channel, voltage-gated, type V, α subunit (SCNSA) Succinate dehydrogenase complex, subunit A, flavoprotein (SDHA), Sarcoglycan, δ (SGCD,) Spectrin repeat containing, nuclear envelope 1(SYNE 1), Spectrin repeat containing, nuclear envelope 2 (SYNE2), Tafazzin (TAZ), Titin-cap (telethonin) (TCAP), Transmembrane protein 43 (TMEM43), Thymopoietin (TMPO), Troponin C type 1 (slow) (TNNC1), Troponin I type 3 (cardiac) (TNNi3), Troponin T type 2 (cardiac) (TNNT2), Tropomyosin 1 (α)Titin (TPM1), TransthyreTIN (TTR), Titin (TTN), Vinculin (VCL), and any combination of portion thereof. Polypeptides or gene that can be introduced for treatment of a cardiovascular condition and/or improved vasculogenesis can be VEGF, SDF1, S100A1, or portions thereof or combinations thereof.

Provided herein are polynucleotide constructs comprising functional polypeptides attached by a linker construct disclosed herein. Also provided are methods for treatment, diagnosis and other therapeutic purposes comprising using or administering to a subject a polynucleotide described herein, or a polypeptide encoded thereby, or conjugates or derivatives thereof. The disclosed methods and compositions may be applied for treatment of diseases and conditions. An example of a condition can be cancer. A cancer or malignancy can include, but is not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's lymphoma, adult lymphocytic leukemia, adult non-Hodgkin's lymphoma, adult primary liver cancer, adult soft tissue sarcoma, aids-related lymphoma, aids-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous t-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non-Hodgkin's lymphoma, nonmelanoma skin cancer, non-small cell lung cancer, occult primary metastatic squamous neck cancer, oropharyngeal cancer, osteo-/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, polycythemia vera, parathyroid cancer, penile cancer, pheochromocytoma, pituitary tumor, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small intestine cancer, soft tissue sarcoma, squamous neck cancer, stomach cancer, supratentorial primitive neuroectodermal and pineal tumors, t-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine sarcoma, vaginal cancer, visual pathway and hypothalamic glioma, vulvar cancer, Waldenstrom' s macroglobulinemia, Wilms' tumor, and any other hyperproliferative disease, besides neoplasia, located in an organ system listed above.

Functional polypeptides connected by a linker polypeptide disclosed herein can be useful in methods and compositions described herein and may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred. Dysplasia can frequently be a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysical dysplasia, Mondini dysplasia, monostatic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia. Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis. In some embodiments, a polypeptide construct encoded by a polynucleotide disclosed herein, comprising at least two functional polypeptides connected by a linker disclosed herein, is used to inhibit growth, progression, and/or metastasis of cancers, in particular those listed above. Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom' s macroglobulinemia, heavy chain disease, and solid tumors including, but not limited to, sarcomas and carcinomas such as fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

In some embodiments, a polypeptide construct encoded by a polynucleotide disclosed herein, comprising at least two functional polypeptides connected by a linker disclosed herein, is used to treat diseases including, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, and also juvenile diabetes.

In some embodiments, a polypeptide construct encoded by a polynucleotide disclosed herein, comprising at least two functional polypeptides connected by a linker disclosed herein, is used to treat infectious diseases. Infectious diseases can be infection by pathogens such as bacteria, rickettsia, mycoplasma, protozoa, fungi, viruses, parasites, or other microbial agents. Examples include human immunodeficiency virus (HIV) causing AIDS, *Mycobacterium* of tuberculosis, *Streptococcus agalactiae*, methicillin-resistant *Staphylococcus aureus, Legionella pneumophilia, Streptococcus pyogenes, Escherichia coli, Neisseria gonorrhoeae, Neisseria meningitides, Pneumococcus, Cryptococcus neoformans, Histoplasma capsulatum, Hemophilis influenzae* B, *Treponema pallidum*, Lyme disease spirochetes, West Nile virus, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*.

In some embodiments, a polypeptide construct encoded by a polynucleotide disclosed herein, comprising at least two functional polypeptides connected by a linker disclosed herein, is used in conjugation with a chemotherapeutic agent, or in addition to, or simultaneously with a chemotherapeutic agent. A "chemotherapeutic agent" or "chemotherapeutic compound" and their grammatical equivalents as used herein, can be a chemical compound useful in the treatment of cancer.

Genes and polypeptides encoded by polynucleotides useful for gene therapy can be introduced into a subject sequentially, concurrently, or a combination thereof. Genes and polypeptides to be administered to a subject can be on a single polynucleotide vector or on separate polynucleotide vectors. In some cases, a multigene vector is used to introduce multiple genes using a single vector construct.

Polypeptide Constructs Encoded by Polynucleotides Described Herein:

Polynucleotide constructs described herein can be utilized to treat cardiovascular disease and/or improve vasculogenesis in a subject. For example, a molecular target for cardiovascular therapy can be VEGF-A, FGF4, Sarcoplasmic reticulum Ca 2+ ATPase, S100A1, beta-adrenergic receptor, Adenylyl-cyclase 6, or combinations thereof. In some cases, genes to be introduced for cardiovascular gene therapy can be SDF1, S100A1, VEGF191, or any combination thereof.

S100 is part of a family of Caβ+-modulated proteins implicated in intracellular regulatory activities. S100A1 can be the most abundant S100 protein isoform in a heart. It can promote cardiac contractile and relaxation function by enhancing activity of both ryanodine receptors (RYRs) and SERCA2a.

S100 can exert profound ionotropic actions through modulation of cardiomyocyte Ca2+ homeostasis and myofilament function independent of beta-adrenergic stimulation. S100A1 can interact in a Ca2+-dependent manner with the RyR and stabilizes the SERCA2a-PLN complex. S100A1 can also diminish the diastolic leak of Ca2+ and influences cardiac titin and mitochondrial F1-ATPase.

In some embodiments, an angiogenic polypeptide or gene can be utilized for cardiovascular therapy or for improved vasculogenesis as described herein. Administration of polynucleotides encoding angiogenic growth factors, such as VEGF-A165, angiopoietins, FGF, 126, HIF-1a26, or combinations thereof. These polypeptides can promote the development of collateral blood vessels in ischemia-related conditions, such as chronic critical limb ischemia, myocardial ischemia, angina, or peripheral arterial occlusive disease. Angiogenic factors can also induce formation of new vascular networks, which can make them suitable therapeutic options for treating acute coronary syndromes and peripheral vascular diseases. Several types of angiogenic factors can exhibit different properties have been explored in therapeutic applications for cardiovascular disease. For example, VEGF and subtypes of VEGF can be used. Subtypes of VEGF can comprise: VEGF-A, VEGF-B, VEGF-C, VEGF-D, placental growth factor (P1GF), and combinations thereof. Some of these factors also yield distinct isoforms. The intracellular signals of these VEGF subtypes can be mediated mainly by three different tyrosine kinase receptors: VEGFR1, VEGFR2, and VEGFR3. Specific interaction between these VEGF subtypes and their cognate cellular receptors can evoke a differential cellular response in endothelial cells and cardiomyocytes. In some cases, an isoform of VEGF-A, VEGF-A165, can have high angiogenic. VEGF-A165 can interact with VEGFR1 and VEGFR2. Interaction of VEGF-A165 with VEGFR1 on endothelial cells can contribute to vascular stability of newly formed vessels. Its interaction with VEGFR2 on endothelial cells can induce angiogenesis, vasculogenesis, and arteriogenesis, vasodilation, cell survival, and increase of cell permeability. Activation of VEGFR2 in newly formed cardiomyocytes can increase expression of anti-apoptotic proteins and reduced expression of pro-apoptotic proteins. In some cases, VEGFR2 activation can induce recruitment of local cardiac stem cells in ischemic areas.

A pro-angiogenic factor or gene can be expressed with a vector of the invention. For example, a pro-angiogenic factor, can be VEGF, basic fibroblast growth factor (bFGF), or transforming growth factor β-1(TGFβ-1), acidic fibroblast growth factor, angiogenin, hepatocyte growth factor, interleukin-8, placental growth factor, platelet-derived growth factor, pleiotropin, proliferin, tumor necrosis factor-alpha, to any combination thereof.

In some cases, cardiac effector genes or polypeptides used and incorporated into cardiac expression vectors of the invention can be selected from any one of as SDF1, S100A1 and VEGF191. In certain cases, a cardiac expression vector of the invention comprises or consists of any two genes selected from SDF1, S100A1 and VEGF191, in any combination of sequential order on the vector. In certain embodiments, a cardiac expression vector comprises a polynucleotide encoding SDF1, S100A1 and; VEGF191, in any combination of sequential order on the vector.

In certain embodiments, an SDF1 coding sequence comprises a polynucleotide encoding an SDF1 polypeptide. In certain embodiments, the SDF1 polypeptide is at least 45%, 50%, 55%, 60%, 65%, 70%, 75%, 80%, 85%, 90%, 95%, 97%, 98%, 99% or 100% identical to SEQ ID NO: 102. In certain cases, an SDF1 coding sequence comprises of an SDF1 codon optimized open reading frame (ORF), SEQ ID NO: 103.

In certain embodiments, a polynucleotide encoding SDF1 is at least 45%, 50%, 55%, 60%, 65%, 70%, 75%, 80%, 85%, 90%, 95%, 97%, 98%, 99% or 100% identical to SEQ ID NO: 103.

In certain cases, a S100A1 coding sequence comprises a polynucleotide encoding an S100A1 polypeptide. In certain embodiments, the S100A1 polypeptide is at least 45%, 50%, 55%, 60%, 65%, 70%, 75%, 80%, 85%, 90%, 95%, 97%, 98%, 99% or 100% identical to SEQ ID NO: 104. In certain embodiments, the S100A1 coding sequence comprises or consists of the S100A1 open reading frame (ORF). In certain cases, a polynucleotide encoding S100A1 is at least 45%, 50%, 55%, 60%, 65%, 70%, 75%, 80%, 85%, 90%, 95%, 97%, 98%, 99% or 100% identical to SEQ ID NO: 105.

In certain embodiments, a VEGF191 coding sequence can comprises a polynucleotide encoding a VEGF191 polypeptide. In certain embodiments, the VEGF191 polypeptide is at least 45%, 50%, 55%, 60%, 65%, 70%, 75%, 80%, 85%, 90%, 95%, 97%, 98%, 99% or 100% identical to SEQ ID NO: 106.

In certain cases, a VEGF191 coding sequence can comprises a VEGF191 open reading frame (ORF). In certain embodiments, the polynucleotide encoding VEGF191 is at least 45%, 50%, 55%, 60%, 65%, 70%, 75%, 80%, 85%, 90%, 95%, 97%, 98%, 99% or 100% identical to SEQ ID NO: 107.

TABLE 4

Polypeptide sequences and polynucleotide sequences

| SEQ ID | Gene Name | SEQUENCE (5' TO 3') |
|---|---|---|
| 102 | SDF-1 alpha | MNAKVVVVLVLVLTALCLSDGKPVSLSYRCPCRFFESHVA RANVKHLKILNTPNCALQIVARLKNNNRQVCIDPKLKWIQ EYLEKALNK |
| 103 | SDF-1 alpha | ATGAATGCCAAGGTCGTTGTGGTGCTTGTACTTGTGCTGA CTGCTCTGTGTCTGAGCGACGGAAAACCAGTCTCCCTCAG CTACAGGTGCCCATGCCGATTCTTCGAATCTCATGTGGCC CGGGCCAATGTGAAGCACTTGAAAATCCTGAATACACCCA ACTGCGCGTTGCAGATCGTGGCCCGCCTGAAAAATAATAA TAGGCAGGTATGTATAGATCCAAAGCTTAAGTGGATCCAG GAGTATCTGGAAAAGGCTCTCAATAAA |
| 104 | S100A1 | MGSELETAMETLINVFHAHSGKEGDKYKLSKKELKELLQT ELSGFLDAQKDVDAVDKVMKELDENGDGEVDFQEYVVLVA ALTVACNNFFWENS |

TABLE 4-continued

Polypeptide sequences and polynucleotide sequences

| SEQ ID | Gene Name | SEQUENCE (5' TO 3') |
|---|---|---|
| 105 | S100A1 | ATGGGCAGCGAACTGGAAACCGCCATGGAGACTTTGATAA<br>ATGTTTTCCACGCGCATAGCGGCAAAGAAGGGGACAAGTA<br>CAAGCTGTCAAAAAAGGAGCTGAAAGAACTGCTGCAGACC<br>GAATTGAGCGGCTTCCTGGACGCTCAGAAAGATGTCGATG<br>CCGTCGACAAAGTGATGAAAGAGCTTGACGAGAACGGTGA<br>CGGTGAAGTCGATTTTCAGGAATATGTGGTGCTGGTGGCC<br>GCCCTTACTGTAGCATGCAACAATTTCTTTTGGGAAAATT<br>CA |
| 106 | VEGF191<br>(amino acids<br>27-191 of<br>this sequence<br>form<br>VEGF165) | MNFLLSWVHWSLALLLYLHHAKWSQAAPMAEGGGQNHHEV<br>VKFMDVYQRSYCHPIETLVDIFQEYPDEIEYIFKPSCVPL<br>MRCGGCCNDEGLECVPTEESNITMQIMRIKPHQGQHIGEM<br>SFLQHNKCECRPKKDRARQENPCGPCSERRKHLFVQDPQT<br>CKCSCKNTDSRCKARQLELNERTCRCDKPRR |
| 107 | VEGF191 | ATGAATTTTCTGCTCTCTTGGGTGCACTGGTCACTGGCAC<br>TGCTGCTGTATCTGCACCATGCAAAATGGTCCCAAGCAGC<br>TCCCATGGCAGAGGGAGGTGGACAGAATCATCATGAGGTT<br>GTCAAATTTATGGATGTCTACCAGCGGAGCTACTGCCACC<br>CAATTGAGACGTTGGTAGACATTTTTCAGGAATATCCAGA<br>CGAGATTGAGTACATTTTCAAGCCTAGCTGTGTGCCCTTG<br>ATGCGATGCGGTGGCTGTTGCAATGATGAGGGACTCGAGT<br>GTGTCCCCACCGAGGAAAGCAATATAACCATGCAAATCAT<br>GCGAATCAAACCCCACCAGGGCCAGCATATCGGCGAGATG<br>TCTTTCTTGCAACATAACAAATGCGAGTGTCGGCCAAAGA<br>AGGACAGGGCTCGCCAGGAAAATCCCTGTGGTCCTTGTTC<br>AGAGCGCAGGAAGCATCTTTTCGTCCAGGATCCGCAGACT<br>TGTAAATGTTCATGCAAGAATACCGATTCTAGGTGTAAGG<br>CGAGGCAACTCGAGCTTAACGAGAGAACCTGTAGGTGTGA<br>CAAACCTAGAAGA |
| 126 | VEGF 165<br>(predicted<br>mature form;<br>i.e.,<br>VEGF191<br>minus signal<br>peptide) | APMAEGGGQNHHEVVKFMDVYQRSYCHPIETLVDIFQEYP<br>DEIEYIFKPSCVPLMRCGGCCNDEGLECVPTEESNITMQI<br>MRIKPHQGQHIGEMSFLQHNKCECRPKKDRARQENPCGPC<br>SERRKHLFVQDPQTCKCSCKNTDSRCKARQLELNERTCRC<br>DKPRR |
| 127 | VEGF165<br>(encoding<br>predicted<br>mature form;<br>i.e.,<br>VEGF 191<br>minus signal<br>peptide) | GCTCCCATGGCAGAGGGAGGTGGACAGAATCATCATGAGG<br>TTGTCAAATTTATGGATGTCTACCAGCGGAGCTACTGCCA<br>CCCAATTGAGACGTTGGTAGACATTTTTCAGGAATATCCA<br>GACGAGATTGAGTACATTTTCAAGCCTAGCTGTGTGCCCT<br>TGATGCGATGCGGTGGCTGTTGCAATGATGAGGGACTCGA<br>GTGTGTCCCCACCGAGGAAAGCAATATAACCATGCAAATC<br>ATGCGAATCAAACCCCACCAGGGCCAGCATATCGGCGAGA<br>TGTCTTTCTTGCAACATAACAAATGCGAGTGTCGGCCAAA<br>GAAGGACAGGGCTCGCCAGGAAAATCCCTGTGGTCCTTGT<br>TCAGAGCGCAGGAAGCATCTTTTCGTCCAGGATCCGCAGA<br>CTTGTAAATGTTCATGCAAGAATACCGATTCTAGGTGTAA<br>GGCGAGGCAACTCGAGCTTAACGAGAGAACCTGTAGGTGT<br>GACAAACCTAGAAGA |

Pharmaceutical Compositions and Formulations:

The compositions described throughout can be formulation into a pharmaceutical medicament and be used to treat a human or mammal, in need thereof, diagnosed with a disease, e.g., cardiovascular disease. In some embodiments, compositions described herein utilized for cardiovascular therapy or for improved vasculogenesis as described herein. These medicaments can be co-administered with one or more vectors.

Vectors comprising polynucleotides described herein, including viral and non-viral vectors containing nucleic acids encoding engineered CRISPR, TALEN, Argonaut, transposon-based, ZEN, meganuclease, or Mega-TAL molecules, transposon and/or transgenes can also be administered directly to an organism for transfection or transduction of cells in vivo. Alternatively, naked DNA or mRNA comprising polynucleotides described herein can be administered. Administration is by any of the routes normally used for introducing a molecule into ultimate contact with blood or tissue cells including, but not limited to, injection, infusion, topical application and electroporation. More than one route can be used to administer a particular composition. Pharmaceutically acceptable carriers are determined in part by the particular composition being administered, as well as by the particular method used to administer the composition.

In some cases, vectors comprising polynucleotides described herein can be administered to a subject in need thereof in conjunction with, or separately with secondary therapies. A secondary therapy can be an agent for improved vasculogenesis, pulmonary hypertension, aldosterone receptor antagonists, angiotensin converting enzyme inhibitors, angiotensin receptor blockers, angiotensin receptor blockers and neprilysin inhibitors, antiadrenergic agents, centrally acting, antiadrenergic agents, peripherally acting antianginal agents, antiarrhythmic agents, group I antiarrhythmic agents, group II antiarrhythmics, group III antiarrhythmics, group IV antiarrhythmics, group V antiarrhythmics, anticholinergic chronotropic agents, antihypertensive combinations, ACE inhibitors with calcium channel blocking agents, ACE inhibitors with thiazides, angiotensin II inhibitors with calcium channel blockers, angiotensin II inhibitors with thiazides, antiadrenergic agents (central) with thiazides, antiadrenergic agents (peripheral) with thiazides, beta blockers with thiazides, potassium sparing diuretics with thiazides, beta-adrenergic blocking agents, cardio selective beta blockers, non-cardioselective beta blockers, calcium channel blocking agents, catecholamines, diuretics, carbonic anhydrase inhibitors, loop diuretics, potassium-sparing diuretics, thiazide diuretics, inotropic agents, peripheral vasodilators, renin inhibitors, sclerosing agents, vasodilators, vasopressin antagonists, vasopressors Anti-angiogenic agents can also be used in conjunction with polynucleotides described herein. Suitable anti-angiogenic agents for use in the disclosed methods and compositions include anti-VEGF antibodies, including humanized and chimeric antibodies, anti-VEGF aptamers and antisense oligonucleotides. In some cases, for example, in the compositions, formulations and methods of treating cancer, the unit dosage of the composition or formulation administered can be 5, 10, 15, 20, 25, 30, 35, 40, 45, 50, 55, 60, 65, 70, 75, 80, 85, 90, 95 or 100 mg.

Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

In some cases, for example, in the compositions, formulations and methods of treating cancer, the unit dosage of the composition or formulation administered can be 5, 10, 15, 20, 25, 30, 35, 40, 45, 50, 55, 60, 65, 70, 75, 80, 85, 90, 95 or 100 mg. In some cases, the total amount of the composition or formulation administered can be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 40, 50, 60, 70, 80, 90, or 100 g.

Methods and Indications

Vectors comprising polynucleotides described herein can be constructed and introduced into a subject as described herein. These vectors can be used for gene therapy. These vectors can be used to treat disease in a recipient (e.g., a human). For example, polynucleotides described herein and/or polypeptides encoded by polynucleotides described herein can be administered to a subject to treat cardiovascular disease or improve vasculogenesis in the subject. A subject treated by a method described herein, or by contact with or administration of a composition described herein can be a mammalian subject who can be a human subject, a non-human primate, a canine mammal, a felid mammal or any other mammal.

Described herein is a method of treating a disease (e.g., cardiovascular disease) in a recipient comprising introducing at least one vector comprising at least one polynucleotides described herein into a subject with cardiovascular disease. In some cases, a vector is introduced to a cell.

In some cases, a cardiovascular disease can be cardiomyopathy. Cardiomyopathy can be defined by a pathologically abnormal myocardium. There can be four major classifications of cardiomyopathy: dilated (DCM), hypertrophic (HCM), restrictive (RCM), and arrhythmogenic RV (ARVC). Cardiomyopathy can be diagnosed through in vivo imaging, with either echocardiography or, increasingly, cardiac MRI. DCM can refer to enlargement of the heart, which often affects all four chambers, especially late in the disease. Most commonly, DCM can be associated with reduced LV function or systolic function, although early in the disease the LV may be dilated, with only minimally reduced function. In contrast, HCM can be characterized by increased LV wall thickness, often targeting the septum that separates the LV from the RV. RCM can be elusive in some cases, in part because the heart may appear morphologically close to normal, with only minor increased wall thickness or modestly decreased LV ejection fraction. The infiltrative process underlying RCM may not be readily detectable in vivo with even the most sensitive imaging technique. RCM can be characterized by impaired filling of the heart, known as diastolic dysfunction, which reduces cardiac output. ARVC can be characterized by reduced function and thinning of the RV with a fibrofatty infiltration that can be seen on MRI. In some cases, a cardiomyopathy patient can be treated with a vector of the invention.

A method provided herein can be used for treating or preventing disease including, but not limited to, cancer, cardiovascular diseases, lung diseases, liver diseases, skin diseases, or neurological diseases. A method provided herein can be used for improved vasculogenesis in a subject.

"Improving" and its grammatical equivalents as used herein can mean any improvement recognized by one of skill in the art. For example, improving cardiovascular disease can mean lessening arrhythmia, which can encompass a decrease, lessening, or diminishing of an undesirable effect or symptom. In another example, improving disease can mean lessening tumor load, which can encompass a decrease, lessening, or diminishing of an undesirable effect or symptom. For example, a subject may experience reduction of a tumor load, extended survival, complete remission, stabilization to name a few improvements.

Another indication of improvement can be the days a subject does not require therapy. For example, after treatment administered provided herein, a recipient can require no therapy for at least or at least about 1, 2, 3, 4, 5, 6, 7, 8, 9, 10 or more days. This can indicate that a treatment was successful. This can also indicate that there is no toxicity associated with the administration of the polynucleic acids described herein.

A subject can require no therapy for at least 1 day. A recipient can also require no therapy for at least 7 days. A recipient can require no therapy for at least 14 days. A recipient can require no therapy for at least 21 days. A recipient can require no therapy for at least 28 days. A recipient can require no therapy for at least 60 days. Furthermore, a recipient can require no therapy for at least 1, 2, 3, 4, 5, 6, 7, 8, 9, 10, or more years.

Another indication of improvement can be the days a recipient requires reduced therapy. For example, after the treatment provided herein, a recipient can require reduced therapy administrations for at least 1, 2, 3, 4, 5, 6, 7, 8, 9, 10 or more days. This can indicate that treatment was successful.

For example, a recipient can require reduced therapy for at least 1 day. A recipient can also require reduced therapy for at least 7 days. A recipient can require reduced therapy for at least 14 days. A recipient can require reduced therapy for at least 21 days. A recipient can require reduced therapy for at least 28 days. A recipient can require reduced therapy for at least 60 days. Furthermore, a recipient can require reduced therapy for at least 1, 2, 3, 4, 5, 6, 7, 8, 9, 10 or more years.

In treatment of cardiac diseased, percutaneous coronary artery catheterization can be a minimally invasive procedure that can allow for homogeneous gene delivery to each region of a heart. In some cases, gene delivery can be impeded in patients with severe coronary artery disease. For example, during coronary artery infusion, a vector can be injected in a catheter without interruption of coronary flow.

In some cases, enhanced vector residence time in coronary circulation can be achievable with coronary venous blockade. For example, antegrade coronary infusion with a short occlusion of both a coronary artery and a coronary vein enhanced myocardial gene expression can enhance vector residence time.

In other cases, to maximize duration of a vector exposure to an endothelium while minimizing systemic distribution, a cardiac recirculation approach can be used. In this case, an extracorporeal device can drain blood from a coronary sinus using an occlusion catheter and return oxygenated coronary venous blood to a left main coronary artery via a peristaltic pump (V-Focus; Osprey Medical Inc.) Utilizing this method can allow for selective administration of endothelial permeabilizing agents without systemic side effects.

In some cases, transfection efficacy can correlate with coronary flow as well as exposure time and vector concentration. For example, antegrade coronary artery infusion supported by an increased coronary flow, for example using an intra-aortic balloon pump, might further enhance cardiac gene transfer In some cases, a direct injection of a vector into the heart can be performed. A vector can be injected epicardially or endocardially into a target area. In some cases, a direct injection can bypass an endothelial barrier. This can result in a high local concentration at an injection site. In some cases, direct injection can avoid exposure to circulating blood. In other cases, a direct injection of a vector into a heart can avoid deactivation of a vector by circulating DNases or neutralizing antibodies. A direct vector injection can also reduce exposure of a vector to off-target organs, although local administration cannot completely avoid some systemic vector distribution. Low volumes at high vector concentrations may also increase vector retention in a myocardium.

In some cases, a vector can be introduced during a thoracotomy. A vector can also be introduced pericardially. In some cases, a vector can be introduced using retrograde perfusion, for instance as disclosed in FIG. 9.

After gene therapy, the transfected cells can be functional in the recipient. Functionality can in some cases determine whether gene therapy was successful. For example, the transfected cells can be functional for at least or at least about 1, 2, 3, 4, 5, 6, 7, 8, 9, 10 or more days. This can indicate that gene therapy was successful. This can also indicate that there is no rejection of the transplanted cells or vectors.

In certain instances, transfected cells can be functional for at least 1 day. Transfected cells can also functional for at least 7 days. Transfected cells can be functional for at least 14 days. Transfected cells can be functional for at least 21 days. Transfected cells can be functional for at least 28 days. Transfected cells can be functional for at least 60 days.

Routes of Administration

Previously, delivery techniques of therapeutics into the heart have included intramyocardial administration (transepicardially or transendocardially) or antegrade delivery into the coronary artery. The transepicardial route suffers the drawback of surgical invasiveness. The transendocardial approach requires complex electromagnetic mapping using systems such as the NOGA device which is not applicable for patients with thinned myocardium, as this technique may cause perforation. Other devices such the Biocardia—Helical infusion catheter or the Celyad—C-Cath also have the limitations of wall thickness.

Antegrade administration into the coronary artery is associated with a lower biologic retention [12], as compared to intramyocardial administration. Additionally, administration of biologics into the coronary artery has been shown to increase risk of coronary embolism and ST segment elevations [13] [14] [15] [16] [17]. Also with pDNA administration, the direct contact with a large blood volume may decrease the effect before entering into the target tissue.

Retrograde Administration

In humans, the coronary sinus drains the venous system of the ventricular cavities, which are responsible for the majority of cardiac contraction. The technique of retrograde delivery into the coronary sinus has been widely used for the administration of cardioplegia solution due in part to superior distribution of the solution throughout the myocardium as compared to antegrade delivery [18]. Additionally, the procedure has been demonstrated clinically safe for administration of oxygenated blood during high risk percutaneous transluminal coronary angioplasty [19] [20] [21]. The process of retrograde administration into the coronary sinus involves temporary occlusion of afferent coronary circulation by means of a balloon catheter followed by administration against the outflowing blood. This results in the solution entering the myocardium via post capillary venules. In contrast to arterioles or capillaries, post-capillary venules have the smallest vessel diameter and conceptually would allow for greatest transfer of material into the interstitium [22]. Physiologically, it is known that post-capillary venules are a major target of immune/inflammatory cell migration across the endothelium, in part due to expression of adhesion molecules such as ELAM-1 [23], ICAM-1 [24], CD18 [25], and CD44 [26], and in part because of biomechanical properties. Patel et al demonstrated in the REVIVE Trial, using the same delivery catheter as proposed in this preclinical study (Cook Regentec), that over 3 billion nucleated cells can safely be delivered in a volume of 60cc into the coronary sinus of patients with end-stage CHF [27].

Gene Therapy by Retrograde Administration

Several studies have successfully utilized retrograde administration in the area of cardiac regeneration. Boekstegers et al [32], delivered adenovirus expressing beta-gal and Luciferase into the porcine myocardium comparing antegrade delivery into the coronary artery or retrograde via the anterior cardiac vein. Significantly elevated expression of the gene in infarct tissue in a homogenous manner was observed via the retrograde method as compared to antegrade. Similar results were reported by Alino et al [33], who observed interstitial expression of eGFP in porcine hearts that were injected in the retrograde manner with naked DNA. In another study, administration of beta-gal encoding plasmid using the retrograde method in pigs resulted in higher myocardial gene expression in comparison to antegrade and intramuscular administration [34]. This superior level of gene expression in comparison to intramyocardial delivery was reproduced in other studies [35]. The use of retrograde administration has also been performed successfully for delivery of protein therapeutics. Von Degenfeld et al [36], reported a porcine study in which retrograde administration of FGF-2 protein was used to prevent experimentally-induced stenosis. Levels of radiolabelled FGF-2 in the myocardium of pigs treated with retrograde were almost twice the levels achieved using antegrade infusion. Additionally, significant improvements in transmural blood flow and regional myocardial function were reported when FGF-2 was administered via the retrograde method. The safe use retrograde delivery of SDF-1α pDNA in heart failure patients was also reported (RETRO-HF).

Accordingly, a preferred embodiment of the present invention comprises use of retrograde administration via the coronary sinus. Another embodiment of the present invention comprises use of intracoronary or intramyocardial routes of administration.

Ultrasound Targeted Microbubble Destruction Gene Delivery (UTMD)

Gas-filled microbubbles are useful ultrasound contrast agents. In some embodiments, microbubbles are used for delivering vectors, genes and/or constructs described herein to tissues and/or organs in a subject.[65] In some cases, the delivery can be organ or tissue-specific. When sonified with ultrasound near their resonance frequency, microbubbles oscillate. With higher ultrasound energies, oscillation amplitudes increase, leading to microbubble destruction. This phenomenon is used to deliver a vector or composition described herein into a target organ, for instance, by administering microbubbles loaded with compositions or gene therapy vectors described herein, for instance by i. v. injection, and subsequently exposing to ultrasound energy resulting in microbubble destruction at a target site.

In an embodiment of UTMD, bioactive molecules, such as plasmid vectors described herein, polynucleotides encoding gene constructs described herein, are added to, for instance, the cationic shells of lipid microbubble contrast agents. These vector-carrying microbubbles can be administered to the subject for instance, intravenously or directly to the left ventricle of the heart amongst other administration options. In some subjects, the microbubbles they can be infused through an intracoronary catheter. The subsequent delivery from the circulation to a target organ occurs by acoustic cavitation at a resonant frequency of the microbubbles. In some embodiments, the mechanical energy generated by the microbubble destruction may result in transient pore formation in or between the endothelial cells of the microvasculature of the targeted region. In some embodiments, the transfection efficiency into and across the endothelial cells is enhanced, and transgene-encoding vectors are deposited into the surrounding tissue. As such, in some cases, wherein a vector described herein is delivered by UTMD, any additional plasmid DNA remaining in the circulation can be degraded by nucleases in the blood, thereby resulting in highly specific target-organ transfection to the organs exposed to ultrasound sonication, and reducing the likelihood of delivery to non-sonicated tissues.

EXAMPLES

Example 1

Transfection of Cardiomyocytes for Att Site Mediated Recombination

Cardiomyocytes were transfected with luciferase vectors with or without (i.e., plus (+) or minus (−)) att-site, and plus (+) or minus (−) SpBC2 recombinase. Luciferase expression was then monitored over time to assess att-site mediated recombination. To determine site specificity and efficacy of SpBC2 and its proposed site of activity (Att-site), cardiomyocytes were co-transfected with a SpBC2 plasmid and a Firefly luciferase ("FLUC" or "Luc") plasmid vector containing att-site around the gene of interest. Controls included were Att-Luc plasmid without SpBC2 (to measure random integration), No-Att-Luc plasmid with SpBC2 (to measure non-att-site specific integration), and No-Att-Luc plasmid without SpBC2 (to measure transient expression). Cells were transfected via DNAfectin (Applied Biological Materials Inc., Richmond, BC, Canada) and cultured over 14 days, periodically sub-culturing cells, testing cells by luciferase assay, and harvesting cells for qPCR assays.

Transfection was performed by utilizing complete growth media and transfection media (Prigrow I without FBS/antibiotics). At least 1 hour prior to transfection, media was removed from cardiomyocytes and replaced with fresh growth media. 3 mL/well in 6 well plate or 1.5 mL/well in 12 well plates. The DNAfectin reagent was warmed to room temperature prior to use and vortexed briefly to mix. The various combinations of DNAfectin-plasmid DNA complexes were prepared in transfection media as follows:

| Plasmid Vector Combination | DNA (µg) |
| --- | --- |
| Att-Luc | 0.375 |
| SPBc2 | 0.375 |
| Att-Luc | 0.375 |
| Stuffer | 0.375 |
| Luc | 0.375 |
| SPBc2 | 0.375 |
| Luc | 0.375 |
| Stuffer | 0.375 |

"Att-Luc" = vector with att site and luciferase gene; "Luc" = vector with luciferase gene, no att site; "SPBc2" = vector encoding SPBc2 recombinase; and, "Stuffer" = (or pStuffer) is a plasmid with the same backbone configuration as pXoX, with the open reading frame (ORF) replaced with a non-expressing, similar-sized non-effector sequence.

DNA was added to the transfection media. The mixture was incubated at room temperature for 20 minutes. 300 µL per well DNAfectin-DNA complex was added to cells.

Passage and Harvest for qPCR, Luciferase Assay 48 hours post-transfection, media was removed from the cells in the 12 well plates. Cells were trypsinized and harvested into microfuge tubes. Cells were then resuspended in 1 mL fresh growth media. Cells were seeded into a fresh 12 well plate at 5e4 cells/well and luciferase was measured. The remaining cells were harvested for qPCR.

Results:

Over a two week course, FLUC expression from the Att-Luc+SPBc2 recombinase decreased roughly 10-fold, while FLUC expression from the other transfection conditions (either without att-site or without recombinase) decreased by 100- to 1000-fold, returning nearly to background levels of expression (data not shown). Att-site mediated recombination of the FLUC GOI (Genes of Interest) into the cardiomyocyte genome was also observed (data not shown).

Example 2

HUVEC Proliferation Assay

A Human Umbilical Vein Endothelial Cell (HUVEC) proliferation assay was used to assess the functionality of VEGF165 expressed by pXoX. Serum-starved HUVECs were treated with conditioned media from patients (dilated, hypertrophic), or healthy iPSC-derived cardiomyocytes transfected with pXoX or a single effector control (pVEGF165 positive control, pSDF-1α negative control). After 96 hours of incubation, HUVEC proliferation was quantitated using a luminescence assay. Assay were repeated three times (e.g., CM-1, CM-2, CM-3).

Figure 5A:
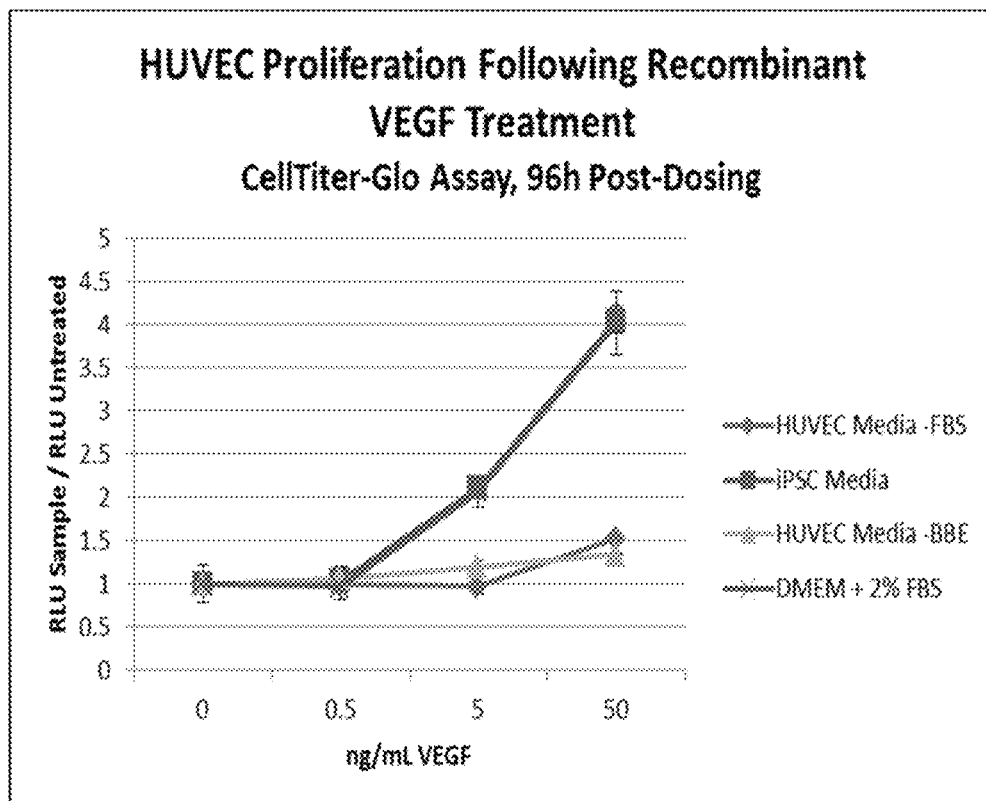
FIG. 5A and FIG. 5B show a HUVEC proliferation assay.
Figure 5B:
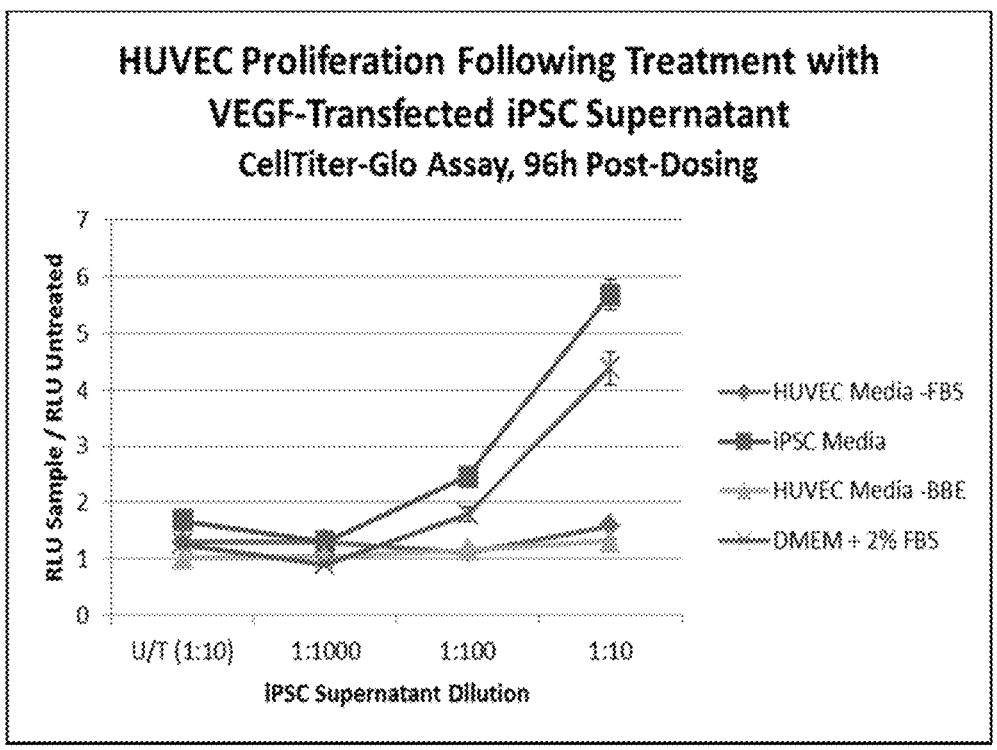
Figure 14A:
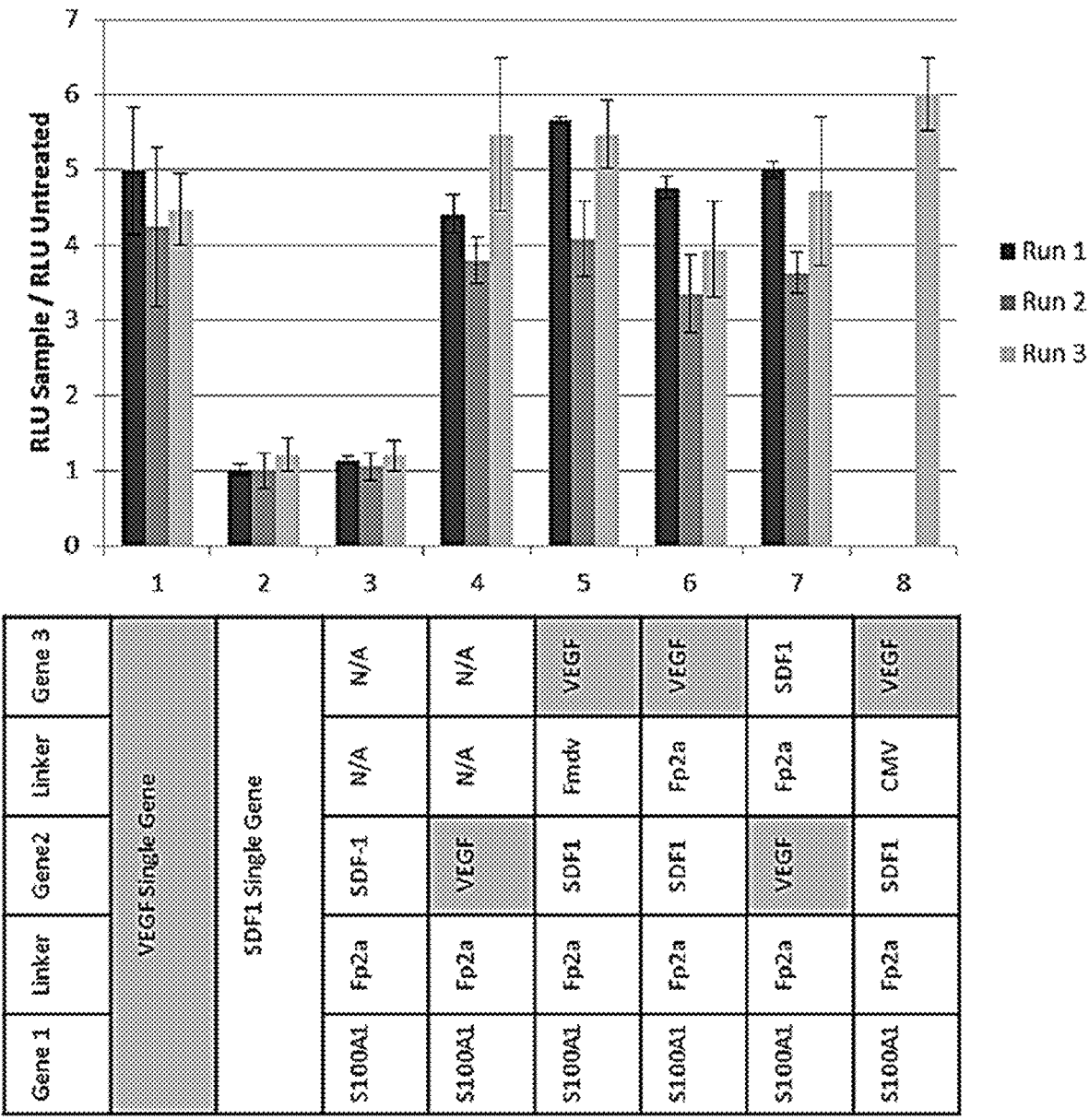
FIG. 14A and FIG. 14B shows a proliferation assay performed on HUVECS.
Figure 14B:
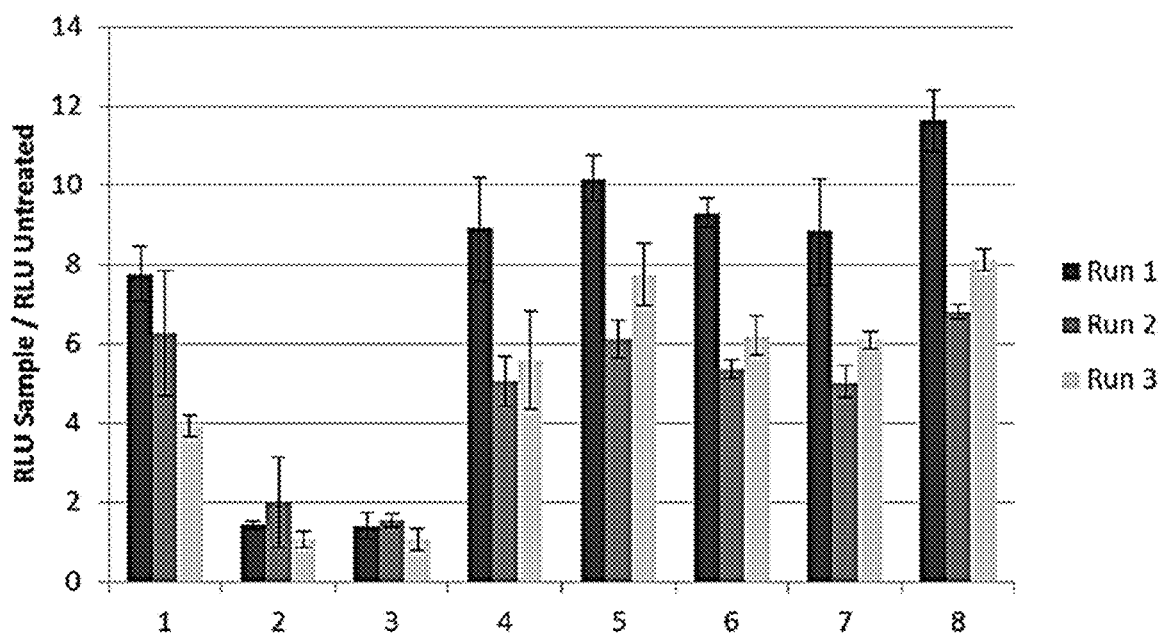

Induced Pluripotent Stem Cells iPSC cardiomyocyte cells were transfected with singe gene, dual-gene, or triple-gene vectors encoding for S100A1 and VEGF; S100A1, SDF1, and VEGF; or VEGF alone. 48 hours post transfection cellular supernatant was collected. HUVECs were seeded on 6-well plates at a density of approximately 1:10, 1:100, and 1:1000 in the supernatant collected from the transfected iPSC cells. 96 hours following introduction of the supernatant, HUVEC proliferation was measured by CellTiter-Glo Assay, FIG. 5A and FIG. 5B show experimental data. FIG. 14A and FIG. 14B show similar results for iPSC cells derived from a dilated cardiomyopathy patient.

Cardiomyocytes from Cardiomyopathy Patients and Healthy Controls

Figure 6:
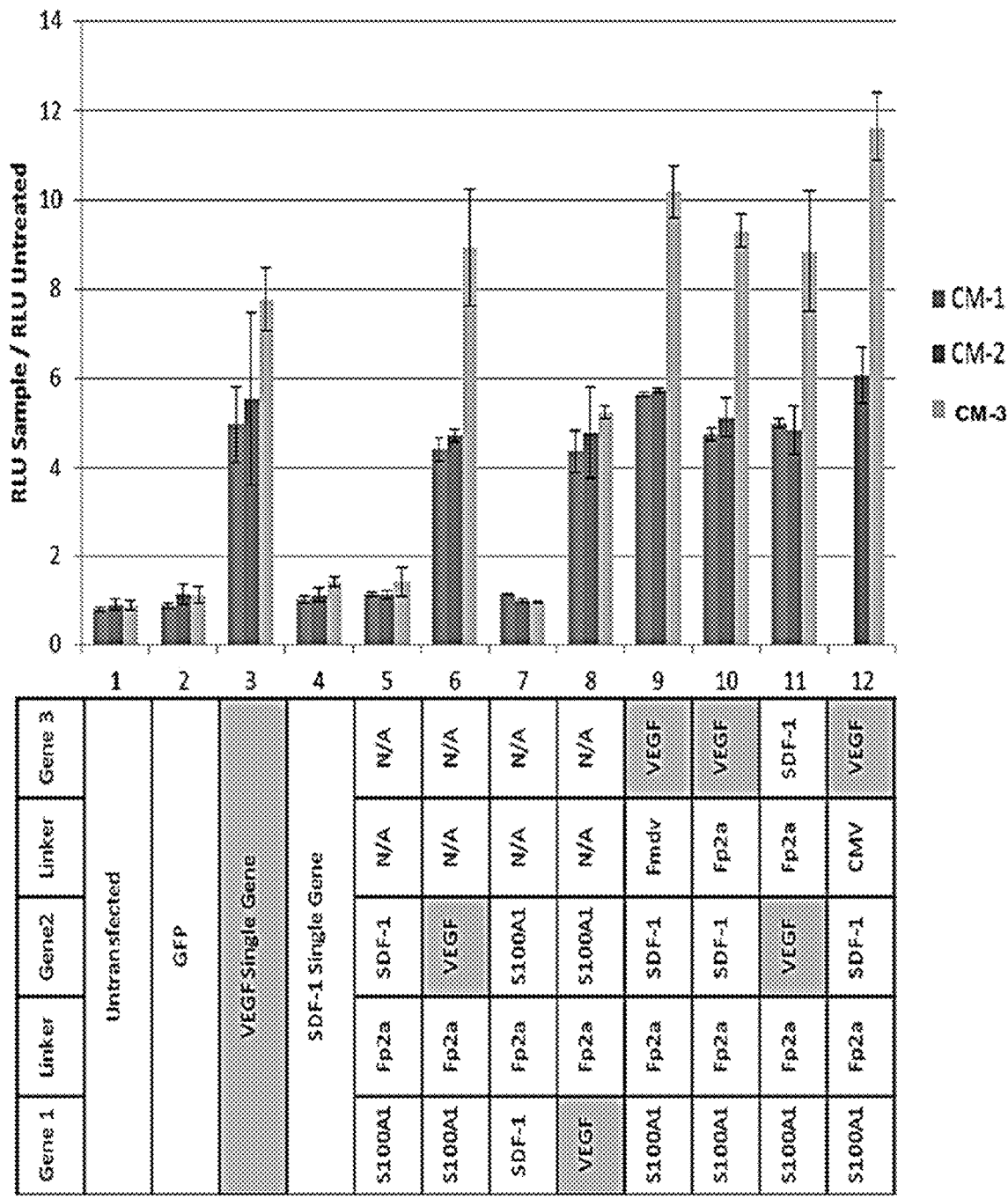
FIG. 6 shows HUVEC proliferation following treatment with transfected Cardiomyocyte-iPSC supernatants. Cardiomyocyte-iPSC were obtained from patients with dilated cardiomyopathy (DCM), (hypertrophy cardiomyopathy (HCM) or healthy controls, demonstrating successful expression and activity of functional polypeptides encoded by polynucleotides described herein, comprising linkers disclosed herein.

Cardiomyocyte-iPSC cells were obtained from patients with dilated cardiomyopathy (DCM), hypertrophy cardiomyopathy (HCM) or healthy controls. iPSC cells were transfected with singe gene, dual-gene, or triple-gene vectors encoding for S100A1 and VEGF; S100A1, SDF1, and VEGF; or VEGF alone. 48 hours post transfection cellular supernatant was collected. HUVECs were seeded on 6-well plates at a density of approximately 1:10, 1:100, and 1:1000 in the supernatant collected from the transfected iPSC cells. 96 hours following introduction of the supernatant, HUVEC proliferation was measured by CellTiter-Glo Assay, FIG. 6 shows experimental data.

Results iPSC-CMs transfected with singe gene, dual-gene, or triple-gene vector constructs showed 4-10-fold increase in HUVEC proliferation in both cases. Thus, results successfully demonstrate that VEGF is functional (i.e., biologically active) when expressed as part of multi-genic linked constructs from dual-gene and triple-gene expression vectors when using linkers provided herein (i.e., induce HUVEC proliferation similar to that observed with a single VEGF165 effector plasmid).

Example 3

Endothelial Tube Formation Assay

The Endothelial Tube Formation Assay (CBA200, Cell Biolabs Inc., San Diego, Calif., USA) will be used in addition to the HUVEC proliferation assay. ECM gel will be thawed at 4° C. and mixed to homogeneity using cooled pipette tips. Cell culture plates (96-well) were bottom-coated with a thin layer of ECM gel (50 µl/well), which will be left to polymerize at 37° C. for 60 min. HUVEC ($2-3\times10^4$ cells) will be seeded into the cell culture plate in supernatant collected from iPSC cardiomyocyte cells that were transfected with singe gene, dual-gene, or triple-gene vectors encoding for S100A1 and VEGF connected by a linker described herein; S100A1, SDF1, and VEGF connected by a linker described herein; or VEGF alone. 150 µl of the supernatant-HUVEC mixture will be added to each well on the solidified ECM gel. The plates will be incubated at 37° C. for 12-18 hr. and the endothelial tubes will be quantified using a fluorescent microscope after staining with Calcein AM. Three microscope fields will be selected at random and photographed. Tube forming ability will be quantified by counting the total number of cell clusters (knots) and branches under a 4× objective and four different fields per well. The results will be expressed as mean fold change of branching compared with the control groups. Each experiment will performed at least three times.

Example 4

SDF-1α Function—Migration Assay

Chemotaxis experiments were performed using a 24-well transwell chemotaxis chamber technique (Millipore, Billerica, Mass., USA). Briefly, Peripheral blood leukocytes (PBLs) were isolated from samples obtained from healthy volunteers and transfected with double gene or triple-gene vectors encoding for S100A1 and VEGF connected by a linker described herein, or S100A1, SDF1, and VEGF connected by a linker described herein. A total of $1\times10^5$ PBLs in 200 µL medium were seeded into the upper chamber (pore size, 8 µm). For the inhibition experiment, half of the PBLs were pre-incubated with 10 nmol/L CXCR4 antagonist (AMD3100) for 30 min prior to seeding. Then, PBLs and medium were transferred into the upper chamber. The chamber was then incubated for 12 h at 37° C. in a humidified atmosphere with 5% $CO_2$. The membrane (Millipore) was removed and its upper surface was wiped away with a cotton swab to remove the immobile PBLs. The membrane was then fixed in neutral formalin for 10 min at room temperature and then stained with 0.1% crystal violet for 5 min. The number of PBLs that have migrated to the lower surface of the membrane was counted in 10 random high-power fields (HPFs) under a light microscope (Nikon Eclipse, Nikon Instruments, Inc., Melville, N.Y., USA).

A chemotactic index (CI) was calculated to express stimulated migration: CI=stimulated migration (number of CSCs per HPF)/random migration (number of CSCs per HPF). Each assay was performed in triplicate wells.

Results

Figure 7:
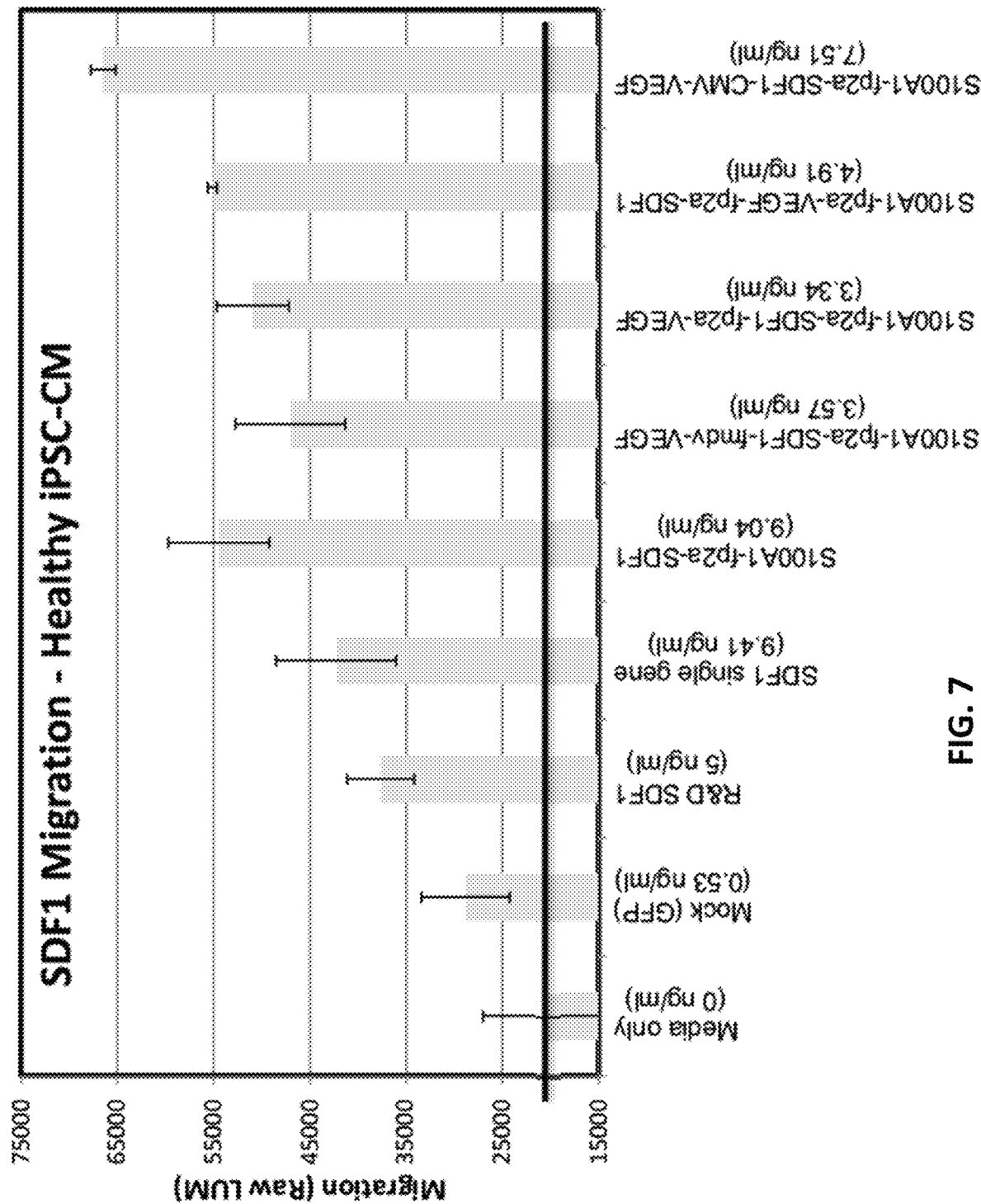
FIG. 7 shows iPSC-CMs transfected with singe gene, double gene, and triple-gene SDF1 polypeptide constructs showing elevated migration of peripheral blood lymphocytes (PBLs), demonstrating successful expression and activity of functional polypeptides encoded by polynucleotides described herein, comprising linkers disclosed herein.
Figure 8:
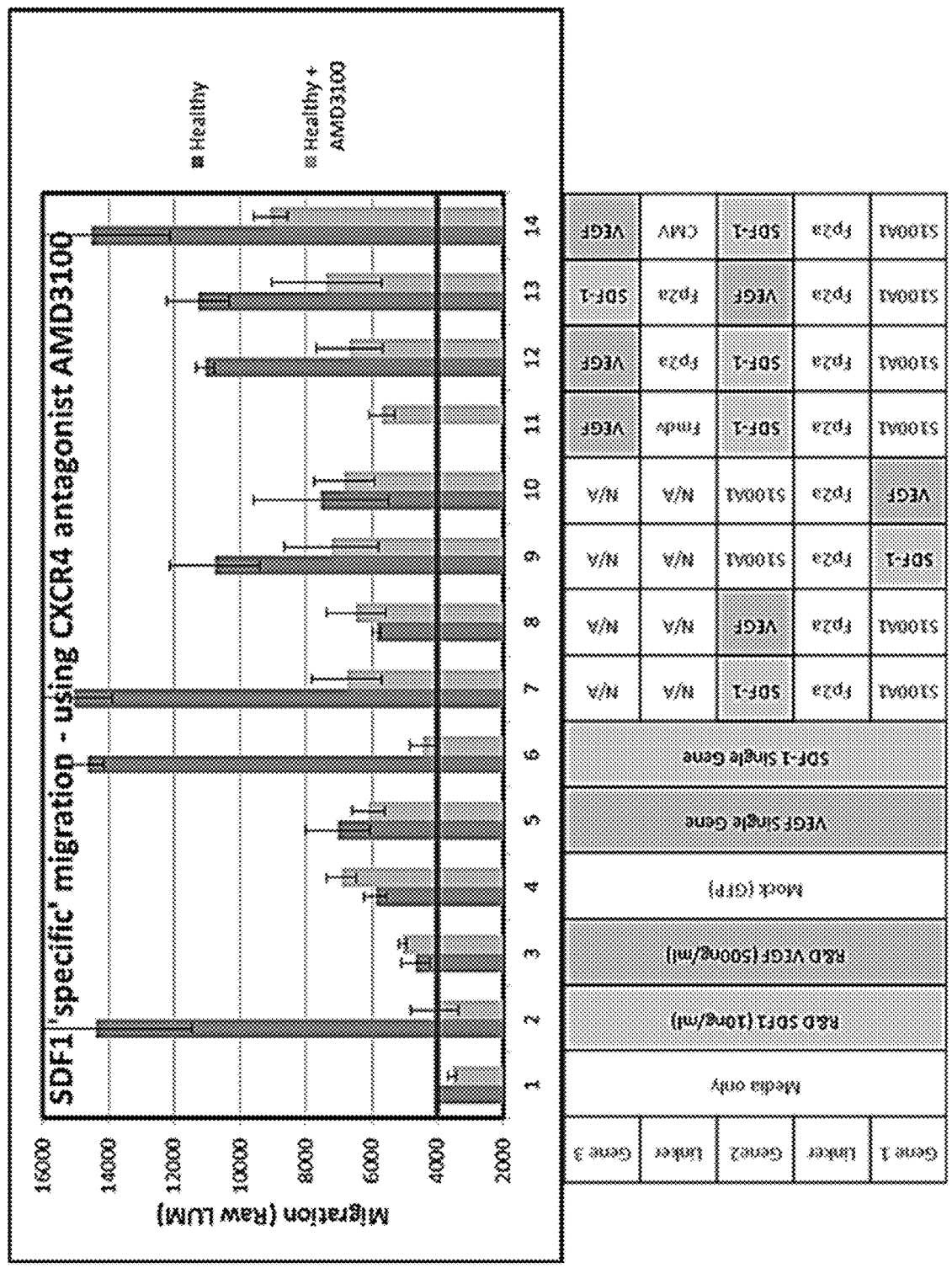
FIG. 8 shows a migration assay where AMD3100 (CXCR4 antagonist) specifically inhibited SDF1-CXCR4 dependent migration. Data shows that SDF1 is functional in double gene and triple-gene constructs, as migration is reduced in presence of AMD3100.

Validation of SDF1 specific migration using AMD3100 (CXCR4 antagonist) was successful. AMD3100 showed complete inhibition of SDF1-CXCR4 dependent migration (sample #2, 6). SDF1 expressed in iPSC-CMs is functional in our double gene and triple-gene constructs, as migration is reduced in presence of AMD3100 (sample #7, 12, 13). FIG. 7 and FIG. 8 show experimental data. A similar experiment performed with VEGF expressing vector constructs shows similar results, FIG. 6. Thus, these results successfully demonstrate that SDF-1α is functional (i.e., biologically active) when expressed as part of multi-genic linked constructs from dual-gene and triple-gene expression vectors when using linkers provided herein.

Example 5A

SDF-1α Function—Jurkat Migration Assay

Transfected Jurkat Cells Produce Functional SDF1 Protein that Supports Cellular Migration SDF-1α was examined for functionality by demonstrating CXCR4-mediated migration of two cell types: Jurkat cells and peripheral blood lymphocytes (PBLs). For Jurkat cell migration, cells in serum-free media were seeded onto the top of transwell inserts. The lower chambers were filled with conditioned media from patients (dilated, hypertrophic) or healthy iPSC-derived cardiomyocytes transfected with pXoX or single effector controls. The number of cells that migrated through the trans-well insert into the lower chamber containing the conditioned media after two hours was quantitated using a luminescence assay.

Figure 10:
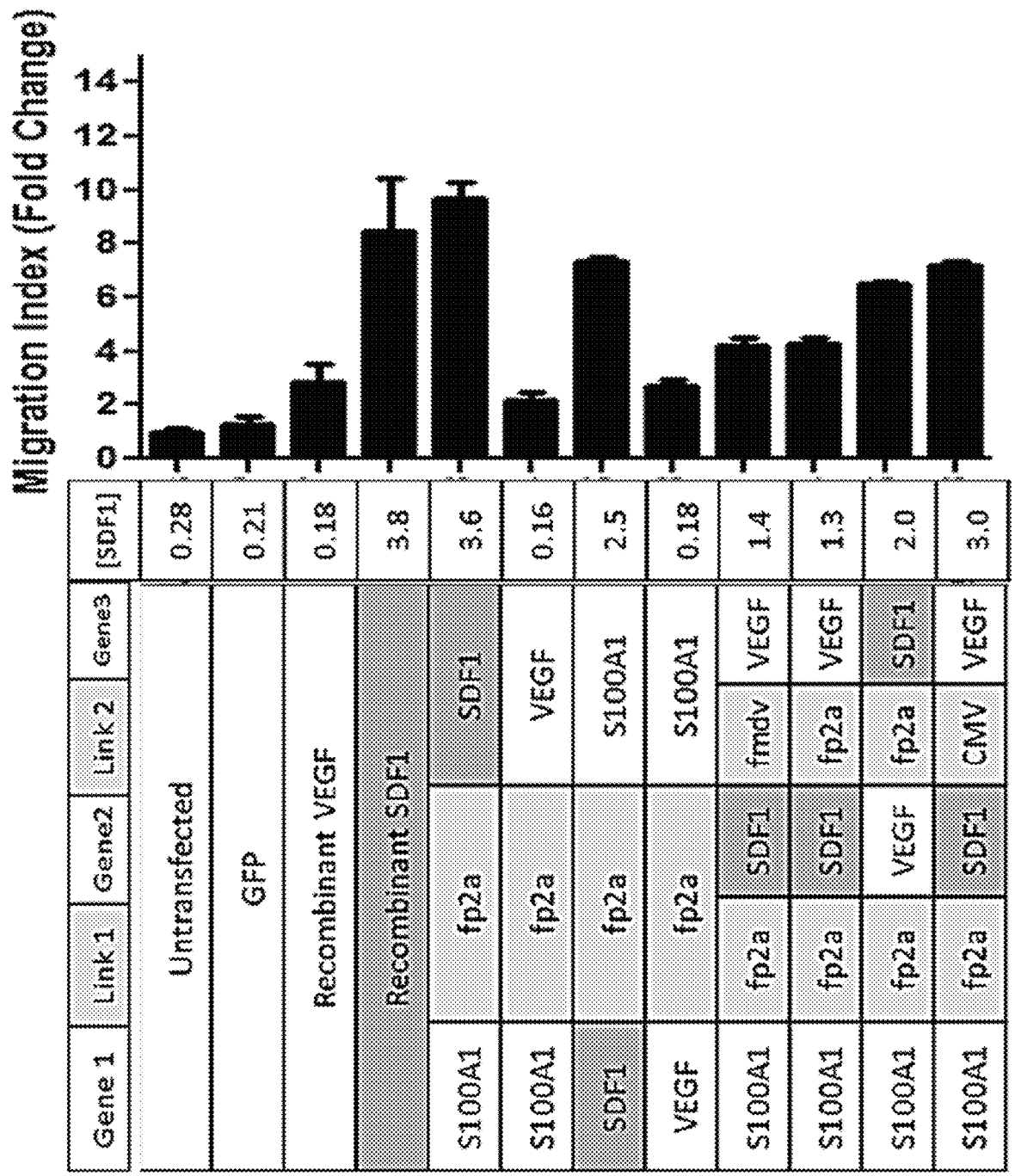
FIG. 10 shows a migration assay in which cardiomyocytes were transfected with double gene and triple-gene constructs expressing SDF1. Jurkat cell migration using supernatant from the iPSC CMs shows that the transfected and SDF1 protein is functional and produces significant migration, demonstrating successful expression and activity of functional polypeptides encoded by polynucleotides described herein, comprising linkers disclosed herein.
Figure 11:
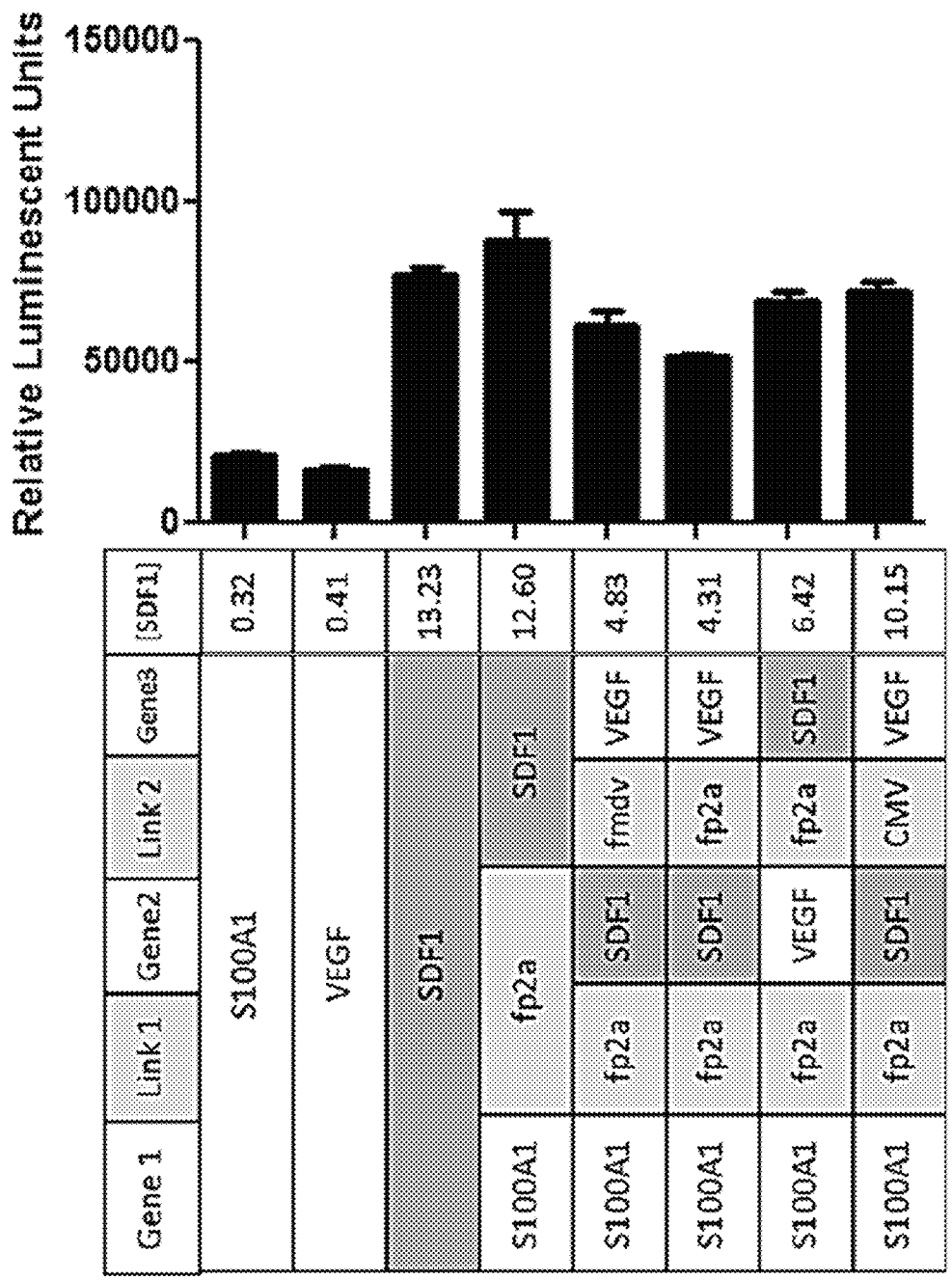
FIG. 11 shows a migration assay in which cardiomyocytes were transfected with double gene and triple-gene constructs expressing SDF1. Jurkat cell migration using supernatant from the iPSC CMs shows that the transfection and SDF1 protein is functional and produces significant migration. Data shows a dose dependent migration of Jurkat cells, demonstrating successful expression and activity of functional polypeptides encoded by polynucleotides described herein, comprising linkers disclosed herein.

Jurkat cells were transfected with singe gene, double gene, and triple-gene gene constructs encoding for SDF1. Jurkat control cells and Jurkat exposed to AMD3100 (CXCR4 antagonist) were measured for migration efficiency 2 hours after the drug was added. FIG. 8 and FIG. 10 show experimental data. A similar experiment performed on Jurkat cells cultured with supernatant from transfected human iPSC with double gene and triple-gene vectors encoding for SDF1 show similar results, FIG. 11.

Results

Jurkat migration towards recombinant SDF1 is CXCR4-dependent. Thus, these results successfully demonstrate that SDF-1α is functional (i.e., biologically active) when expressed as part of multi-genic linked constructs from dual-gene and triple-gene expression vectors when using linkers provided herein.

Example 5B

Figure 12:
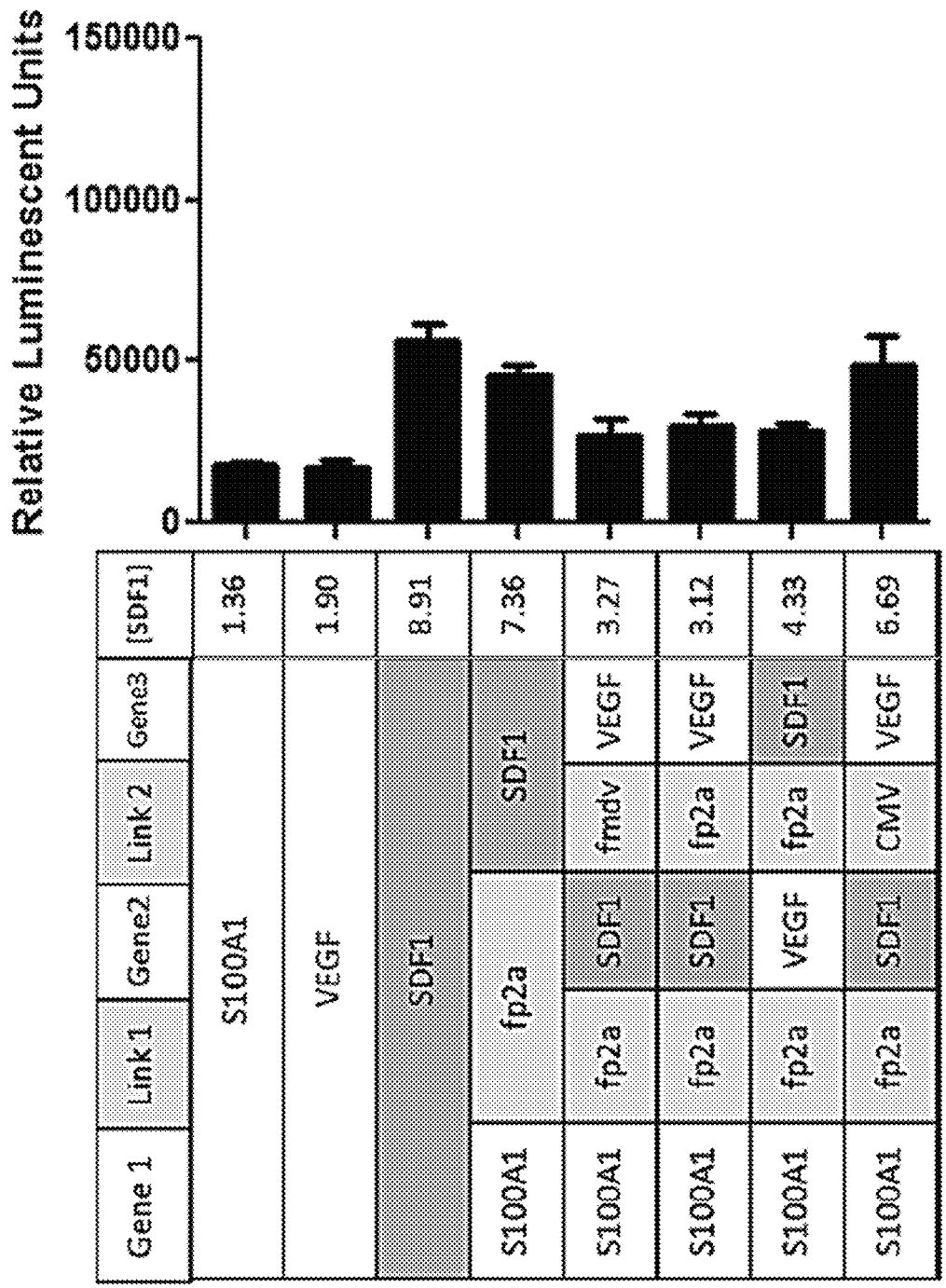
FIG. 12 shows cardiomyocytes from a dilated cardiomyopathy subject were transfected with double gene and triple-gene constructs encoding for SDF1. Data show SDF1 dependent Jurkat cell migration. SDF1 expressed by double gene and triple-gene vector constructs in Dilated Cardiomyopathy iPSC-CMs is functional.
Figure 13:
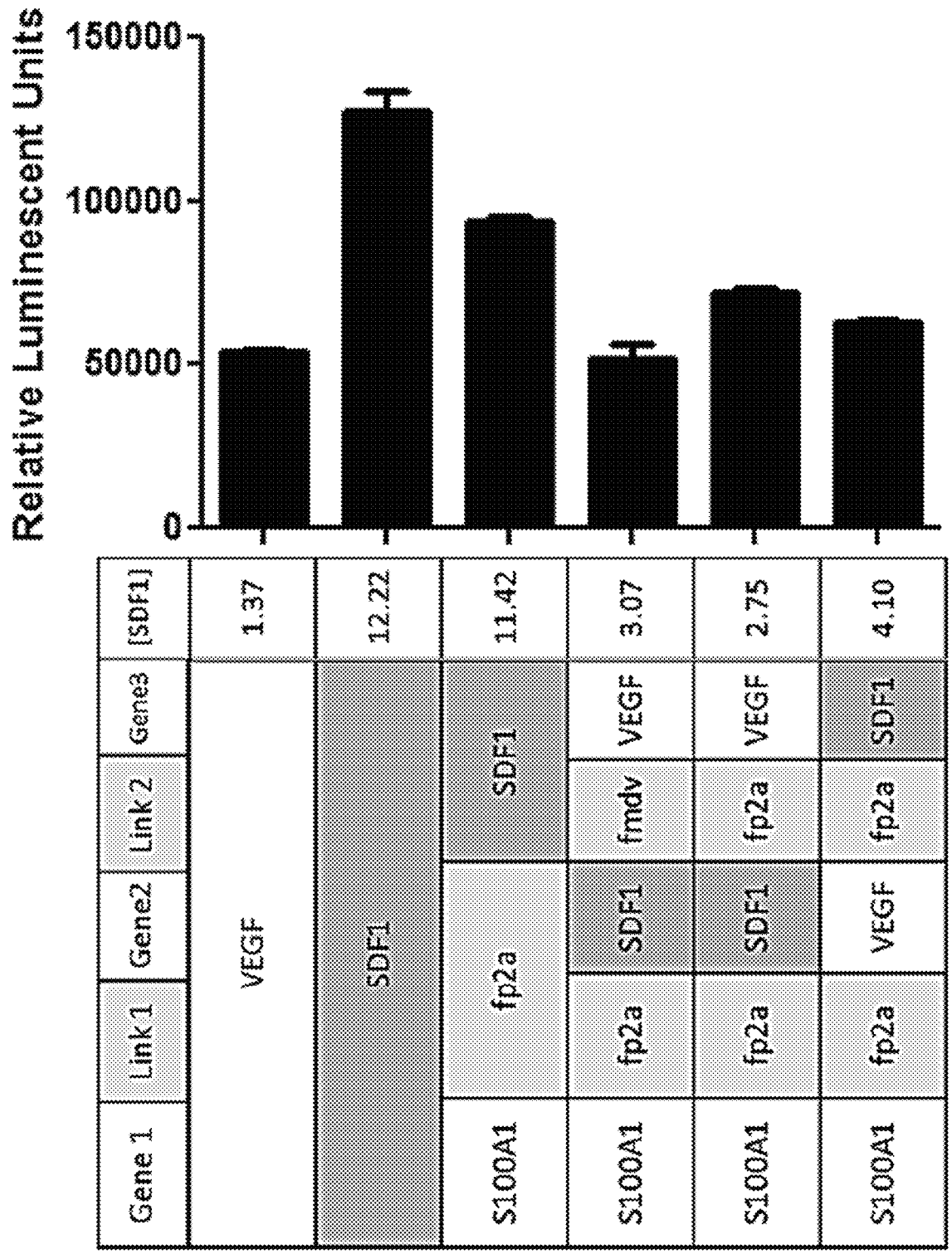
FIG. 13 shows cardiomyocytes from a hypertrophic cardiomyopathy subject were transfected with double gene and triple-gene constructs encoding for SDF1. Data show SDF1 dependent Jurkat cell migration. SDF1 expressed by double gene and triple-gene vector constructs in hypertrophic cardiomyopathy iPSC-CMs is functional.

Transfected Cardiomyocytes from Cardiomyopathy Patients Produce Functional SDF1 Protein that Supports Cellular Migration Cardiomyocyte-iPSC cells (iPSC-CM) were obtained from patients with dilated cardiomyopathy (DCM), hypertrophy cardiomyopathy (HCM) or healthy controls. iPSC cells were transfected with singe gene, dual-gene (double-gene), or triple-gene vectors encoding for S100A1 and VEGF connected by a linker described herein; S100A1, SDF1, and VEGF connected by a linker described herein; or VEGF alone. 48 hours post transfection cellular supernatant was collected. Jurkat cells were seeded on 6-well plates at a density of approximately 1:10, 1:100, and 1:1000 in the supernatant collected from the transfected iPSC cells. 96 hours following introduction of the supernatant, Jurkat cell migration was measured, FIG. 12 shows experimental data in a dilated cardiomyopathy model. FIG. 13 shows experimental data in a hypertrophy cardiomyopathy model.

Results iPSC-CM transfected with singe gene, dual-gene, or triple-gene vector constructs showed 4-10-fold increase in HUVEC proliferation in both cases.

Example 6

ELISA

Transfected 293T Cells Produce Quantifiable Protein Levels 293T cells were transfected via Fugene 6 (Promega) with Xogenex single-gene, dual-gene (double-gene), triple (triple-gene) gene constructs and the appropriate control constructs. Cell supernatant and lysate were harvested at desired time point(s). 293T cells were transfected with vector constructs encoding for S100A, SDF1, VEGF191, or various combinations thereof connected by a linker described herein, utilizing vectors differing in the presence or absence of Kozak sequences, linkers (Furin-AP-F2A, GSG-P2A, Furin-APVKQGSG-P2A) (SEQ ID NO: 119), or none, as summarized in FIGS. 15-17. Concentrations of protein produced were measured by ELISA.

Figure 15A:
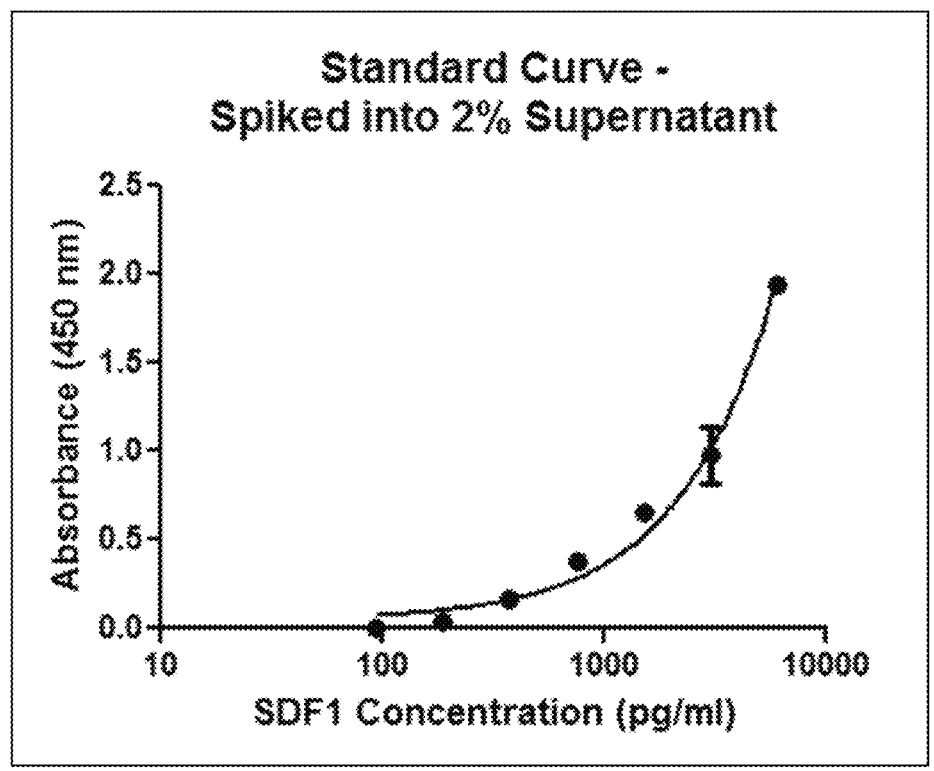
FIG. 15A and FIG. 15B depict SDF1 protein expression in 293 T cells transfected with a double gene vector encoding for S100A1-SDF1.
Figure 15B:
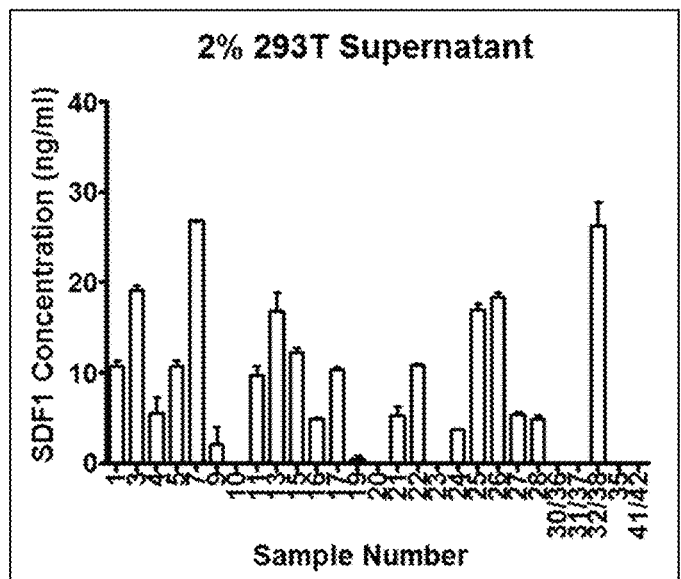
Figure 16A:
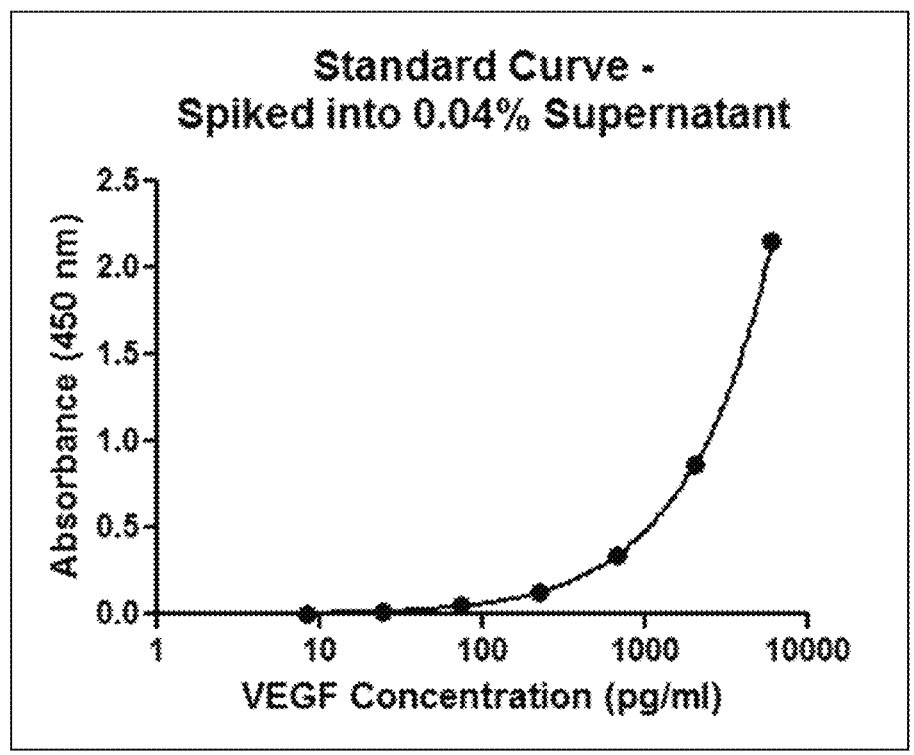
FIG. 16A and FIG. 16B depict VEGF protein expression in 293 T cells transfected with a double gene vector encoding for S100A1-VEGF191.
Figure 16B:
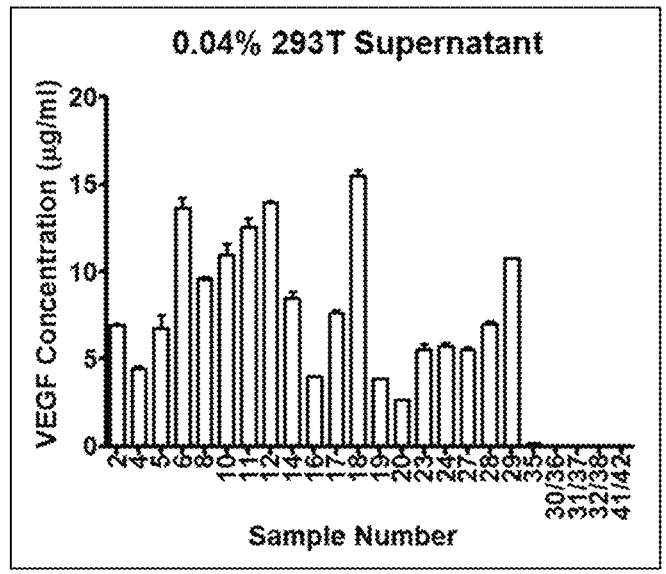
Figure 17A:
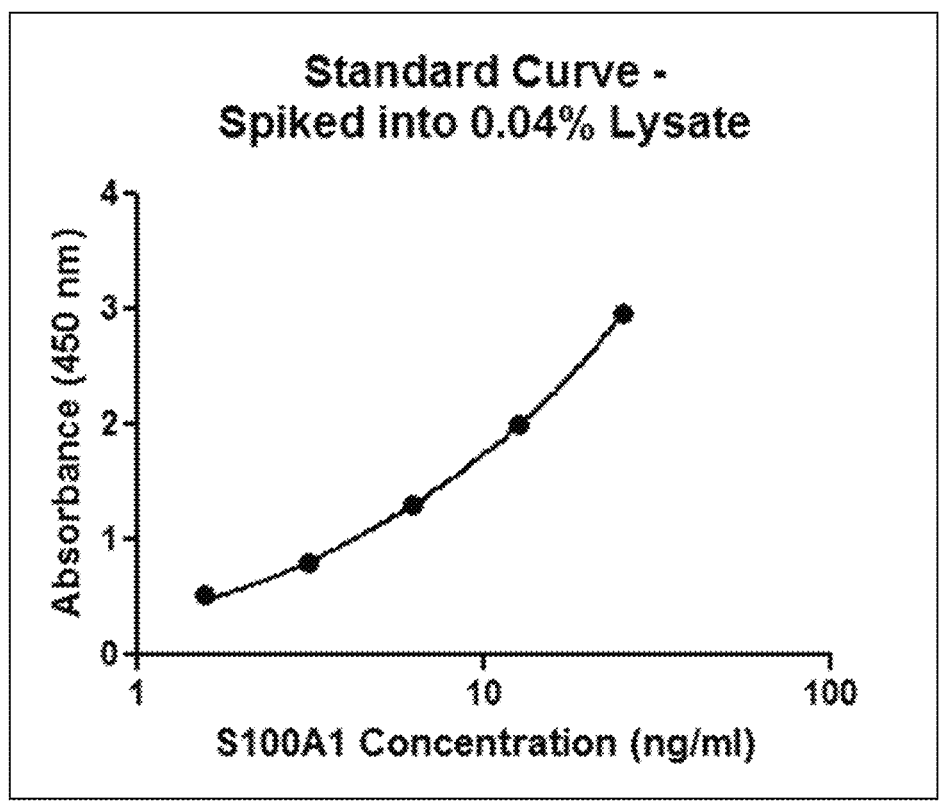
FIG. 17A and FIG. 17B depict S100A1 protein expression in 293 T cells transfected with a double gene vector encoding for S100A1-SDF1.
Figure 17B:
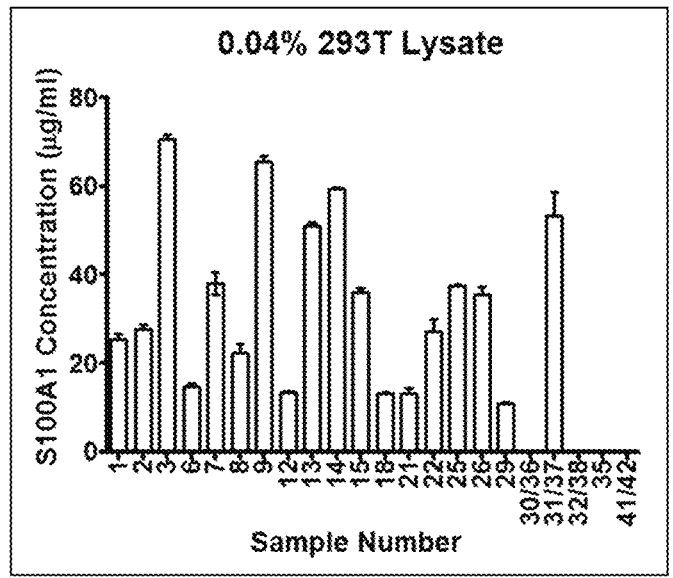

Results 293T cells transfected with double gene vectors encoding for S100A, SDF1, VEGF191, or various combinations thereof produce measurable levels of protein. FIG. 15A and FIG. 15B show levels of SDF1 protein. FIG. 16A and FIG. 16B show levels of VEGF protein. FIG. 17A and FIG. 17B show levels of S100A1 protein.

Example 7

Triple-Gene Expression Constructs

A matrix (variety) of dual-gene (double-gene), triple-gene, and quadruple-gene (four-gene) constructs were designed as shown below in Table 5.

TABLE 5

Matrix of multi-gene plasmid construct designs

| # | 5' Promoter | Gene-1 | Linker | Gene-2 | Optional 2$^{nd}$ Linker, Promoter, or Intervening Sequence | 3Optional Gene-3 |
|---|---|---|---|---|---|---|
| 1 | CAG | S100A1 | fp2a | SDF1α | fmdv | VEGF191 |
| 2 | CAG | S100A1 | fp2a | SDF1α | p2a | VEGF191 |
| 3 | CAG | S100A1 | fp2a | VEGF191 | p2a | SDF1α |
| 4 | CAG | S100A1 | fp2a | SDF1α | fp2a | VEGF191 |
| 5 | CAG | S100A1 | fp2a | VEGF191 | fp2a | SDF1α |
| 6 | CAG | S100A1 | fp2a | SDF1α | IRES | VEGF191 |
| 7 | CAG | S100A1 | fp2a | VEGF191 | IRES | SDF1α |
| 8 | CAG | S100A1 | fp2a | SDF1α | CMV | VEGF191 |
| 9 | CAG | S100A1 | fp2a | VEGF191 | CMV | SDF1α |
| 10 | CAG | S100A1 | fp2a | SDF1α | CMV | S100A1 |
| 11 | CAG | S100A1 | fp2a | VEGF191 | CMV | S100A1 |

| *Linked to 3' end of above: | Optional 3$^{rd}$ Linker | Optional Gene-4 |
|---|---|---|
| #10 | fp2a | VEGF191 |
| #11 | fp2a | SDF1α |

*Optional 3$^{rd}$ Linker and Gene-4 to increase S100A1 valency (i.e., increase production of S100A1 dimers)

Polypeptide expression and cleavage efficiency was tested in model cell types (i.e., 293T cells, SV40-transformed cardiomyocytes, and iPSC-derived cardiomyocytes from each of healthy donors, donors (patients) having dilated cardiomyopathy and hypertrophic cardiomyopathy. A summary of expression results, cleavage efficiency results, and expression considerations for various linker (i e linkinu effluence) combinations is shown below in Table 6.

TABLE 6

Polypeptide Cleavage/Linker/Gene of Interest (GOI) Expression Differentials

| Linker Composition | GOI Polypeptide Expression Levels (ELISA Assay) | GOI Polypeptide/ Linker Cleavage (Western Blot/ Immunoblot Assay) | Consider Biological Aspects of: | Overall Performance Ranking |
|---|---|---|---|---|
| f2pa-fp2a | High | Complete cleavage all 3 GOIs | Presence of 2A C-terminal tail | #1 |

TABLE 6-continued

Polypeptide Cleavage/Linker/Gene of Interest (GOI) Expression Differentials

| Linker Composition | GOI Polypeptide Expression Levels (ELISA Assay) | GOI Polypeptide/ Linker Cleavage (Western Blot/ Immunoblot Assay) | Consider Biological Aspects of: | Overall Performance Ranking |
|---|---|---|---|---|
| f2pa-fmdv | High | Complete cleavage all 3 GOIs | Presence of 2A C-terminal tail | #2 |
| f2pa-CMV | High | Complete cleavage all 3 GOIs | Differing stoichiometric expression ratios of GOIs and promoter silencing | #3 |
| f2pa-CMV-fp2a | High | Complete cleavage all 3 GOIs | Differing stoichiometric expression ratios of GOIs and promoter silencing | #4 |
| f2pa-p2a | Very high | Poor cleavage between $2^{nd}$ and $3^{rd}$ GOIs | n/a | n/a |
| f2pa-IRES | Poor ($3^{rd}$ GOI; 3' of IRES) | n/a | n/a | n/a |

Lead Construct Configurations:

(5')-CAG Promoter-S100A1-fp2a (linker)-SDF1α-fp2a (linker)-VEGF191 -(3')

(5')-CAG Promoter-S100A1-fp2a (linker)-VEGF191-fp2a (linker)-SDF1α-(3')

ELISA Assay—Expression of S100A1 from Triple-Gene Constructs

Figure 18:
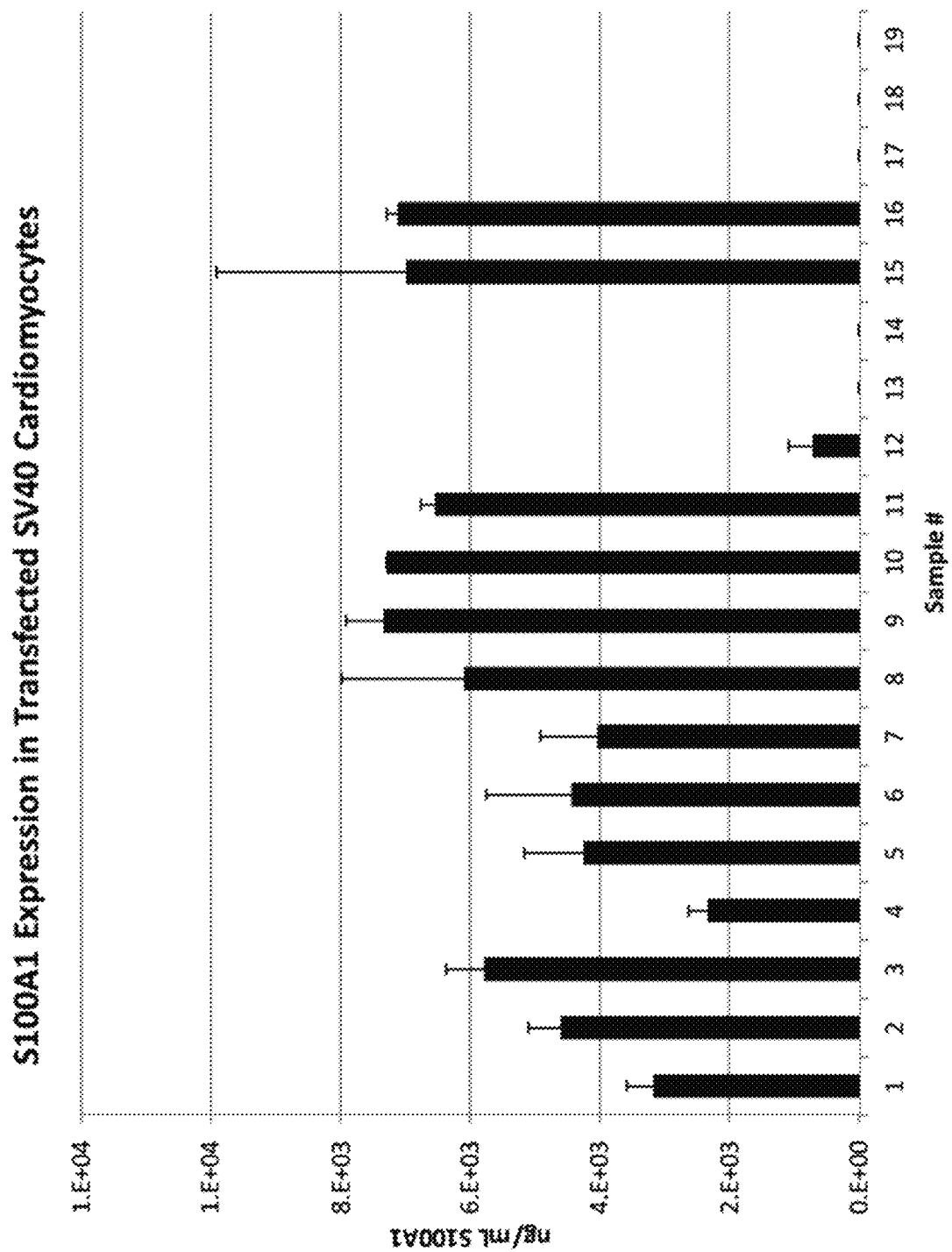
FIG. 18 shows a bar graph of S100A1 concentrations as produced by cardiomyocytes transfected with single-gene, double-gene and triple-gene constructs.

ELISA assays were performed to quantify expression of S100A1 from triple-gene pXoX constructs in comparison to single-gene pXoX controls and previously identified lead candidate, dual-gene constructs. SV40 transformed cardiomyocytes were transfected with each of the test plasmid constructs and cell supernatants and lysates were harvested at desired time point(s). The cardiomyocytes were transfected with vector constructs encoding for S100A, SDF1α, VEGF191, or various combinations thereof connected by linker sequences described herein and indicated below in Table 7 as respective first, second, and third linker sequences (e.g., fp2a, fmdv, p2a, IRES, CMV, or no linking sequence). Concentrations of protein produced were measured by ELISA. See, FIG. 18; sample numbers correspond to sample numbers shown in Table 7 below.

Configuration of constructs and S100A1 expression results are shown in Table 7 (below).

TABLE 7

S100A1 Polypeptide Expression From Triple-Gene Compared To Other Constructs.

| Sample | Name | Linker | GOI | S100A1 ng/mL |
|---|---|---|---|---|
| 1 | Triple 1 | fp2a-fmdv | S100A1-SDF1-VEGF | 3176 |
| 2 | Triple 2 | fp2a-p2a | S100A1-SDF1-VEGF | 4616 |
| 3 | Triple 3 | fp2a-p2a | S100A1-VEGF-SDF1 | 5792 |
| 4 | triple 4 | fp2a-fp2a | S100A1-SDF1-VEGF | 2335 |
| 5 | Triple 5 | fp2a-fp2a | S100A1-VEGF-SDF1 | 4258 |
| 6 | Triple 6 | fp2a-IRES | S100A1-SDF1-VEGF | 4440 |
| 7 | Triple 7 | fp2a-IRES | S100A1-VEGF-SDF1 | 4042 |
| 8 | Triple 8 | fp2a-CMV | S100A1-SDF1-VEGF | 6096 |
| 9 | Triple 9 | fp2a-CMV | S100A1-VEGF-SDF1 | 7342 |
| 10 | Triple 10 | fp2a-CMV-fp2a | S100A1-SDF1-S100A1-VEGF | 7290 |
| 11 | Triple 11 | fp2a-CMV-fp2a | S100A1-VEFG-S100A1-SDF1 | 6541 |
| 12 | Single Gene Control | N/A | S100A1 | 724 |
| 13 | Single Gene Control | N/A | SDF1 | 0 |
| 14 | Single Gene Control | N/A | VEGF | 0 |
| 15 | Dual Lead #13 | fp2a | S100A1-SDF1 | 6988 |
| 16 | Dual Lead #14 | fp2a | S100A1-VEGF | 7121 |
| 17* | Dual Lead #15 | fp2a | SDF1-S100A1 | 0 |
| 18 | GFP | N/A | GFP | 0 |
| 19 | Untransfected | N/A | N/A | 0 |

ELISA Assay—Expression of SDF1α from Triple-Gene Constructs

Figure 19:
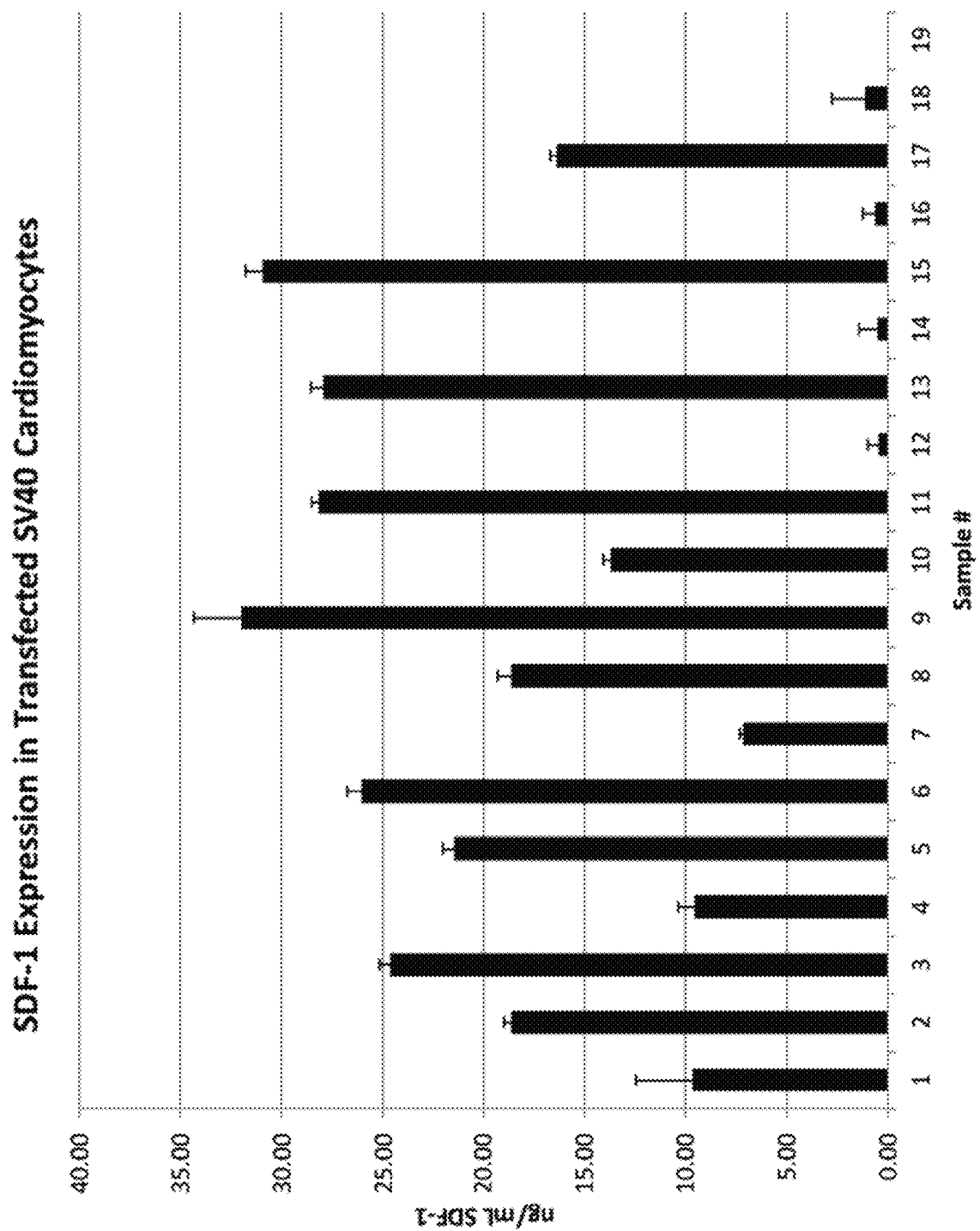
FIG. 19 shows a bar graph of SDF-1α concentrations as produced by cardiomyocytes transfected with single-gene, double-gene and triple-gene constructs.

ELISA assays were performed to quantify expression of SDF1α☐from triple-gene pXoX constructs in comparison to single-gene pXoX controls and previously identified lead candidate, dual-gene constructs. SV40 transformed cardiomyocytes were transfected with each of the test plasmid constructs and cell supernatants and lysates were harvested at desired time point(s). The cardiomyocytes were transfected with vector constructs encoding for S100A, SDF1α, VEGF191, or various combinations thereof connected by linker sequences described herein and indicated below in Table 8 as respective first, second, and third linker sequences (e.g., fp2a, fmdv, p2a, IRES, CMV, or no linking sequence). Concentrations of protein produced were measured by ELISA. See, FIG. 19; sample numbers correspond to sample numbers shown in Table 8 below.

TABLE 8

SDF1α Polypeptide Expression From Triple-Gene Compared To Other Constructs.

| Sample | Name | Linker | GOI | SDF1α ng/mL |
|---|---|---|---|---|
| 1 | Triple 1 | fp2a-fmdv | S100A1-SDF1-VEGF | 9.66 |
| 2 | Triple 2 | fp2a-p2a | S100A1-SDF1-VEGF | 18.63 |
| 3 | Triple 3 | fp2a-p2a | S100A1-VEGF-SDF1 | 24.65 |
| 4 | Triple 4 | fp2a-fp2a | S100A1-SDF1-VEGF | 9.55 |
| 5 | Triple 5 | fp2a-fp2a | S100A1-VEGF-SDF1 | 21.45 |
| 6 | Triple 6 | fp2a-IRES | S100A1-SDF1-VEGF | 26.07 |

TABLE 8-continued

SDF1α Polypeptide Expression From Triple-Gene Compared To Other Constructs.

| Sample | Name | Linker | GOI | SDF1α ng/mL |
|---|---|---|---|---|
| 7 | Triple 7 | fp2a-IRES | S100A1-VEGF-SDF1 | 7.16 |
| 8 | Triple 8 | fp2a-CMV | S100A1-SDF1-VEGF | 18.64 |
| 9 | Triple 9 | fp2a-CMV | S100A1-VEGF-SDF1 | 31.99 |
| 10 | Triple 10 | fp2a-CMV-fp2a | S100A1-SDF1-S100A1-VEGF | 13.73 |
| 11 | Triple 11 | fp2a-CMV-fp2a | S100A1-VEFG-S100A1-SDF1 | 28.17 |
| 12 | Single Gene Control | N/A | S100A1 | 0.46 |
| 13 | Single Gene Control | N/A | SDF1 | 27.95 |
| 14 | Single Gene Control | N/A | VEGF | 0.51 |
| 15 | Dual Lead #13 | fp2a | S100A1-SDF1 | 30.94 |
| 16 | Dual Lead #14 | fp2a | S100A1-VEGF | 0.64 |
| 17 | Dual Lead #15 | fp2a | SDF1-S100A1 | 16.40 |
| 18 | GFP Control | N/A | GFP | 1.12 |
| 19 | Untransfected | N/A | N/A | 0 |

ELISA Assay—Expression of VEGF191 from Triple-Gene Constructs

ELISA assays were performed to quantify expression of VEGF191 from triple-gene pXoX constructs in comparison to single-gene pXoX controls and previously identified lead candidate, dual-gene constructs. SV40 transformed cardiomyocytes were transfected with each of the test plasmid constructs and cell supernatants and lysates were harvested at desired time point(s). The cardiomyocytes were transfected with vector constructs encoding for S100A, SDF1α, VEGF191, or various combinations thereof connected by linker sequences described herein and indicated below in Table 9 as respective first, second, and third linker sequences (e.g., fp2a, fmdv, p2a, IRES, CMV, or no linking sequence). Concentrations of protein produced were measured by ELISA. See, FIG. 20; sample numbers correspond to sample numbers shown in Table 9 below.

TABLE 9

VEGF191 Polypeptide Expression From Triple-Gene Compared To Other Constructs.

| Sample | Name | Linker | GOI | VEGF191 ng/mL |
|---|---|---|---|---|
| 1 | Triple 1 | fp2a-fmdv | S100A1-SDF1-VEGF | 197.1 |
| 2 | Triple 2 | fp2a-p2a | S100A1-SDF1-VEGF | 281.9 |
| 3 | Triple 3 | fp2a-p2a | S100A1-VEGF-SDF1 | 169.6 |
| 4 | Triple 4 | fp2a-fp2a | S100A1-SDF1-VEGF | 73.1 |
| 5 | Triple 5 | fp2a-fp2a | S100A1-VEGF-SDF1 | 99.9 |
| 6 | Triple 6 | fp2a-IRES | S100A1-SDF1-VEGF | 24.0 |
| 7 | Triple 7 | fp2a-IRES | S100A1-VEGF-SDF1 | 111.2 |
| 8 | Triple 8 | fp2a-CMV | S100A1-SDF1-VEGF | 226.5 |
| 9 | Triple 9 | fp2a-CMV | S100A1-VEGF-SDF1 | 149.4 |
| 10 | Triple 10 | fp2a-CMV-fp2a | S100A1-SDF1-S100A1-VEGF | 231.0 |
| 11 | Triple 11 | fp2a-CMV-fp2a | S100A1-VEFG-S100A1-SDF1 | 239.6 |
| 12 | Single Gene Control | N/A | S100A1 | 1.5 |
| 13 | Single Gene Control | N/A | SDF1 | 1.7 |
| 14 | Single Gene Control | N/A | VEGF | 427.5 |
| 15 | Dual Lead #13 | fp2a | S100A1-SDF1 | 1.1 |
| 16 | Dual Lead #14 | fp2a | S100A1-VEGF | 265.3 |
| 17 | Dual Lead #15 | fp2a | SDF1-S100A1 | 1.4 |
| 18 | GFP Control | N/A | GFP | 1.1 |
| 19 | Untransfected | N/A | N/A | 5.5 |

Western Blot (Immunoblot) Assays Verify Efficient Cleavage of S100A1, SDF-1a and VEGF191 from Triple-gene Constructs Confirmation of the appropriate size and sequence of individual effector proteins within the relevant cell types was demonstrated by immunoblot and mass spectrometry analyses (as described further herein). Multiple pertinent cell lines were transfected with pXoX and either cell lysates (for S100A1) or conditioned media (for SDF-1α and VEGF165) were analyzed. Controls for immunoblot analyses were lysates/conditioned media from cells transfected with the appropriate single effector (pS100A1, pSDF-1α, pVEGF165) and the corresponding commercially available, purified, recombinant protein.

SDS-PAGE/immunoblot results were consistent across all tested cell lines (293T, SV40 immortalized cardiomyocytes, iPSC-derived cardiomyocytes from healthy individual, dilated cardiomyopathy patient, hypertrophy cardiomyopathy patient). Immunoblot data from SV40 immortalized cardiomyocytes is shown below in FIGS. 21-23 with arrows indicating the expected size of each of the indicated effector proteins.

For each GOI, immunoblot analysis was performed using standard procedures according to manufacturer's instructions. Detection reagent conditions were as follows:

S100A1 detection—Anti-S100A1 antibody (R&D Systems, Inc.) diluted 1:200, incubated with blot overnight at 4 degrees C.; anti-sheep HRP (horse radish peroxidase) antibody (KPL Inc., Gaithersburg, Md., USA) diluted 1:20,000, incubated with blot at room temperature (RT) 30 minutes; signal detection via LUMIGLO® Ultra (KPL Inc.);

SDF-1α detection—Anti-SDF-1α antibody (R&D Systems, Inc.) diluted 1:2000, incubated with blot overnight at 4 degrees C.; anti-goat HRP (Jackson ImmunoResearch Laboratories, Inc., West Grov, Pa., USA) antibody diluted 1:20,000, incubated with blot at room temperature (RT) 30 minutes; signal detection via LUMIGLO® Ultra (KPL Inc.).

VEGF detection—Anti-VEGF antibody (Abcam, Plc., Cambridge, Mass.) diluted 1:2000, incubated with blot overnight at 4 degrees C.; anti-rabbit HRP (Jackson ImmunoResearch Laboratories, Inc.) antibody diluted 1:20,000, incubated with blot at room temperature (RT) 30 minutes; signal detection via LUMIGLO® Ultra (KPL Inc.).

Figure 21:
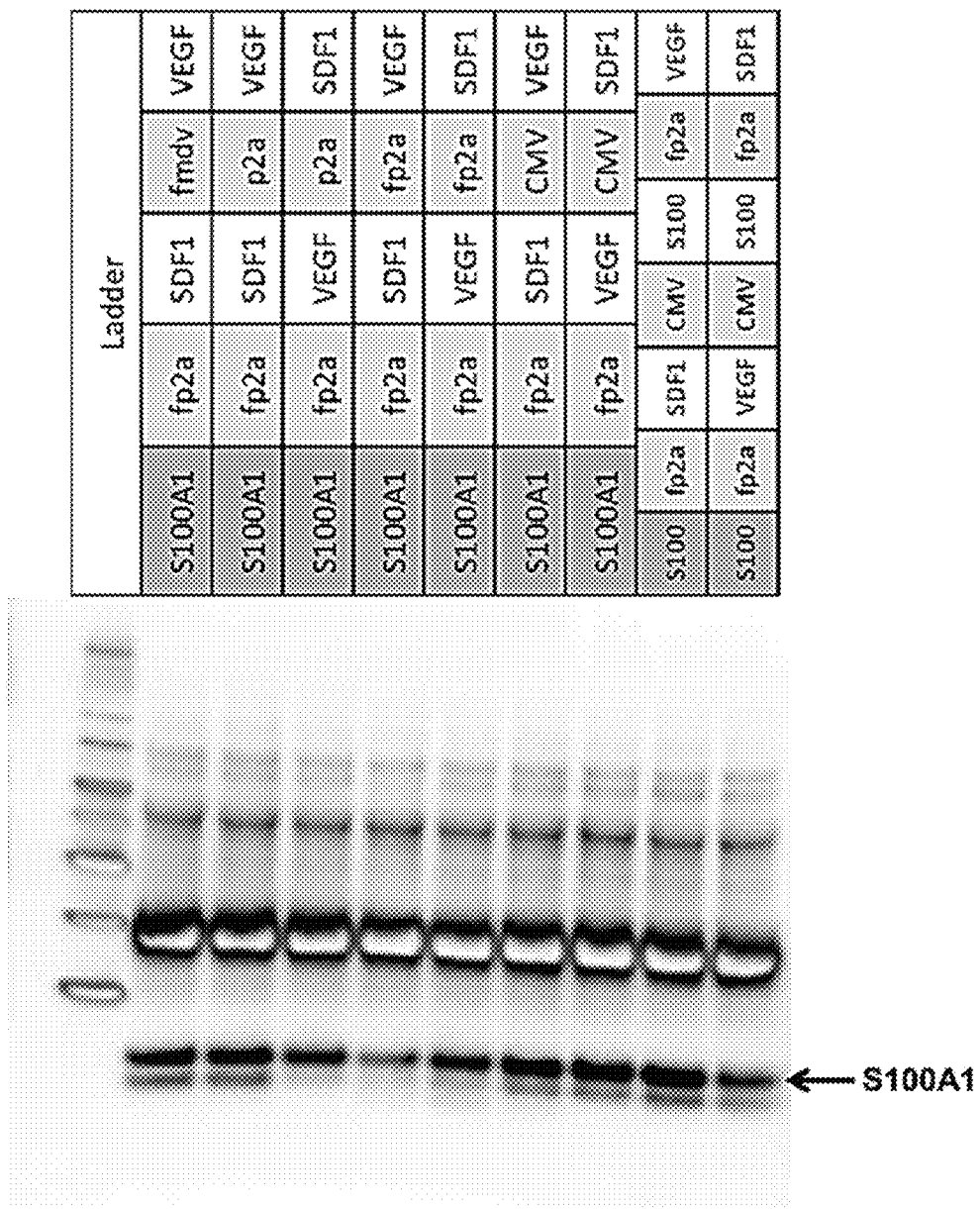
FIG. 21 shows Western blot (immunoblot) detection of S100A1 polypeptide cleavage as produced by cardiomyocytes transfected with single-gene, double-gene and triple-gene constructs.
Figure 22:
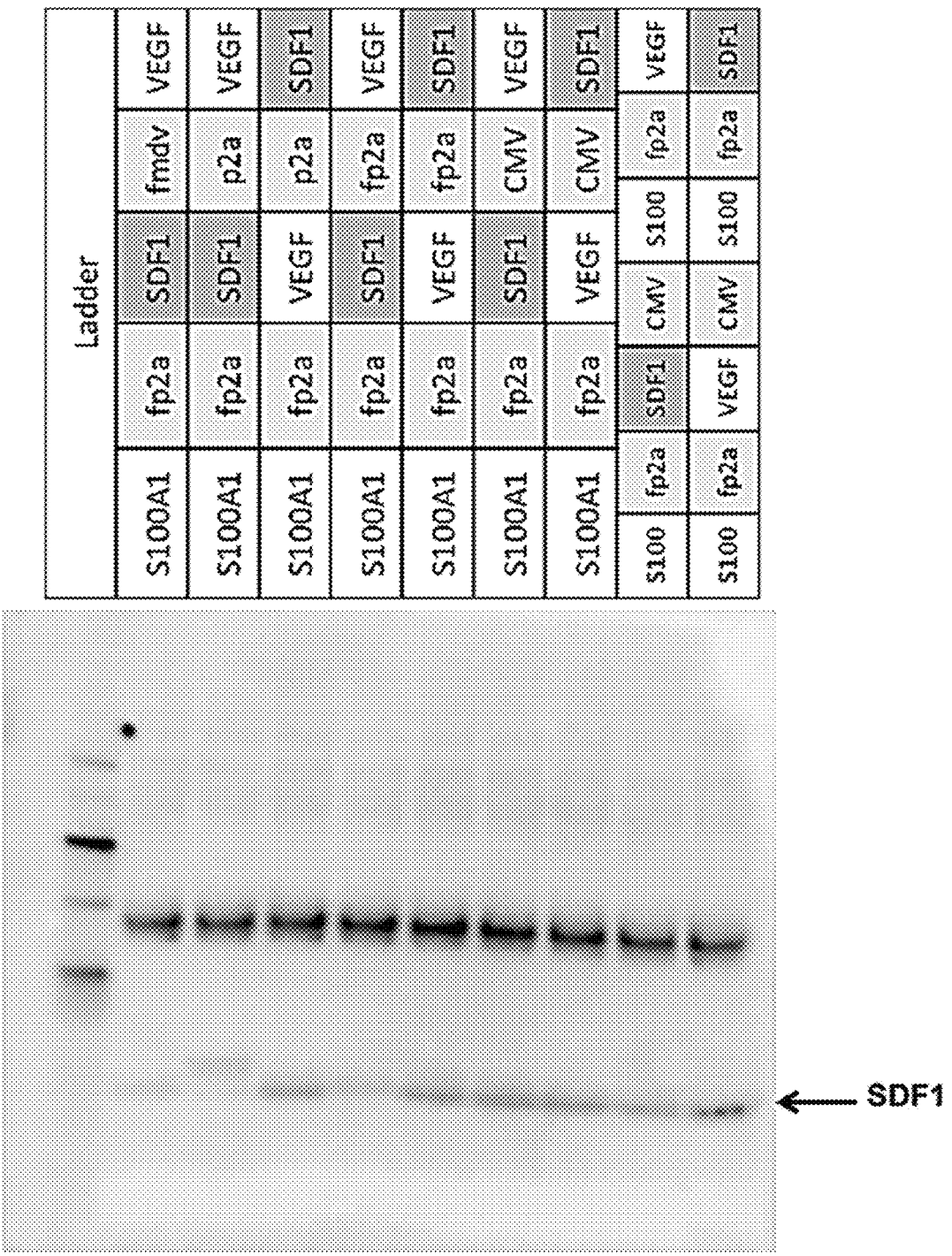
FIG. 22 shows Western blot (immunoblot) detection of SDF-1α polypeptide cleavage as produced by cardiomyocytes transfected with single-gene, double-gene and triple-gene constructs.
Figure 23:
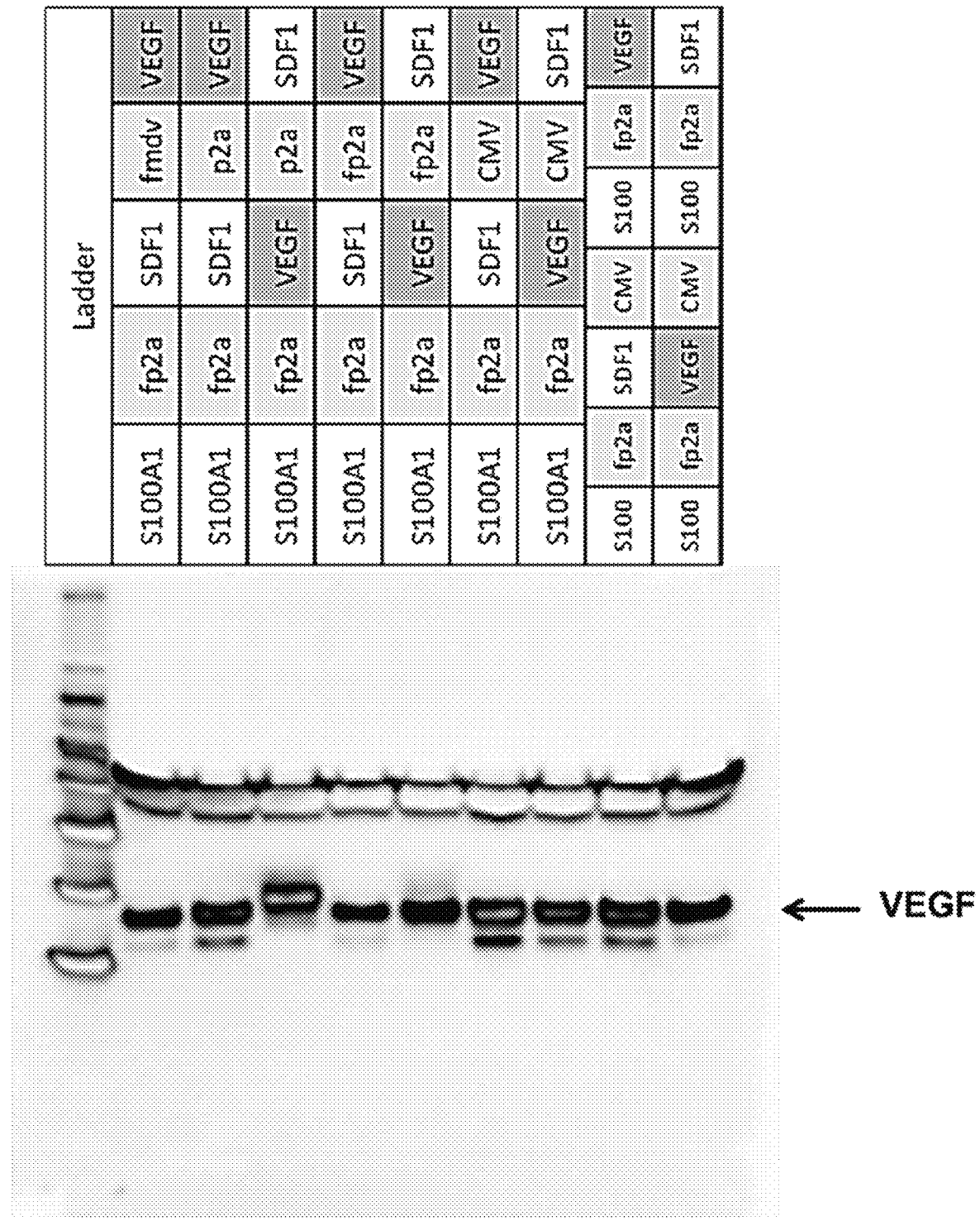
FIG. 23 shows Western blot (immunoblot) detection of VEGF polypeptide cleavage as produced by cardiomyocytes transfected with single-gene, double-gene and triple-gene constructs.

Example immunoblots are shown in FIGS. 21, 22 and 23.

TABLE 10

Samples from cells expressing the various constructs are shown in lanes 1-9 (lane "L" showing a polypeptide molecular weight control ladder (220, 120, 100, 80, 60, 50, 40, 30, 20, 14, 6, and 3 kDa markers)).

| Lane | GOI | Linker | GOI | Linker | GOI | Linker | GOI |
|---|---|---|---|---|---|---|---|
| L | Ladder - Molecular Weight Marker | | | | | | |
| 1 | S100A1 | fp2a | SDF1α | fmdv | VEGF191 | | |
| 2 | S100A1 | fp2a | SDF1α | p2a | VEGF191 | | |
| 3 | S100A1 | fp2a | VEGF191 | p2a | SDF1α | | |
| 4 | S100A1 | fp2a | SDF1α | fp2a | VEGF191 | | |
| 5 | S100A1 | fp2a | VEGF191 | fp2a | SDF1α | | |
| 6 | S100A1 | fp2a | SDF1α | CMV | VEGF191 | | |
| 7 | S100A1 | fp2a | VEGF191 | CMV | SDF1α | | |
| 8 | S100A1 | fp2a | SDF1α | CMV | S100A1 | fp2a | VEGF191 |
| 9 | S100A1 | fp2a | VEGF191 | CMV | S100A1 | fp2a | SDF1α |

Results indicate that each of the three GOIs are cleaved efficiently as expressed from triple-gene constructs.

Mass Spectometry Assay—Multi-gene Expression Products were Evaluated by Mass Spectrometry.

Cleavage products of lead candidates were verified using mass spectrometry. Trypsin, chymotrypsin and elastase digestion was performed using standard procedures. Each gel digest was further analyzed by nano LC/MS/MS* with a Waters NanoAcquity HPLC system (Waters Corp., Milford, Mass., USA) interfaced to a ThermoFisher Q Exactive HF (ThermoFisher Scientific, Waltham, Mass., USA). Data was processed using Mascot database. Mascot DAT files were parsed into the Scaffold software for validation, filtering and to create a nonredundant list per sample. Data were filtered using a minimum protein value of 90%, a minimum peptide value of 50% (Prophet scores) and requiring at least two unique peptides per protein. Consistent with the above described Western blot (immunoblot) analysis, the mass spectrometry results further verified proteolytic cleavage of S100A1, SDF-1 and VEGF when expressed from lead dual-gene and triple-gene constructs; see, Table 11.

*LC/MS/MS indicates liquid chromatography (LC) with mass spectrometry (MS). MS/MS is a combination of two mass analyzers in one mass spectrometry instrument. The first MS filters for precursor ions followed by a fragmentation of the precursor ion with high energy and, for example, nitrogen gas. A second mass analyzer then filters for product ions generated by the fragmentation. Advantage of MS/MS is increased sensitivity.

TABLE 11

Summary of Polypeptide Cleavage Analyzed by Mass Spectrometry for Lead Candidate Constructs

| | Construct Configuration (Optional promoter type)-GOI#1-linker-GOI#2-linker-GOI#3 | S100A1 Cleavage | SDF Cleavage | VEGF Cleavage |
|---|---|---|---|---|
| Lead Dual #13 | (CAG)-S100A1-fp2a-SDF1 | Yes | Yes | n/a |
| Lead Dual #14 | (CAG)-S100A1-fp2a-VEGF | Yes | n/a | Yes |
| Triple #1 | (CAG)-S100A1-fp2a-SDF1-fmdv-VEGF | Yes | Yes | Yes |
| Triple #2 | (CAG)-S100A1-fp2a-SDF1-p2a-VEGF | Yes | Yes | Yes |
| Triple #3 | (CAG)-S100A1-fp2a-SDF1-CMV-VEGF | Yes | Yes | Yes |
| Triple #4 | (CAG)-S100A1-fp2a-SDF1-fp2a-VEGF | Yes | Yes | Yes |
| Triple #5 | (CAG)-S100A1-fp2a-VEGF-fp2a-SDF1 | Yes | Yes | Yes |

Mass spectrometry (MS) was also used to assess the presence or absence of linker amino acid residues at the end (C-terminus) of each GOI. MS was performed as indicated above. Results are shown below in Table 12.

TABLE 12

MS Analysis of C-terminal Linker Amino Acid Residues for Lead Candidate Constructs

| | Construct Configuration (Optional promoter type)-GOI#1-linker-GOI#2-linker-GOI#3 | Presence of Linker AA residues (C-termini)?* | | |
|---|---|---|---|---|
| | | S100A1 | SDF | VEGF |
| Dual Leads | (CAG)-S100A1-fp2a-SDF1 | Yes | no | n/a |
| | (CAG)-S100A1-fp2a-VEGF | Yes | n/a | no |
| Primary Triple Leads | (CAG)-S100A1-fp2a-SDF1-fp2a-VEGF | Yes | no | no |
| | (CAG)-S100A1-fp2a-VEGF-fp2a-SDF1 | Yes | no | Yes |
| Secondary Triple Leads | (CAG)-S100A1-fp2a-SDF1-fmdv-VEGF | Yes | no | no |
| | (CAG)-S100A1-fp2a-SDF1-CMV-VEGF | Yes | no | no |
| Tertiary Triple Leads | (CAG)-S100A1-CMV-SDF1-fp2a-VEGF | n/a | no | no |
| | (CAG)-S100A1-CMV-VEGF-fp2a-SDF1 | n/a | no | Yes |

*"Yes" indicates presence of > (greater than) 2 amino acid (AA) residues on C-terminal tail (which may be referred to herein as a "linker tail"); "No" indicates presence of < or = (less than or equal to) 2A on C-terminal tail.

Western Blot (Immunoblot) Analysis of S100A1 Polypeptide Dimerization

Figure 24:
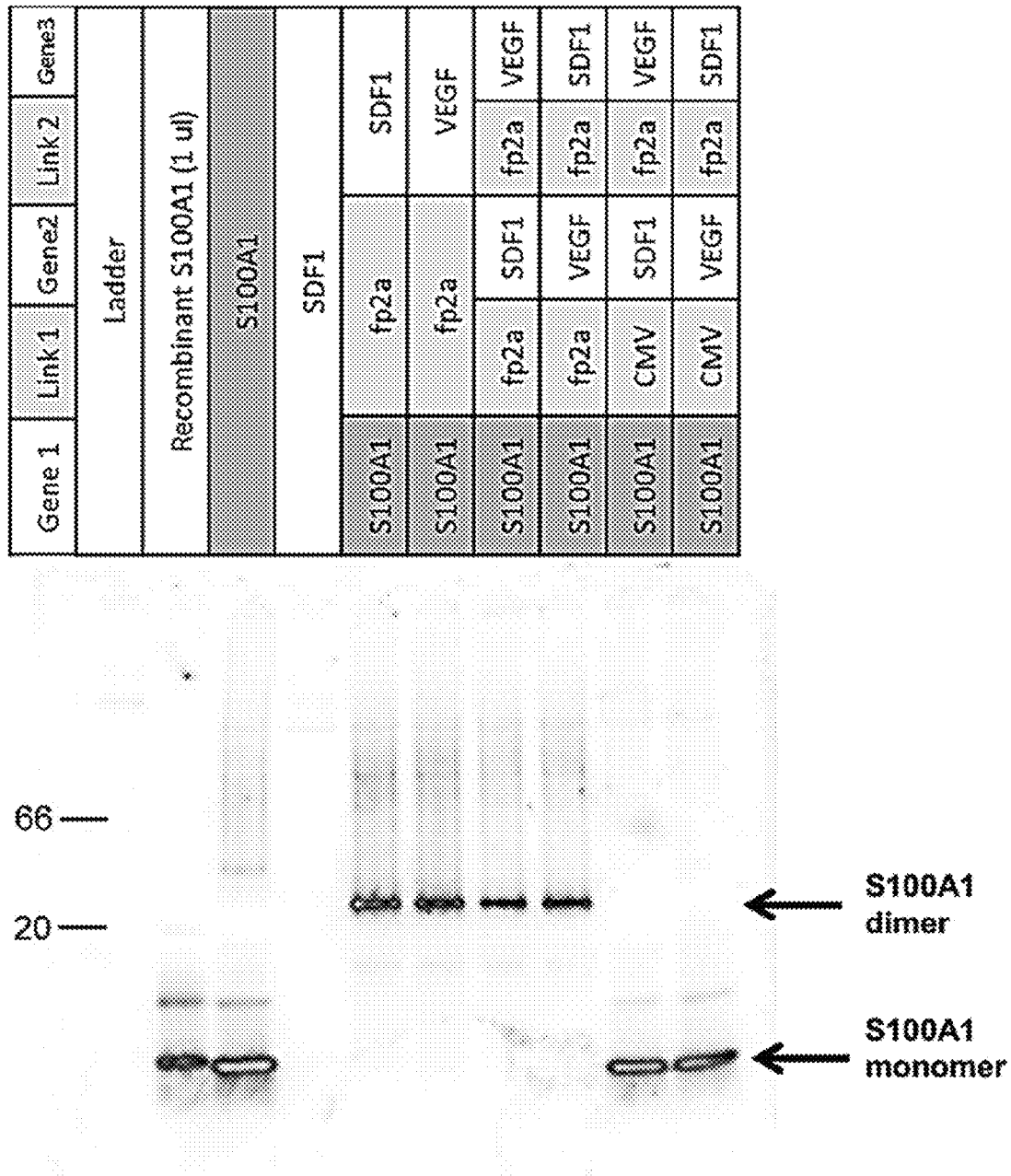
FIG. 24 shows formation of dimeric S100A1 expressed from triple-gene constructs, using linkers of the invention, as detected via non-denaturing PAGE and immunoblotting.
Figure 25A:
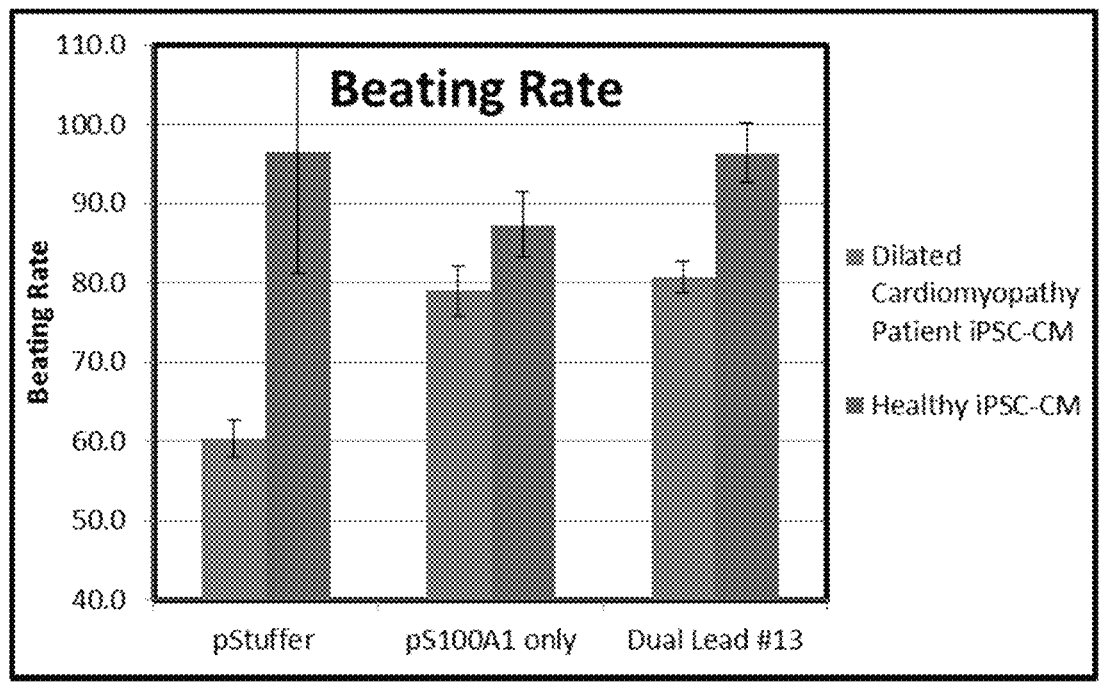
FIG. 25A and FIG. 25B show a comparison of iPSC cells from a dilated cardiomyopathy patients vs. a healthy control in terms of FIG. 25A. beat rate of iPSC cells transfected with pStuffer, a vector encoding for pS100A1, or a vector encoding for S100A1 comprising a 2A tail.
Figure 25B:
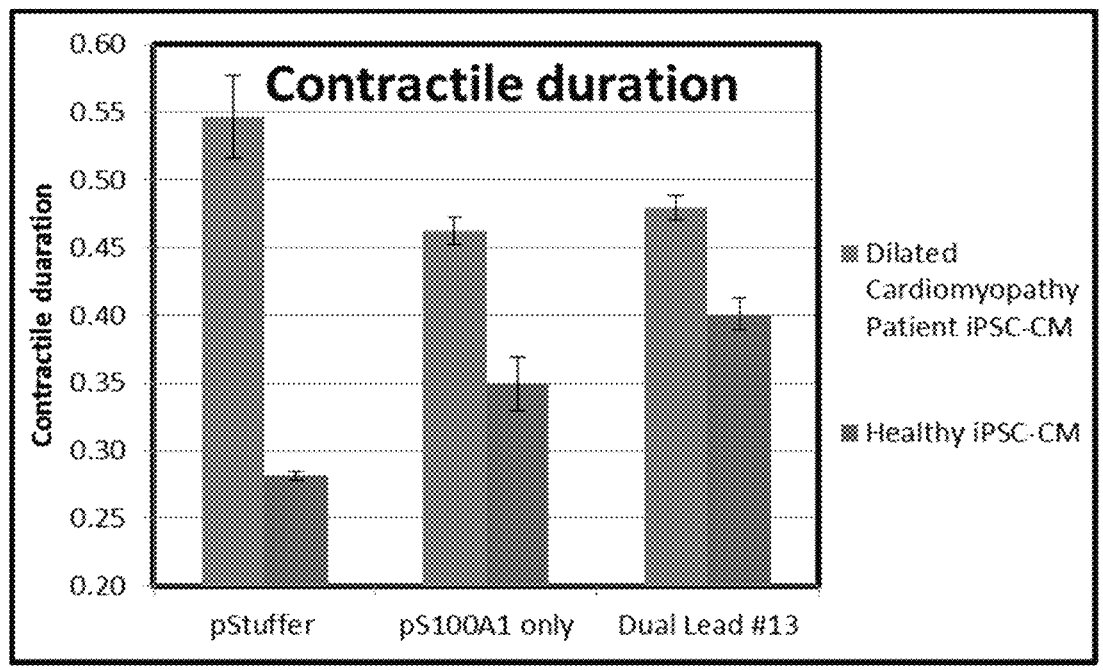
Figures 26A, 26B, 26C:
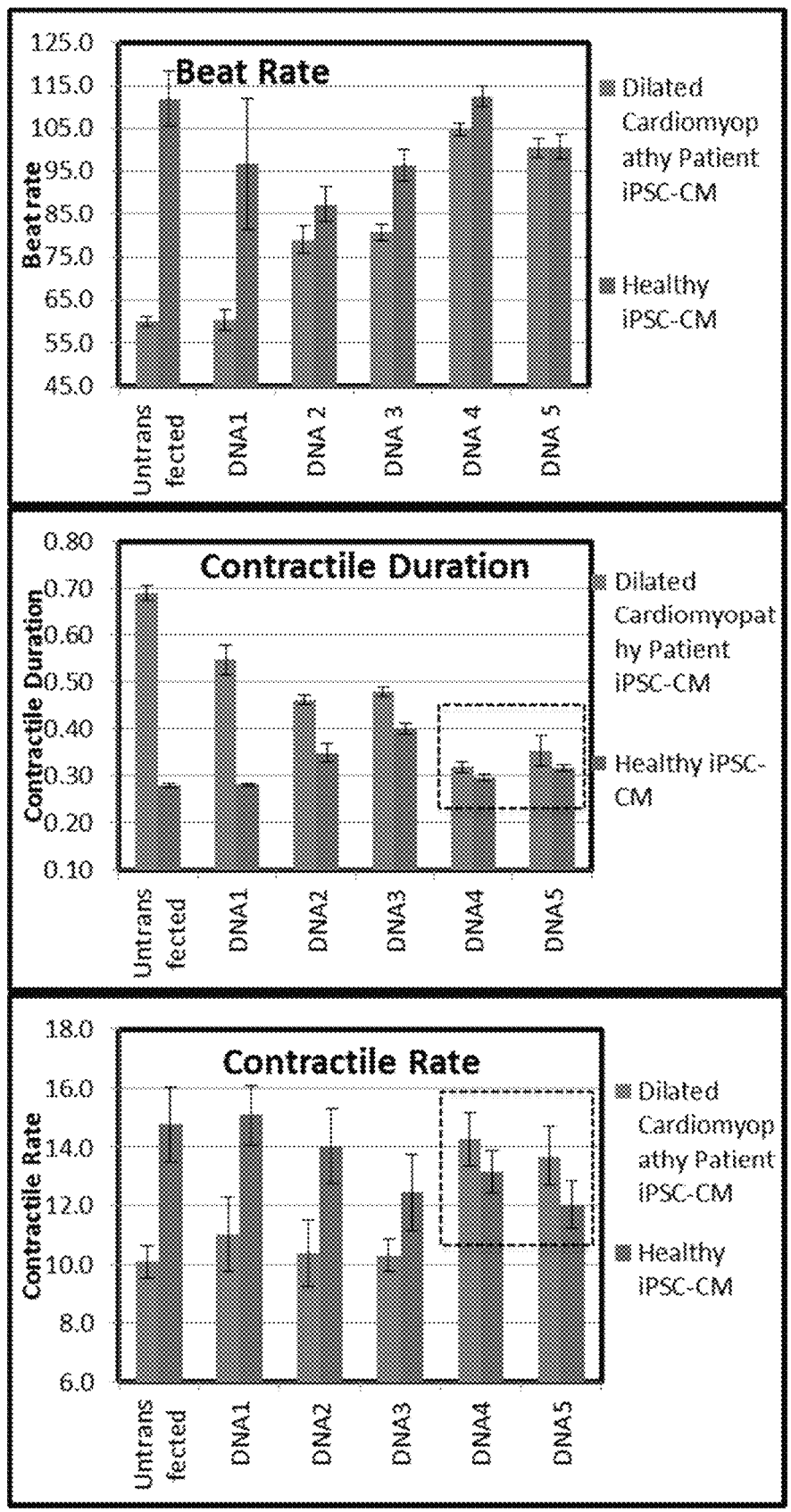
FIG. 26A, FIG. 26B, and FIG. 26C show a comparison of iPSC cells from a dilated cardiomyopathy patients vs. a healthy control in terms of FIG. 26A. beat rate of iPSC cells transfected with DNA1 (CAGStufferNXB-V2), DNA2 (CAG-S100A1 (no kozak), DNA3 (CAG-S100A1-fp2a-SDF1), DNA4 (CAG-S100A1-fp2a-SDF1-fp2a-VEGF), DNA 5(CAG-S100A1-CMV-SDF1-fp2a-VEGF191), or an untransfected control.

Non-denaturing PolyAcrylamide Gel Electrophoresis (PAGE) was performed to assess dimer formation of S100A1 polypeptides expressed from dual-gene and triple gene constructs. Conditioned media of transfected 293T cells was analyzed by native-PAGE/immunoblot for monomeric and dimeric levels of S100A1. Results demonstrate that the S100A1 cleaved from lead dual and lead triple candidates is predominantly in a dimeric form, whereas S100A1 expressed by the single effector construct pS100A1 and by triple-gene constructs having a CMV linker C-terminal to S100A1 is predominantly monomeric; see, FIG. 24.

Notably, a unique aspect of the present invention is provided and enabled by the specific sequential order of polypeptides encoded by constructs of the invention. Thus, in one aspect of the invention, specifically placing S100A1 protein first achieves and allows functional expression of biologically active S100A1 molecules because the remaining 2A tail on S100A1 was, surprisingly, discovered not to interfere with S100A1 biological activity. In contrast, it was discovered that placing S100A1 as the second gene resulted in incomplete cleavage of genes expressed via the construct.

Accordingly, analysis of pXoX expression using mass spectrometry, as indicated below in Table 13 showed that S100A1 was the only effector that did not exhibit furin cleavage resulting in removal of the C-terminal 2A peptide. Hence, there is no 2A C-terminal tail left on SDF1a or VEGF. Only S100A1 has a 2A linker-tail present. The exact ending amino acid sequence is PG. It cleaves between G and P of ending PGP sequence. Hence, the C-terminal linker tail on S100A1 as expressed from pXoX comprises the sequence (from N- to C-terminus) S101A1 polypeptide fused to-RAKRAPVKQGSGATNFSLLKQAGDVEENPG (SEQ ID NO: 123); which may be referred to herein as the "2A tail". For example, in one embodiment, from the initial methionine of S100A1 to the C-terminal end of the fp2a cleaved linker tail a first GOI of the invention comprises the sequence:

(SEQ ID NO: 124)
MGSELETAMETLINVFHAHSGKEGDKYKLSKKELKELLQTELSGFLDAQK

DVDAVDKVMKELDENGDGEVDFQEYVVLVAALTVACNNFFWENSRAKRAP

VKQGSGATNFSLLKQAGDVEENPG.

However, as provided via data presented herein, it has been demonstrated that this S100A1 tail is 'inert'—i.e. does not affect S100A1 function (biological activity).

TABLE 13

Mass Spectrometry Analyses of Proteins Expressed From pXoX

| Effectors in pXoX | Cellular location | Expected proteolytic cleavage | Absence of 2A Tail |
|---|---|---|---|
| S100A1 | Intracellular | Yes | No |
| SDF-1α | Secreted | Yes | Yes |
| VEGF165 | Secreted | Yes | Yes |

Example 8

Triple-Gene Vector Transfection 293T cells were plated at 750,000 cells per well in a 6 well plate and incubated overnight at plates to 37° C./5% CO$_2$ incubator overnight. The following day, the cells were transfected using FuGENE 6 (Promega) with single (singegene), dual (double-gene), triple (triple-gene), Table 14, gene constructs and the appropriate control constructs using plasmid vector at 100 ng/ml diluted in OptiMEM media (LifeTechnologies). After transfection, the cells were incubated. Cell supernatant and lysate were harvested at desired at 72 hours.

TABLE 14 pXoX Triple-Gene Vector Sequence

| SEQ ID No. | Construct | Sequence |
|---|---|---|
| 108 | pXoX | TAACTATAACGGTCCTAAGGTAGCGACGTACGAACCGTTGGGCGCGCCTGGGGA TAGCGATCGCTGCTGGCGCGGTCCGCTATGAGGTCTCTGATAGACCACAGACGC GTCGACATTGATTATTGACTAGTTATTAATAGTAATCAATTACGGGTCATTAG TTCATAGCCCATATATGGAGTTCCGCGTTACATAACTTACGGTAAATGGCCCGC CTGGCTGACCGCCCAACGACCCCCGCCCATTGACGTCAATAATGACGTATGTTC CCATAGTAACGCCAATAGGGACTTTCCATTGACGTCAATGGGTGGAGTATTTAC GGTAAACTGCCCACTTGGCAGTACATCAAGTGTATCATATGCCAAGTACGCCCC CTATTGACGTCAATGACGGTAAATGGCCCGCCTGGCATTATGCCCAGTACATGA CCTTATGGGACTTTCCTACTTGGCAGTACATCTACGTATTAGTCATCGCTATTA CCATGGTCGAGGTGAGCCCCACGTTCTGCTTCACTCTCCCCATCTCCCCCCCCT CCCCACCCCCAATTTTGTATTTATTTATTTTTTAATTATTTTGTGCAGCGATGG GGGCGGGGGGGGGGGGGGCGCGCGCCAGGCGGGGCGGGGCGGGGCGAGGGGC GGGGCGGGGCGAGGCGGAGAGGTGCGGCGGCAGCCAATCAGAGCGGCGCGCTCC GAAAGTTTCCTTTTATGGCGAGGCGGCGGCGGCGGCGGCCCTATAAAAAGCGAA GCGCGCGGCGGGCGGGAGTCGCTGCGCGCTGCCTTCGCCCCGTGCCCCGCTCCG CCGCCGCCTCGCGCCGCCCGCCCCGGCTCTGACTGACCGCGTTACTCCCACAGG TGAGCGGGCGGGACGGCCCTTCTCCTCCGGGCTGTAATTAGCGCTTGGTTTAAT GACGGCTTGTTTCTTTTCTGTGGCTGCGTGAAAGCCTTGAGGGGCTCCGGGAGG GCCCTTTGTGCGGGGGGAGCGGCTCGGGGGGTGCGTGCGTGTGTGTGCGTGG GGAGCGCCGCGTGCGGCTCCGCGCTGCCCGGCGGCTGTGAGCGCTGCGGGCGCG GCGCGGGGCTTTGTGCGCTCCGCAGTGTGCGCGAGGGGAGCGCGGCCGGGGGCG GTGCCCCGCGGTGCGGGGGGGGCTGCGAGGGGAACAAAGGCTGCGTGCGGGGTG TGTGCGTGGGGGGGTGAGCAGGGGGTGTGGGCGCGTCGGTCGGGCTGCAACCCC CCCTGCACCCCCCTCCCCGAGTTGCTGAGCACGGCCCGGCTTCGGGTGCGGGGC TCCGTACGGGGCGTGGCGCGGGGCTCGCCGTGCCGGGCGGGGGGTGGCGGCAGG TGGGGGTGCCGGGCGGGGCGGGGGCCGCCTCGGGCCGGGGAGGGCTCGGGGGAGG GGCGCGGCGGCCCCCGGAGCGCCGGCGGCTGTCGAGGCGCGGCGAGCCGCAGCC ATTGCCTTTTATGGTAATCGTGCGAGAGGGCGCAGGGACTTCCTTTGTCCCAAA TCTGTGCGGAGCCGAAATCTGGGAGGCGCCGCCGCACCCCCTCTAGCGGGCGCG GGGCGAAGCGGTGCGGCGCCGGCAGGAAGGAAATGGGCGGGGAGGGCCTTCGTG CGTCGCCGCGCCGCCGTCCCCTTCTCCCTCTCCAGCCTCGGGGCTGTCCGCGGG GGGACGGCTGCCTTCGGGGGGGACGGGGCAGGGCGGGGTTCGGCTTCTGGCGTG |

TABLE 14-continued pXoX Triple-Gene Vector Sequence

| SEQ ID No. | Construct | Sequence |
|---|---|---|
| | | TGACCGGCGGCTCTAGAGCCTCTGCTAACCATGTTCATGCCTTCTTCTTTTTCC |
| | | TACAGCTCCTGGGCAACGTGCTGGTTATTGTGCTGTCTCATCATTTTGGCAAAG |
| | | AATTCCCTGCAGGAAATTGAGCCCGCAGCCTCCCGCTTCGCTCTCTGCTCCTCC |
| | | TGTTCGACAGTCAGCCGCATCTTCTTTTGCGTCGCCAGCCGAGCCACATCGCTC |
| | | AGACACCGCTAGCATGGGCAGCGAACTGGAAACCGCCATGGAGACTTTGATAAA |
| | | TGTTTTCCACGCGCATAGCGGCAAAGAAGGGGACAAGTACAAGCTGTCAAAAAA |
| | | GGAGCTGAAAGAACTGCTGCAGACCGAATTGAGCGGCTTCCTGGACGCTCAGAA |
| | | AGATGTCGATGCCGTCGACAAAGTGATGAAAGAGCTTGACGAGAACGGTGACGG |
| | | TGAAGTCGATTTTCAGGAATATGTGGTGCTGGTGGCCGCCCTTACTGTAGCATG |
| | | CAACAATTTCTTTTGGGAAAATTCACGTGCAAAGCGTGCACCGGTGAAACAGGG |
| | | AAGCGGAGCTACTAACTTCAGCCTGCTGAAGCAGGCTGGAGACGTGGAGGAGAA |
| | | CCCTGGACCTATGAATGCCAAGGTCGTTGTGGTGCTTGTACTTGTGCTGACTGC |
| | | TCTGTGTCTGAGCGACGGAAAACCAGTCTCCCTCAGCTACAGGTGCCCATGCCG |
| | | ATTCTTCGAATCTCATGTGGCCCGGGCCAATGTGAAGCACTTGAAAATCCTGAA |
| | | TACACCCAACTGCGCGTTGCAGATCGTGGCCCGCCTGAAAAATAATAATAGGCA |
| | | GGTATGTATAGATCCAAAGCTTAAGTGGATCCAGGAGTATCTGGAAAAGGCTCT |
| | | CAATAAACGTGCAAAGCGTGCACCGGTGAAACAGGGAAGCGGAGCTACTAACTT |
| | | CAGCCTGCTGAAGCAGGCTGGAGACGTGGAGGAGAACCCTGGACCTATGAATTT |
| | | TCTGCTCTCTTGGGTGCACTGGTCACTGGCACTGCTGCTGTATCTGCACCATGC |
| | | AAAATGGTCCCAAGCAGCTCCCATGGCAGAGGGAGGTGGACAGAATCATCATGA |
| | | GGTTGTCAAATTTATGGATGTCTACCAGCGGAGCTACTGCCACCCAATTGAGAC |
| | | GTTGGTAGACATTTTTCAGGAATATCCAGACGAGATTGAGTACATTTTCAAGCC |
| | | TAGCTGTGTGCCCTTGATGCGATGCGGTGGCTGTTGCAATGATGAGGGACTCGA |
| | | GTGTGTCCCCACCGAGGAAAGCAATATAACCATGCAAATCATGCGAATCAAACC |
| | | CCACCAGGGCCAGCATATCGGCGAGATGTCTTTCTTGCAACATAACAAATGCGA |
| | | GTGTCGGCCAAAGAAGGACAGGGCTCGCCAGGAAAATCCCTGTGGTCCTTGTTC |
| | | AGAGCGCAGGAAGCATCTTTTCGTCCAGGATCCGCAGACTTGTAAATGTTCATG |
| | | CAAGAATACCGATTCTAGGTGTAAGGCGAGGCAACTCGAGCTTAACGAGAGAAC |
| | | CTGTAGGTGTGACAAACCTAGAAGATAAATCGATTACGCTCCTCTACTCTTTGA |
| | | GACATCACTGGCCTATAATAAATGGGTTAATTTATGTAACAAAATTGCCTTGGC |
| | | TTGTTAACTTTATTAGACATTCTGATGTTTGCATTGTGTAAATACTGTTGTATT |
| | | GGAAAAGCGTGCCAAGATGGATTATTGTAATTCAGTGTCTTTTTTAGTAGCGTC |
| | | ACGTGCCAAACACTGTTAGTCACAGAGGGCATGAGACAGCCTGTGCTGGAACAG |
| | | CTCAGTTCATAGGGCTATGGAGATGGGGAGAAAGGGGCGCTTCTGTCAGAGACA |
| | | AGCTGTGGTCTGGGAAGGCCTTAGCACTAAAAGCACCACAATGAGAAGCAACCG |
| | | CCAGAAGCAGGGCCCGCAGGCCTTTGTTCCAGCTGCAAAGAGAAAGGAAAAAGT |
| | | GGGGAATAAGAGTTGGGGCTGCGGAGGGGGTGGGGAGCATTGTGCAGGTTCCGT |
| | | ACTTGAACAGAAAGCAGGGACCAACACAAGGAAGGCTCGAGCTGGCGGAATAGG |
| | | TTCCAATCTGTCGCGGCCGCATTACCCTGTTATCCCTAATCTCGTTTAACTATG |
| | | ACTCTCTTAAGGTAGCCAAATTCCGGAACTATAAATTGCGTTGCGCTCACTGCC |
| | | CGCTTTCCAGTCGGGAAACCTGTCGTGCCAGCTGCATAAATGAATCGGCCAACG |
| | | CGCGGGGAGAGGCGGTTTGCGTATTGGGCGCGCTTCCGCTTCCTCGCTCACTGA |
| | | CTCGCTGCGCTCGGTCGTTCGGCTGCGGCGAGCGGTATCAGCTCACTCAAAGGC |
| | | GGTAATACGGTTATCCACAGAATCAGGGGATAACGCAGGAAAGAACATGTGAGC |
| | | AAAAGGCCAGCAAAAGGCCAGGAACCGTAAAAAGGCCGCGTTGCTGGCGTTTTT |
| | | CCATAGGCTCCGCCCCCCTGACGAGCATCACAAAAATCGACGCTCAAGTCAGAG |
| | | GTGGCGAAACCCGACAGGACTATAAAGATACCAGGCGTTTCCCCCTGGAAGCTC |
| | | CCTCGTGCGCTCTCCTGTTCCGACCCTGCCGCTTACCGGATACCTGTCCGCCTT |
| | | TCTCCCTTCGGGAAGCGTGGCGCTTTCTCATAGCTCACGCTGTAGGTATCTCAG |
| | | TTCGGTGTAGGTCGTTCGCTCCAAGCTGGGCTGTGTGCACGAACCCCCCGTTCA |
| | | GCCCGACCGCTGCGCCTTATCCGGTAACTATCGTCTTGAGTCCAACCCGGTAAG |
| | | ACACGACTTATCGCCACTGGCAGCAGCCACTGGTAACAGGATTAGCAGAGCGAG |
| | | GTATGTAGGCGGTGCTACAGAGTTCTTGAAGTGGTGGCCTAACTACGGCTACAC |
| | | TAGAAGAACAGTATTTGGTATCTGCGCTCTGCTGAAGCCAGTTACCTTCGGAAA |
| | | AAGAGTTGGTAGCTCTTGATCCGGCAAACAAACCACCGCTGGTAGCGGTGGTTT |
| | | TTTTGTTTGCAAGCAGCAGATTACGCGCAGAAAAAAAGGATCTCAAGAAGATCC |
| | | TTTGATCTTTTCTACGGGGTCTGACGCTCAGTGGAACGAAAACTCACGTTAAGG |
| | | GATTTTGGTCATGAGATTATCAAAAAGGATCTTCACCTAGATCCTTTTAAATTA |
| | | AAAATGAAGTTTTAAATCAATCTAAAGTATATATGAGTAAACTTGGTCTGACAT |
| | | GCGCATCTGACGCTCAGTGGAACGAAAACTCACGTTAAGGGATTTTGGTCATGC |
| | | CTCAGAAGAACTCGTCAAGAAGGCGATAGAAGGCGATGCGCTGCGAATCGGGAG |
| | | CGGCGATACCGTAAAGCACGAGGAAGCGGTCAGCCCATTCGCCGCCAAGCTCTT |
| | | CAGCAATATCACGGGTAGCCAACGCTATGTCCTGATAGCGGTCCGCCACACCCA |
| | | GCCGGCCACAGTCGATGAATCCAGAAAAGCGGCCATTTTCCACCATGATATTCG |
| | | GCAAGCAGGCATCGCCATGGGTCACGACGAGATCCTCGCCGTCGGGCATGCGCG |
| | | CCTTGAGCCTGGCGAACAGTTCGGCTGGCGCGAGCCCCTGATGCTCTTCGTCCA |
| | | GATCATCCTGATCGACAAGACCGGCTTCCATCCGAGTACGTGCTCGCTCGATGC |
| | | GATGTTTCGCTTGGTGGTCGAATGGGCAGGTAGCCGGATCAAGCGTATGCAGCC |
| | | GCCGCATTGCATCAGCCATGATGGATACTTTCTCGGCAGGAGCAAGGTGAGATG |
| | | ACAGGAGATCCTGCCCCGGCACTTCGCCCAATAGCAGCCAGTCCCTTCCCGCTT |
| | | CAGTGACAACGTCGAGCACAGCTGCGCAAGGAACGCCCGTCGTGGCCAGCCACG |
| | | ATAGCCGCGCTGCCTCGTCCTGCAGTTCATTCAGGGCACCGGACAGGTCGGTCT |
| | | TGACAAAAAGAACCGGGCGCCCCTGCGCTGACAGCCGGAACACGGCGGCATCAG |
| | | AGCAGCCGATTGTCTGTTGTGCCCAGTCATAGCCGAATAGCCTCTCCACCCAAG |
| | | CGGCCGGAGAACCTGCGTGCAATCCATCTTGTTCAATCATGCGAAACGATCCTC |
| | | ATTCATTTATCAGGGTTATTGTCTCATGAGCGGATACATATTTGAATGTATTTA |

TABLE 14-continued pXoX Triple-Gene Vector Sequence

| SEQ ID No. | Construct | Sequence |
|---|---|---|
| | | GGCTGAGCATCTATGTCGGGTGCGGAGAAAGAGGTAATGAAATGGCAGGCGCCT TTTTCGTTAGATATGTAGTAAGTATCTTAATATACAGCTTTATCTGTTTTTTAA GATACTTACTACTTTTCTTAGTGGAAACTATTAGTGGCTGTTAATTAAGCTAGT ACTACCCAAGATTTGACAGAATGCATCGTTTGCATTCGAA |

Results

As effectors from pXoX are expressed as single multigene mRNA, the relative expression of each effector is fixed. To determine the relative expression levels of each effector of pXoX, several relevant cell lines were transfected, and protein expression assessed by ELISA. Cells were transfected with plasmids for each individual effector (pS100A1, pSDF-1α or pVEGF165) or all three effectors (pXoX).

Accordingly, as shown in Table 15, a variety of cells transfected with pXoX triple-gene vector encoding S100A1, SDF-1, and VEGF165, produced measurable levels of protein as detected via ELISA assays. Cell types tested included 293T cells, SV40 transformed Cardiomyocytes, iPSαC-CMs (Cardiomyocytes) from healthy individual, iPSC-CMs from dilated cardiomyopathy patient, and iPSC-CMs from hypertrophy cardiomyopathy patient.

At 72 hours post-transfection, media and cell lysates were collected and analyzed separately to evaluate expression of the secreted proteins (VEGF165 and SDF-1α) or the intracellular proteins (S100A1). Table 15 below shows the protein levels of each effector compared to levels achieved by plasmids expressing each effector individually, expressed as ng/mL.

Table 15: Detection of Polypeptide Expression from Single-Gene and Triple-Gene Expression Plasmids in Variety of Cell Types.

TABLE 16

Detection of Polypeptide Expression from Single-Gene and Triple-Gene Expression Plasmids in Variety of Cell Types.

| | Plasmid Construct | S100A1 [ng/mL] | SDF-1α [ng/mL] | VEGF165 [ng/mL] |
|---|---|---|---|---|
| 293T cells | Mock | 0.0 | 0.0 | 0.0 |
| | pS100A1 only | 182.6 | 0.0 | 0.0 |
| | pSDF-1α only | 0.0 | 114.3 | 0.0 |
| | pVEGF165 only | 0.0 | 0.0 | >600.0 |
| | pXoX | 1466.6 | 92.2 | >600.0 |
| SV40 Cardiomyocytes | Mock | 0.0 | 0.6 | 0.4 |
| | pS100A1 only | 57.8 | 0.1 | 0.4 |
| | pSDF-1α only | 0.0 | 20.9 | 0.4 |
| | pVEGF165 only | 0.0 | 0.2 | 386.1 |
| | pXoX | 155.3 | 7.4 | 50.0 |
| iPSC-CMs from Healthy individual | Mock | 0.0 | 0.3 | 0.0 |
| | pS100A1 only | 1182.0 | 0.3 | 0.0 |
| | pSDF-1α only | 0.0 | 13.2 | 0.0 |
| | pVEGF165 only | 0.0 | 0.4 | 190.5 |
| | pXoX | 1082.4 | 4.3 | 17.3 |
| iPSC-CMs from Dilated Cardiomyopathy patient | Mock | 0.0 | 0.1 | 0.0 |
| | pS100A1 only | 518.0 | 0.7 | 0.0 |
| | pSDF-1α only | 0.0 | 6.0 | 0.0 |
| | pVEGF165 only | 0.0 | 1.0 | 191.0 |
| | pXoX | 257.0 | 1.9 | 15.6 |
| iPSC-CMs from Hypertrophy Cardiomyopathy patient | Mock | 23.3 | 0.1 | 0.0 |
| | pS100A1 only | 361.7 | 0.1 | 0.0 |
| | pSDF-1α only | 23.2 | 7.7 | 0.0 |
| | pVEGF165 only | 19.4 | 0.7 | 180.5 |
| | pXoX | 118.0 | 1.6 | 13.6 |

Example 8

Cardiomyocyte Transfection

SV40 Immortalized Cardiomyocytes

SV40 Immortalized Cardiomyocytes were transfected via DNAfectin Plus (ABM) with Xogenex single-gene, dual-gene (double-gene), triple-gene constructs wherein at least two genes are connected by a linker described herein, and the appropriate control constructs. A 6 well plate was coated with extracellular matrix (ABM) overnight. 24 hours later, cardiomyocytes were seeded on the 6 well plate at 225,000 cells/well into each ECM-coated well. The cells were incubated overnight at 37° C./5% $CO_2$. 72 hours later, media was collected from the cells into a 2 mL deep well block and stored for ELISA for detected and quantification of protein production.

iPSC Cardiomyocytes iPSC Cardiomyocytes were transfected via GeneJammer transfection reagent (Agilent) with Xogenex single-gene, dual-gene (double-gene), triple-gene constructs and the appropriate control constructs. A 12 well plate was coated with Fibronectin (ThermoScientific) and incubated at 37° C./5% $CO_2$ for 1 hour. DNase was reconstituted in UltraPure water to a final concentration of 10 mg/mL Cardiomyocytes were trypsinzed using TrypLE and 1× DNase I and incubated for 5 minutes at 37° C. or until cells detached from the flask. iPSC cells were seeded at 4e5 cells/well into each Fibronectin-coated well of the 12 well plates. Plated cells were incubated at 37° C./5% $CO_2$ incubator for 24 hours. The following day, the cardiomyocytes were transfected using plasmid DNA at 2 μg (pXoX and controls).

Results

Immortalized and primary cardiomyocytes transfected with a triple-gene vector encoding for S100A, SDF1, VEGF165, produced measurable levels of protein, FIG. 21.

Example 9

Quantifying Protein Production by Transfected Cardiomyocytes

Lysates from 293T cells, SV40 CMs and iPSC CMs were diluted 1:100 in BuPH Carbonate-Bicarbonate buffer pack (0.2M) (ThermoFisher) and analyzed by ELISA assay.

Results

S100A1, SDF-1α, and VEGF165 proteins were detected in cellular lysates of transfected 293T cells, SV40 CMs and iPSC CMs, FIG. 21.

Example 10

Beating Rate and Contractile Duration

To evaluate efficacy of pXoX and function of S100A1 expressed by pXoX, the contraction properties of iPSC-cardiomyocytes derived from a healthy individual and a dilated cardiomyopathy patient (carrying a R173W mutation in the cardiac TNNT2 gene) transfected with pXoX or appropriate controls were measured on a Sony S18000 Live Cell Imaging System. Cellular contraction was recorded as high-resolution and high-frame rate videos (2048*2048 pixels, 150 fps, 10 second per well). The contraction videos were further analyzed with Sony S18000C analyzer software, and the contractile parameters were pulled out for each individual well. Responsiveness of iPSC-CMs to β-adrenergic stimulation, Isoproterenol (ISO, 100 nM) was measured based on contraction properties that were recorded within 30-minutes of incubation. Three contraction parameters were evaluated during the study: beat rate, contraction rate (velocity), and contraction duration.

Results

The beating rate and contractile duration indicate that the presence of a 2A tail at the 3' end of a vector encoding for S100A1 does not affect the function of S100A1, FIG. 18A and FIG. 18B. In a separate experiment, the beating rate and contractile duration shown, FIG. 19A, FIG. 19B, and FIG. 19C show the restoration of DCM contractile properties to healthy control levels by the protein produced from transfected iPSC-CM cells.

Thus, these results demonstrate that in vitro contraction properties of iPSC-cardiomyocytes derived from a dilated cardiomyopathy patient were improved with pS100A1, pS100A1-SDF-1α, and pXoX, as compared with pStuffer and non-transfection controls. (pStuffer is a plasmid with the same backbone configuration as pXoX, with the open reading frame (ORF) replaced with a non-expressing, similar-sized stuffer sequence.)

pS100A1 and pS100A1-SDF-1α displayed comparable functional output (increased beating rate, improved contractile duration), suggesting that presence of 2A tail at 3' end of S100A1 in pS100A1-SDF-1α and pXoX does not affect S100A1 function.

pXoX was most effective in restoring contractile properties of dilated cardiomyopathy patient to levels observed in healthy individuals, suggesting effectors in pXoX are complementary.

Example 11

Recombinase Titrations

Figure 28:
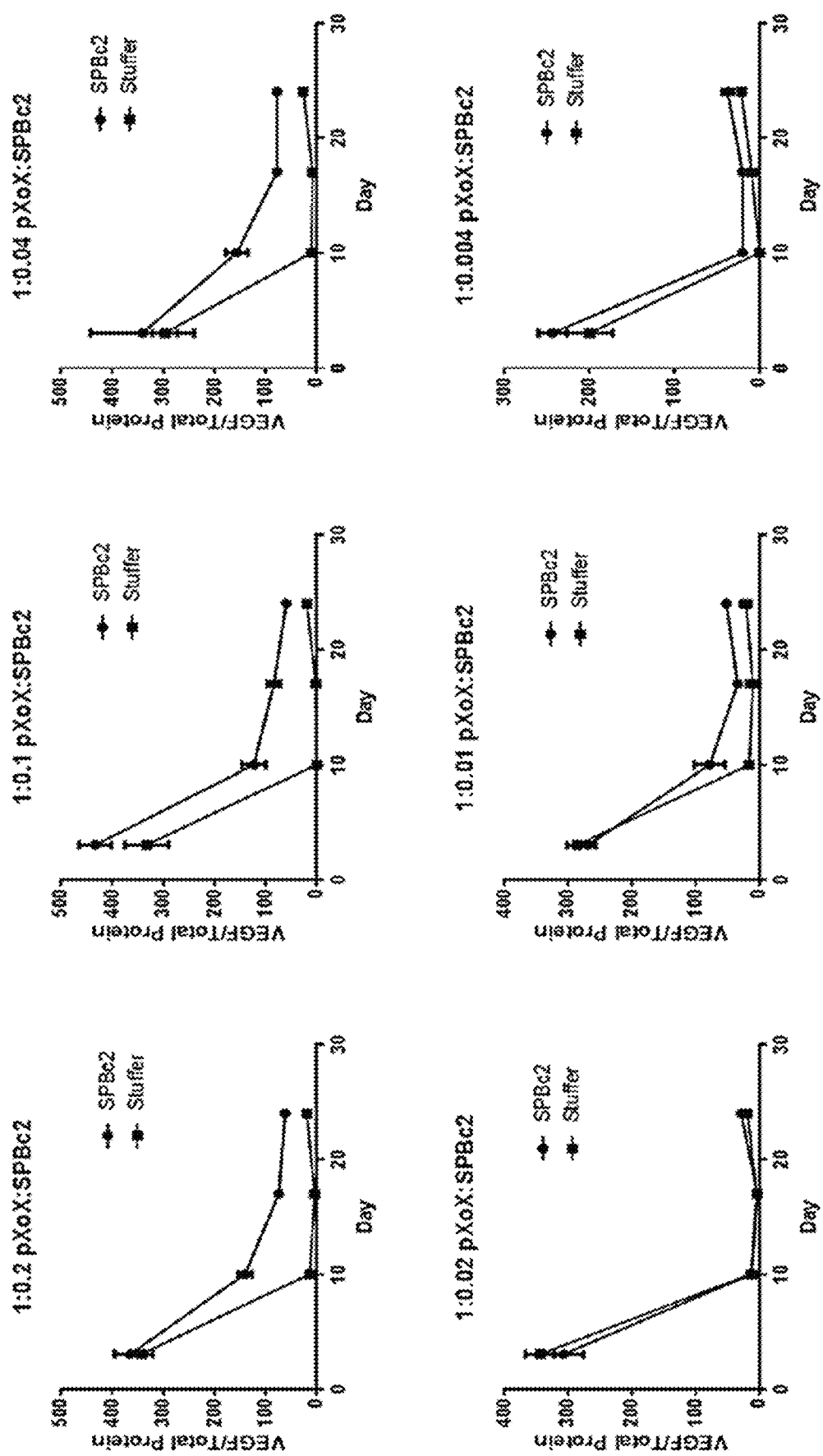
FIG. 28 shows data for expression of VEGF in a recombinase titration experiments. Data indicates integration of VEGF into genomic DNA.

FIG. 28 shows data for expression of VEGF in a recombinase titration experiments in which ELISA analysis was performed to detect the persistence of expression of VEGF when transfected into SV40 transformed cardiomyocytes with varying ratios of the pXoX triple-gene expression vector to recombinase. On Day 3 post-transfection, there was no significant difference in VEGF expression between the SPBc2 and Stuffer groups. On Days 10, 17, and 24 post-transfection, the SPBc2 groups showed significantly more VEGF secretion than the control (Stuffer) groups when the luciferase: recombinase ratio was 1:0.2-1:0.04.

Figure 29:
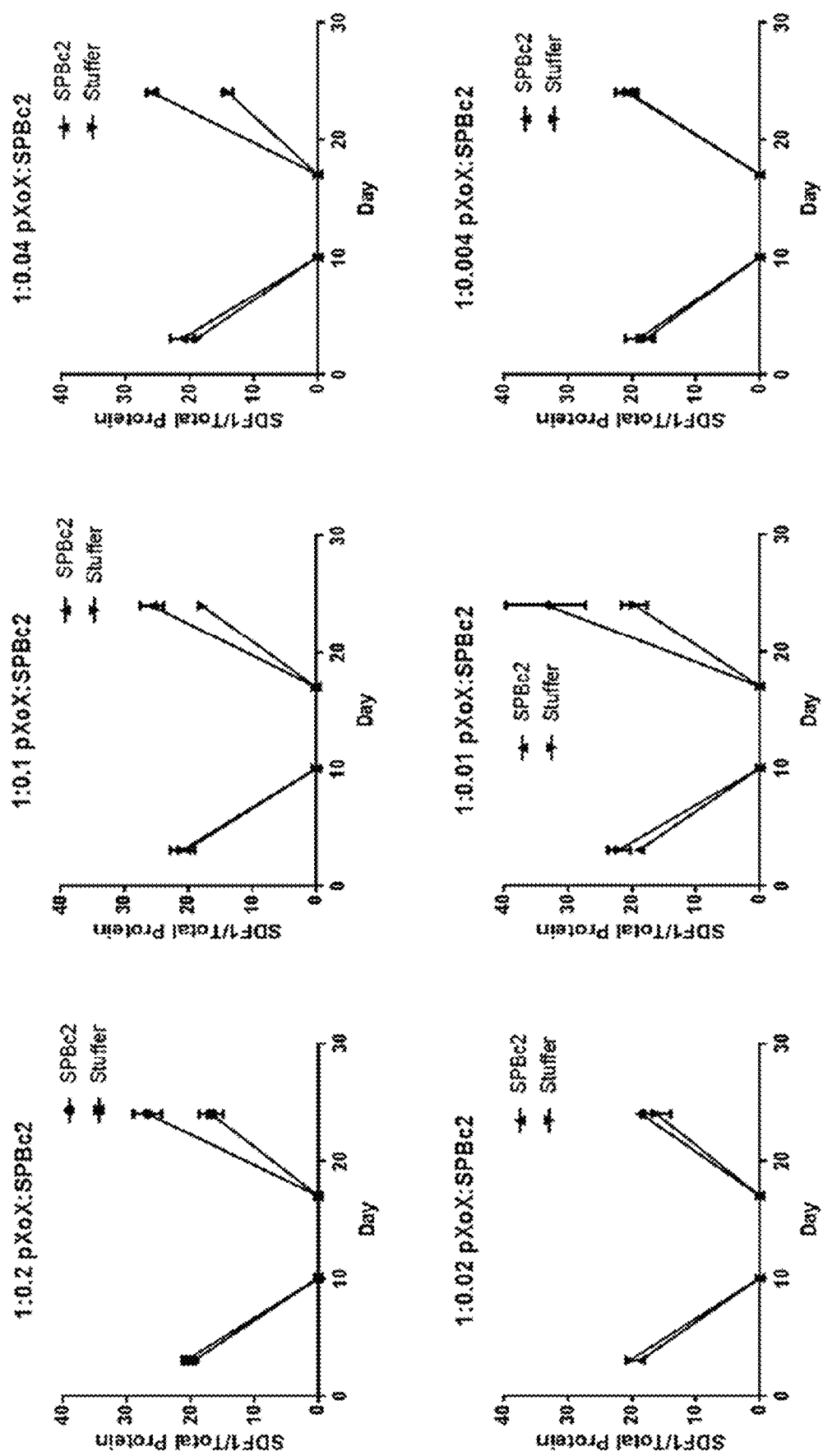
FIG. 29 shows data for expression of SDF-1α in a recombinase titration experiments. Data indicates integration of SDF-1α into genomic DNA.

FIG. 29 shows data for expression of SDF-1α in a recombinase titration experiments in which ELISA analysis was performed to detect the persistence of expression of SDF-1α when transfected into SV40 transformed cardiomyocytes with varying ratios of the pXoX triple-gene expression vector to recombinase. On Day 3 post-transfection, there was no significant difference in SDF1 expression between the SPBc2 and Stuffer groups. SDF1 protein levels were below the limit of detection Days 10 and 17 post-transfection. SDF1 protein levels were detected Day 24 post-transfection at which point, the SPBc2 groups showed significantly more SDF1 secretion than the control (Stuffer) groups when the luciferase: recombinase ratio was 1:0.2-1:0.04.

Figure 30:
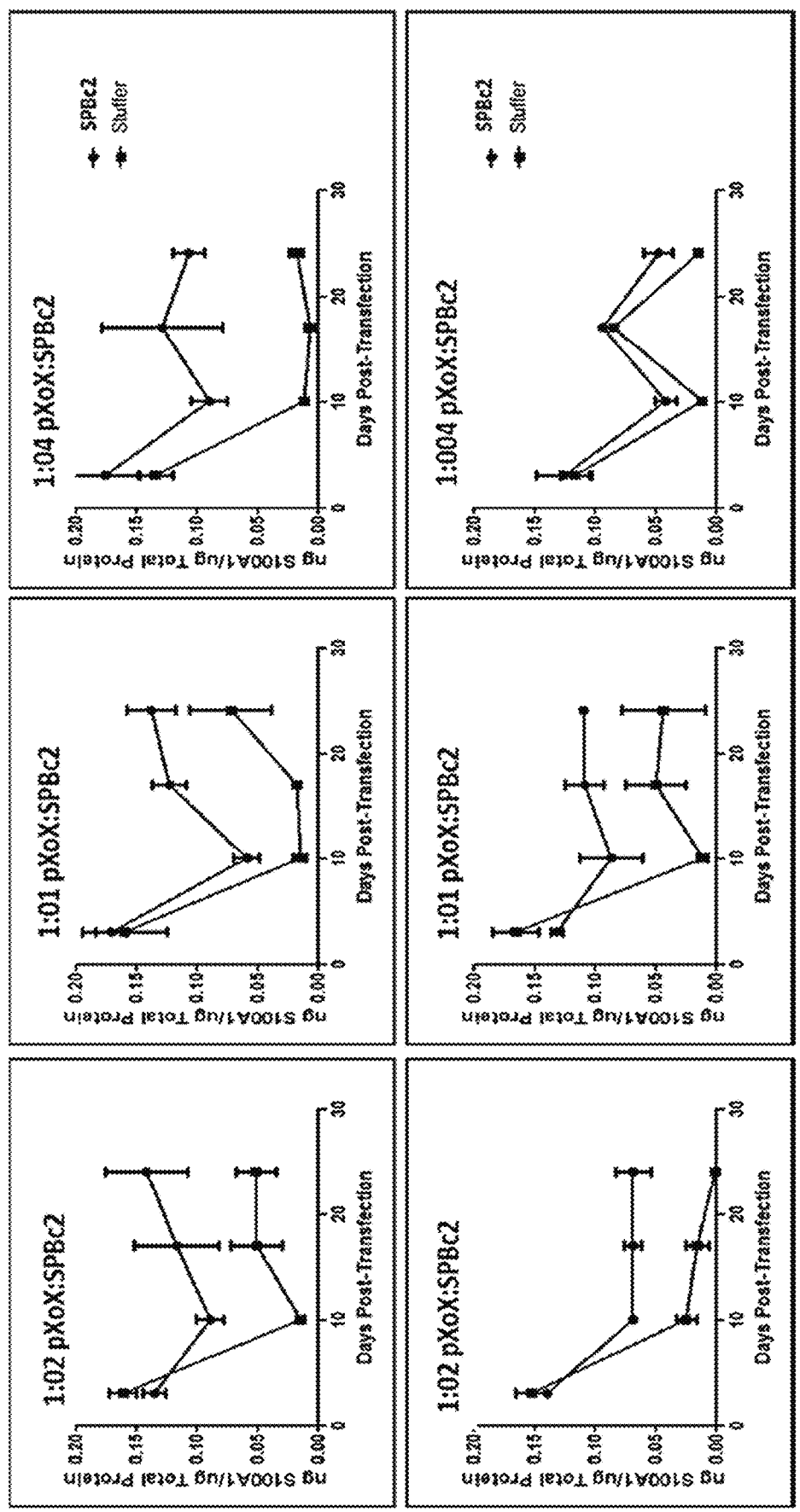
FIG. 30 shows data for expression of S100A1 in a recombinase titration experiments. Data indicates integration of S100A1 into genomic DNA.

FIG. 30 shows data for expression of S100A1 in cardiomyocytes transfected with and without recombinase. On Day 3 post-transfection, there was no significant difference in S100A1 expression between the SPBc2 and Stuffer groups. On Days 10, 17, and 24 post-transfection, the SPBc2 groups showed significantly more S100A1 secretion than the control (Stuffer) groups.

Example 12

Plasmid Backbone Expression Study in Rats pXoX has a standard plasmid backbone with a kanamycin resistance gene. Additionally, expression of the effector proteins is driven by the hybrid CAG promoter and utilizes a synthetic 3'UTR/polyA tail. To verify the ability of this backbone configuration to maintain gene expression in the heart over time, the effector ORF in pXoX was replaced with a luciferase (fLuc) reporter gene (pCAG-fLuc) and was evaluated by live animal imaging for duration of luciferase expression after plasmid injection into the heart. A similar plasmid with the CMV promoter and a non-expressing stuffer sequence (pCMV-stuffer) was used as a control for plasmid size and background fLuc expression.

For this expression study, plasmid DNA (250 µg) was injected into the left ventricular wall of 12-14 week-old female Sprague Dawley rats (n=5 per group). Rats were monitored over time and luciferase expression levels were measured using a live in vivo imaging system (IVIS). Luciferase activity in rats injected with pCAG-fLuc were initially 2-logs higher than background levels seen in rats injected with the control pCMV-fLuc construct. Expression levels gradually dropped over 28 days after dosing as expected with transiently expressing plasmids. These findings indicate that this plasmid backbone is capable of initiating protein expression which gradually diminishes to near control levels around Day 28. Data not shown.

Example 13

Delivery Method—Retrograde Infusion via the Coronary Sinus in Pigs

Retrograde infusion via the coronary sinus is the proposed method of delivery for non-viral plasmid constructs (such as, but not limited to, pXoX) to the heart. The technical complexity of this delivery method precludes its assessment in small animal models such as mice and rats. As such, pigs are proposed for use in pharmacology and toxicology/biodistribution studies. To test the feasibility of this method, a pilot study was performed in pigs as test subjects. Using standard interventional techniques, a balloon catheter (Cook Regentec) was placed over the wire into the coronary sinus. The balloon was inflated, occlusion was confirmed, and infusion of the luciferase reporter plasmid followed. Three different doses (40 mg, 80 mg, and 120 mg) were tested with a plasmid concentration of 1 mg/mL. Total of 9 animals were studied, providing for 3 replicates for each dose. In each animal infusion occurred in 10 mL increments until all volume was administered. The infusion was at 10mL/min and post infusion balloon occlusion was for 10 minutes.

Figure 9:
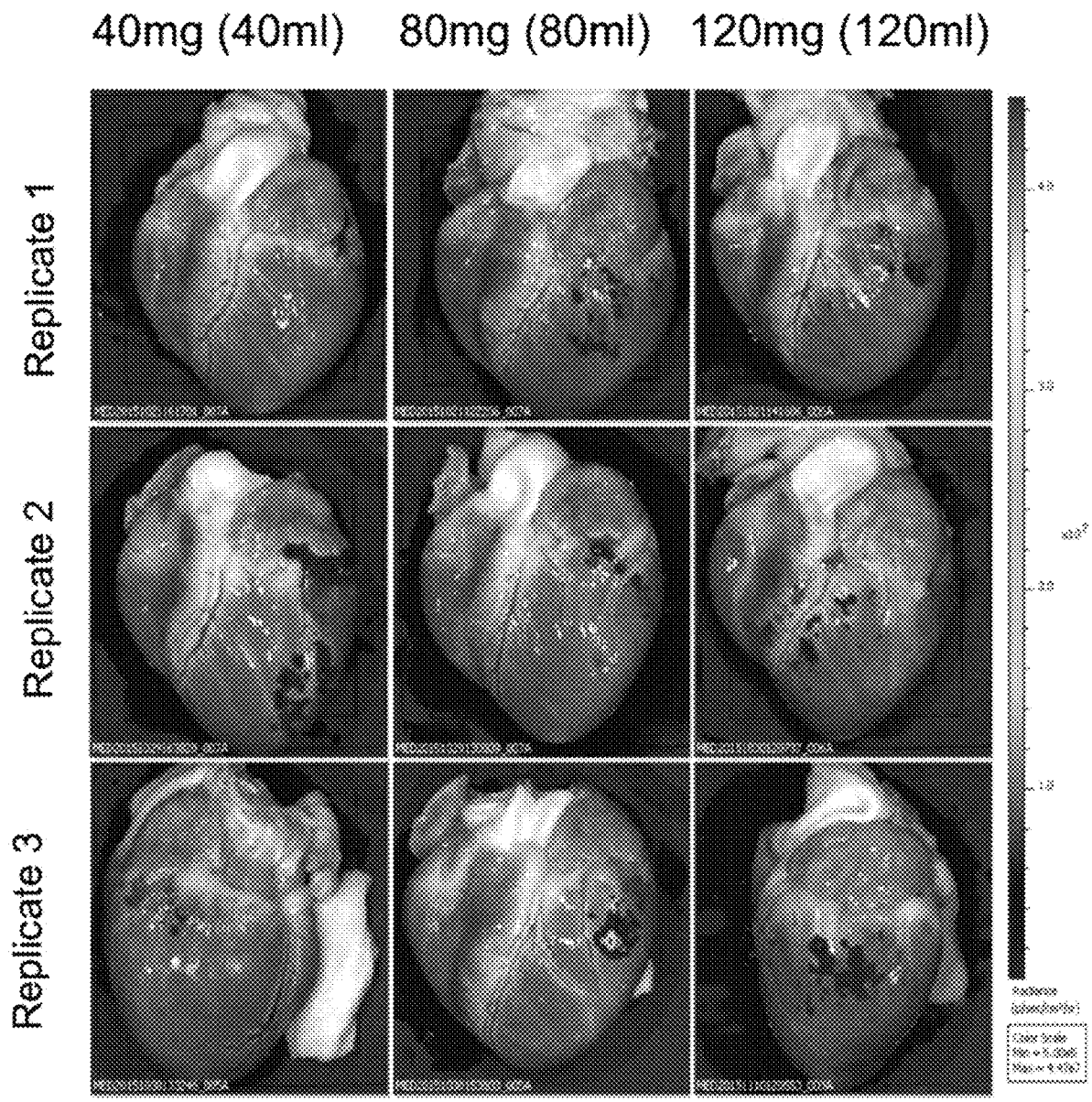
FIG. 9 shows a porcine study in which bioluminescence images illustrate retrograde perfusion through the coronary sinus of a reporter plasmid, also incorporating a linker described herein, results in delivery to the heart and expression of the delivered reporter gene after 24 hours. The radiance intensity and distribution 24-hours post-retrograde infusion of luciferase-expressing plasmids through the porcine heart coronary sinus. Three plasmid doses (40, 80, and 120 mg) were tested in triplicate.

Approximately 24 hours following plasmid infusion, the great cardiac vein was catheterized and a D-Luciferin substrate solution (approximately 0.125 mg/ml concentration) was infused into the coronary venous system. Animals were then euthanized and hearts explanted. The explanted hearts were subsequently evaluated for bioluminescence via CCD camera counts using the IVIS® Lumina imaging system. Bioluminescent images showing luciferase radiance intensity and distribution at 24 hour post injection of isolated hearts is depicted in FIG. 9, indicating plasmid mediated luciferase expression by the heart cells occurs within 24 hours after dosing.

Further biodistribution of the plasmid mediated luciferase expression was studied in heart and lung tissue sections. RT-PCR data further confirmed luciferase expression only in heart left ventricle in pigs in the 120 mg treatment group (data not shown). No animals died before planned sacrifice. Accordingly, this study illustrated that delivery of non-viral plasmids such as pXoX is safe, practical and results in limited systemic distribution of the plasmid.

Example 14

In Vivo Cardiomyocytes regeneration by pXoX in adriamycin-induced cardiomyopathy using ultrasound targeted microbubble destruction (UTMD) method [64]Adriamycin induced cardiomyopathy in rats is a well established model for congestive heart failure (CHF). Ultrasound targeted microbubble destruction (UTMD) method was used to deliver pXoX (which expresses biologically active SDF1α, S100A1, and VEGF) to rat hearts in adriamycin-induced cardiomyopathy. A total of 16 rats with established adriamycin-induced cardiomyopathy were divided into 2 groups of eight. Each group was treated with one of the 2 plasmids: (1) pStuffer, or (2) pXoX. pStuffer is a negative control plasmid with the same backbone configuration as pXoX, with the open reading frame (ORF) replaced with a non-expressing, similar-sized "stuffer" sequence. Plasmid-containing lipid-stabilized microbubbles were prepared in a solution of 1,2-dipalmitoylsn-glycero-3-phosphatidylcholine 2.5 mg/ml, 1,2-dipalmitoyl-sn-glycero-3-phosphatidylethanolamine 0.5 mg/ml, and 10% glycerol mixed with 2 mg of plasmid dissolved in 50 ml of lipofectamine 3000 (Invitrogen, Carlsbad, Calif.). Aliquots of 0.5 ml of this phospholipid-plasmid solution were placed in 1.5 ml clear vials; the remaining head space was filled with the perfluoropropane gas (Air Products, Inc, Allentown, Pa.). Each vial was incubated at 4° C. for 30 min and then mechanically shaken for 30 s by a dental amalgamator (Vialmix™, Bristol-Myers Squibb Medical Imaging N. Billerica, Mass.).Echocardiographic measurements of fractional shortening, LV posterior wall thickness and interventricular septal end diastole and end systole (IVSd) were made from digital images acquired with a 12 MHz broadband transducer (S12 probe, Philips Ultrasound, Bothell, Wash.) in M-mode under 2D parasternal short axis of the left ventricle view.

Figure 31A:
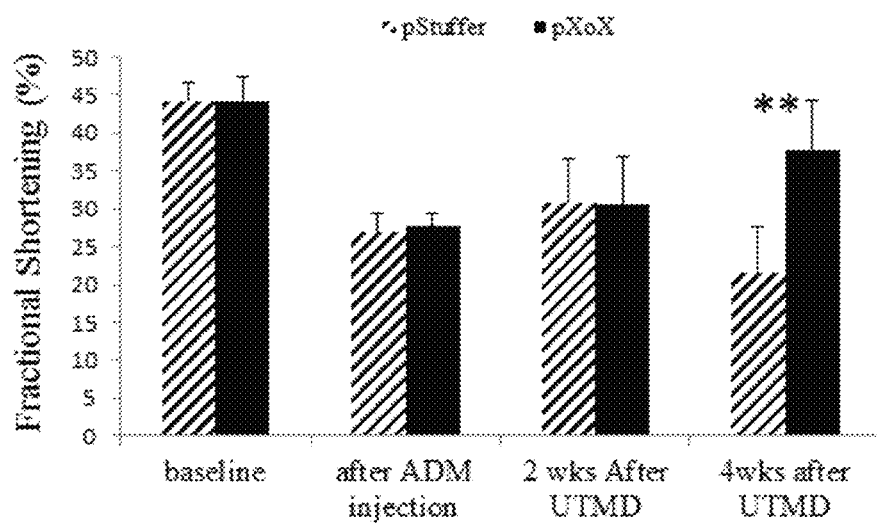
FIG. 31A shows results as a function of percent fractional shortening.
Figure 31B:
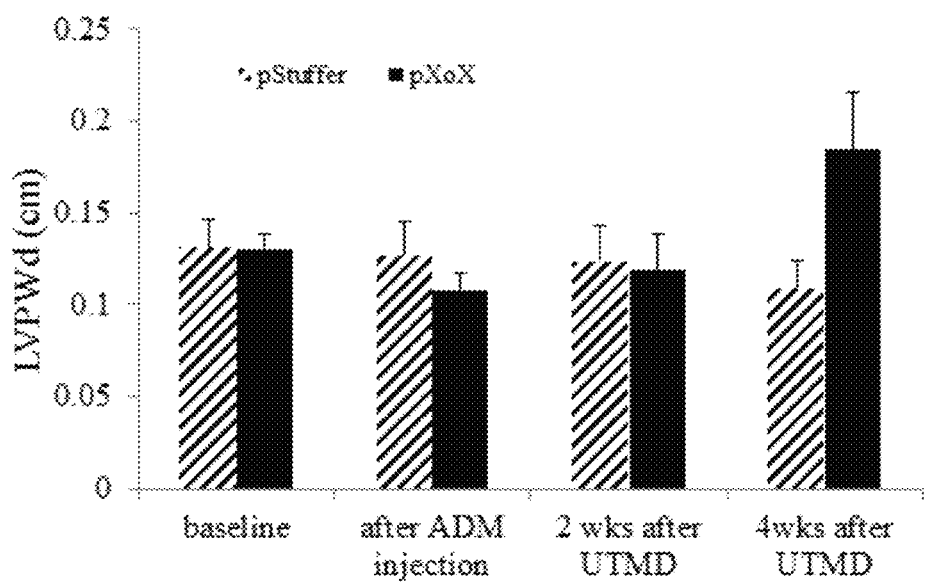
FIG. 31B shows left ventricle posterior wall thickness (cm) of the pStuffer construct as compared to the pXoX construct.
Figure 31C:
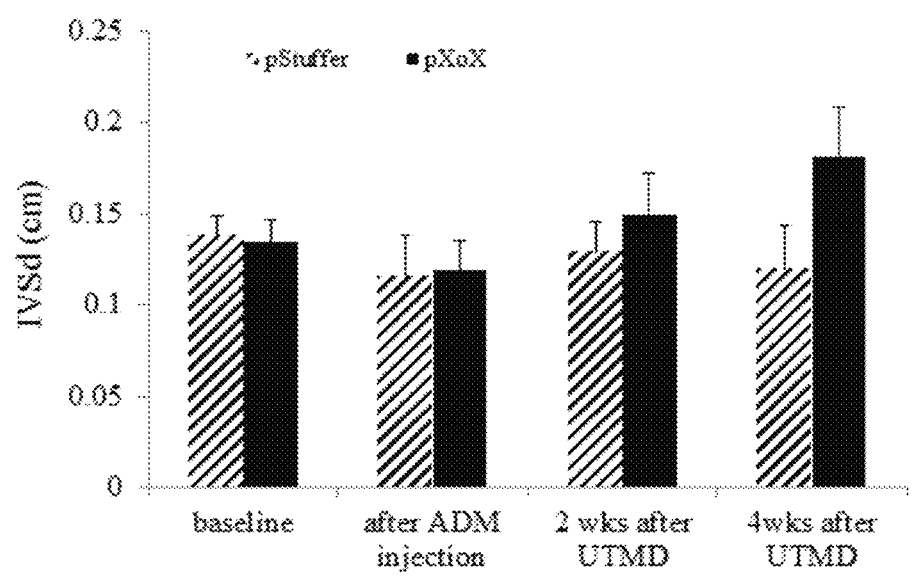
FIG. 31C shows IVSd (cm) of the pStuffer construct as compared to pXoX construct. Values are presented as mean±SEM. **$P<0.001$ vs pStuffer.

Results of echocardiographic measurement of cardiac structure and function demonstrate that UTMD-pXoX gene therapy restores fractional shortening index, LV posterior wall diameter, and IVSd, FIG. 31A, FIG. 31B, and FIG. 31C. Values are presented as mean±SEM. **$P<0.001$ vs pStuffer. Results show that echocardiographic measurement demonstrated reversal of established ADM cardiomyopathy after a single UTMD-pXoX treatment, thereby indicating successful in vivo treatment of cardiomyopathy in a congestive heart failure model by administration of the (triple-gene with linkers) pXoX construct which expresses biologically active SDF1α, S100A1, and VEGF.

Figure 32:
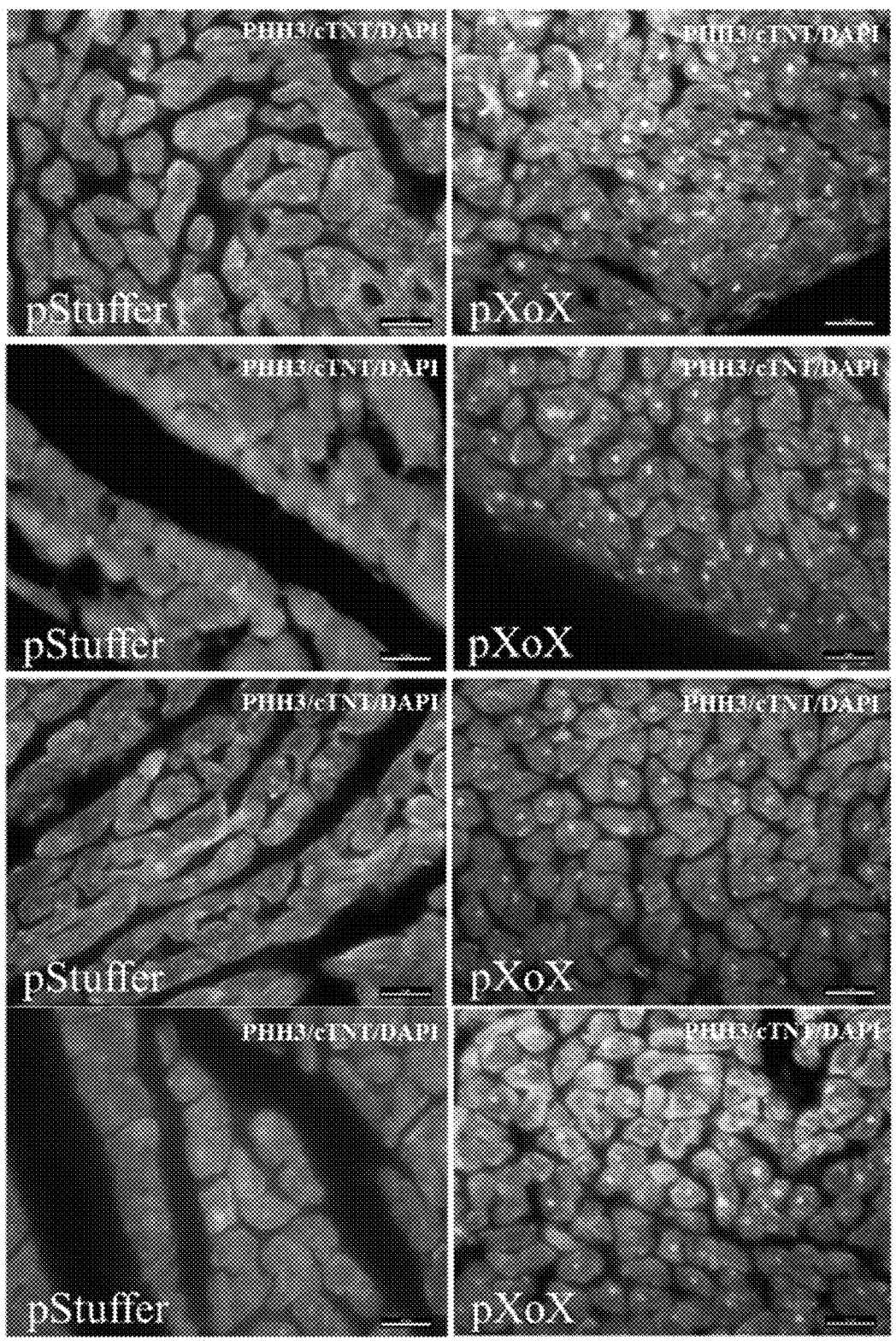
FIG. 32 shows results of nuclear localization of PHH3 (phospho-histone H3 (Ser10)) Mitotic marker signal in cardiac cells demonstrating cardiomyocyte regeneration. Representative images of 4 out of 8 rats per plasmid. Scale bar is 25 μm.
Figure 33:
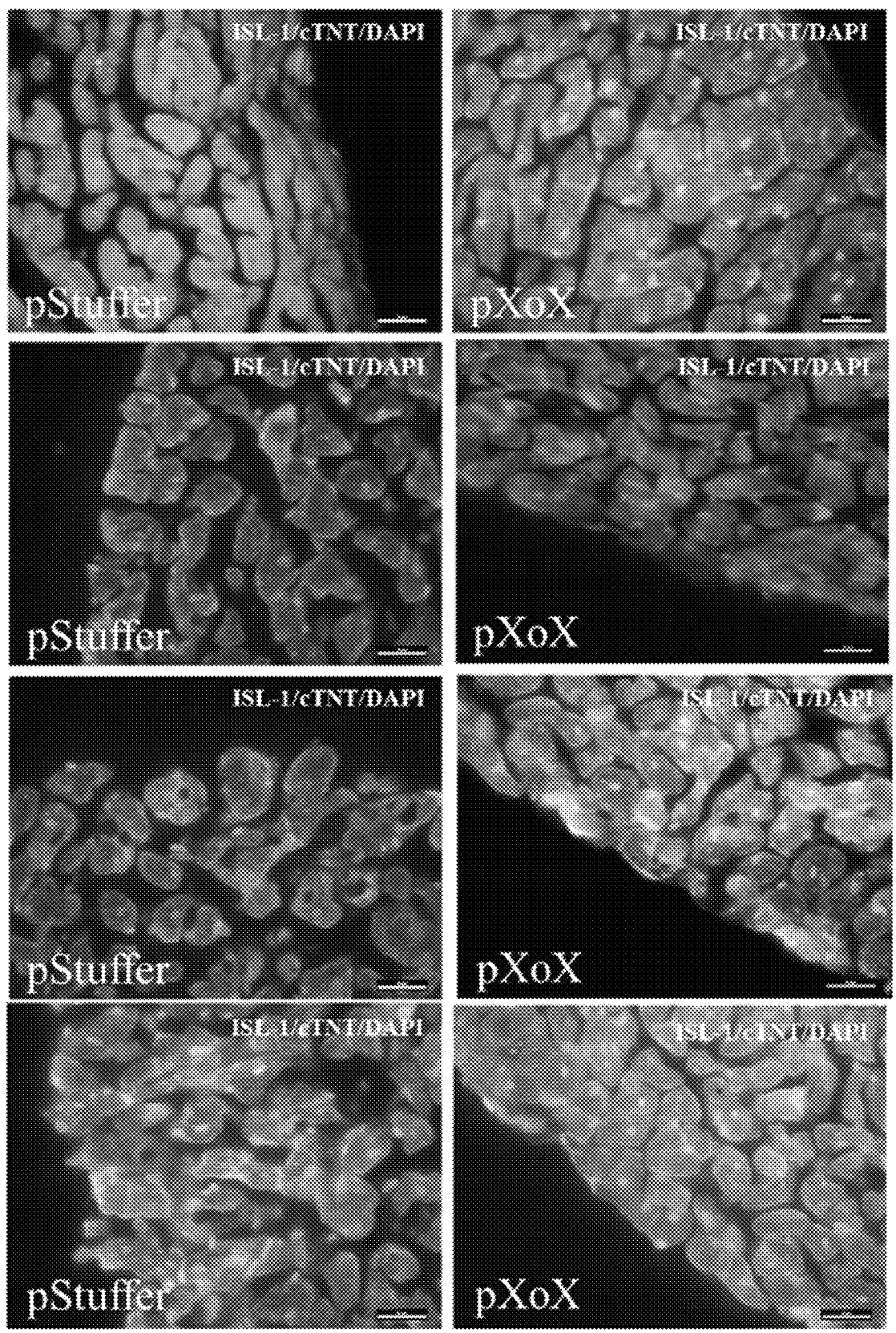
FIG. 33 shows imaging results demonstrating negative results of ISL-1, a marker of early cardiac progenitor cells confirming progenitor cells are not involved in regeneration. Observed cardiomyocyte regeneration is, therefore, a result of UTMD-pXoX gene therapy. Representative images of 4 out of 8 rats per plasmid. Scale bar is 25 μm.

Results of nuclear localization of PHH3 (phospho-histone H3 (Ser10)) Mitotic marker signal in cardiac cells of rats receiving the pStuffer or pXoX plasmid are shown in FIG. 32 and demonstrate cardiomyocyte regeneration. PHH3 Mitotic marker confirmed proliferation of adult rat cardiac muscle cells with established heart failure using UTMD-pXoX. Negative results of ISL-1, a marker of early cardiac progenitor cells confirms progenitor cells are not involved in regeneration in the same rats, FIG. 33. Negative results of ISL-1 confirmed cardiomyocytes regeneration is truly a result of UTMD-pXoX gene therapy.

These results indicate that administration of the pXoX construct which expresses biologically active SDF1α, S100A1, and VEGF is useful in cardiomyocyte regeneration and successful treatment of cardiomyopathy in a congestive heart failure models. The results also indicate that Ultrasound targeted microbubble destruction (UTMD) is a successful method of administering the vectors and gene constructs described herein, for instance including multi-gene constructs such as pXoX for treatment of cardiac conditions and other pathologies.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

[1] J. L. Hellawell and K. B. Marguiles, "Myocardial reverse remodeling," Cardiovasc Ther, vol. 30, no. 3, pp. 172-181, 2012.

[2] D. Rohde, J. Ritterhoff, M. Voelkers, H. Katus, T. G. Parker and P. Most, "S100A1: a multifaceted therapeutic target in cardiovascular disease," J Cardiovasc Transl Res, vol. 3, no. 5, pp. 525-537, 2010.

[3] S. T. Pleger, P. Most, M. Boucher and S. Soltys, "Stable myocardial-specific AAV6-S100A1 gene therapy results in chronic functional heart failure rescue," Circulation, vol. 115, no. 19, pp. 2506-2515, 2007.

[4] A. Remppis, T. Greten, B. Schafer and P. Hunziker, "Altered expression of the Ca 2+-binding protein S100A1 in human cardiomyopathy," Biochim Biophys Acta, vol. 1313, no. 3, pp. 253-257, 1996.

[5] D. Rohde, H. Brinks, J. Ritterhoff, G. Qui, S. Ren and P. Most, "S100A1 gene therapy for heart failure: a novel strategy on the verge of clinical trials," J Mol Cell Cardiol, vol. 50, no. 5, pp. 777-784, 2011.

[6] C. Weber, I. Neacsu, B. Krautz, P. Schlegel, S. Sauer, P. Raake, J. Ritterhoff, A. Jungmann, A. B. Remppis, M. Stangassinger, W. J. Koch, H. A. Katus, O. J. Muller, P. Most and S. T. Pleger, "Therapeutic safety of high myocardial expression levels of the molecular inotrope S100A1 in a preclinical heart failure model," Gene Ther, vol. 21, pp. 131-138, 2014.

[7] M. S. Penn, J. Pastore, T. Miller and R. Aras, "SDF-1 in myocardial repair," Gene Ther, vol. 19, no. 6, pp. 583-587, 2012.

[8] M. S. Penn, F. O. Mendelsohn, G. L. Schaer, W. Sherman, M. Farr, J. Pastore, D. Rouy, R. Clemens, R. Aras and D.

W. Losordo, "An open-label dose escalation study to evaluate the safety of administration of nonviral stromal cell-derived factor-1 plasmid to treat symptomatic ischemic heart failure," Circ Res, vol. 112, no. 5, pp. 816-825, 2013.

[9] E. S. Chung, L. Miller, A. N. Patel, R. D. Anderson, F. 0. Mendelsohn, J. Traverse, K. H. Silver, J. Shin, G. Ewald, M. J. Farr and S. Anwaruddin, "Changes in ventricular remodelling and clinical status during the year following a single administration of stromal cell-derived factor-1 non-viral gene therapy in chronic ischaemic heart failure patients: the STOP-HF randomized Phase II trial," Eur Heart J, vol. 36, pp. 2228-2238, 2015.

[10] Z. Taimeh, J. Loughran, E. J. Birks and R. Bolli, "Vascular endothelial growth factor in heart failure," Nat Rev Cardiol, vol. 10, no. 9, pp. 519-530, 2013.

[11] J. X. Yu, X. F. Huang, W. M. Lv, C. S. Ye, X. Z. Peng, H. Zhang, L. B. Xiao and S. M. Wang, "Combination of stromal-derived factor-1a and vascular endothelial growth factor gene-modified endothelial progenitor cells is more effective for ischemic neovascularization," J Vasc Surg, vol. 50, no. 3, pp. 608-616, 2009.

[12] E. Perin, G. V. Silva, J. A. Assad, D. Vela, L. M. Buja, A. L. Sousa, S. Litovsky, J. Lin, W. K. Vaughn, S. Coulter and M. R. Fernandes, "Comparison of intracoronary and transendocardial delivery of allogeneic mesenchymal cells in a canine model of acute myocardial infarction," J Mol Cell Cardiol, vol. 44, no. 3, pp. 486-95, 2008.

[13] S. Robinson, P. W. Cho, H. I. Levitsky, J. L. Olson, R. H. Hruban, M. A. Acker and P. D. Kessler, "Arterial delivery of genetically labelled skeletal myoblasts to the murine heart: long-term survival and phenotypic modification of implanted myoblasts," Cell Transplant, vol. 5, no. 1, pp. 77-91, 1996.

[14] K. Suzuki, N. J. Brand, R. T. Smolenski, J. Jayakumar, B. Murtuza and M. H. Yacoub, "Development of a novel method for cell transplantation through the coronary artery," Circulation, vol. 102, no. 19 Suppl 3, pp. 111359-64, 2000.

[15] K. Suzuki, B. Murtuza, N. Suzuki, R. T. Smolenski and M. H. Yacoub, "Intracoronary infusion of skeletal myoblasts improves cardiac function in doxorubicin-induced heart failure," Circulation, vol. 104, no. 12 Suppl 1, pp. 1213-7, 2001.

[16] P. Musialek, L. Tekieli, M. Kostkiewicz, M. Majka, W. Szot, Z. Walter and M. Olszowska, "Randomized transcoronary delivery of CD34(+) cells with perfusion versus stop-flow method in patients with recent myocardial infarction: Early cardiac retention of (m)Tc-labeled cells activity," J Nuclear Cardiol, vol. 18, no. 1, pp. 104-16, 2011.

[17] P. W. Musialek, A. B. Tracz, K. Skotnicki, P. Zmudka, Z. Pieniazek and W. M. Szostek, "Transcoronary stem cell delivery using physiological endothelium-targeting perfusion technique: the rationale and a pilot study involving a comparison with conventional over-the-wire balloon coronary occlusions in patients after recent myocardial infarcti," Kardiol Pol, vol. 64, no. 5, pp. 489-98, 2006.

[18] L. Noyez, J. A. van Son, J. T. Van Der Werf, J. Knape, J. Gimbrere, W. N. van Asten, L. K. Lacquet and W. Flameng, "Retrograde versus antegrade delivery of cardioplegic solution in myocardial revascularization. A clinical trial in patients with three-vessel coronary artery disease who underwent myocardial revascularization with extensive use of the internal mammary art," J Thorac Cardiovasc Surg, vol. 105, no. 5, pp. 854-63, 1993.

[19] P. Boekstegers, W. Giehrl, G. von Degenfeld and G. Steinbeck, "Selective suction and pressure-regulated retroinfusion: an effective and safe approach to retrograde protection against myocardial ischemia in patients undergoing normal and high risk percutaneous transluminal coronary angioplasty," J Am Coll Cardiol, vol. 31, no. 7, pp. 1525-33, 1998.

[20] T. Pohl, W. Giehrl, B. Reichart, C. Kupatt, P. Raake, S. Paul, H. Reichenspurner, G. Steinbeck and P. Boekstegers, "Retroinfusion-supported stenting in high-risk patients for percutaneous intervention and bypass surgery: results of the prospective randomized myoprotect I study," Cath Cardiovasc Intervent, vol. 62, no. 3, pp. 323-30, 2004.

[21] R. Incorvati, S. G. Tauberg, M. J. Pecora, R. S. Macherey, S. B. Dianzumba, B. C. Donohue and M. W. Krucoff, "Clinical applications of coronary sinus retroperfusion during high risk percutaneous transluminal coronary angioplasty," J Am Coll Cardiol, vol. 22, no. 1, pp. 127-34, 1993.

[22] Z. a. G. M. Lokmic, "Visualisation and stereological assessment of blood and lymphatic vessels," Histolog Histopathol, vol. 26, no. 6, pp. 781-96, 2011.

[23] D. Rohde, W. Schluter-Wigger, V. Mielke, P. von den Driesch, B. von Gaudecker and W. Sterry, "Infiltration of both T cells and neutrophils in the skin is accompanied by the expression of endothelial leukocyte adhesion molecule-1 (ELAM-1): an immunohistochemical and ultrastructural study," J Invest Dermatol, vol. 98, no. 5, pp. 794-9, 1992.

[24] S. Anderson, R. Shiner, M. D. Brown and 0. Hudlicka, "ICAM-1 expression and leukocyte behavior in the microcirculation of chronically ischemic rat skeletal muscles," Microvasc Res, vol. 71, no. 3, pp. 205-11, 2006.

[25] H. Habazettl, C. Kupatt, S. Zahler, B. F. Becker and K. Messmer, "Selectins and beta 2-integrins mediate post-ischaemic venular adhesion of polymorphonuclear leukocytes, but not capillary plugging, in isolated hearts," Pflugers Arch, vol. 438, no. 4, pp. 479-85, 1999.

[26] J. Lesley, I. Gal, D. J. Mahoney, M. R. Cordell, M. S. Rugg, R. Hyman, A. J. Day and K. Mikecz, "TSG-6 modulates the interaction between hyaluronan and cell surface CD44," J Biol Chem, vol. 279, no. 24, pp. 25745-54, 2004.

[27] A. N. Patel, S. Mittal, G. Turan, A. A. Winters, T. D. Henry, H. Ince and N. Trehan, "REVIVE Trial: Retrograde Delivery of Autologous Bone Marrow in Patients With Heart Failure," Stem Cells Transl Med, vol. 4, pp. 1021-1027, 2015.

[28] R. E. Henschler, E. Deak and E. Seifried, "Homing of Mesenchymal Stem Cells," Infusionsther Transfusionsmed, vol. 35, no. 4, pp. 306-312, 2008.

[29] B. Ruster, S. Gottig, R. J. Ludwig, R. Bistrian, S. Muller, E. Seifried, J. Gille and R. Henschler, "Mesenchymal stem cells display coordinated rolling and adhesion behavior on endothelial cells," Blood, vol. 108, no. 12, pp. 3938-44, 2006.

[30] C. Hart, D. Drewel, G. Mueller, J. Grassinger, M. Zaiss, L. A. Kunz-Schughart, R. Andreesen, A. Reichle, E. Holler and B. Hennemann, "Expression and function of homing-essential molecules and enhanced in vivo homing ability of human peripheral blood-derived hematopoietic progenitor cells after stimulation with stem cell factor," Stem Cells, vol. 22, no. 4, pp. 580-9, 2004.

[31] C. Rampon, N. Weiss, C. Deboux, N. Chaverot, F. Miller, D. Buchet, H. Tricoire-Leignel, S. Cazaubon, B.-V. Evercooren and P.-0. Couraud, "Molecular mechanism of systemic delivery of neural precursor cells to the brain: assembly of brain endothelial apical cups and control of transmigration by CD44," Stem Cells, vol. 26, no. 7, pp. 1673-82, 2008.

[32] E. Bachrach, A. L. Perez, Y. H. Choi, B. M. Illigens, S. J. Jun, P. D. Nido, F. X. McGowan, S. Li, A. Flint, J. Chamberlain and L. M. Kunkel, "Muscle engraftment of myogenic progenitor cells following intraarterial transplantation," Muscle Nerve, vol. 34, no. 1, pp. 44-52, 2006.

[33] P. Boekstegers, G. Von Degenfeld, D. Giehrl, R. Heinrich, C. Hullin, G. Kupatt, G. Steinbeck, G. Baretton, G. Middeler, H. Katus and W. M. Franz, "Myocardial gene transfer by selective pressure-regulated retroinfusion of coronary veins," Gene Ther, vol. 7, no. 3, pp. 232-40, 2000.

[34] S. Alino, M. Jose Herrero, V. Bodi, I. Noguera, L. Mainar, F. Dasi, A. Sempere, M. Sanchez, A. Diaz, L. Sabater and S. Lledo, "Naked DNA delivery to whole pig cardiac tissue by coronary sinus retrograde injection employing non-invasive catheterization," J Gene Med, vol. 12, no. 11, pp. 920-6, 2010.

[35] E. Youssef, P. Zhang, P. I. Rogers, P. Tremble, J. Rokovich, B. H. Johnstone, K. L. March and D. Hou, "Enhancing myocardial plasmid expression by retrograde coronary venous delivery," Cath Cardiovasc Intervent, vol. 65, no. 4, pp. 528-34, 2005.

[36] P. Raake, G. von Degenfeld, R. Hinkel, R. Vachenauer, T. Sandner, S. Beller, M. Andrees, C. Kupatt, G. Schuler and P. Boekstegers, "Myocardial gene transfer by selective pressure-regulated retroinfusion of coronary veins: comparison with surgical and percutaneous intramyocardial gene delivery," J Am Coll Cardiol, vol. 44, no. 5, pp. 1124-9, 2004.

[37] G. von Degenfeld, P. Raake, C. Kupatt, C. Leberhz, R. Hinkel, F. J. Gildehaus, W. MUnzing, A. Kranz, J. Waltenberger, M. Simoes and M. Schwaiger, "Selective pressure-regulated retroinfusion of fibroblast growth factor-2 into the coronary vein enhances regional myocardial blood flow and function in pigs with chronic myocardial ischemia," J Am Coll Cardiol, vol. 42, no. 6, pp. 1120-8, 2003.

[38] K. Suzuki, B. Murtuza, S. Fukushima, R. T. Smolenski, A. Varela-Carver, S. R. Coppen and M. H. Yacoub, "Targeted cell delivery into infarcted rat hearts by retrograde intracoronary infusion: distribution, dynamics, and influence on cardiac function," Circulation, vol. 110, no. 11 Suppl 1, pp. 11225-30, 2004.

[39] J. George, J. Goldberg, M. Joseph, N. Abdulhameed, J. Crist, H. Das and V. J. Pompili, "Transvenous intramyocardial cellular delivery increases retention in comparison to intracoronary delivery in a porcine model of acute myocardial infarction," J Intery Cardiol, vol. 21, no. 5, pp. 424-31, 2008.

[40] C. Thompson, B. A. Nasseri, J. Makower, S. Houser, M. McGarry, T. Lamson, I. Pomerantseva, J. Y. Chang, H. K. Gold, J. P. Vacanti and S. N. Oesterle, "Percutaneous transvenous cellular cardiomyoplasty: A novel nonsurgical approach for myocardial cell transplantation," J Am Coll Cardiol, vol. 41, no. 11, pp. 1964-71, 2003.

[41] P. W. Raake, R. Hinkel, S. Muller, S. Delker, R. Kreuzpointner, C. Kupatt, H. A. Katus, J. A. Kleinschmidt, P. Boekstegers and 0. J. Muller, "Cardiospecific long-term gene expression in a porcine model after selective pressure-regulated retroinfusion of adeno-associated viral (AAV) vectors," Gene Ther, vol. 15, no. 1, pp. 12-7, 2008.

[42] J. Tuma, R. Fernandez-Viria, A. Carrasco, J. Castillo, C. Cruz, A. Carrillo, J. Ercilla, C. Yarleque, J. Cunza, T. D. Henry and A. N. Patel, "Safety and feasibility of percutaneous retrograde coronary sinus delivery of autologous bone marrow mononuclear cell transplantation in patients with chronic refractory angina," J Transl Med, vol. 9, p. 183, 2011.

[43] N. T. Wright, K. M. Varney, K. C. Ellis, J. Markowitz, R. K. Gitti, D. B. Zimmer and D. J. Weber, "The three-dimensional solution structure of Ca(2+)-bound S100A1 as determined by NMR spectroscopy," J Mol Biol, vol. 353, no. 2, pp. 410-426, 2005.

[44] R. Donato, "Functional roles of S100 proteins, calcium-binding proteins of the EF-hand type," Biochim Biophys Acta, vol. 1450, no. 3, pp. 191-231, 1999.

[45] D. B. Zimmer, P. Wright Sadosky and D. J. Weber, "Molecular mechanisms of S100-target protein interactions," Microsc Res Tech, vol. 60, no. 6, pp. 552-559, 2003.

[46] L. Hove-Madsen and D. M. Bers, "Sarcoplasmic reticulum Ca2+uptake and thapsigargin sensitivity in permeabilized rabbit and rat ventricular myocytes," Circ Res, vol. 73, no. 5, pp. 820-828, 1993.

[47] J. James, Y. Zhang, K. Wright, S. Witt and E. Glascock, "Transgenic rabbits expressing mutant essential light chain do not develop hypertrophic cardiomyopathy.," J Mol Cell Cardiol, vol. 34, no. 7, pp. 872-882, 2002.

[48] J. Woda, S. J. Fisher, J. Pastore and A. N. Patel, "Coronary Sinus Delivery of SDF-1 Plasmid for the Treatment of Heart Failure," American Society of Gene and Cell Therapy, p. poster presentation, 2014.

[49] M. Hedman, J. Hartikainen, M. Syvanne, J. Stjernvall, A. Hedman, A. Kivela, E. Vanninen, H. Mussalo, E. Kauppila, S. Simula and 0. Narvanen, "Safety and Feasibility of Catheter-Based Local Intracoronary Vascular Endothelial Growth Factor Gene Transfer in the Prevention of Postangioplasty and In-Stent Restenosis and in the Treatment of Chronic Myocardial Ischemia. Phase II Results of the Kuopio," Circulation, vol. 107, pp. 2677-2683, 2003.

[50] M. G. Katz, A. S. Fargnoli, A. P. Kendle, R. J. Hajjar and C. R. Bridges, "Gene Therapy in Cardiac Surgery: Clinical Trials, Challenges and Perspectives," Ann Thorac Surg, vol. 101, pp. 2407-2416, 2016.

[51] P. Kolsut, M. Malecki, P. Zelazny, B. Teresiriska, P. Firek, P. Janik and Z. Religa, "Gene therapy of coronary artery disease with phvegf165—early outcome," Kardiol Pol, vol. 59, pp. 373-384, 2003.

[52] M. Ruel, R. S. Beanlands, M. Lortie, V. Chan, N. Camack, E. J. Suuronen, F. D. Rubens, J. N. DaSilva, F. W. Sellke, D. J. Stewart and T. G. Mesana, "Concomitant treatment with oral L-arginine improves the efficacy of surgical angiogenesis in patients with severe diffuse coronary artery disease: the Endothelial Modulation in Angiogenic Therapy randomized controlled trial," J Thorac Cardiovasc Surg, vol. 135, pp. 762-770, 2008.

[53] S. T. Pleger, C. Shan, J. Ksienzyk, R. Bekeredjian, P. Boekstegers, R. Hinkel, S. Schinkel, B. Leuchs, J. Ludwig, G. Qiu and C. Weber, "Cardiac AAV9-S100A1 gene therapy rescues post-ischemic heart failure in a preclinical large animal model," Sci Transl Med, vol. 3, no. 92, pp. 92ra64-92ra64, 2011.

[54] R. J. Lee, M. L. Springer, W. E. Blanco-Bose, R. Shaw, P. C. Ursell and H. M. Blau, "VEGF Gene Delivery to Myocardium: Deleterious Effects of Unregulated Expression," Circulation, vol. 102, pp. 898-901, 2000.

[55] J. J. Lopez, R. Laham, A. Stamler, J. D. Pearlman, S. Bunting, A. Kaplan, J. P. Carrozza, F. W. Sellke and M. Simons, "VEGF administration in chronic myocardial ischemia in pigs," Cardiovasc Res, pp. 272-281, 1998.

[56] M. Katz, A. Fargnoli, R. Williams and C. Bridges, "Gene Therapy Delivery Systems for Enhancing Viral and Nonviral Vectors for Cardiac Diseases:and Nonviral Vectors for Cardiac Diseases: Current Concepts and Future Applications," Human Gene Ther, vol. 24, pp. 914-927, 2013.

[57] Brinks H, D. Rohde, M. Voelkers, G. Qiu and S. Pleger, "S100A1 genetically targeted therapy reverses dysfunction of human failing cardiomyocytes," J Am Coll Cardiol, vol. 58, no. 9, pp. 966-973, 2011.

[58] F. J. Giordano, "Retrograde coronary perfusion: a superior route to deliver therapeutics to the heart?," J Am Coll Cardiol, vol. 42, no. 6, pp. 1129-1131, 2003.

[59] Y. Wang, F. Wang, R. Wang, P. Zhao and Q. Xia, "2A self-cleaving peptide-based multi-gene expression system in the silkworm Bombyx mori," Sci Rep, vol. 5, no. 16273, pp. 1-10, 2015.

[60] M. C. Scimia, A. M. Gumpert and W. J. Koch, "Cardiovascular gene therapy for myocardial infarction," Expert Opin Biol Ther, vol. 14, no. 2, pp. 183-195, 2014.

[61] I. Marenholz, C. W. Heizmann, G. Fritz, "S100 proteins in mouse and man: from evolution to function and pathology (including an update of the nomenclature)," Biochem Biophys Res Commun. vol. 322, no. 4, pp. 1111-22, 2004.

[62] T. Nagasawa, "CXCL12/SDF-1 and CXCR4," Front. Immunol, vol. 6, pp. 301, 2015.

[63] David I.R. Holmes, I. Zachary, "The Vascular Endothelial Growth Factor (VEGF) Family: Angiogenic Factors in Health and Disease." Genome Biol. Vol. 6, no.2, pp. 209, (2005).

[64] S. Chen, J. Chen, P Huang, XL Meng, . Clayton, JS Shen, PA Graybum, "Myocardial regeneration in adriamycin cardiomyopathy by nuclear expression of GLP1 using ultrasound targeted microbubble destruction." Biochem Biophys Res Commun. Vol. 458, no. 4, pp. 823-9, 2015.

[65] C.R. Mayer, N. A. Geis, H. A. Katus, R. Bekeredjian, "Ultrasound targeted microbubble destruction for drug and gene delivery." Expert Opin Drug Deliv., vol. 5, no.10, pp.1121-38, 2008.

SEQUENCE LISTING

<160> NUMBER OF SEQ ID NOS: 127

<210> SEQ ID NO 1
<211> LENGTH: 5350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaatacgg actttccatt     300
gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctcccccccc     540
tccccacccc caatttttgta tttatttatt ttttaattat tttgtgcagc gatggggcg      600 gggggggggg gggcgcgcgc caggcggggc ggggcggggc gaggggcggg gcggggcgag     660
gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcgggcg ggacggccct tctcctccgg gctgtaatta     900
gcgcttggtt taatgacggc tcgtttcttt tctgtggctg cgtgaaagcc ttaaagggct     960
ccgggagggc cctttgtgcg gggggagcg gctcgggggg tgcgtgcgtg tgtgtgtgcg    1020
tggggagcgc cgcgtgcggc ccgcgctgcc cggcggctgt gagcgctgcg ggcgcggcgc    1080
```

-continued

| | | | | |
|---|---|---|---|---|
| ggggctttgt | gcgctccgcg | tgtgcgcgag | gggagcgcgg | ccggggggcgg | tgccccgcgg | 1140 |
| tgcggggggg | ctgcgagggg | aacaaaggct | gcgtgcgggg | tgtgtgcgtg | ggggggtgag | 1200 |
| caggggggtgt | gggcgcggcg | gtcgggctgt | aaccccccccc | tgcacccccc | tccccgagtt | 1260 |
| gctgagcacg | gcccggcttc | gggtgcgggg | ctccgtgcgg | ggcgtggcgc | ggggctcgcc | 1320 |
| gtgccgggcg | gggggtggcg | gcaggtgggg | gtgccgggcg | gggcggggcc | gcctcgggcc | 1380 |
| ggggagggct | cggggggaggg | gcgcggcggc | cccggagcgc | cggcggctgt | cgaggcgcgg | 1440 |
| cgagccgcag | ccattgcctt | ttatggtaat | cgtgcgagag | ggcgcaggga | cttcctttgt | 1500 |
| cccaaatctg | gcggagccga | aatctgggag | gcgccgccgc | accccctcta | gcgggcgcgg | 1560 |
| gcgaagcggt | gcggcgccgg | caggaaggaa | atgggcgggg | agggccttcg | tgcgtcgccg | 1620 |
| cgccgccgtc | cccttctcca | tctccagcct | cggggctgcc | gcaggggac | ggctgccttc | 1680 |
| ggggggggacg | gggcagggcg | gggttcggct | tctggcgtgt | gaccggcggc | tctagagcct | 1740 |
| ctgctaacca | tgttcatgcc | ttcttctttt | tcctacagct | cctgggcaac | gtgctggttg | 1800 |
| ttgtgctgtc | tcatcatttt | ggcaaagaat | tccctgcagg | aaattgagcc | cgcagcctcc | 1860 |
| cgcttcgctc | tctgctcctc | ctgttcgaca | gtcagccgca | tcttcttttg | cgtcgccagc | 1920 |
| cgagccacat | cgctcagaca | ccgctagcat | gggcagcgaa | ctggaaaccg | ccatggagac | 1980 |
| tttgataaat | gttttccacg | cgcatagcgg | caaagaaggg | gacaagtaca | agctgtcaaa | 2040 |
| aaaggagctg | aaagaactgc | tgcagaccga | attgagcggc | ttcctggacg | ctcagaaaga | 2100 |
| tgtcgatgcc | gtcgacaaag | tgatgaaaga | gcttgacgag | aacggtgacg | gtgaagtcga | 2160 |
| ttttcaggaa | tatgtggtgc | tggtggccgc | ccttactgta | gcatgcaaca | atttcttttg | 2220 |
| ggaaaattca | agagccaaga | gggcaccggt | gaaacagact | ttgaattttg | accttctgaa | 2280 |
| gttggcagga | gacgttgagt | ccaaccctgg | gcccatgaat | gccaaggtcg | ttgtggtgct | 2340 |
| tgtacttgtg | ctgactgctc | tgtgtctgag | cgacggaaaa | ccagtctccc | tcagctacag | 2400 |
| gtgcccatgc | cgattcttcg | aatctcatgt | ggcccgggcc | aatgtgaagc | acttgaaaat | 2460 |
| cctgaataca | cccaactgcg | cgttgcagat | cgtggcccgc | ctgaaaaata | taataggca | 2520 |
| ggtatgtatc | gatccaaagc | ttaagtggat | ccaggagtat | ctggaaaagg | ctctcaataa | 2580 |
| ataaatcgat | tacgctcctc | tactctttga | dacatcactg | gcctataata | aatgggttaa | 2640 |
| tttatgtaac | aaaattgcct | tggcttgtta | acttttattag | acattctgat | gttttgcattg | 2700 |
| tgtaaatact | gttgtattgg | aaaagcgtgc | caagatggat | tattgtaatt | cagtgtcttt | 2760 |
| tttagtagcg | tcacgtgcca | aacactgtta | gtcacagagg | gcatgagaca | gcctgtgctg | 2820 |
| gaacagctca | gttcataggg | ctatggagat | ggggagaaag | gggcgcttct | gtcagagaca | 2880 |
| agctgtggtc | tgggaaggcc | ttagcactaa | aagcaccaca | atgagaagca | accgccagaa | 2940 |
| gcagggcccg | caggcctttg | ttccagctgc | aaagagaaag | gaaaaagtgg | ggaataagag | 3000 |
| ttggggctgc | ggagggggtg | gggagcattg | tgcaggttcc | gtacttgaac | agaaagcagg | 3060 |
| gaccaacaca | aggaaggctc | gagctggcgg | aataggttcc | aatctgtcgc | ggccgcatta | 3120 |
| ccctgttatc | cctaatctcg | tttaactatg | actctcttaa | ggtagccaaa | ttccggaact | 3180 |
| ataaattgcg | ttgcgctcac | tgcccgcttt | ccagtcggga | aacctgtcgt | gccagctgca | 3240 |
| taaatgaatc | ggccaacgcg | cggggagagg | cggtttgcgt | attgggcgcg | cttccgcttc | 3300 |
| ctcgctcact | gactcgctgc | gctcggtcgt | tcggctgcgg | cgagcggtat | cagctcactc | 3360 |
| aaaggcggta | atacggttat | ccacagaatc | aggggataac | gcaggaaaga | acatgtgagc | 3420 |
| aaaaggccag | caaaaggcca | ggaaccgtaa | aaaggccgcg | ttgctggcgt | ttttccatag | 3480 |

| | |
|---|---|
| gctccgcccc cctgacgagc atcacaaaaa tcgacgctca agtcagaggt ggcgaaaccc | 3540 |
| gacaggacta taaagatacc aggcgtttcc ccctggaagc tccctcgtgc gctctcctgt | 3600 |
| tccgaccctg ccgcttaccg gatacctgtc cgcctttctc ccttcgggaa gcgtggcgct | 3660 |
| ttctcatagc tcacgctgta ggtatctcag ttcggtgtag gtcgttcgct ccaagctggg | 3720 |
| ctgtgtgcac gaaccccccg ttcagcccga ccgctgcgcc ttatccggta actatcgtct | 3780 |
| tgagtccaac ccgtaagac acgacttatc gccactggca gcagccactg gtaacaggat | 3840 |
| tagcagagcg aggtatgtag gcggtgctac agagttcttg aagtggtggc ctaactacgg | 3900 |
| ctacactaga agaacagtat ttggtatctg cgctctgctg aagccagtta ccttcggaaa | 3960 |
| aagagttggt agctcttgat ccggcaaaca accaccgct ggtagcggtg gttttttgt | 4020 |
| ttgcaagcag cagattacgc gcagaaaaaa aggatctcaa gaagatcctt tgatcttttc | 4080 |
| tacggggtct gacgctcagt ggaacgaaaa ctcacgttaa gggattttgg tcatgagatt | 4140 |
| atcaaaaagg atcttcacct agatcctttt aaattaaaaa tgaagtttta atcaatcta | 4200 |
| aagtatatat gagtaaactt ggtctgacat gcgcatctga cgctcagtgg aacgaaaact | 4260 |
| cacgttaagg gattttggtc atgcctcaga agaactcgtc aagaaggcga tagaaggcga | 4320 |
| tgcgctgcga atcgggagcg gcgataccgt aaagcacgag gaagcggtca gcccattcgc | 4380 |
| cgccaagctc ttcagcaata tcacgggtag ccaacgctat gtcctgatag cggtccgcca | 4440 |
| cacccagccg gccacagtcg atgaatccag aaaagcggcc attttccacc atgatattcg | 4500 |
| gcaagcaggc atcgccatgg gtcacgacga gatcctcgcc gtcgggcatg cgcgccttga | 4560 |
| gcctggcgaa cagttcggct ggcgcgagcc cctgatgctc ttcgtccaga tcatcctgat | 4620 |
| cgacaagacc ggcttccatc cgagtacgtg ctcgctcgat gcgatgtttc gcttggtggt | 4680 |
| cgaatgggca ggtagccgga tcaagcgtat gcagccgccg cattgcatca gccatgatgg | 4740 |
| atactttctc ggcaggagca aggtgagatg acaggagatc ctgccccggc acttcgccca | 4800 |
| atagcagcca gtcccttccc gcttcagtga caacgtcgag cacagctgcg caaggaacgc | 4860 |
| ccgtcgtggc cagccacgat agccgcgctg cctcgtcctg cagttcattc agggcaccgg | 4920 |
| acaggtcggt cttgacaaaa agaaccgggc gcccctgcgc tgacagccgg aacacggcgg | 4980 |
| catcagagca gccgattgtc tgttgtgccc agtcatagcc gaatagcctc tccacccaag | 5040 |
| cggccggaga acctgcgtgc aatccatctt gttcaatcat gcgaaacgat cctcattcat | 5100 |
| ttatcagggt tattgtctca tgagcggata catatttgaa tgtatttagg ctgagcatct | 5160 |
| atgtcgggtc cggagaaaga ggtaatgaaa tggcaggcgc ctttttcgtt agatatgtag | 5220 |
| taagtatctt aatatacagc tttatctgtt ttttaagata cttactactt tccttagtgg | 5280 |
| aaactattag tggctgttaa ttaagctagt actacccaag atttgacaga atgcatcgtt | 5340 |
| tgcattcgaa | 5350 |

<210> SEQ ID NO 2
<211> LENGTH: 5350
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 2

| | |
|---|---|
| ctagcatgaa tgccaaggtc gttgtggtgc ttgtacttgt gctgactgct ctgtgtctga | 60 |

```
gcgacggaaa accagtctcc ctcagctaca ggtgcccatg ccgattcttc gaatctcatg      120
tggcccgggc caatgtgaag cacttgaaaa tcctgaatac acccaactgc gcgttgcaga      180
tcgtggcccg cctgaaaaat aataataggc aggtatgtat cgatccaaag cttaagtgga      240
tccaggagta tctggaaaag gctctcaata aaagagccaa gagggcaccg gtgaaacaga      300
ctttgaattt tgaccttctg aagttggcag gagacgttga gtccaaccct gggcccatgg      360
gcagcgaact ggaaaccgcc atggagactt tgataaatgt tttccacgcg catagcggca      420
aagaagggga caagtacaag ctgtcaaaaa aggagctgaa agaactgctg cagaccgaat      480
tgagcggctt cctggacgct cagaaagatg tcgatgccgt cgacaaagtg atgaaagagc      540
ttgacgagaa cggtgacggt gaagtcgatt ttcaggaata tgtggtgctg gtggccgccc      600
ttactgtagc atgcaacaat ttcttttggg aaaattcata aatcgattac gctcctctac      660
tctttgagac atcactggcc tataataaat gggttaattt atgtaacaaa attgccttgg      720
cttgttaact ttattagaca ttctgatgtt tgcattgtgt aaatactgtt gtattggaaa      780
agcgtgccaa gatggattat tgtaattcag tgtctttttt agtagcgtca cgtgccaaac      840
actgttagtc acagagggca tgagacagcc tgtgctggaa cagctcagtt catagggcta      900
tggagatggg gagaaagggg cgcttctgtc agagacaagc tgtggtctgg aaggccttag      960
gcactaaaag caccacaatg agaagcaacc gccagaagca gggcccgcag gcctttgttc     1020
cagctgcaaa gagaaaggaa aaagtgggga ataagagttg gggctgcgga gggggtgggg     1080
agcattgtgc aggttccgta cttgaacaga aagcagggac caacacaagg aaggctcgag     1140
ctggcggaat aggttccaat ctgtcgcggc cgcattaccc tgttatccct aatctcgttt     1200
aactatgact ctcttaaggt agccaaattc cggaactata aattgcgttg cgctcactgc     1260 ccgcttttcca gtcgggaaac ctgtcgtgcc agctgcataa atgaatcggc caacgcgcgg     1320
ggagaggcgg tttgcgtatt gggcgcgctt ccgcttcctc gctcactgac tcgctgcgct     1380
cggtcgttcg gctgcggcga gcggtatcag ctcactcaaa ggcggtaata cggttatcca     1440
cagaatcagg ggataacgca ggaaagaaca tgtgagcaaa aggccagcaa aaggccagga     1500
accgtaaaaa ggccgcgttg ctggcgtttt tccataggct ccgcccccct gacgagcatc     1560
acaaaaatcg acgctcaagt cagaggtggc gaaacccgac aggactataa agataccagg     1620
cgtttccccc tggaagctcc ctcgtgcgct ctcctgttcc gaccctgccg cttaccggat     1680
acctgtccgc ctttctccct tcgggaagcg tggcgctttc tcatagctca cgctgtaggt     1740
atctcagttc ggtgtaggtc gttcgctcca agctgggctg tgtgcacgaa ccccccgttc     1800
agcccgaccg ctgcgcctta tccggtaact atcgtcttga gtccaacccg gtaagacacg     1860
acttatcgcc actggcagca gccactggta acaggattag cagagcgagg tatgtaggcg     1920
gtgctacaga gttcttgaag tggtggccta actacggcta cactagaaga acagtatttg     1980
gtatctgcgc tctgctgaag ccagttacct tcggaaaaag agttggtagc tcttgatccg     2040
gcaaacaaac caccgctggt agcggtggtt tttttgtttg caagcagcag attacgcgca     2100
gaaaaaaagg atctcaagaa gatcctttga tcttttctac ggggtctgac gctcagtgga     2160
acgaaaactc acgttaaggg attttggtca tgagattatc aaaaaggatc ttcacctaga     2220
tccttttaaa ttaaaaatga agttttaaat caatctaaag tatatatgag taaacttggt     2280
ctgacatgcg catctgacgc tcagtggaac gaaaactcac gttaagggat tttggtcatg     2340
cctcagaaga actcgtcaag aaggcgatag aaggcgatgc gctgcgaatc gggagcggcg     2400
ataccgtaaa gcacgaggaa gcggtcagcc cattcgccgc caagctcttc agcaatatca     2460
```

```
cgggtagcca acgctatgtc ctgatagcgg tccgccacac ccagccggcc acagtcgatg    2520
aatccagaaa agcggccatt ttccaccatg atattcggca agcaggcatc gccatgggtc    2580
acgacgagat cctcgccgtc gggcatgcgc gccttgagcc tggcgaacag ttcggctggc    2640
gcgagcccct gatgctcttc gtccagatca tcctgatcga caagaccggc ttccatccga    2700
gtacgtgctc gctcgatgcg atgtttcgct tggtggtcga atgggcaggt agccggatca    2760
agcgtatgca gccgccgcat tgcatcagcc atgatggata cttctcggc aggagcaagg    2820 tgagatgaca ggagatcctg ccccggcact cgcccaata gcagccagtc ccttcccgct    2880
tcagtgacaa cgtcgagcac agctgcgcaa ggaacgcccg tcgtggccag ccacgatagc    2940
cgcgctgcct cgtcctgcag ttcattcagg gcaccggaca ggtcggtctt gacaaaaaga    3000
accgggcgcc cctgcgctga cagccggaac acggcggcat cagagcagcc gattgtctgt    3060
tgtgcccagt catagccgaa tagcctctcc acccaagcgg ccggagaacc tgcgtgcaat    3120
ccatcttgtt caatcatgcg aaacgatcct cattcattta tcagggttat tgtctcatga    3180
gcggatacat atttgaatgt atttaggctg agcatctatg tcgggtgcgg agaaagaggt    3240
aatgaaatgg caggcgcctt tttcgttaga tatgtagtaa gtatcttaat atacagcttt    3300
atctgttttt taagatactt actactttc ttagtggaaa ctattagtgg ctgttaatta    3360
agctagtact acccaagatt tgacagaatg catcgtttgc attcgaataa ctataacggt    3420
cctaaggtag cgacgtacga accgttgggc gcgcctgggg atagcgatcg ctgctggcgc    3480
ggtccgctat gaggtctctg atagaccaca gacgcgtcga cattgattat tgactagtta    3540
ttaatagtaa tcaattacgg ggtcattagt tcatagccca tatatggagt tccgcgttac    3600
ataacttacg gtaaatggcc cgcctggctg accgcccaac gaccccgccc cattgacgtc    3660
aataatgacg tatgttccca tagtaacgcc aatagggact ttccattgac gtcaatgggt    3720
ggactattta cggtaaactg cccacttggc agtacatcaa gtgtatcata tgccaagtac    3780
gccccctatt gacgtcaatg acggtaaatg gcccgcctgg cattatgccc agtacatgac    3840
cttatgggac tttcctactt ggcagtacat ctacgtatta gtcatcgcta ttaccatggg    3900
tcgaggtgag ccccacgttc tgcttcactc tccccatctc ccccccctcc ccaccccaa    3960 ttttgtattt atttattttt taattatttt gtgcagcgat gggggcgggg gggggggggg    4020
cgcgcgccag gcggggcggg gcggggcgag gggcggggcg gggcgaggcg gagaggtgcg    4080
gcggcagcca atcagagcgg cgcgctccga aagtttcctt ttatggcgag gcggcggcgg    4140 cggcggcccct ataaaaagcg aagcgcgcgg cgggcgggag tcgctgcgtt gccttcgccc    4200
cgtgccccgc tccgcgccgc ctcgcgccgc ccgccccggc tctgactgac cgcgttactc    4260
ccacaggtga gcgggcggga cggcccttct cctccgggct gtaattagcg cttggtttaa    4320
tgacggctcg tttcttttct gtggctgcgt gaaagcctta aagggctccg ggagggccct    4380
ttgtgcgggg gggagcggct cgggggggtgc gtgcgtgtgt gtgtgcgtgg ggagcgccgc    4440
gtgcggcccg cgctgcccgg cggctgtgag cgctgcgggc gcggcgcggg gctttgtgcg    4500
ctccgcgtgt gcgcgagggg agcgcggccg gggcggtgc ccgcggtgc ggggggctg    4560 cgaggggaac aaaggctgcg tgcggggtgt gtgcgtgggg gggtgagcag ggggtgtggg    4620
cgcggcggtc gggctgtaac cccccctgc accccctcc ccgagttgct gagcacggcc    4680
cggcttcggg tgcgggctc cgtgcgggggc gtggcgcggg gctcgccgtg ccggcgggg    4740 ggtggcggca ggtgggggtg ccgggcgggg cggggccgcc tcgggccggg gagggctcgg    4800
```

| | |
|---|---|
| gggaggggcg cggcggcccc ggagcgccgg cggctgtcga ggcgcggcga gccgcagcca | 4860 |
| ttgcctttta tggtaatcgt gcgagagggc gcagggactt cctttgtccc aaatctggcg | 4920 |
| gagccgaaat ctgggaggcg ccgccgcacc ccctctagcg ggcgcgggcg aagcggtgcg | 4980 |
| gcgccggcag gaaggaaatg ggcggggagg gccttcgtgc gtcgccgcgc cgccgtcccc | 5040 |
| ttctccatct ccagcctcgg ggctgccgca ggggacggc tgccttcggg ggggacgggg | 5100 |
| cagggcgggg ttcggcttct ggcgtgtgac cggcggctct agagcctctg ctaaccatgt | 5160 |
| tcatgccttc ttcttttcc tacagctcct gggcaacgtg ctggttgttg tgctgtctca | 5220 |
| tcatttggc aaagaattcc ctgcaggaaa ttgagcccgc agcctcccgc ttcgctctct | 5280 |
| gctcctcctg ttcgacagtc agccgcatct tcttttgcgt cgccagccga gccacatcgc | 5340 |
| tcagacaccg | 5350 |

<210> SEQ ID NO 3
<211> LENGTH: 5641
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3

| | |
|---|---|
| ctagcatgaa tgccaaggtc gttgtggtgc ttgtacttgt gctgactgct ctgtgtctga | 60 |
| gcgacggaaa accagtctcc ctcagctaca ggtgcccatg ccgattcttc gaatctcatg | 120 |
| tggcccgggc caatgtgaag cacttgaaaa tcctgaatac acccaactgc gcgttgcaga | 180 |
| tcgtggcccg cctgaaaaat aataataggc aggtatgtat cgatccaaag cttaagtgga | 240 |
| tccaggagta tctggaaaag gctctcaata aaagagccaa gagggcaccg gtgaaacaga | 300 |
| ctttgaattt tgaccttctg aagttggcag agacgttga gtccaaccct gggcccatga | 360 |
| attttctgct ctcttgggtg cactggtcac tggcactgct gctgtatctg caccatgcaa | 420 |
| aatggtccca agcagctccc atggcagagg aggtggaca gaatcatcat gaggttgtca | 480 |
| aatttatgga tgtctaccag cggagctact gccacccaat tgagacgttg gtagacattt | 540 |
| tcaggaata tccagacgag attgagtaca ttttcaagcc tagctgtgtg cccttgatgc | 600 |
| gatgcggtgg ctgttgcaat gatgagggac tcgagtgtgt ccccaccgag aaagcaata | 660 |
| taccatgca atcatgcga atcaaacccc accagggcca gcatatcggc gagatgtctt | 720 |
| tcttgcaaca taacaaatgc gagtgtcggc caaagaagga cagggctcgc caggaaaatc | 780 |
| cctgtggtcc ttgttcagag cgcaggaagc atcttttcgt ccaggatccg cagacttgta | 840 |
| aatgttcatg caagaatacc gattctaggt gtaaggcgag gcaactcgag cttaacgaga | 900 |
| gaacctgtag gtgtgacaaa cctagaagat aaatcgatta cgctcctcta ctctttgaga | 960 |
| catcactggc ctataataaa tgggttaatt tatgtaacaa aattgccttg gcttgttaac | 1020 |
| tttattagac attctgatgt ttgcattgtg taaatactgt tgtattggaa aagcgtgcca | 1080 |
| agatggatta ttgtaattca gtgtcttttt tagtagcgtc acgtgccaaa cactgttagt | 1140 |
| cacagagggc atgagacagc ctgtgctgga acagctcagt tcatagggct atggagatgg | 1200 |
| ggagaaaggg gcgcttctgt cagagacaag ctgtggtctg ggaaggcctt agcactaaaa | 1260 |
| gcaccacaat gagaagcaac cgccagaagc agggcccgca ggcctttgtt ccagctgcaa | 1320 |
| agagaaagga aaaagtgggg aataagagtt ggggctgcgg aggggtggg gagcattgtg | 1380 |
| caggttccgt acttgaacag aaagcaggga ccaacacaag gaaggctcga gctggcggaa | 1440 |

```
taggttccaa tctgtcgcgg ccgcattacc ctgttatccc taatctcgtt taactatgac   1500
tctcttaagg tagccaaatt ccggaactat aaattgcgtt gcgctcactg cccgctttcc   1560
agtcgggaaa cctgtcgtgc cagctgcata atgaatcggc caacgcgcg gggagaggcg   1620 gtttgcgtat tgggcgcgct tccgcttcct cgctcactga ctcgctgcgc tcggtcgttc   1680
ggctgcggcg agcggtatca gctcactcaa aggcggtaat acggttatcc acagaatcag   1740
gggataacgc aggaaagaac atgtgagcaa aaggccagca aaaggccagg aaccgtaaaa   1800
aggccgcgtt gctggcgttt ttccataggc tccgcccccc tgacgagcat cacaaaaatc   1860
gacgctcaag tcagaggtgg cgaaacccga caggactata agataccag gcgtttcccc   1920 ctggaagctc cctcgtgcgc tctcctgttc cgaccctgcc gcttaccgga tacctgtccg   1980
cctttctccc ttcgggaagc gtggcgcttt ctcatagctc acgctgtagg tatctcagtt   2040
cggtgtaggt cgttcgctcc aagctgggct gtgtgcacga accccccgtt cagcccgacc   2100
gctgcgcctt atccggtaac tatcgtcttg agtccaaccc ggtaagacac gacttatcgc   2160
cactggcagc agccactggt aacaggatta gcagagcgag gtatgtaggc ggtgctacag   2220
agttcttgaa gtggtggcct aactacggct acactagaag aacagtattt ggtatctgcg   2280
ctctgctgaa gccagttacc ttcggaaaaa gagttggtag ctcttgatcc ggcaaacaaa   2340
ccaccgctgg tagcggtggt ttttttgttt gcaagcagca gattacgcgc agaaaaaaag   2400
gatctcaaga agatcctttg atcttttcta cggggtctga cgctcagtgg aacgaaaact   2460
cacgttaagg gattttggtc atgagattat caaaaaggat cttcacctag atcctttttaa   2520 attaaaaatg aagttttaaa tcaatctaaa gtatatatga gtaaacttgg tctgacatgc   2580
gcatctgacg ctcagtggaa cgaaaactca cgttaaggga ttttggtcat gcctcagaag   2640
aactcgtcaa gaaggcgata gaaggcgatg cgctgcgaat cgggagcggc gataccgtaa   2700
agcacgagga gcggtcagc ccattcgccg ccaagctctt cagcaatatc acgggtagcc   2760
aacgctatgt cctgatagcg gtccgccaca cccagccggc cacagtcgat gaatccagaa   2820
aagcggccat tttccaccat gatattcggc aagcaggcat cgccatgggt cacgacgaga   2880
tcctcgccgt cgggcatgcg cgccttgagc ctggcgaaca gttcggctgg cgcgagcccc   2940
tgatgctctt cgtccagatc atcctgatcg acaagaccgg cttccatccg agtacgtgct   3000
cgctcgatgc gatgtttcgc ttggtggtcg aatgggcagg tagccggatc aagcgtatgc   3060
agccgccgca ttgcatcagc catgatggat actttctcgg caggagcaag gtgagatgac   3120
aggagatcct gccccggcac ttcgcccaat agcagccagt cccttcccgc ttcagtgaca   3180
acgtcgagca cagctgcgca aggaacgccc gtcgtggcca gccacgatag ccgcgctgcc   3240
tcgtcctgca gttcattcag ggcaccggac aggtcggtct tgacaaaaag aaccgggcgc   3300
ccctgcgctg acagccggaa cacggcggca tcagagcagc cgattgtctg ttgtgcccag   3360
tcatagccga atagcctctc cacccaagcg gccgagaaac ctgcgtgcaa tccatcttgt   3420
tcaatcatgc gaaacgatcc tcattcattt atcagggtta ttgtctcatg agcggataca   3480
tatttgaatg tatttaggct gagcatctat gtcgggtgcg gagaaagagg taatgaaatg   3540
gcaggcgcct ttttcgttag atatgtagta agtatcttaa tatacagctt tatctgtttt   3600
ttaagatact tactacttttt cttagtggaa actattagtg gctgttaatt aagctagtac   3660
tacccaagat ttgacagaat gcatcgtttg cattcgaata actataacgg tcctaaggta   3720
gcgacgtacg aaccgttggg cgcgcctggg gatagcgatc gctgctggcg cggtccgcta   3780
```

```
tgaggtctct gatagaccac agacgcgtcg acattgatta ttgactagtt attaatagta    3840
atcaattacg gggtcattag ttcatagccc atatatggag ttccgcgtta cataacttac    3900
ggtaaatggc ccgcctggct gaccgcccaa cgaccccgc ccattgacgt caataatgac     3960
gtatgttccc atagtaacgc caatagggac tttccattga cgtcaatggg tggactattt    4020
acggtaaact gcccacttgg cagtacatca agtgtatcat atgccaagta cgccccctat    4080
tgacgtcaat gacggtaaat ggcccgcctg gcattatgcc cagtacatga ccttatggga    4140
ctttcctact tggcagtaca tctacgtatt agtcatcgct attaccatgg gtcgaggtga    4200
gccccacgtt ctgcttcact ctccccatct ccccccctc cccaccccca attttgtatt    4260
tatttatttt ttaattattt tgtgcagcga tgggggcggg ggggggggg gcgcgcgcca    4320
ggcggggcgg ggcggggcga ggggcgggc ggggcgaggc ggagaggtgc ggcggcagcc   4380
aatcagagcg gcgcgctccg aaagtttcct tttatggcga ggcggcggcg gcggcggccc    4440
tataaaaagc gaagcgcgcg gcgggcggga gtcgctgcgt tgccttcgcc ccgtgccccg    4500
ctccgcgccg cctcgcgccg cccgcccgg ctctgactga ccgcgttact cccacaggtg     4560
agcgggcggg acggcccttc tcctccgggc tgtaattagc gcttggttta atgacggctc    4620
gttctttttc tgtggctgcg tgaaagcctt aaagggctcc gggagggccc tttgtgcggg    4680
ggggagcggc tcgggggtg cgtgcgtgtg tgtgtgcgtg gggagcgccg cgtgcggccc      4740
gcgctgcccg gcgctgtga gcgctgcggg cgcggcgcgg ggctttgtgc gctccgcgtg    4800
tgcgcgaggg gagcgcggcc ggggggcggtg ccccgcggtg cgggggggct gcgaggggaa    4860
caaaggctgc gtgcggggtg tgtgcgtggg gggtgagca gggggtgtgg gcgcggcggt     4920
cgggctgtaa ccccccctg caccccctc cccgagttgc tgagcacggc ccggcttcgg     4980
gtgcggggct ccgtgcgggg cgtggcgcgg ggctcgccgt gccgggcggg gggtggcggc    5040
aggtggggt gccgggcggg gcggggccgc ctcgggccgg ggagggctcg gggagggc     5100
gcggcggccc cggagcgccg gcggctgtcg aggcgcggcg agccgcagcc attgcctttt    5160
atggtaatcg tgcgagaggg cgcagggact tcctttgtcc caaatctggc ggagccgaaa    5220
tctgggaggc gccgccgcac cccctctagc gggcgcggg gaagcggtgc ggcgccggca    5280
ggaaggaaat gggcggggag ggccttcgtg cgtcgccgcg ccgccgtccc cttctccatc     5340
tccagcctcg gggctgccgc agggggacgg ctgccttcgg gggggacggg gcagggcggg   5400
gttcggcttc tggcgtgtga ccggcggctc tagagcctct gctaaccatg ttcatgcctt    5460
cttcttttc ctacagctcc tgggcaacgt gctggttgtt gtgctgtctc atcattttgg    5520
caaagaattc cctgcaggaa attgagcccg cagcctcccg cttcgctctc tgctcctcct    5580
gttcgacagt cagccgcatc ttcttttgcg tcgccagccg agccacatcg ctcagacacc    5640
g                                                                    5641
```

<210> SEQ ID NO 4
<211> LENGTH: 5641
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

```
taactataac ggtcctaagg tagcgacgta cgaaccgttg ggcgcgcctg gggatagcga     60
tcgctgctgg cgcggtccgc tatgaggtct ctgatagacc acagacgcgt cgacattgat    120
```

```
tattgactag ttattaatag taatcaatta cggggtcatt agttcatagc ccatatatgg      180
agttccgcgt tacataactt acggtaaatg cccgcctgg ctgaccgccc aacgacccc       240 gcccattgac gtcaataatg acgtatgttc ccatagtaac gccaataggg actttccatt    300
gacgtcaatg ggtggactat ttacggtaaa ctgcccactt ggcagtacat caagtgtatc    360
atatgccaag tacgcccct attgacgtca atgacggtaa atggcccgcc tggcattatg    420
cccagtacat gaccttatgg gactttccta cttggcagta catctacgta ttagtcatcg    480
ctattaccat gggtcgaggt gagccccacg ttctgcttca ctctccccat ctcccccccc    540
tccccacccc caattttgta tttatttatt ttttaattat tttgtgcagc gatgggggcg    600
gggggggggg gggcgcgcgc caggcggggc ggggcggggc gaggggcggg gcggggcgag    660
gcggagaggt gcggcggcag ccaatcagag cggcgcgctc cgaaagtttc cttttatggc    720
gaggcggcgg cggcggcggc cctataaaaa gcgaagcgcg cggcgggcgg gagtcgctgc    780
gttgccttcg ccccgtgccc cgctccgcgc cgcctcgcgc cgcccgcccc ggctctgact    840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct    960
ccgggagggc cctttgtgcg ggggggagcg gctcgggggg tgcgtgcgtg tgtgtgtgcg   1020
tggggagcgc cgcgtgcggc ccgcgctgcc cggcggctgt gagcgctgcg ggcgcggcgc   1080
ggggctttgt gcgctccgcg tgtgcgcgag gggagcgcgg ccggggcgg tgccccgcgg    1140 tgcggggggg ctgcgagggg aacaaaggct gcgtgcgggg tgtgtgcgtg ggggggtgag   1200 caggggtgt gggcgcggcg gtcgggctgt aaccccccc tgcaccccc tccccgagtt      1260 gctgagcacg gcccggcttc gggtgcgggg ctccgtgcgg ggcgtggcgc ggggctcgcc   1320
gtgccgggcg ggggtggcg gcaggtgggg gtgccgggcg gggcggggcc gcctcgggcc    1380
ggggagggct cggggaggg gcgcggcggc cccggagcgc cggcggctgt cgaggcgcgg    1440
cgagccgcag ccattgcctt ttatggtaat cgtgcgagag ggcgcaggga cttcctttgt   1500
cccaaatctg gcggagccga aatctgggag gcgccgccgc accccctcta gcgggcgcgg   1560
gcgaagcggt gcggcgccgg caggaaggaa atgggcgggg agggccttcg tgcgtcgccg   1620
cgccgccgtc cccttctcca tctccagcct cggggctgcc gcaggggac ggctgccttc    1680 gggggggacg gggcagggcg gggttcggct tctggcgtgt gaccggcggc tctagagcct   1740
ctgctaacca tgttcatgcc ttcttctttt tcctacagct cctgggcaac gtgctggttg   1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcat gaatttctg ctctcttggg tgcactggtc    1980
actggcactg ctgctgtatc tgcaccatgc aaaatggtcc caagcagctc ccatggcaga   2040
gggaggtgga cagaatcatc atgaggttgt caaatttatg gatgtctacc agcggagcta   2100
ctgccaccca attgagacgt tggtagacat ttttcaggaa tatccagacg agattgagta   2160
cattttcaag cctagctgtg tgcccttgat gcgatgcgt ggctgttgca atgatgaggg    2220
actcgagtgt gtccccaccg aggaaagcaa tataaccatg caaatcatgc gaatcaaacc   2280
ccaccagggc cagcatatcg gcgagatgtc tttcttgcaa cataacaaat gcgagtgtcg   2340
gccaaagaag gacagggctc gccaggaaaa tccctgtggt ccttgttcag agcgcaggaa   2400
gcatcttttc gtccaggatc cgcagacttg taaatgttca tgcaagaata ccgattctag   2460
```

```
gtgtaaggcg aggcaactcg agcttaacga gagaacctgt aggtgtgaca aacctagaag   2520
aagagccaag agggcaccgg tgaaacagac tttgaatttt gaccttctga agttggcagg   2580
agacgttgag tccaaccctg ggcccatgaa tgccaaggtc gttgtggtgc ttgtacttgt   2640
gctgactgct ctgtgtctga gcgacggaaa accagtctcc ctcagctaca ggtgcccatg   2700
ccgattcttc gaatctcatg tggcccgggc caatgtgaag cacttgaaaa tcctgaatac   2760
acccaactgc gcgttgcaga tcgtggcccg cctgaaaaat aataataggc aggtatgtat   2820
cgatccaaag cttaagtgga tccaggagta tctggaaaag gctctcaata aataaatcga   2880
ttacgctcct ctactctttg agacatcact ggcctataat aaatgggtta atttatgtaa   2940
caaaattgcc ttggcttgtt aactttatta gacattctga tgtttgcatt gtgtaaatac   3000
tgttgtattg gaaaagcgtg ccaagatgga ttattgtaat tcagtgtctt ttttagtagc   3060
gtcacgtgcc aaacactgtt agtcacagag gcatgagac agcctgtgct ggaacagctc   3120
agttcatagg gctatggaga tggggagaaa ggggcgcttc tgtcagagac aagctgtggt   3180
ctgggaaggc cttagcacta aaagcaccac aatgagaagc aaccgccaga agcagggccc   3240
gcaggccttt gttccagctg caaagagaaa ggaaaaagtg gggaataaga gttgggctg   3300 cggagggggt ggggagcatt gtgcaggttc cgtacttgaa cagaaagcag gaccaacac   3360 aaggaaggct cgagctggcg aataggttc caatctgtcg cggccgcatt accctgttat   3420
ccctaatctc gtttaactat gactctctta aggtagccaa attccggaac tataaattgc   3480
gttgcgctca ctgcccgctt ccagtcggg aaacctgtcg tgccagctgc ataaatgaat   3540
cggccaacgc gcggggagag gcggtttgcg tattgggcgc gcttccgctt cctcgctcac   3600
tgactcgctg cgctcggtcg ttcggctgcg gcgagcggta tcagctcact caaaggcggt   3660
aatacggtta tccacagaat cagggggataa cgcaggaaag aacatgtgag caaaaggcca   3720
gcaaaaggcc aggaaccgta aaaaggccgc gttgctggcg ttttccata ggctccgccc   3780 ccctgacgag catcacaaaa atcgacgctc aagtcagagg tggcgaaacc cgacaggact   3840
ataaagatac caggcgtttc ccctggaag ctccctcgtg cgctctcctg ttccgaccct   3900
gccgcttacc ggatacctgt ccgcctttct cccttcggga agcgtggcgc tttctcatag   3960
ctcacgctgt aggtatctca gttcggtgta ggtcgttcgc tccaagctgg gctgtgtgca   4020 cgaaccccc gttcagcccg accgctgcgc cttatccggt aactatcgtc ttgagtccaa   4080
cccggtaaga cacgacttat cgccactggc agcagccact ggtaacagga ttagcagagc   4140
gaggtatgta ggcggtgcta cagagttctt gaagtggtgg cctaactacg gctacactag   4200
aagaacagta tttggtatct gcgctctgct gaagccagtt accttcggaa aaagagttgg   4260
tagctcttga tccggcaaac aaaccaccgc tggtagcggt ggtttttttg tttgcaagca   4320
gcagattacg cgcagaaaaa aaggatctca agaagatcct ttgatctttt ctacggggtc   4380
tgacgctcag tggaacgaaa actcacgtta agggattttg gtcatgagat tatcaaaaag   4440
gatcttcacc tagatccttt taaattaaaa atgaagtttt aaatcaatct aaagtatata   4500
tgagtaaact tggtctgaca tgcgcatctg acgctcagtg gaacgaaaac tcacgttaag   4560
ggattttggt catgcctcag aagaactcgt caagaaggcg atagaaggcg atgcgctgcg   4620
aatcgggagc ggcgataccg taaagcacga ggaagcggtc agcccattcg ccgccaagct   4680
cttcagcaat atcacgggta gccaacgcta tgtcctgata gcggtccgcc acacccagcc   4740
ggccacagtc gatgaatcca gaaaagcggc cattttccac catgatattc ggcaagcagg   4800
catcgccatg ggtcacgacg agatcctcgc cgtcgggcat gcgcgccttg agcctggcga   4860
```

```
acagttcggc tggcgcgagc ccctgatgct cttcgtccag atcatcctga tcgacaagac    4920
cggcttccat ccgagtacgt gctcgctcga tgcgatgttt cgcttggtgg tcgaatgggc    4980
aggtagccgg atcaagcgta tgcagccgcc gcattgcatc agccatgatg gatactttct    5040
cggcaggagc aaggtgagat gacaggagat cctgccccgg cacttcgccc aatagcagcc    5100
agtcccttcc cgcttcagtg acaacgtcga gcacagctgc gcaaggaacg cccgtcgtgg    5160
ccagccacga tagccgcgct gcctcgtcct gcagttcatt cagggcaccg acaggtcgg     5220 tcttgacaaa aagaaccggg cgccctgcg ctgacagccg gaacacggcg gcatcagagc     5280
agccgattgt ctgttgtgcc cagtcatagc cgaatagcct ctccacccaa gcggccggag    5340
aacctgcgtg caatccatct tgttcaatca tgcgaaacga tcctcattca tttatcaggg    5400
ttattgtctc atgagcggat acatatttga atgtatttag gctgagcatc tatgtcgggt    5460
gcggagaaag aggtaatgaa atggcaggcg cctttttcgt tagatatgta gtaagtatct    5520
taatatacag ctttatctgt tttttaagat acttactact tttcttagtg gaaactatta    5580
gtggctgtta attaagctag tactacccaa gatttgacag aatgcatcgt ttgcattcga    5640
a                                                                    5641

<210> SEQ ID NO 5
<211> LENGTH: 5332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaataggg actttccatt     300
gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc     540 tccccacccc caattttgta tttatttatt ttttaattat tttgtgcagc gatggggcg     600 ggggggggg gggcgcgcgc caggcgggc ggggcgggc gagggcggg gcggggcgag        660 gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcggcg ggacggccct tctcctccgg gctgtaatta     900
gcgcttggtt taatgacggc tcgtttcttt tctgtggctg cgtgaaagcc ttaaagggct     960
cggggagggc cctttgtgcg gggggagcg gctcggggg tgcgtgcgtg tgtgtgtgcg     1020 tgggagcgc cgcgtgcggc ccgcgctgcc cggcggctgt gagcgctgcg ggcgcggcgc     1080
ggggctttgt gcgctccgcg tgtgcgcgag gggagcgcgg ccggggcgg tgcccgcgg     1140
```

```
tgcgggggg   ctgcgagggg   aacaaaggct   gcgtgcgggg   tgtgtgcgtg   gggggggtgag    1200 caggggggtgt  gggcgcggcg   gtcgggctgt   aaccccccc   tgcacccccc   tccccgagtt    1260
gctgagcacg   gcccggcttc   gggtgcgggg   ctccgtgcgg   ggcgtggcgc   ggggctcgcc    1320
gtgccgggcg   gggggtggcg   gcaggtgggg   gtgccgggcg   gggcggggcc   gcctcgggcc    1380
ggggagggct   cggggggaggg  gcgcggcggc   cccggagcgc   cggcggctgt   cgaggcgcgg    1440
cgagccgcag   ccattgcctt   ttatggtaat   cgtgcgagag   ggcgcaggga   cttcctttgt    1500
cccaaatctg   gcggagccga   aatctgggag   gcgccgccgc   acccctcta   gcgggcgcgg    1560 gcgaagcggt   gcggcgccgg   caggaaggaa   atgggcgggg   agggccttcg   tgcgtcgccg    1620
cgccgccgtc   cccttctcca   tctccagcct   cggggctgcc   gcaggggggac   ggctgccttc    1680 gggggggacg   gggcagggcg   gggttcggct   tctggcgtgt   gaccggcggc   tctagagcct    1740
ctgctaacca   tgttcatgcc   ttcttctttt   tcctacagct   cctgggcaac   gtgctggttg    1800
ttgtgctgtc   tcatcatttt   ggcaaagaat   tccctgcagg   aaattgagcc   cgcagcctcc    1860
cgcttcgctc   tctgctcctc   ctgttcgaca   gtcagccgca   tcttcttttg   cgtcgccagc    1920
cgagccacat   cgctcagaca   ccgctagcat   gggcagcgaa   ctggaaaccg   ccatggagac    1980
tttgataaat   gttttccacg   cgcatagcgg   caaagaaggg   gacaagtaca   agctgtcaaa    2040
aaaggagctg   aaagaactgc   tgcagaccga   attgagcggc   ttcctggacg   ctcagaaaga    2100
tgtcgatgcc   gtcgacaaag   tgatgaaaga   gcttgacgag   aacggtgacg   gtgaagtcga    2160
ttttcaggaa   tatgtggtgc   tggtggccgc   ccttactgta   gcatgcaaca   atttctttg    2220 ggaaaattca   ggaagcggag   ctactaactt   cagcctgctg   aagcaggctg   gagacgtgga    2280
ggagaaccct   ggacctatga   atgccaaggt   cgttgtggtg   cttgtacttg   tgctgactgc    2340
tctgtgtctg   agcgacggaa   aaccagtctc   cctcagctac   aggtgcccat   gccgattctt    2400
cgaatctcat   gtggcccggg   ccaatgtgaa   gcacttgaaa   atcctgaata   cacccaactg    2460
cgcgttgcag   atcgtggccc   gcctgaaaaa   taataatagg   caggtatgta   tcgatccaaa    2520
gcttaagtgg   atccaggagt   atctggaaaa   ggctctcaat   aaataaatcg   attacgctcc    2580
tctactcttt   gagacatcac   tggcctataa   taaatgggtt   aatttatgta   acaaaattgc    2640
cttggcttgt   taactttat   agacattctg   atgtttgcat   tgtgtaaata   ctgttgtatt    2700
ggaaaagcgt   gccaagatgg   attattgtaa   ttcagtgtct   tttttagtag   cgtcacgtgc    2760
caaacactgt   tagtcacaga   gggcatgaga   cagcctgtgc   tggaacagct   cagttcatag    2820
ggctatggag   atgggagaa   aggggcgctt   ctgtcagaga   caagctgtgg   tctgggaagg    2880
ccttagcact   aaaagcacca   caatgagaag   caaccgccag   aagcagggcc   cgcaggcctt    2940
tgttccagct   gcaaagagaa   aggaaaaagt   ggggaataag   agttggggct   gcggagggg    3000 tggggagcat   tgtgcaggtt   ccgtacttga   acagaaagca   gggaccaaca   caaggaaggc    3060
tcgagctggc   ggaataggtt   ccaatctgtc   gcggccgcat   taccctgtta   tccctaatct    3120
cgtttaacta   tgactctctt   aaggtagcca   aattccggaa   ctataaattg   cgttgcgctc    3180
actgcccgct   ttccagtcgg   gaaacctgtc   gtgccagctg   cataaatgaa   tcggccaacg    3240
cgcggggaga   ggcggtttgc   gtattgggcg   cgcttccgct   tcctcgctca   ctgactcgct    3300
gcgctcggtc   gttcggctgc   ggcgagcggt   atcagctcac   tcaaaggcgg   taatacggtt    3360
atccacagaa   tcaggggata   acgcaggaaa   gaacatgtga   gcaaaaggcc   agcaaaaggc    3420
caggaaccgt   aaaaaggccg   cgttgctggc   gtttttccat   aggctccgcc   ccctgacga    3480 gcatcacaaa   aatcgacgct   caagtcagag   gtggcgaaac   ccgacaggac   tataaagata    3540
```

```
ccaggcgttt cccctggaa gctccctcgt gcgctctcct gttccgaccc tgccgcttac    3600
cggataccgt tccgcctttc tcccttcggg aagcgtggcg ctttctcata gctcacgctg    3660
taggtatctc agttcggtgt aggtcgttcg ctccaagctg gctgtgtgc acgaacccc     3720 cgttcagccc gaccgctgcg ccttatccgg taactatcgt cttgagtcca acccggtaag    3780
acacgactta tcgccactgg cagcagccac tggtaacagg attagcagag cgaggtatgt    3840
aggcggtgct acagagttct tgaagtggtg cctaactac ggctacacta gaagaacagt    3900
atttggtatc tgcgctctgc tgaagccagt taccttcgga aaaagagttg gtagctcttg    3960
atccggcaaa caaccaccg ctggtagcgg tggttttttt gtttgcaagc agcagattac    4020
gcgcagaaaa aaggatctc aagaagatcc tttgatcttt tctacggggt ctgacgctca    4080
gtggaacgaa actcacgtt aagggatttt ggtcatgaga ttatcaaaaa ggatcttcac    4140
ctagatcctt ttaaattaaa aatgaagttt taaatcaatc taaagtatat atgagtaaac    4200
ttggtctgac atgcgcatct gacgctcagt ggaacgaaaa ctcacgttaa gggattttgg    4260
tcatgcctca gaagaactcg tcaagaaggc gatagaaggc gatgcgctgc gaatcgggag    4320
cggcgatacc gtaaagcacg aggaagcggt cagcccattc gccgccaagc tcttcagcaa    4380
tatcacgggt agccaacgct atgtcctgat agcggtccgc cacacccagc cggccacagt    4440
cgatgaatcc agaaaagcgg ccattttcca ccatgatatt cggcaagcag gcatcgccat    4500
gggtcacgac gagatcctcg ccgtcgggca tgcgcgcctt gagcctggcg aacagttcgg    4560
ctggcgcgag cccctgatgc tcttcgtcca gatcatcctg atcgacaaga ccggcttcca    4620
tccgagtacg tgctcgctcg atgcgatgtt tcgcttggtg gtcgaatggg caggtagccg    4680
gatcaagcgt atgcagccgc cgcattgcat cagccatgat ggatactttc tcggcaggag    4740
caaggtgaga tgacaggaga tcctgccccg gcacttcgcc caatagcagc cagtcccttc    4800
ccgcttcagt gacaacgtcg agcacagctg cgcaaggaac gcccgtcgtg gccagccacg    4860
atagccgcgc tgcctcgtcc tgcagttcat tcagggcacc ggacaggtcg gtcttgacaa    4920
aaagaaccgg gcgcccctgc gctgacagcc ggaacacggc ggcatcagag cagccgattg    4980
tctgttgtgc ccagtcatag ccgaatagcc tctccaccca gcggccgga gaacctgcgt    5040 gcaatccatc ttgttcaatc atgcgaaacg atcctcattc atttatcagg gttattgtct    5100
catgagcgga tacatatttg aatgtattta ggctgagcat ctatgtcggg tgcggagaaa    5160
gaggtaatga atggcaggc gccttttcg ttagatatgt agtaagtatc ttaatataca    5220
gctttatctg ttttttaaga tacttactac ttttcttagt ggaaactatt agtggctgtt    5280
aattaagcta gtactaccca agatttgaca gaatgcatcg tttgcattcg aa           5332
```

<210> SEQ ID NO 6
<211> LENGTH: 5332
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
```

```
agttccgcgt tacataactt acggtaaatg gcccgcctgg ctgaccgccc aacgaccccc    240
gcccattgac gtcaataatg acgtatgttc ccatagtaac gccaataggg actttccatt    300
gacgtcaatg ggtggactat ttacggtaaa ctgcccactt ggcagtacat caagtgtatc    360
atatgccaag tacgccccct attgacgtca atgacggtaa atggcccgcc tggcattatg    420
cccagtacat gaccttatgg gactttccta cttggcagta catctacgta ttagtcatcg    480
ctattaccat gggtcgaggt gagccccacg ttctgcttca ctctccccat ctccccccc    540 tccccacccc caattttgta tttatttatt ttttaattat tttgtgcagc gatggggggcg    600 gggggggggg gggcgcgcgc caggcggggc ggggcggggc gaggggcggg gcggggcgag    660
gcggagaggt gcggcggcag ccaatcagag cggcgcgctc cgaaagtttc cttttatggc    720
gaggcggcgg cggcggcggc cctataaaaa gcgaagcgcg cggcgggcgg gagtcgctgc    780
gttgccttcg ccccgtgccc cgctccgcgc cgcctcgcgc cgcccgcccc ggctctgact    840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct    960
ccgggagggc cctttgtgcg ggggggagcg gctcgggggg tgcgtgcgtg tgtgtgtgcg   1020
tggggagcgc cgcgtgcggc ccgcgctgcc cggcggctgt gagcgctgcg ggcgcggcgc   1080
ggggctttgt gcgctccgcg tgtgcgcgag gggagcgcgg ccggggggcgg tgccccgcgg   1140 tgcgggggggg ctgcgagggg aacaaaggct gcgtgcgggg tgtgtgcgtg gggggtgag   1200 caggggggtgt gggcgcggcg gtcgggctgt aaccccccccc tgcaccccccc tccccgagtt   1260 gctgagcacg gccggcttc gggtgcgggg ctccgtgcgg ggcgtggcgc ggggctcgcc   1320
gtgccgggcg gggggtggcg gcaggtgggg gtgccgggcg gggcggggcc gcctcgggcc   1380
ggggagggct cgggggaggg gcgcggcggc cccggagcgc cggcggctgt cgaggcgcgg   1440
cgagccgcag ccattgcctt ttatggtaat cgtgcgagag ggcgcaggga cttcctttgt   1500
cccaaatctg gcggagccga aatctgggag gcgccgccgc accccctcta gcgggcgcgg   1560
gcgaagcggt gcggcgccgg caggaaggaa atgggcgggg agggccttcg tgcgtcgccg   1620
cgccgccgtc cccttctcca tctccagcct cggggctgcc gcaggggggac ggctgccttc   1680 ggggggggacg gggcagggcg gggttcggct tctggcgtgt gaccggcggc tctagagcct   1740
ctgctaacca tgttcatgcc ttcttctttt tcctacagct cctgggcaac gtgctggttg   1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcat gaatgccaag gtcgttgtgg tgcttgtact   1980
tgtgctgact gctctgtgtc tgagcgacgg aaaaccagtc tccctcagct acaggtgccc   2040
atgccgattc ttcgaatctc atgtggcccg ggccaatgtg aagcacttga aaatcctgaa   2100
tacacccaac tgcgcgttgc agatcgtggc ccgcctgaaa aataataata ggcaggtatg   2160
tatcgatcca aagcttaagt ggatccagga gtatctggaa aaggctctca ataaggaag   2220 cggagctact aacttcagcc tgctgaagca ggctggagac gtggaggaga accctggacc   2280
tatgggcagc gaactggaaa ccgccatgga ctttgataa atgttttcc acgcgcatag   2340 cggcaaagaa ggggacaagt acaagctgtc aaaaaaggag ctgaaagaac tgctgcagac   2400
cgaattgagc ggcttcctgg acgctcagaa agatgtcgat gccgtcgaca aagtgatgaa   2460
agagcttgac gagaacggtg acggtgaagt cgattttcag gaatatgtgg tgctggtggc   2520
cgcccttact gtagcatgca acaatttctt ttgggaaaat tcataaatcg attacgctcc   2580
```

```
tctactctttt gagacatcac tggcctataa taaatgggtt aatttatgta acaaaattgc    2640
cttggcttgt taactttatt agacattctg atgtttgcat tgtgtaaata ctgttgtatt    2700
ggaaaagcgt gccaagatgg attattgtaa ttcagtgtct tttttagtag cgtcacgtgc    2760
caaacactgt tagtcacaga gggcatgaga cagcctgtgc tggaacagct cagttcatag    2820
ggctatggag atgggagaa aggggcgctt ctgtcagaga caagctgtgg tctggaagg      2880 ccttagcact aaaagcacca caatgagaag caaccgccag aagcagggcc cgcaggcctt    2940
tgttccagct gcaaagagaa aggaaaaagt ggggaataag agttgggget gcggagggg    3000 tggggagcat tgtgcaggtt ccgtacttga acagaaagca gggaccaaca caaggaaggc    3060
tcgagctggc ggaataggtt ccaatctgtc gcggccgcat taccctgtta tccctaatct    3120
cgtttaacta tgactctctt aaggtagcca aattccggaa ctataaattg cgttgcgctc    3180
actgcccgct ttccagtcgg gaaacctgtc gtgccagctg cataaatgaa tcggccaacg    3240
cgcggggaga ggcggtttgc gtattgggcg cgcttccgct tcctcgctca ctgactcgct    3300
gcgctcggtc gttcggctgc ggcgagcggt atcagctcac tcaaaggcgg taatacggtt    3360
atccacagaa tcaggggata acgcaggaaa gaacatgtga gcaaaaggcc agcaaaaggc    3420
caggaaccgt aaaaaggccg cgttgctggc gtttttccat aggctccgcc cccctgacga    3480
gcatcacaaa aatcgacgct caagtcagag gtggcgaaac ccgacaggac tataaagata    3540
ccaggcgttt ccccctggaa gctccctcgt gcgctctcct gttccgaccc tgccgcttac    3600
cggatacctg tccgcctttc tcccttcggg aagcgtggcg ctttctcata gctcacgctg    3660
taggtatctc agttcggtgt aggtcgttcg ctccaagctg ggctgtgtgc acgaaccccc    3720
cgttcagccc gaccgctgcg ccttatccgg taactatcgt cttgagtcca acccggtaag    3780
acacgactta tcgccactgg cagcagccac tggtaacagg attagcagag cgaggtatgt    3840
aggcggtgct acagagttct tgaagtggtg gcctaactac ggctacacta agaacagt     3900 atttggtatc tgcgctctgc tgaagccagt taccttcgga aaaagagttg gtagctcttg    3960
atccggcaaa caaaccaccg ctggtagcgg tggtttttt gtttgcaagc agcagattac     4020
gcgcagaaaa aaaggatctc aagaagatcc tttgatcttt tctacggggt ctgacgctca    4080
gtggaacgaa aactcacgtt aagggatttt ggtcatgaga ttatcaaaaa ggatcttcac    4140
ctagatcctt ttaaattaaa aatgaagttt taaatcaatc taaagtatat atgagtaaac    4200
ttggtctgac atgcgcatct gacgctcagt ggaacgaaaa ctcacgttaa gggatttgg     4260 tcatgcctca gaagaactcg tcaagaaggc gatagaaggc gatgcgctgc gaatcggag     4320 cggcgatacc gtaaagcacg aggaagcggt cagcccattc gccgccaagc tcttcagcaa    4380
tatcacgggt agccaacgct atgtcctgat agcggtccgc cacacccagc cggccacagt    4440
cgatgaatcc agaaaagcgg ccattttcca ccatgatatt cggcaagcag gcatcgccat    4500
gggtcacgac gagatcctcg ccgtcgggca tgcgcgcctt gagcctggcg aacagttcgg    4560
ctggcgcgag cccctgatgc tcttcgtcca gatcatcctg atcgacaaga ccggcttcca    4620
tccgagtacg tgctcgctcg atgcgatgtt tcgcttggtg gtcgaatggg caggtagccg    4680
gatcaagcgt atgcagccgc cgcattgcat cagccatgat ggatactttc tcggcaggag    4740
caaggtgaga tgacaggaga tcctgccccg gcacttcgcc caatagcagc cagtcccttc    4800
ccgcttcagt gacaacgtcg agcacagctg cgcaaggaac gcccgtcgtg gccagccacg    4860
atagccgcgc tgcctcgtcc tgcagttcat tcagggcacc ggacaggtcg gtcttgacaa    4920
```

| | | | | |
|---|---|---|---|---|
| aaagaaccgg | gcgcccctgc | gctgacagcc | ggaacacggc | ggcatcagag cagccgattg | 4980 |
| tctgttgtgc | ccagtcatag | ccgaatagcc | tctccaccca | agcggccgga gaacctgcgt | 5040 |
| gcaatccatc | ttgttcaatc | atgcgaaacg | atcctcattc | atttatcagg gttattgtct | 5100 |
| catgagcgga | tacatatttg | aatgtattta | ggctgagcat | ctatgtcggg tgcggagaaa | 5160 |
| gaggtaatga | aatggcaggc | gccttttcg | ttagatatgt | agtaagtatc ttaatataca | 5220 |
| gctttatctg | tttttaaga | tacttactac | ttttcttagt | ggaaactatt agtggctgtt | 5280 |
| aattaagcta | gtactaccca | agatttgaca | gaatgcatcg | tttgcattcg aa | 5332 |

<210> SEQ ID NO 7
<211> LENGTH: 5623
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

| | | | | |
|---|---|---|---|---|
| ctagcatgaa | tgccaaggtc | gttgtggtgc | ttgtacttgt | gctgactgct ctgtgtctga | 60 |
| gcgacggaaa | accagtctcc | ctcagctaca | ggtgcccatg | ccgattcttc gaatctcatg | 120 |
| tggcccgggc | caatgtgaag | cacttgaaaa | tcctgaatac | acccaactgc gcgttgcaga | 180 |
| tcgtggcccg | cctgaaaaat | aataataggc | aggtatgtat | cgatccaaag cttaagtgga | 240 |
| tccaggagta | tctggaaaag | gctctcaata | aaggaagcgg | agctactaac ttcagcctgc | 300 |
| tgaagcaggc | tggagacgtg | gaggagaacc | ctggacctat | gaattttctg ctctcttggg | 360 |
| tgcactggtc | actggcactg | ctgctgtatc | tgccaccatg | caaaatggtcc caagcagctc | 420 |
| ccatggcaga | gggaggtgga | cagaatcatc | atgaggttgt | caaatttatg gatgtctacc | 480 |
| agcggagcta | ctgccacccca | attgagacgt | tggtagacat | ttttcaggaa tatccagacg | 540 |
| agattgagta | cattttcaag | cctagctgtg | tgcccttgat | gcgatgcggt ggctgttgca | 600 |
| atgatgaggg | actcgagtgt | gtccccaccg | aggaaagcaa | tataaccatg caaatcatgc | 660 |
| gaatcaaacc | ccaccaggggc | cagcatatcg | gcgagatgtc | tttcttgcaa cataacaaat | 720 |
| gcgagtgtcg | gccaaagaag | gacagggctc | gccaggaaaa | tccctgtggt ccttgttcag | 780 |
| agcgcaggaa | gcatctttc | gtccaggatc | cgcagacttg | taaatgttca tgcaagaata | 840 |
| ccgattctag | gtgtaaggcg | aggcaactcg | agcttaacga | gagaacctgt aggtgtgaca | 900 |
| aacctagaag | ataaatcgat | tacgctcctc | tactctttga | gacatcactg gcctataata | 960 |
| aatgggttaa | tttatgtaac | aaaattgcct | tggcttgtta | actttattag acattctgat | 1020 |
| gtttgcattg | tgtaaatact | gttgtattgg | aaaagcgtgc | caagatggat tattgtaatt | 1080 |
| cagtgtcttt | tttagtagcg | tcacgtgcca | aacactgtta | gtcacagagg gcatgagaca | 1140 |
| gcctgtgctg | gaacagctca | gttcataggg | ctatggagat | ggggagaaag gggcgcttct | 1200 |
| gtcagagaca | agctgtggtc | tgggaaggcc | ttagcactaa | aagcaccaca atgagaagca | 1260 |
| accgccagaa | gcagggcccg | caggccttg | ttccagctgc | aaagagaaag gaaaagtgg | 1320 |
| ggaataagag | ttggggctgc | ggagggggtg | gggagcattg | tgcaggttcc gtacttgaac | 1380 |
| agaaagcagg | gaccaacaca | aggaaggctc | gagctggcgg | aataggttcc aatctgtcgc | 1440 |
| ggccgcatta | ccctgttatc | cctaatctcg | tttaactatg | actctcttaa ggtagccaaa | 1500 |
| ttccggaact | ataaattgcg | ttgcgctcac | tgcccgcttt | ccagtcggga aacctgtcgt | 1560 |
| gccagctgca | taaatgaatc | ggccaacgcg | cggggagagg | cggtttgcgt attgggcgcg | 1620 |

```
cttccgcttc ctcgctcact gactcgctgc gctcggtcgt tcggctgcgg cgagcggtat    1680
cagctcactc aaaggcggta atacggttat ccacagaatc aggggataac gcaggaaaga    1740
acatgtgagc aaaaggccag caaaaggcca ggaaccgtaa aaaggccgcg ttgctggcgt    1800
ttttccatag gctccgcccc cctgacgagc atcacaaaaa tcgacgctca agtcagaggt    1860
ggcgaaaccc gacaggacta taaagatacc aggcgtttcc ccctggaagc tccctcgtgc    1920
gctctcctgt tccgaccctg ccgcttaccg gatacctgtc cgcctttctc ccttcgggaa    1980
gcgtggcgct ttctcatagc tcacgctgta ggtatctcag ttcggtgtag gtcgttcgct    2040
ccaagctggg ctgtgtgcac gaaccccccg ttcagcccga ccgctgcgcc ttatccggta    2100
actatcgtct tgagtccaac ccggtaagac acgacttatc gccactggca gcagccactg    2160
gtaacaggat tagcagagcg aggtatgtag gcggtgctac agagttcttg aagtggtggc    2220
ctaactacgg ctacactaga agaacagtat ttggtatctg cgctctgctg aagccagtta    2280
ccttcggaaa aagagttggt agctcttgat ccggcaaaca aaccaccgct ggtagcggtg    2340
gtttttttgt ttgcaagcag cagattacgc gcagaaaaaa aggatctcaa gaagatcctt    2400
tgatcttttc tacggggtct gacgctcagt ggaacgaaaa ctcacgttaa gggattttgg    2460
tcatgagatt atcaaaaagg atcttcacct agatcctttt aaattaaaaa tgaagtttta    2520
aatcaatcta aagtatatat gagtaaactt ggtctgacat gcgcatctga cgctcagtgg    2580
aacgaaaact cacgttaagg gattttggtc atgcctcaga agaactcgtc aagaaggcga    2640
tagaaggcga tgcgctgcga atcgggagcg cgataccgt aaagcacgag gaagcggtca    2700
gcccattcgc cgccaagctc ttcagcaata tcacgggtag ccaacgctat gtcctgatag    2760
cggtccgcca cacccagccg gccacagtcg atgaatccag aaaagcggcc attttccacc    2820
atgatattcg gcaagcaggc atcgccatgg gtcacgacga atcctcgcc gtcgggcatg    2880 cgcgccttga gcctggcgaa cagttcggct ggcgcgagcc cctgatgctc ttcgtccaga    2940
tcatcctgat cgacaagacc ggcttccatc cgagtacgtg ctcgctcgat gcgatgtttc    3000
gcttggtggt cgaatgggca ggtagccgga tcaagcgtat gcagccgccg cattgcatca    3060
gccatgatgg atactttctc ggcaggagca aggtgagatg acaggagatc ctgccccggc    3120
acttcgccca atagcagcca gtcccttccc gcttcagtga caacgtcgag cacagctgcg    3180
caaggaacgc ccgtcgtggc cagccacgat agccgcgctg cctcgtcctg cagttcattc    3240
agggcaccgg acaggtcggt cttgacaaaa agaaccgggc gcccctgcgc tgacagccgg    3300 aacacgcgg catcagagca gccgattgtc tgttgtgccc agtcatagcc gaatagcctc    3360
tccacccaag cggccggaga acctgcgtgc aatccatctt gttcaatcat gcgaaacgat    3420
cctcattcat ttatcaggt tattgtctca tgagcggata catatttgaa tgtatttagg    3480
ctgagcatct atgtcgggtg cggagaaaga ggtaatgaaa tggcaggcgc cttttcgtt    3540 agatatgtag taagtatctt aatatacagc tttatctgtt ttttaagata cttactactt    3600
ttcttagtgg aaactattag tggctgttaa ttaagctagt actacccaag atttgacaga    3660
atgcatcgtt tgcattcgaa taactataac ggtcctaagg tagcgacgta cgaaccgttg    3720
ggcgcgcctg gggatagcga tcgctgctgg cgcggtccgc tatgaggtct ctgatagacc    3780
acagacgcgt cgacattgat tattgactag ttattaatag taatcaatta cggggtcatt    3840
agttcatagc ccatatatgg agttccgcgt tacataactt acggtaaatg gcccgcctgg    3900
ctgaccgccc aacgaccccc gcccattgac gtcaataatg acgtatgttc ccatagtaac    3960
```

```
gccaataggg actttccatt gacgtcaatg ggtggactat ttacggtaaa ctgcccactt    4020
ggcagtacat caagtgtatc atatgccaag tacgccccct attgacgtca atgacggtaa    4080
atggcccgcc tggcattatg cccagtacat gaccttatgg gactttccta cttggcagta    4140
catctacgta ttagtcatcg ctattaccat gggtcgaggt gagccccacg ttctgcttca    4200
ctctccccat ctcccccccc tccccacccc caattttgta tttatttatt ttttaattat    4260
tttgtgcagc gatgggggcg ggggggggg gggcgcgcgc caggcggggc ggggcggggc    4320
gaggggcggg gcggggcgag gcggagaggt gcggcggcag ccaatcagag cggcgcgctc    4380
cgaaagtttc cttttatggc gaggcggcgg cggcggcggc cctataaaaa gcgaagcgcg    4440
cggcgggcgg gagtcgctgc gttgccttcg ccccgtgccc cgctccgcgc cgcctcgcgc    4500
cgcccgcccc ggctctgact gaccgcgtta ctcccacagg tgagcgggcg ggacggccct    4560
tctcctccgg gctgtaatta gcgcttggtt taatgacggc tcgtttcttt tctgtggctg    4620
cgtgaaagcc ttaaagggct ccgggagggc cctttgtgcg gggggagcg gctcggggg    4680 tgcgtgcgtg tgtgtgtgcg tggggagcgc cgcgtgcggc ccgcgctgcc cggcggctgt    4740
gagcgctgcg ggcgcggcgc ggggctttgt gcgctccgcg tgtgcgcgag gggagcgcgg    4800 ccggggggcgg tgccccgcgg tgcggggggg ctgcgaggg aacaaaggct gcgtgcgggg    4860
tgtgtgcgtg ggggggtgag caggggtgt gggcgcggcg gtcgggctgt aaccccccc    4920 tgcaccccc tccccgagtt gctgagcacg gcccggcttc gggtgcgggg ctccgtgcgg    4980
ggcgtggcgc ggggctcgcc gtgccgggcg ggggtggcg gcaggtgggg gtgccgggcg    5040
gggcggggcc gcctcgggcc ggggagggct cggggaggg gcgcggcggc ccggagcgc    5100 cggcggctgt cgaggcgcgg cgagccgcag ccattgcctt ttatggtaat cgtgcgagag    5160
ggcgcaggga cttcctttgt cccaaatctg gcggagccga aatctgggag gcgccgccgc    5220
accccctcta gcgggcgcgg gcgaagcggt gcggcgccgg caggaaggaa atgggcgggg    5280
agggccttcg tgcgtcgccg cgccgccgtc cccttctcca tctccagcct cggggctgcc    5340
gcagggggac ggctgccttc gggggggacg gggcagggcg gggttcggct tctggcgtgt    5400
gaccggcggc tctagagcct ctgctaacca tgttcatgcc ttcttctttt tcctacagct    5460
cctgggcaac gtgctggttg ttgtgctgtc tcatcatttt ggcaaagaat tccctgcagg    5520
aaattgagcc cgcagcctcc cgcttcgctc tctgctcctc ctgttcgaca gtcagccgca    5580
tcttcttttg cgtcgccagc cgagccacat cgctcagaca ccg                      5623

<210> SEQ ID NO 8
<211> LENGTH: 5623
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
ctagcatgaa ttttctgctc tcttgggtgc actggtcact ggcactgctg ctgtatctgc       60
accatgcaaa atggtcccaa gcagctccca tggcagaggg aggtggacag aatcatcatg      120
aggttgtcaa atttatggat gtctaccagc ggagctactg ccacccaatt gagacgttgg      180
tagacatttt tcaggaatat ccagacgaga ttgagtacat tttcaagcct agctgtgtgc      240
ccttgatgcg atgcggtggc tgttgcaatg atgagggact cgagtgtgtc cccaccgagg      300
aaagcaatat aaccatgcaa atcatgcgaa tcaaacccca ccagggccag catatcggcg      360
```

```
agatgtcttt cttgcaacat aacaaatgcg agtgtcggcc aaagaaggac agggctcgcc    420
aggaaaatcc ctgtggtcct tgttcagagc gcaggaagca tcttttcgtc caggatccgc    480
agacttgtaa atgttcatgc aagaataccg attctaggtg taaggcgagg caactcgagc    540
ttaacgagag aacctgtagg tgtgacaaac ctagaagagg aagcggagct actaacttca    600
gcctgctgaa gcaggctgga gacgtggagg agaaccctgg acctatgaat gccaaggtcg    660
ttgtggtgct tgtacttgtg ctgactgctc tgtgtctgag cgacggaaaa ccagtctccc    720
tcagctacag gtgcccatgc cgattcttcg aatctcatgt ggcccgggcc aatgtgaagc    780
acttgaaaat cctgaataca cccaactgcg cgttgcagat cgtggcccgc ctgaaaaata    840
ataataggca ggtatgtatc gatccaaagc ttaagtggat ccaggagtat ctggaaaagg    900
ctctcaataa ataaatcgat tacgctcctc tactctttga cattcactg gcctataata    960 aatgggttaa tttatgtaac aaaattgcct tggcttgtta actttattag acattctgat   1020
gtttgcattg tgtaaatact gttgtattgg aaaagcgtgc caagatggat tattgtaatt   1080
cagtgtcttt tttagtagcg tcacgtgcca aacactgtta gtcacagagg gcatgagaca   1140
gcctgtgctg gaacagctca gttcataggg ctatggagat ggggagaaag gggcgcttct   1200
gtcagagaca agctgtggtc tgggaaggcc ttagcactaa aagcaccaca atgagaagca   1260
accgccagaa gcagggcccg caggcctttg ttccagctgc aaagagaaag gaaaagtgg    1320 ggaataagag ttgggctgc ggaggggtg gggagcattg tgcaggttcc gtacttgaac    1380
agaaagcagg gaccaacaca aggaaggctc gagctggcgg aataggttcc aatctgtcgc   1440
ggccgcatta ccctgttatc cctaatctcg tttaactatg actctcttaa ggtagccaaa   1500
ttccggaact ataaattgcg ttgcgctcac tgcccgcttt ccagtcggga aacctgtcgt   1560
gccagctgca taaatgaatc ggccaacgcg cggggagagg cggtttgcgt attgggcgcg   1620
cttccgcttc ctcgctcact gactcgctgc gctcggtcgt tcggctgcgg cgagcggtat   1680
cagctcactc aaaggcggta atacggttat ccacagaatc aggggataac gcaggaaaga   1740
acatgtgagc aaaaggccag caaaaggcca ggaaccgtaa aaaggccgcg ttgctggcgt   1800
ttttccatag gctccgcccc cctgacgagc atcacaaaaa tcgacgctca agtcagaggt   1860
ggcgaaaccc gacaggacta taaagatacc aggcgtttcc ccctggaagc tccctcgtgc   1920
gctctcctgt tccgaccctg ccgcttaccg gatacctgtc cgcctttctc ccttcgggaa   1980
gcgtggcgct ttctcatagc tcacgctgta ggtatctcag ttcggtgtag gtcgttcgct   2040
ccaagctggg ctgtgtgcac gaaccccccg ttcagcccga ccgctgcgcc ttatccggta   2100
actatcgtct tgagtccaac ccggtaagac acgacttatc gccactggca gcagccactg   2160
gtaacaggat tagcagagcg aggtatgtag gcggtgctac agagttcttg aagtggtggc   2220
ctaactacgg ctacactaga agaacagtat ttggtatctg cgctctgctg aagccagtta   2280
ccttcggaaa aagagttggt agctcttgat ccggcaaaca aaccaccgct ggtagcggtg   2340
gtttttttgt ttgcaagcag cagattacgc gcagaaaaaa aggatctcaa gaagatcctt   2400
tgatcttttc tacggggtct gacgctcagt ggaacgaaaa ctcacgttaa gggattttgg   2460
tcatgagatt atcaaaaagg atcttcacct agatcctttt aaattaaaaa tgaagtttta   2520
aatcaatcta agtatatat gagtaaactt ggtctgacat gcgcatctga cgctcagtgg   2580
aacgaaaact cacgttaagg gattttggtc atgcctcaga agaactcgtc aagaaggcga   2640
tagaaggcga tgcgctgcga atcgggagcg gcgataccgt aaagcacgag gaagcggtca   2700
```

```
gcccattcgc cgccaagctc ttcagcaata tcacgggtag ccaacgctat gtcctgatag    2760
cggtccgcca cacccagccg gccacagtcg atgaatccag aaaagcggcc attttccacc    2820
atgatattcg gcaagcaggc atcgccatgg gtcacgacga gatcctcgcc gtcgggcatg    2880
cgcgccttga gcctggcgaa cagttcggct ggcgcgagcc cctgatgctc ttcgtccaga    2940
tcatcctgat cgacaagacc ggcttccatc cgagtacgtg ctcgctcgat gcgatgtttc    3000
gcttggtggt cgaatgggca ggtagccgga tcaagcgtat gcagccgccg cattgcatca    3060
gccatgatgg atactttctc ggcaggagca aggtgagatg acaggagatc ctgccccggc    3120
acttcgccca atagcagcca gtcccttccc gcttcagtga caacgtcgag cacagctgcg    3180
caaggaacgc ccgtcgtggc cagccacgat agccgcgctg cctcgtcctg cagttcattc    3240
agggcaccgg acaggtcggt cttgacaaaa agaaccgggc gccctgcgc tgacagccgg    3300 aacacggcgg catcagagca gccgattgtc tgttgtgccc agtcatagcc gaatagcctc    3360
tccacccaag cggccggaga acctgcgtgc aatccatctt gttcaatcat gcgaaacgat    3420
cctcattcat ttatcagggt tattgtctca tgagcggata catatttgaa tgtatttagg    3480
ctgagcatct atgtcgggtg cggagaaaga ggtaatgaaa tggcaggcgc ctttttcgtt    3540
agatatgtag taagtatctt aatatacagc tttatctgtt ttttaagata cttactactt    3600
ttcttagtgg aaactattag tggctgttaa ttaagctagt actacccaag atttgacaga    3660
atgcatcgtt tgcattcgaa taactataac ggtcctaagg tagcgacgta cgaaccgttg    3720
ggcgcgcctg gggatagcga tcgctgctgg cgcggtccgc tatgaggtct ctgatagacc    3780
acagacgcgt cgacattgat tattgactag ttattaatag taatcaatta cggggtcatt    3840
agttcatagc ccatatatgg agttccgcgt tacataactt acggtaaatg gcccgcctgg    3900
ctgaccgccc aacgacccccc gcccattgac gtcaataatg acgtatgttc ccatagtaac    3960
gccaataggg actttccatt gacgtcaatg ggtggactat ttacggtaaa ctgcccactt    4020
ggcagtacat caagtgtatc atatgccaag tacgccccct attgacgtca atgacggtaa    4080
atggcccgcc tggcattatg cccagtacat gaccttatgg gactttccta cttggcagta    4140
catctacgta ttagtcatcg ctattaccat gggtcgaggt gagcccccacg ttctgcttca    4200 ctctccccat ctccccccccc tccccacccc caattttgta tttatttatt ttttaattat    4260
tttgtgcagc gatgggggcg ggggggggg gggcgcgcgc caggcggggc ggggcggggc    4320
gaggggcggg gcggggcgag gcggagaggt gcggcggcag ccaatcagag cggcgcgctc    4380
cgaaagtttc cttttatggc gaggcggcgg cggcggcggc cctataaaaa gcgaagcgcg    4440
cggcgggcgg gagtcgctgc gttgccttcg ccccgtgccc cgctccgcgc cgcctcgcgc    4500
cgcccgcccc ggctctgact gaccgcgtta ctcccacagg tgagcgggcg gacggcccct    4560
tctcctccgg gctgtaatta gcgcttggtt taatgacggc tcgtttcttt tctgtggctg    4620
cgtgaaagcc ttaaagggct cccggagggc cctttgtgcg gggggagcg gctcgggggg    4680 tgcgtgcgtg tgtgtgtgcg tggggagcgc gcgtgcggc ccgcgctgcc cggcggctgt    4740
gagcgctgcg ggcgcggcgc ggggctttgt gcgctccgcg tgtgcgcgag gggagcgcgg    4800 ccggggggcgg tgcccgcgg tgcggggggg ctgcgagggg aacaaaggct gcgtgcggg    4860 tgtgtgcgtg gggggtgag caggggtgt gggcgcggcg gtcgggctgt aaccccccccc    4920 tgcaccccccc tccccgagtt gctgagcacg gccggcttc gggtgcgggg ctccgtgcgg    4980
ggcgtggcgc ggggctcgcc gtgccggggcg gggggtgggcg gcaggtgggg gtgccggggcg   5040 gggcggggcc gcctcggggcc ggggagggct cggggaggg gcgcggcggc cccggagcgc    5100
```

```
cggcggctgt cgaggcgcgg cgagccgcag ccattgcctt ttatggtaat cgtgcgagag    5160
ggcgcaggga cttcctttgt cccaaatctg gcggagccga atctgggag gcgccgccgc    5220 accccctcta gcgggcgcgg gcgaagcggt gcggcgccgg caggaaggaa atgggcgggg    5280
agggccttcg tgcgtcgccg cgccgccgtc cccttctcca tctccagcct cggggctgcc    5340 gcaggggac ggctgccttc ggggggacg gggcagggcg gggttcggct tctggcgtgt    5400
gaccggcggc tctagagcct ctgctaacca tgttcatgcc ttcttctttt tcctacagct    5460
cctgggcaac gtgctggttg ttgtgctgtc tcatcatttt ggcaaagaat tccctgcagg    5520
aaattgagcc cgcagcctcc cgcttcgctc tctgctcctc ctgttcgaca gtcagccgca    5580 tcttctttg cgtcgccagc cgagccacat cgctcagaca ccg                      5623
```

<210> SEQ ID NO 9
<211> LENGTH: 5359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaatagg actttccatt     300 gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc     540 tccccacccc caattttgta tttatttatt ttttaattat tttgtgcagc gatggggcg     600 ggggggggg gggcgcgcgc caggcggggc gggcgggc gagggcggg gcggggcgag     660 gcggagaggt gcggcggcag ccaatcagag cggcgcgctc cgaaagtttc cttttatggc     720
gaggcggcgg cggcggcggc cctataaaaa gcaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcgggcg ggacggccct tctcctccgg gctgtaatta     900
gcgcttggtt taatgacggc tcgtttcttt tctgtggctg cgtgaaagcc ttaaagggct     960
ccgggagggc cctttgtgcg ggggggagcg gctcggggg tgcgtgcgtg tgtgtgtgcg    1020 tgggagcgc cgcgtgcggc ccgcgctgcc cggcggctgt gagcgctgcg ggcgcggcgc    1080
ggggctttgt gcgctccgcg tgtgcgcgag gggagcgcgg ccggggcgg tgccccgcgg    1140 tgcggggggg ctgcgagggg aacaaaggct gcgtgcgggg tgtgtgcgtg ggggggtgag    1200
cagggggtgt gggcgcggcg gtcgggctgt aaccccccc tgcaccccc tccccgagtt    1260 gctgagcacg gcccggcttc gggtgcgggg ctccgtgcgg ggcgtggcgc ggggctcgcc    1320
gtgccgggcg ggggtggcg gcaggtgggg gtgccgggcg gggcggggcc gcctcgggcc    1380
ggggagggct cggggaggg gcgcggcggc cccggagcgc cggcggctgt cgaggcgcgg    1440
```

```
cgagccgcag ccattgcctt ttatggtaat cgtgcgagag ggcgcaggga cttcctttgt    1500
cccaaatctg gcggagccga aatctgggag gcgccgccgc accccctcta gcgggcgcgg    1560
gcgaagcggt gcggcgccgg caggaaggaa atgggcgggg agggccttcg tgcgtcgccg    1620
cgccgccgtc cccttctcca tctccagcct cggggctgcc gcaggggac ggctgccttc     1680 gggggggacg gggcagggcg gggttcggct tctggcgtgt gaccggcggc tctagagcct    1740
ctgctaacca tgttcatgcc ttcttctttt tcctacagct cctgggcaac gtgctggttg    1800
ttgtgctgtc tcatcatttt ggcaaagaat tccctgcagg aaattgagcc cgcagcctcc    1860
cgcttcgctc tctgctcctc ctgttcgaca gtcagccgca tcttcttttg cgtcgccagc    1920
cgagccacat cgctcagaca ccgctagcat gggcagcgaa ctggaaaccg ccatggagac    1980
tttgataaat gttttccacg cgcatagcgg caaagaaggg gacaagtaca agctgtcaaa    2040
aaaggagctg aaagaactgc tgcagaccga attgagcggc ttcctggacg ctcagaaaga    2100
tgtcgatgcc gtcgacaaag tgatgaaaga gcttgacgag aacggtgacg gtgaagtcga    2160
ttttcaggaa tatgtggtgc tggtggccgc ccttactgta gcatgcaaca atttcttttg    2220
ggaaaattca cgtgcaaagc gtgcaccggt gaaacaggga agcggagcta ctaacttcag    2280
cctgctgaag caggctggag acgtggagga gaaccctgga cctatgaatg ccaaggtcgt    2340
tgtggtgctt gtacttgtgc tgactgctct gtgtctgagc gacggaaaac cagtctccct    2400
cagctacagg tgcccatgcc gattcttcga atctcatgtg gcccgggcca atgtgaagca    2460
cttgaaaatc ctgaatacac ccaactgcgc gttgcagatc gtggcccgcc tgaaaaataa    2520
taataggcag gtatgtatcg atccaaagct taagtggatc caggagtatc tggaaaaggc    2580
tctcaataaa taaatcgatt acgctcctct actctttgag acatcactgg cctataataa    2640
atgggttaat ttatgtaaca aaattgcctt ggcttgttaa ctttattaga cattctgatg    2700
tttgcattgt gtaaatactg ttgtattgga aaagcgtgcc aagatggatt attgtaattc    2760
agtgtctttt ttagtagcgt cacgtgccaa acactgttag tcacagaggg catgagacag    2820
cctgtgctgg aacagctcag ttcatagggc tatggagatg gggagaaagg ggcgcttctg    2880
tcagagacaa gctgtggtct gggaaggcct tagcactaaa agcaccacaa tgagaagcaa    2940
ccgccagaag cagggcccgc aggcctttgt tccagctgca aagagaaagg aaaaagtggg    3000
gaataagagt tggggctgcg gaggggtgg ggagcattgt gcaggttccg tacttgaaca     3060
gaaagcaggg accaacacaa ggaaggctcg agctggcgga ataggttcca atctgtcgcg    3120
gccgcattac cctgttatcc ctaatctcgt ttaactatga ctctcttaag gtagccaaat    3180
tccggaacta taaattgcgt tgcgctcact gcccgctttc cagtcgggaa acctgtcgtg    3240
ccagctgcat aaatgaatcg gccaacgcgc ggggagaggc ggtttgcgta ttgggcgcgc    3300
ttccgcttcc tcgctcactg actcgctgcg ctcggtcgtt cggctgcggc gagcggtatc    3360
agctcactca aaggcggtaa tacggttatc cacagaatca ggggataacg caggaaagaa    3420
catgtgagca aaaggccagc aaaaggccag gaaccgtaaa aaggccgcgt tgctggcgtt    3480
tttccatagg ctccgccccc ctgacgagca tcacaaaaat cgacgctcaa gtcagaggtg    3540
gcgaaacccg acaggactat aaagatacca ggcgtttccc cctggaagct ccctcgtgcg    3600
ctctcctgtt ccgaccctgc cgcttaccgg atacctgtcc gcctttctcc cttcgggaag    3660
cgtggcgctt tctcatagct cacgctgtag gtatctcagt tcggtgtagg tcgttcgctc    3720
caagctgggc tgtgtgcacg aaccccccgt tcagcccgac cgctgcgcct tatccggtaa    3780
ctatcgtctt gagtccaacc cggtaagaca cgacttatcg ccactggcag cagccactgg    3840
```

```
taacaggatt agcagagcga ggtatgtagg cggtgctaca gagttcttga agtggtggcc   3900
taactacggc tacactagaa gaacagtatt tggtatctgc gctctgctga agccagttac   3960
cttcggaaaa agagttggta gctcttgatc cggcaaacaa accaccgctg gtagcggtgg   4020 ttttttgtt tgcaagcagc agattacgcg cagaaaaaaa ggatctcaag aagatccttt   4080
gatcttttct acggggtctg acgctcagtg gaacgaaaac tcacgttaag ggattttggt   4140
catgagatta tcaaaaagga tcttcaccta gatcctttta aattaaaaat gaagttttaa   4200
atcaatctaa agtatatatg agtaaacttg gtctgacatg cgcatctgac gctcagtgga   4260
acgaaaactc acgttaaggg attttggtca tgcctcagaa gaactcgtca agaaggcgat   4320
agaaggcgat gcgctgcgaa tcgggagcgg cgataccgta aagcacgagg aagcggtcag   4380
cccattcgcc gccaagctct tcagcaatat cacgggtagc caacgctatg tcctgatagc   4440
ggtccgccac acccagccgg ccacagtcga tgaatccaga aaagcggcca ttttccacca   4500
tgatattcgg caagcaggca tcgccatggg tcacgacgag atcctcgccg tcgggcatgc   4560
gcgccttgag cctggcgaac agttcggctg gcgcgagccc ctgatgctct tcgtccagat   4620
catcctgatc gacaagaccg gcttccatcc gagtacgtgc tcgctcgatg cgatgtttcg   4680
cttggtggtc gaatgggcag gtagccggat caagcgtatg cagccgccgc attgcatcag   4740
ccatgatgga tactttctcg gcaggagcaa ggtgagatga caggagatcc tgccccggca   4800
cttcgcccaa tagcagccag tcccttcccg cttcagtgac aacgtcgagc acagctgcgc   4860
aaggaacgcc cgtcgtggcc agccacgata gccgcgctgc ctcgtcctgc agttcattca   4920
gggcaccgga caggtcggtc ttgacaaaaa gaaccgggcg cccctgcgct gacagccgga   4980
acacggcggc atcagagcag ccgattgtct gttgtgccca gtcatagccg aatagcctct   5040
ccacccaagc ggccggagaa cctgcgtgca atccatcttg ttcaatcatg cgaaacgatc   5100
ctcattcatt tatcagggtt attgtctcat gagcggatac atatttgaat gtatttaggc   5160
tgagcatcta tgtcgggtgc ggagaaagag gtaatgaaat ggcaggcgcc ttttcgtta   5220 gatatgtagt aagtatctta atatacagct ttatctgttt tttaagatac ttactacttt   5280
tcttagtgga aactattagt ggctgttaat taagctagta ctacccaaga tttgacagaa   5340
tgcatcgttt gcattcgaa                                                5359
```

<210> SEQ ID NO 10
<211> LENGTH: 5359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

```
ctagcatgaa tgccaaggtc gttgtggtgc ttgtacttgt gctgactgct ctgtgtctga     60
gcgacggaaa accagtctcc ctcagctaca ggtgcccatg ccgattcttc gaatctcatg    120
tggcccgggc caatgtgaag cacttgaaaa tcctgaatac acccaactgc gcgttgcaga    180
tcgtggcccg cctgaaaaat aataataggc aggtatgtat cgatccaaag cttaagtgga    240
tccaggagta tctggaaaag gctctcaata acgtgcaaa gcgtgcaccg gtgaaacagg    300
gaagcggagc tactaacttc agcctgctga agcaggctgg agacgtggag gagaaccctg    360
gacctatggg cagcgaactg gaaaccgcca tggagacttt gataaatgtt ttccacgcgc    420
```

| | |
|---|---|
| atagcggcaa agaagqggac aagtacaagc tgtcaaaaaa ggagctgaaa gaactgctgc | 480 |
| agaccgaatt gagcggcttc ctggacgctc agaaagatgt cgatgccgtc gacaaagtga | 540 |
| tgaaagagct tgacgagaac ggtgacggtg aagtcgattt tcaggaatat gtggtgctgg | 600 |
| tggccgcccT tactgtagca tgcaacaatt tctttTggga aaattcataa atcgattacg | 660 |
| ctcctctact ctttgagaca tcactggcct ataataaatg ggttaattta tgtaacaaaa | 720 |
| ttgccttggc ttgttaactt tattagacat tctgatgttt gcattgtgta aatactgttg | 780 |
| tattggaaaa gcgtgccaag atggattatt gtaattcagt gtcttttTTA gtagcgtcac | 840 |
| gtgccaaaca ctgttagtca cagagggcat gagacagcct gtgctggaac agctcagttc | 900 |
| ataqggctat ggagatgggg agaaaggggc gcttctgtca gagacaagct gtggtctggg | 960 |
| aaggccttag cactaaaagc accacaatga aagcaaccg ccagaagcag ggcccgcagg | 1020 |
| cctttgttcc agctgcaaag agaaaggaaa aagtggggaa taagagttgg ggctgcggag | 1080 |
| ggggtgggga gcattgtgca ggttccgtac ttgaacagaa agcagggacc aacacaagga | 1140 |
| aggctcgagc tggcggaata ggttccaatc tgtcgcggcc gcattaccct gttatccctA | 1200 |
| atctcgttta actatgactc tcttaaggta gccaaattcc ggaactataa attgcgttgc | 1260 |
| gctcactgcc cgctttccag tcgggaaacc tgtcgtgcca gctgcataaa tgaatcggcc | 1320 |
| aacgcgcggg gagaggcggt ttgcgtattg ggcgcgcttc cgcttcctcg ctcactgact | 1380 |
| cgctgcgctc ggtcgttcgg ctgcggcgag cggtatcagc tcactcaaag gcggtaatac | 1440 |
| ggttatccac agaatcaggg gataacgcag gaaagaacat gtgagcaaaa ggccagcaaa | 1500 |
| aggccaggaa ccgtaaaaag gccgcgttgc tggcgtTTTT ccataggctc cgcccccctg | 1560 |
| acgagcatca caaaaatcga cgctcaagtc agaggtggcg aaacccgaca ggactataaa | 1620 |
| gataccaggc gtttccccct ggaagctccc tcgtgcgctc tcctgttccg accctgccgc | 1680 |
| ttaccggata cctgtccgcc tttctccctt cgggaagcgt ggcgctttct catagctcac | 1740 |
| gctgtaggta tctcagttcg gtgtaggtcg ttcgctccaa gctgggctgt gtgcacgaac | 1800 |
| cccccgttca gcccgaccgc tgcgccttat ccggtaacta tcgtcttgag tccaacccgg | 1860 |
| taagacacga cttatcgcca ctggcagcag ccactggtaa caggattagc agagcgaggt | 1920 |
| atgtaggcgg tgctacagag ttcttgaagt ggtggcctaa ctacggctac actagaagaa | 1980 |
| cagtatttgg tatctgcgct ctgctgaagc cagttacctt cggaaaaaga gttggtagct | 2040 |
| cttgatccgg caaacaaacc accgctggta gcggtggttt TTTtgtttgc aagcagcaga | 2100 |
| ttacgcgcag aaaaaaagga tctcaagaag atcctttgat cttttctacg ggtctgacg | 2160 |
| ctcagtggaa cgaaaactca cgttaaggga ttttggtcat gagattatca aaaggatct | 2220 |
| tcacctagat ccttttaaat taaaaatgaa gttttaaatc aatctaaagt atatatgagt | 2280 |
| aaacttggtc tgacatgcgc atctgacgct cagtggaacg aaaactcacg ttaagggatt | 2340 |
| ttggtcatgc tcagaagaa ctcgtcaaga aggcgataga aggcgatgcg ctgcgaatcg | 2400 |
| ggagcggcga taccgtaaag cacgaggaag cggtcagccc attcgccgcc aagctcttca | 2460 |
| gcaatatcac gggtagccaa cgctatgtcc tgatagcggt ccgccacacc cagccggcca | 2520 |
| cagtcgatga atccagaaaa gcggccattt tccaccatga tattcggcaa gcaggcatcg | 2580 |
| ccatgggtca cgacgagatc ctcgccgtcg gcatgcgcg ccttgagcct ggcgaacagt | 2640 |
| tcggctggcg cgagcccctg atgctcttcg tccagatcat cctgatcgac aagaccggct | 2700 |
| tccatccgag tacgtgctcg ctcgatgcga tgtttcgctt ggtggtcgaa tgggcaggta | 2760 |
| gccggatcaa gcgtatgcag ccgccgcatt gcatcagcca tgatggatac tttctcggca | 2820 |

```
ggagcaaggt gagatgacag gagatcctgc cccggcactt cgcccaatag cagccagtcc    2880
cttcccgctt cagtgacaac gtcgagcaca gctgcgcaag gaacgcccgt cgtggccagc    2940
cacgatagcc gcgctgcctc gtcctgcagt tcattcaggg caccggacag gtcggtcttg    3000
acaaaaagaa ccgggcgccc ctgcgctgac agccggaaca cggcggcatc agagcagccg    3060
attgtctgtt gtgcccagtc atagccgaat agcctctcca cccaagcggc cggagaacct    3120
gcgtgcaatc catcttgttc aatcatgcga aacgatcctc attcatttat cagggttatt    3180
gtctcatgag cggatacata tttgaatgta tttaggctga gcatctatgt cgggtgcgga    3240
gaaagaggta atgaaatggc aggcgccttt ttcgttagat atgtagtaag tatcttaata    3300
tacagcttta tctgtttttt aagatactta ctactttttct tagtggaaac tattagtggc    3360
tgttaattaa gctagtacta cccaagattt gacagaatgc atcgtttgca ttcgaataac    3420
tataacggtc ctaaggtagc gacgtacgaa ccgttgggcg cgcctgggga tagcgatcgc    3480
tgctggcgcg gtccgctatg aggtctctga tagaccacag acgcgtcgac attgattatt    3540
gactagttat taatagtaat caattacggg gtcattagtt catagcccat atatggagtt    3600
ccgcgttaca taacttacgg taaatggccc gcctggctga cgcccaacg accccccgccc    3660 attgacgtca ataatgacgt atgttcccat agtaacgcca atagggactt tccattgacg    3720
tcaatgggtg gactatttac ggtaaactgc ccacttggca gtacatcaag tgtatcatat    3780
gccaagtacg cccccctattg acgtcaatga cggtaaatgg cccgcctggc attatgccca    3840
gtacatgacc ttatgggact ttcctacttg gcagtacatc tacgtattag tcatcgctat    3900
taccatgggt cgaggtgagc cccacgttct gcttcactct ccccatctcc cccccctccc    3960
cacccccaat tttgtattta tttatttttt aattatttg tgcagcgatg ggggcggggg    4020 ggggggggc gcgcgccagg cggggcgggg cgggcgaggg ggcggggcgg ggcgaggcgg    4080
agaggtgcgg cggcagccaa tcagagcggc gcgctccgaa agtttccttt tatggcgagg    4140
cggcggcggc ggcggcccta taaaaagcga agcgcgcggc gggcgggagt cgctgcgttg    4200
ccttcgcccc gtgccccgct ccgcgccgcc tcgcgccgcc cgccccggct ctgactgacc    4260
gcgttactcc cacaggtgag cgggcgggac ggcccttctc ctccgggctg taattagcgc    4320
ttggtttaat gacggctcgt ttcttttctg tggctgcgtg aaagccttaa agggctccgg    4380
gagggccctt tgtgcggggg ggagcggctc ggggggtgcg tgcgtgtgtg tgtgcgtggg    4440
gagcgccgcg tgcggcccgc gctgcccggc ggctgtgagc gctgcgggcg cggcgcgggg    4500
ctttgtgcgc tccgcgtgtg cgcgagggga gcgcggccgg gggcggtgcc ccgcggtgcg    4560 gggggggctgc gagggggaaca aaggctgcgt gcgggtgtg tgcgtggggg ggtgagcagg    4620
gggtgtgggc gcggcggtcg ggctgtaacc cccccctgca ccccccctccc cgagttgctg    4680 agcacggccc ggcttcgggt gcggggctcc gtgcggggcg tggcgcgggg ctcgccgtgc    4740
cgggcggggg gtgcggcag gtgggggtgc cgggcggggc ggggccgcct cgggccgggg    4800
agggctcggg ggagggggcgc ggcggccccg gagcgccggc ggctgtcgag gcgcggcgag    4860
ccgcagccat tgccttttat ggtaatcgtg cgagagggcg cagggacttc ctttgtccca    4920
aatctggcgg agccgaaatc tgggaggcgc cgccgcaccc cctctagcgg gcgcgggcga    4980
agcggtgcgg cgccggcagg aaggaaatgg gcggggaggg ccttcgtgcg tcgccgcgcc    5040
gccgtcccct tctccatctc cagcctcggg gctgccgcag ggggacggct gccttcgggg    5100
gggacggggc agggcggggt tcggcttctg gcgtgtgacc ggcggctcta gagcctctgc    5160
```

```
taaccatgtt catgccttct tcttttcct acagctcctg ggcaacgtgc tggttgttgt    5220
gctgtctcat cattttggca aagaattccc tgcaggaaat tgagcccgca gcctcccgct    5280
tcgctctctg ctcctcctgt tcgacagtca gccgcatctt cttttgcgtc gccagccgag    5340
ccacatcgct cagacaccg                                                  5359
```

<210> SEQ ID NO 11
<211> LENGTH: 5650
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
ctagcatgaa tgccaaggtc gttgtggtgc ttgtacttgt gctgactgct ctgtgtctga      60
gcgacggaaa accagtctcc ctcagctaca ggtgcccatg ccgattcttc gaatctcatg     120
tggcccgggc caatgtgaag cacttgaaaa tcctgaatac acccaactgc gcgttgcaga     180
tcgtggcccg cctgaaaaat aataataggc aggtatgtat cgatccaaag cttaagtgga     240
tccaggagta tctggaaaag gctctcaata acgtgcaaaa gcgtgcaccg gtgaaacagg     300
gaagcggagc tactaacttc agcctgctga gcaggctgg agacgtggag gagaaccctg     360
gacctatgaa ttttctgctc tcttgggtgc actggtcact ggcactgctg ctgtatctgc     420
accatgcaaa atggtcccaa gcagctccca tggcagaggg aggtggacag aatcatcatg     480
aggttgtcaa atttatggat gtctaccagc ggagctactg ccacccaatt gagacgttgg     540
tagacatttt tcaggaatat ccagacgaga ttgagtacat tttcaagcct agctgtgtgc     600
ccttgatgcg atgcggtggc tgttgcaatg atgagggact cgagtgtgtc cccaccgagg     660
aaagcaatat aaccatgcaa atcatgcgaa tcaaacccca ccagggccag catatcggcg     720
agatgtcttt cttgcaacat aacaaatgcg agtgtcggcc aaagaaggac agggctcgcc     780
aggaaaatcc ctgtggtcct tgttcagagc gcaggaagca tcttttcgtc caggatccgc     840
agacttgtaa atgttcatgc aagaataccg attctaggtg taaggcgagg caactcgagc     900
ttaacgagag aacctgtagg tgtgacaaac ctagaagata aatcgattac gctcctctac     960
tctttgagac atcactggcc tataataaat gggttaattt atgtaacaaa attgccttgg    1020
cttgttaact ttattagaca ttctgatgtt tgcattgtgt aaatactgtt gtattggaaa    1080
agcgtgccaa gatggattat tgtaattcag tgtctttttt agtagcgtca cgtgccaaac    1140
actgttagtc acagagggca tgagacagcc tgtgctggaa cagctcagtt catagggcta    1200
tggagatggg gagaaagggg cgcttctgtc agagacaagc tgtggtctgg aaggccttta    1260
gcactaaaag caccacaatg agaagcaacc gccagaagca gggcccgcag gcctttgttc    1320
cagctgcaaa gagaaaggaa aaagtgggga ataagagttg gggctgcgga ggggtggg     1380 agcattgtgc aggttccgta cttgaacaga aagcagggac caacacaagg aaggctcgag    1440
ctggcggaat aggttccaat ctgtcgcggc cgcattaccc tgttatccct aatctcgttt    1500
aactatgact ctcttaaggt agccaaattc cggaactata aattgcgttg cgtcactgc    1560 ccgcttttcca gtcgggaaac ctgtcgtgcc agctgcataa atgaatcggc caacgcgcgg    1620
ggagaggcgg tttgcgtatt gggcgcgctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
```

```
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagacacg   2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt ttttgtttg caagcagcag attacgcgca   2400 gaaaaaagg atctcaagaa gatcctttga tcttttctac ggggtctgac gctcagtgga   2460
acgaaaactc acgttaaggg attttggtca tgagattatc aaaaaggatc ttcacctaga   2520
tccttttaaa ttaaaaatga agttttaaat caatctaaag tatatatgag taaacttggt   2580
ctgacatgcg catctgacgc tcagtggaac gaaaactcac gttaagggat tttggtcatg   2640
cctcagaaga actcgtcaag aaggcgatag aaggcgatgc gctgcgaatc gggagcggcg   2700
ataccgtaaa gcacgaggaa gcggtcagcc cattcgccgc caagctcttc agcaatatca   2760
cgggtagcca acgctatgtc ctgatagcgg tccgccacac ccagccggcc acagtcgatg   2820
aatccagaaa agcggccatt ttccaccatg atattcggca agcaggcatc gccatgggtc   2880
acgacgagat cctcgccgtc gggcatgcgc gccttgagcc tggcgaacag ttcggctggc   2940
gcgagcccct gatgctcttc gtccagatca tcctgatcga caagaccggc ttccatccga   3000
gtacgtgctc gctcgatgcg atgtttcgct tggtggtcga atgggcaggt agccggatca   3060
agcgtatgca gccgccgcat tgcatcagcc atgatggata ctttctcggc aggagcaagg   3120
tgagatgaca ggagatcctg ccccggcact tcgcccaata gcagccagtc ccttcccgct   3180
tcagtgacaa cgtcgagcac agctgcgcaa ggaacgcccg tcgtggccag ccacgatagc   3240
cgcgctgcct cgtcctgcag ttcattcagg gcaccggaca ggtcggtctt gacaaaaaga   3300
accgggcgcc cctgcgctga cagccggaac acggcggcat cagagcagcc gattgtctgt   3360
tgtgcccagt catagccgaa tagcctctcc acccaagcgg ccggagaacc tgcgtgcaat   3420
ccatcttgtt caatcatgcg aaacgatcct cattcattta tcagggttat tgtctcatga   3480
gcggatacat atttgaatgt atttaggctg agcatctatg tcgggtgcgg agaaagaggt   3540
aatgaaatgg caggcgcctt tttcgttaga tatgtagtaa gtatcttaat atacagcttt   3600
atctgttttt taagatactt actactttc ttagtggaaa ctattagtgg ctgttaatta   3660
agctagtact acccaagatt tgacagaatg catcgtttgc attcgaataa ctataacggt   3720
cctaaggtag cgacgtacga accgttgggc gcgcctgggg atagcgatcg ctgctggcgc   3780
ggtccgctat gaggtctctg atagaccaca gacgcgtcga cattgattat tgactagtta   3840
ttaatagtaa tcaattacgg ggtcattagt tcatagccca tatatggagt tccgcgttac   3900
ataacttacg gtaaatggcc cgcctggctg accgcccaac gacccccgcc cattgacgtc   3960
aataatgacg tatgttccca tagtaacgcc aatagggact ttccattgac gtcaatgggt   4020
ggactattta cggtaaactg cccacttggc agtacatcaa gtgtatcata tgccaagtac   4080
gccccctatt gacgtcaatg acggtaaatg gcccgcctgg cattatgccc agtacatgac   4140
```

```
cttatgggac tttcctactt ggcagtacat ctacgtatta gtcatcgcta ttaccatggg   4200
tcgaggtgag ccccacgttc tgcttcactc tccccatctc ccccccctcc caccccaa    4260 ttttgtattt atttattttt taattatttt gtgcagcgat gggggcgggg ggggggggggg 4320 cgcgcgccag gcggggcggg gcggggcgag gggcggggcg gggcgaggcg gagaggtgcg  4380
gcggcagcca atcagagcgg cgcgctccga aagtttcctt ttatggcgag cggcggcgg   4440 cggcggccct ataaaagcg aagcgcgcgg cgggcgggag tcgctgcgtt gccttcgccc   4500
cgtgccccgc tccgcgccgc ctcgcgccgc ccgccccggc tctgactgac cgcgttactc  4560
ccacaggtga gcgggcggga cggcccttct cctccgggct gtaattagcg cttggtttaa  4620
tgacggctcg tttctttcct gtggctgcgt gaaagcctta aagggctccg ggagggccct  4680
ttgtgcgggg gggagcggct cggggggtgc gtgcgtgtgt gtgtgcgtgg ggagcgccgc  4740
gtgcggcccg cgctgcccgg cggctgtgag cgctgcgggc gcggcgcggg gctttgtgcg  4800
ctccgcgtgt gcgcgagggg agcgcggccg ggggcggtgc cccgcggtgc ggggggggctg 4860 cgagggggaac aaaggctgcg tgcggggtgt gtgcgtgggg gggtgagcag ggggtgtggg 4920
cgcggcggtc gggctgtaac cccccctgc acccccctcc ccgagttgct gagcacggcc   4980
cggcttcggg tgcggggctc cgtgcggggc gtggcgcggg gctcgccgtg ccgggcgggg  5040
ggtggcggca ggtgggggtg ccggcgggg cggggccgcc tcgggccggg gagggctcgg   5100
gggaggggcg cggcggcccc ggagcgccgg cggctgtcga ggcgcggcga gccgcagcca  5160
ttgcctttta tggtaatcgt gcgagagggc gcagggactt cctttgtccc aaatctggcg  5220
gagccgaaat ctgggaggcg ccgccgcacc ccctctagcg ggcgcgggcg aagcggtgcg  5280
gcgccggcag gaaggaaatg ggcggggagg gccttcgtgc gtcgccgcgc cgccgtcccc  5340
ttctccatct ccagcctcgg ggctgccgca ggggacggc tgccttcggg ggggacgggg   5400
cagggcgggg ttcggcttct ggcgtgtgac cggcggctct agagcctctg ctaaccatgt  5460
tcatgccttc ttcttttttcc tacagctcct gggcaacgtg ctggttgttg tgctgtctca  5520
tcattttggc aaagaattcc ctgcaggaaa ttgagcccgc agcctcccgc ttcgctctct   5580
gctcctcctg ttcgacagtc agccgcatct tcttttgcgt cgccagccga gccacatcgc  5640
tcagacaccg                                                         5650
```

<210> SEQ ID NO 12
<211> LENGTH: 5650
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

```
taactataac ggtcctaagg tagcgacgta cgaaccgttg ggcgcgcctg gggatagcga    60
tcgctgctgg cgcggtccgc tatgaggtct ctgatagacc acagacgcgt cgacattgat   120
tattgactag ttattaatag taatcaatta cggggtcatt agttcatagc ccatatatgg   180
agttccgcgt tacataactt acggtaaatg gcccgcctgg ctgaccgccc aacgacccc    240 gcccattgac gtcaataatg acgtatgttc ccatagtaac gccaataggg actttccatt   300
gacgtcaatg ggtggactat ttacggtaaa ctgcccactt ggcagtacat caagtgtatc   360
atatgccaag tacgccccct attgacgtca atgacggtaa atggcccgcc tggcattatg   420
cccagtacat gaccttatgg gactttccta cttggcagta catctacgta ttagtcatcg   480
```

```
ctattaccat gggtcgaggt gagccccacg ttctgcttca ctctccccat ctccccccc     540
tccccacccc caattttgta tttatttatt ttttaattat tttgtgcagc gatgggggcg    600
gggggggggg gggcgcgcgc caggcggggc ggggcggggc gagggcgggg gcggggcgag    660
gcggagaggt gcggcggcag ccaatcagag cggcgcgctc cgaaagtttc cttttatggc    720
gaggcggcgg cggcggcggc cctataaaaa gcgaagcgcg cggcgggcgg gagtcgctgc    780
gttgccttcg ccccgtgccc cgctccgcgc cgcctcgcgc cgcccgcccc ggctctgact    840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct    960
ccgggagggc cctttgtgcg ggggggagcg gctcgggggg tgcgtgcgtg tgtgtgtgcg   1020
tggggagcgc cgccgtgcgg ccgcgctgcc cggcggctgt gagcgctgcg ggcgcggcgc   1080
ggggctttgt gcgctccgcg tgtgcgcgag gggagcgcgg ccggggggcgg tgccccgcgg   1140
tgcgggggggg ctgcgagggg aacaaaggct gcgtgcgggg tgtgtgcgtg ggggggtgag   1200
caggggggtgt gggcgcggcg gtcgggctgt aaccccccccc tgcaccccccc tccccgagtt   1260
gctgagcacg gcccggcttc gggtgcgggg ctccgtgcgg ggcgtggcgc ggggctcgcc   1320
gtgccgggcg gggggtggcg gcaggtgggg gtgccgggcg gggcggggcc gcctcgggcc   1380
ggggagggct cgggggaggg gcggcggcgg cccggagcgc cggcggctgt cgaggcgcgg   1440
cgagccgcag ccattgcctt ttatggtaat cgtgcgagag ggcgcaggga cttcctttgt   1500
cccaaatctg gcggagccga aatctgggag gcgccgccgc accccctcta gcgggcgcgg   1560
gcgaagcggt gcggcgccgg caggaaggaa atgggcgggg agggccttcg tgcgtcgccg   1620
cgccgccgtc cccttctcca tctccagcct cggggctgcc gcaggggggac ggctgccttc   1680
ggggggggacg gggcagggcg gggttcggct tctggcgtgt gaccggcggc tctagagcct   1740
ctgctaacca tgttcatgcc ttcttctttt tcctacagct cctgggcaac gtgctggttg   1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcat gaattttctg ctctcttggg tgcactggtc   1980
actggcactg ctgctgtatc tgcaccatgc aaaatggtcc caagcagctc ccatggcaga   2040
gggaggtgga cagaatcatc atgaggttgt caaatttatg gatgtctacc agcggagcta   2100
ctgccaccca attgagacgt tggtagacat ttttcaggaa tatccagacg agattgagta   2160
cattttcaag cctagctgtg tgcccttgat gcgatgcgt ggctgttgca atgatgaggg   2220
actcgagtgt gtccccaccg aggaaagcaa tataaccatg caaatcatgc gaatcaaacc   2280
ccaccagggc cagcatatcg gcgagatgtc tttcttgcaa cataacaaat gcgagtgtcg   2340
gccaaagaag gacagggctc gccaggaaaa tccctgtggt ccttgttcag agcgcaggaa   2400
gcatctttc gtccaggatc cgcagacttg taaatgttca tgcaagaata ccgattctag    2460
gtgtaaggcg aggcaactcg agcttaacga gagaacctgt aggtgtgaca aacctagaag   2520
acgtgcaaag cgtgcaccgg tgaaacaggg aagcggagct actaacttca gcctgctgaa   2580
gcaggctgga gacgtggagg agaaccctgg acctatgaat gccaaggtcg ttgtggtgct   2640
tgtacttgtg ctgactgctc tgtgtctgag cgacggaaaa ccagtctccc tcagctacag   2700
gtgcccatgc cgattcttcg aatctcatgt ggcccgggcc aatgtgaagc acttgaaaat   2760
cctgaataca cccaactgcg cgttgcagat cgtggcccgc ctgaaaaata ataataggca   2820
```

```
ggtatgtatc gatccaaagc ttaagtggat ccaggagtat ctggaaaagg ctctcaataa    2880
ataaatcgat tacgctcctc tactctttga gacatcactg gcctataata aatgggttaa    2940
tttatgtaac aaaattgcct tggcttgtta actttattag acattctgat gtttgcattg    3000
tgtaaatact gttgtattgg aaaagcgtgc aagatggat tattgtaatt cagtgtcttt     3060
tttagtagcg tcacgtgcca aacactgtta gtcacagagg gcatgagaca gcctgtgctg    3120
gaacagctca gttcataggg ctatggagat ggggagaaag gggcgcttct gtcagagaca    3180
agctgtggtc tgggaaggcc ttagcactaa aagcaccaca atgagaagca accgccagaa    3240
gcagggcccg caggcctttg ttccagctgc aaagagaaag gaaaaagtgg ggaataagag    3300
ttggggctgc ggagggggtg gggagcattg tgcaggttcc gtacttgaac agaaagcagg    3360
gaccaacaca aggaaggctc gagctggcgg aataggttcc aatctgtcgc ggccgcatta    3420
ccctgttatc cctaatctcg tttaactatg actctcttaa ggtagccaaa ttccggaact    3480
ataaattgcg ttgcgctcac tgcccgcttt ccagtcggga aacctgtcgt gccagctgca    3540
taaatgaatc ggccaacgcg cggggagagg cggtttgcgt attgggcgcg cttccgcttc    3600
ctcgctcact gactcgctgc gctcggtcgt tcggctgcgg cgagcggtat cagctcactc    3660
aaaggcggta atacggttat ccacagaatc aggggataac gcaggaaaga acatgtgagc    3720
aaaaggccag caaaaggcca ggaaccgtaa aaaggccgcg ttgctggcgt ttttccatag    3780
gctccgcccc cctgacgagc atcacaaaaa tcgacgctca agtcagaggt ggcgaaaccc    3840
gacaggacta taaagatacc aggcgtttcc ccctggaagc tccctcgtgc gctctcctgt    3900
tccgaccctg ccgcttaccg gatacctgtc cgcctttctc ccttcgggaa gcgtggcgct    3960
ttctcatagc tcacgctgta ggtatctcag ttcggtgtag gtcgttcgct ccaagctggg    4020
ctgtgtgcac gaaccccccg ttcagcccga ccgctgcgcc ttatccggta actatcgtct    4080
tgagtccaac ccggtaagac acgacttatc gccactggca gcagccactg gtaacaggat    4140
tagcagagcg aggtatgtag gcggtgctac agagttcttg aagtggtggc ctaactacgg    4200
ctacactaga agaacagtat ttggtatctg cgctctgctg aagccagtta ccttcggaaa    4260
aagagttggt agctcttgat ccggcaaaca aaccaccgct ggtagcggtg gtttttttgt    4320
ttgcaagcag cagattacgc gcagaaaaaa aggatctcaa gaagatcctt tgatcttttc    4380
tacgggtct gacgctcagt ggaacgaaaa ctcacgttaa gggattttgg tcatgagatt     4440
atcaaaaagg atcttcacct agatcctttt aaattaaaaa tgaagtttta atcaatcta     4500
aagtatatat gagtaaactt ggtctgacat gcgcatctga cgctcagtgg aacgaaaact    4560
cacgttaagg gattttggtc atgcctcaga agaactcgtc aagaaggcga tagaaggcga    4620
tgcgctgcga atcgggagcg gcgataccgt aaagcacgag gaagcggtca gcccattcgc    4680
cgccaagctc ttcagcaata tcacgggtag ccaacgctat gtcctgatag cggtccgcca    4740
cacccagccg gccacagtcg atgaatccag aaaagcggcc attttccacc atgatattcg    4800
gcaagcaggc atcgccatgg gtcacgacga gatcctcgcc gtcgggcatg cgcgccttga    4860
gcctggcgaa cagttcggct ggcgcgagcc cctgatgctc ttcgtccaga tcatcctgat    4920
cgacaagacc ggcttccatc cgagtacgtg ctcgctcgat gcgatgtttc gcttggtggt    4980
cgaatgggca ggtagccgga tcaagcgtat gcagccgccg cattgcatca gccatgatgg    5040
atactttctc ggcaggagca aggtgagatg acaggagatc ctgccccggc acttcgccca    5100
atagcagcca gtcccttccc gcttcagtga acaacgtcgag cacagctgcg caaggaacgc    5160
ccgtcgtggc cagccacgat agccgcgctg cctcgtcctg cagttcattc agggcaccgg    5220
```

| | |
|---|---|
| acaggtcggt cttgacaaaa agaaccgggc gcccctgcgc tgacagccgg aacacggcgg | 5280 |
| catcagagca gccgattgtc tgttgtgccc agtcatagcc gaatagcctc tccacccaag | 5340 |
| cggccggaga acctgcgtgc aatccatctt gttcaatcat gcgaaacgat cctcattcat | 5400 |
| ttatcagggt tattgtctca tgagcggata catatttgaa tgtatttagg ctgagcatct | 5460 |
| atgtcgggtg cggagaaaga ggtaatgaaa tggcaggcgc cttttcgtt agatatgtag | 5520 |
| taagtatctt aatatacagc tttatctgtt ttttaagata cttactactt ttcttagtgg | 5580 |
| aaactattag tggctgttaa ttaagctagt actacccaag atttgacaga atgcatcgtt | 5640 |
| tgcattcgaa | 5650 |

<210> SEQ ID NO 13
<211> LENGTH: 5665
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

| | |
|---|---|
| ctagcatgaa ttttctgctc tcttgggtgc actggtcact ggcactgctg ctgtatctgc | 60 |
| accatgcaaa atggtcccaa gcagctccca tggcagaggg aggtggacag aatcatcatg | 120 |
| aggttgtcaa atttatggat gtctaccagc ggagctactg ccacccaatt gagacgttgg | 180 |
| tagacatttt tcaggaatat ccagacgaga ttgagtacat tttcaagcct agctgtgtgc | 240 |
| ccttgatgcg atgcggtggc tgttgcaatg atgagggact cgagtgtgtc cccaccgagg | 300 |
| aaagcaatat aaccatgcaa atcatgcgaa tcaaacccca ccagggccag catatcggcg | 360 |
| agatgtcttt cttgcaacat aacaaatgcg agtgtcggcc aaagaaggac agggctcgcc | 420 |
| aggaaaatcc ctgtggtcct tgttcagagc gcaggaagca tcttttcgtc caggatccgc | 480 |
| agacttgtaa atgttcatgc aagaataccg attctaggtg taaggcgagg caactcgagc | 540 |
| ttaacgagag aacctgtagg tgtgacaaac ctagaagacg tgcaaagcgt gcaccggtga | 600 |
| aacagggaag cggagctact aacttcagcc tgctgaagca ggctggagac gtggaggaga | 660 |
| accctggacc tatgggcagc gaactggaaa ccgccatgga gactttgata aatgttttcc | 720 |
| acgcgcatag cggcaaagaa ggggacaagt acaagctgtc aaaaaaggag ctgaaagaac | 780 |
| tgctgcagac cgaattgagc ggcttcctgg acgctcagaa agatgtcgat gccgtcgaca | 840 |
| aagtgatgaa agagcttgac gagaacggtg acggtgaagt cgattttcag gaatatgtgg | 900 |
| tgctggtggc cgcccttact gtagcatgca caatttctt ttgggaaaat tcataaatcg | 960 |
| attacgctcc tctactcttt gagacatcac tggcctataa taatgggtt aatttatgta | 1020 |
| acaaaattgc cttggcttgt taactttatt agacattctg atgtttgcat tgtgtaaata | 1080 |
| ctgttgtatt ggaaaagcgt gccaagatgg attattgtaa ttcagtgtct tttttagtag | 1140 |
| cgtcacgtgc caaacactgt tagtcacaga gggcatgaga cagcctgtgc tggaacagct | 1200 |
| cagttcatag ggctatggag atggggagaa aggggcgctt ctgtcagaga caagctgtgg | 1260 |
| tctgggaagg ccttagcact aaaagcacca caatgagaag caaccgccag aagcagggcc | 1320 |
| cgcaggcctt tgttccagct gcaaagagaa aggaaaaagt ggggaataag agttgggggct | 1380 |
| gcggaggggg tggggagcat tgtgcaggtt ccgtacttga acagaaagca gggaccaaca | 1440 |
| caaggaaggc tcgagctggc ggaataggtt ccaatctgtc gcggccgcat taccctgtta | 1500 |

```
tccctaatct cgtttaacta tgactctctt aaggtagcca aattccggaa ctataaattg    1560
cgttgcgctc actgcccgct ttccagtcgg gaaacctgtc gtgccagctg cataaatgaa    1620
tcggccaacg cgcggggaga ggcggttttgc gtattgggcg cgcttccgct tcctcgctca    1680
ctgactcgct gcgctcggtc gttcggctgc ggcgagcgg atcagctcac tcaaaggcgg     1740
taatacggtt atccacagaa tcaggggata acgcaggaaa gaacatgtga gcaaaaggcc    1800
agcaaaaggc caggaaccgt aaaaaggccg cgttgctggc gttttccat aggctccgcc     1860 cccctgacga gcatcacaaa aatcgacgct caagtcagag gtggcgaaac ccgacaggac    1920
tataaagata ccaggcgttt ccccctggaa gctccctcgt gcgctctcct gttccgaccc    1980
tgccgcttac cggatacctg tccgcctttc tcccttcggg aagcgtggcg ctttctcata    2040
gctcacgctg taggtatctc agttcggtgt aggtcgttcg ctccaagctg ggctgtgtgc    2100
acgaaccccc cgttcagccc gaccgctgcg ccttatccgg taactatcgt cttgagtcca    2160
acccggtaag acacgactta tcgccactgg cagcagccac tggtaacagg attagcagag    2220
cgaggtatgt aggcggtgct acagagttct tgaagtggtg gcctaactac ggctacacta    2280
gaagaacagt atttggtatc tgcgctctgc tgaagccagt taccttcgga aaaagagttg    2340
gtagctcttg atccggcaaa caaaccaccg ctggtagcgg tggttttttt gtttgcaagc    2400
agcagattac gcgcagaaaa aaaggatctc aagaagatcc tttgatcttt tctacggggt    2460
ctgacgctca gtggaacgaa aactcacgtt aagggatttt ggtcatgaga ttatcaaaaa    2520
ggatcttcac ctagatcctt ttaaattaaa aatgaagttt taaatcaatc taaagtatat    2580
atgagtaaac ttggtctgac atgcgcatct gacgctcagt ggaacgaaaa ctcacgttaa    2640
gggattttgg tcatgcctca gaagaactcg tcaagaaggc gatagaaggc gatgcgctgc    2700 gaatcggag cggcgatacc gtaaagcacg aggaagcgt cagcccattc gccgccaagc      2760
tcttcagcaa tatcacgggt agccaacgct atgtcctgat agcggtccgc cacacccagc    2820
cggccacagt cgatgaatcc agaaaagcgg ccattttcca ccatgatatt cggcaagcag    2880
gcatcgccat gggtcacgac gagatcctcg ccgtcgggca tgcgcgcctt gagcctggcg    2940
aacagttcgg ctggcgcgag ccctgatgc tcttcgtcca gatcatcctg atcgacaaga    3000
ccggcttcca tccgagtacg tgctcgctcg atgcgatgtt tcgcttggtg gtcgaatggg    3060
caggtagccg gatcaagcgt atgcagccgc cgcattgcat cagccatgat ggatactttc    3120
tcggcaggag caaggtgaga tgacaggaga tcctgccccg gcacttcgcc caatagcagc    3180
cagtcccttc ccgcttcagt gacaacgtcg agcacagctg cgcaaggaac gcccgtcgtg    3240
gccagccacg atagccgcgc tgcctcgtcc tgcagttcat tcagggcacc ggacaggtcg    3300
gtcttgacaa aaagaaccgg gcgcccctgc gctgacagcc ggaacacggc ggcatcagag    3360
cagccgattg tctgttgtgc ccagtcatag ccgaatagcc tctccaccca agcggccgga    3420
gaacctgcgt gcaatccatc ttgttcaatc atgcgaaacg atcctcattc atttatcagg    3480
gttattgtct catgagcgga tacatatttg aatgtattta ggctgagcat ctatgtcggg    3540
tgcggagaaa gaggtaatga aatggcaggc gccttttcg ttagatatgt agtaagtatc     3600
ttaatataca gctttatctg ttttttaaga tacttactac ttttcttagt ggaaactatt    3660
agtggctgtt aattaagcta gtactaccca agatttgaca gaatgcatcg tttgcattcg    3720
aataactata acggtcctaa ggtagcgacg tacgaaccgt tgggcgcgcc tggggatagc    3780
gatcgctgct ggcgcggtcc gctatgaggt ctctgataga ccacagacgc gtcgacattg    3840
attattgact agtattaat agtaatcaat tacggggtca ttagttcata gcccatatat     3900
```

| | |
|---|---|
| ggagttccgc gttacataac ttacggtaaa tggcccgcct ggctgaccgc ccaacgaccc | 3960 |
| ccgcccattg acgtcaataa tgacgtatgt tcccatagta acgccaatag ggactttcca | 4020 |
| ttgacgtcaa tgggtggact atttacggta aactgcccac ttggcagtac atcaagtgta | 4080 |
| tcatatgcca agtacgcccc ctattgacgt caatgacggt aaatggcccg cctggcatta | 4140 |
| tgcccagtac atgaccttat gggactttcc tacttggcag tacatctacg tattagtcat | 4200 |
| cgctattacc atgggtcgag gtgagcccca cgttctgctt cactctcccc atctcccccc | 4260 |
| cctccccacc cccaattttg tatttattta ttttttaatt attttgtgca gcgatggggg | 4320 |
| cggggggggg ggggcgcgc gccaggcggg gcggggcggg gcgaggggcg gggcgggcg | 4380 |
| aggcggagag gtgcggcggc agccaatcag agcggcgcgc tccgaaagtt tccttttatg | 4440 |
| gcgaggcggc ggcggcggcg gccctataaa aagcgaagcg cgcggcgggc gggagtcgct | 4500 |
| gcgttgcctt cgccccgtgc cccgctccgc gccgcctcgc gccgcccgcc ccggctctga | 4560 |
| ctgaccgcgt tactcccaca ggtgagcggg cgggacggcc cttctcctcc gggctgtaat | 4620 |
| tagcgcttgg tttaatgacg gctcgtttct tttctgtggc tgcgtgaaag ccttaaaggg | 4680 |
| ctccggagg gccctttgtg cgggggggag cggctcgggg ggtgcgtgcg tgtgtgtgtg | 4740 |
| cgtggggagc gccgcgtgcg gcccgcgctg cccggcggct gtgagcgctg cgggcgcggc | 4800 |
| gcggggcttt gtgcgctccg cgtgtgcgcg agggagcgc ggccggggc ggtgccccgc | 4860 |
| ggtgcggggg ggctgcgagg ggaacaaagg ctgcgtgcgg ggtgtgtgcg tgggggggtg | 4920 |
| agcaggggt gtgggcgcgg cggtcgggct gtaacccccc cctgcacccc cctccccgag | 4980 |
| ttgctgagca cggcccggct tcgggtgcgg ggctccgtgc ggggcgtggc gcggggctcg | 5040 |
| ccgtgccggg cggggggtgg cggcaggtgg gggtgccggg cggggcgggg ccgcctcggg | 5100 |
| ccggggaggg ctcgggggag gggcgcggcg gccccggagc gccggcggct gtcgaggcgc | 5160 |
| ggcgagccgc agccattgcc ttttatggta atcgtgcgag agggcgcagg gacttccttt | 5220 |
| gtcccaaatc tggcggagcc gaaatctggg aggcgccgcc gcaccccctc tagcgggcgc | 5280 |
| gggcgaagcg gtgcggcgcc ggcaggaagg aaatgggcgg ggagggcctt cgtgcgtcgc | 5340 |
| cgcgccgccg tccccttctc catctccagc ctcgggctg ccgcaggggg acggctgcct | 5400 |
| tcgggggga cggggcaggg cggggttcgg cttctggcgt gtgaccggcg gctctagagc | 5460 |
| ctctgctaac catgttcatg ccttcttctt tttcctacag ctcctgggca acgtgctggt | 5520 |
| tgttgtgctg tctcatcatt ttggcaaaga attccctgca ggaaattgag cccgcagcct | 5580 |
| cccgcttcgc tctctgctcc tcctgttcga cagtcagccg catcttcttt tgcgtcgcca | 5640 |
| gccgagccac atcgctcaga caccg | 5665 |

<210> SEQ ID NO 14
<211> LENGTH: 5656
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

| | |
|---|---|
| taactataac ggtcctaagg tagcgacgta cgaaccgttg ggcgcgcctg gggatagcga | 60 |
| tcgctgctgg cgcggtccgc tatgaggtct ctgatagacc acagacgcgt cgacattgat | 120 |
| tattgactag ttattaatag taatcaatta cggggtcatt agttcatagc ccatatatgg | 180 |

```
agttccgcgt tacataactt acggtaaatg gcccgcctgg ctgaccgccc aacgaccccc    240
gcccattgac gtcaataatg acgtatgttc ccatagtaac gccaataggg actttccatt    300
gacgtcaatg ggtggactat ttacggtaaa ctgcccactt ggcagtacat caagtgtatc    360
atatgccaag tacgccccct attgacgtca atgacggtaa atggcccgcc tggcattatg    420
cccagtacat gaccttatgg gactttccta cttggcagta catctacgta ttagtcatcg    480
ctattaccat gggtcgaggt gagccccacg ttctgcttca ctctccccat ctcccccccc    540
tccccacccc caattttgta tttatttatt ttttaattat tttgtgcagc gatgggggcg    600 ggggggggg gggcgcgcgc caggcggggc ggggcggggc gaggggcggg gcggggcgag    660
gcggagaggt gcggcggcag ccaatcagag cggcgcgctc cgaaagtttc cttttatggc    720
gaggcggcgg cggcggcggc cctataaaaa gcgaagcgcg cggcgggcgg gagtcgctgc    780
gttgccttcg ccccgtgccc cgctccgcgc cgcctcgcgc cgcccgcccc ggctctgact    840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct    960
ccgggagggc cctttgtgcg gggggagcg gctcgggggg tgcgtgcgtg tgtgtgtgcg   1020
tggggagcgc cgcgtgcggc ccgcgctgcc cggcggctgt gagcgctgcg ggcgcggcgc   1080
ggggctttgt gcgctccgcg tgtgcgcgag gggagcgcgg ccggggggcgg tgccccgcgg   1140 tgcggggggg ctgcgagggg aacaaaggct gcgtgcgggg tgtgtgcgtg gggggtgag   1200 caggggggtgt gggcgcggcg gtcgggctgt aaccccccc tgcaccccc tccccgagtt   1260 gctgagcacg gcccggcttc gggtgcgggg ctccgtgcgg ggcgtggcgc ggggctcgcc   1320
gtgccgggcg gggggtggcg gcaggtgggg gtgccgggcg gggcggggcc gcctcgggcc   1380
ggggagggct cggggaggg gcgcggcggc cccggagcgc cggcggctgt cgaggcgcgg   1440
cgagccgcag ccattgcctt ttatggtaat cgtgcgagag ggcgcaggga cttcctttgt   1500
cccaaatctg gcggagccga aatctgggag gcgccgccgc accccctcta gcgggcgcgg   1560
gcgaagcggt gcggcgccgg caggaaggaa atgggcgggg agggccttcg tgcgtcgccg   1620
cgccgccgtc cccttctcca tctccagcct cggggctgcc gcaggggac ggctgccttc    1680 ggggggacg gggcagggcg gggttcggct tctggcgtgt gaccggcggc tctagagcct   1740
ctgctaacca tgttcatgcc ttcttctttt tcctacagct cctgggcaac gtgctggttg   1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcat gggcagcgaa ctggaaaccg ccatggagac   1980
tttgataaat gttttccacg cgcatagcgg caaagaaggg gacaagtaca agctgtcaaa   2040
aaaggagctg aaagaactgc tgcagaccga attgagcggc ttcctggacg ctcagaaaga   2100
tgtcgatgcc gtcgacaaag tgatgaaaga gcttgacgag aacggtgacg tgaagtcga   2160 ttttcaggaa tatgtggtgc tggtggccgc ccttactgta gcatgcaaca atttcttttg   2220
ggaaaattca agagccaaga gggcaccggt gaaacagact ttgaattttg accttctgaa   2280
gttggcagga gacgttgagt ccaaccctgg gcccatgaat tttctgctct cttgggtgca   2340
ctggtcactg gcactgctgc tgtatctgca ccatgcaaaa tggtcccaag cagctcccat   2400
ggcagaggga ggtggacaga atcatcatga ggttgtcaaa tttatggatg tctaccagcg   2460
gagctactgc cacccaattg agacgttggt agacattttt caggaatatc agacgagat   2520 tgagtacatt ttcaagccta gctgtgtgcc cttgatgcga tgcggtggct gttgcaatga   2580
```

```
tgagggactc gagtgtgtcc ccaccgagga agcaatata  accatgcaaa tcatgcgaat    2640
caaaccccac cagggccagc atatcggcga gatgtctttc ttgcaacata acaaatgcga    2700
gtgtcggcca aagaaggaca gggctcgcca ggaaaatccc tgtggtcctt gttcagagcg    2760
caggaagcat cttttcgtcc aggatccgca gacttgtaaa tgttcatgca agaataccga    2820
ttctaggtgt aaggcgaggc aactcgagct taacgagaga acctgtaggt gtgacaaacc    2880
tagaagataa atcgattacg ctcctctact ctttgagaca tcactggcct ataataaatg    2940
ggttaattta tgtaacaaaa ttgccttggc ttgttaactt tattagacat tctgatgttt    3000
gcattgtgta aatactgttg tattggaaaa gcgtgccaag atggattatt gtaattcagt    3060 gtcttttta  gtagcgtcac gtgccaaaca ctgttagtca cagagggcat gagacagcct    3120
gtgctggaac agctcagttc atagggctat ggagatgggg agaaagggggc gcttctgtca   3180 gagacaagct gtggtctggg aaggccttag cactaaaagc accacaatga gaagcaaccg    3240
ccagaagcag ggcccgcagg cctttgttcc agctgcaaag agaaaggaaa aagtggggaa    3300
taagagttgg ggctgcggag ggggtgggga gcattgtgca ggttccgtac ttgaacagaa    3360
agcagggacc aacacaagga aggctcgagc tggcggaata ggttccaatc tgtcgcggcc    3420
gcattaccct gttatcccta atctcgttta actatgactc tcttaaggta gccaaattcc    3480
ggaactataa attgcgttgc gctcactgcc cgctttccag tcgggaaacc tgtcgtgcca    3540
gctgcataaa tgaatcggcc aacgcgcggg gagaggcggt ttgcgtattg ggcgcgcttc    3600
cgcttcctcg ctcactgact cgctgcgctc ggtcgttcgg ctgcggcgag cggtatcagc    3660
tcactcaaag gcggtaatac ggttatccac agaatcaggg gataacgcag gaaagaacat   3720
gtgagcaaaa ggccagcaaa aggccaggaa ccgtaaaaag gccgcgttgc tggcgttttt    3780
ccataggctc cgcccccctg acgagcatca caaaaatcga cgctcaagtc agaggtggcg    3840
aaacccgaca ggactataaa gataccaggc gtttccccct ggaagctccc tcgtgcgctc    3900
tcctgttccg accctgccgc ttaccggata cctgtccgcc tttctccctt cgggaagcgt    3960
ggcgctttct catagctcac gctgtaggta tctcagttcg gtgtaggtcg ttcgctccaa    4020
gctgggctgt gtgcacgaac cccccgttca gcccgaccgc tgcgccttat ccggtaacta    4080
tcgtcttgag tccaacccgg taagacacga cttatcgcca ctggcagcag ccactggtaa    4140
caggattagc agagcgaggt atgtaggcgg tgctacagag ttcttgaagt ggtggcctaa    4200
ctacggctac actagaagaa cagtatttgg tatctgcgct ctgctgaagc cagttacctt    4260
cggaaaaaga gttggtagct cttgatccgg caaacaaacc accgctggta gcggtggttt    4320
ttttgtttgc aagcagcaga ttacgcgcag aaaaaaagga tctcaagaag atcctttgat    4380
cttttctacg gggtctgacg ctcagtggaa cgaaaactca cgttaaggga ttttggtcat    4440
gagattatca aaaaggatct tcacctagat ccttttaaat taaaaatgaa gttttaaatc    4500
aatctaaagt atatatgagt aaacttggtc tgacatgcgc atctgacgct cagtggaacg    4560
aaaactcacg ttaagggatt tggtcatgc  ctcagaagaa ctcgtcaaga aggcgataga    4620
aggcgatgcg ctgcgaatcg ggagcggcga taccgtaaag cacgaggaag cggtcagccc    4680
attcgccgcc aagctcttca gcaatatcac gggtagccaa cgctatgtcc tgatagcggt    4740
ccgccacacc cagccggcca cagtcgatga atccagaaaa gcggccattt tccaccatga    4800
tattcggcaa gcaggcatcg ccatgggtca cgacgagatc ctcgccgtcg gcatgcgcg    4860 ccttgagcct ggcgaacagt tcggctggcg cgagcccctg atgctcttcg tccagatcat    4920
```

```
cctgatcgac aagaccggct tccatccgag tacgtgctcg ctcgatgcga tgtttcgctt    4980
ggtggtcgaa tgggcaggta gccggatcaa gcgtatgcag ccgccgcatt gcatcagcca    5040
tgatggatac tttctcggca ggagcaaggt gagatgacag gagatcctgc cccggcactt    5100
cgcccaatag cagccagtcc cttcccgctt cagtgacaac gtcgagcaca gctgcgcaag    5160
gaacgcccgt cgtggccagc cacgatagcc gcgctgcctc gtcctgcagt tcattcaggg    5220
caccggacag gtcggtcttg acaaaaagaa ccgggcgccc ctgcgctgac agccggaaca    5280
cggcggcatc agagcagccg attgtctgtt gtgcccagtc atagccgaat agcctctcca    5340
cccaagcggc cggagaacct gcgtgcaatc catcttgttc aatcatgcga aacgatcctc    5400
attcatttat cagggttatt gtctcatgag cggatacata tttgaatgta tttaggctga    5460
gcatctatgt cgggtgcgga gaagaggta atgaaatggc aggcgccttt ttcgttagat      5520
atgtagtaag tatcttaata tacagcttta tctgtttttt aagatactta ctactttct     5580 tagtggaaac tattagtggc tgttaattaa gctagtacta cccaagatt  gacagaatgc    5640 atcgtttgca ttcgaa                                                     5656

<210> SEQ ID NO 15
<211> LENGTH: 5656
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgacccc      240 gcccattgac gtcaataatg acgtatgttc ccatagtaac gccaataggg actttccatt     300
gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc     540 tccccacccc caattttgta tttatttatt ttttaattat tttgtgcagc gatggggcg      600 ggggggggg gggcgcgcgc caggcggggc ggggcgggc gaggggcggg gcggggcgag       660
gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct     960 ccggagggc cctttgtgcg ggggagcg gctcggggg tgcgtgcgtg tgtgtgtgcg       1020 tggagcgc cgcgtgcggc ccgcgctgcc cggcggctgt gagcgctgcg ggcgcggcgc    1080
ggggctttgt gcgctccgcg tgtgcgcgag gggagcgcgg ccgggggcgg tgccccgcgg   1140
tgcggggggg ctgcgagggg aacaaaggct gcgtgcgggg tgtgtgcgtg ggggggtgag   1200 caggggtgt gggcgcggcg gtcgggctgt aaccccccc tgcaccccc tccccgagtt     1260
```

```
gctgagcacg gcccggcttc gggtgcgggg ctccgtgcgg ggcgtggcgc ggggctcgcc    1320
gtgccgggcg gggggtggcg gcaggtgggg gtgccgggcg gggcggggcc gcctcgggcc    1380
ggggagggct cggggagggg gcgcggcggc cccggagcgc cggcggctgt cgaggcgcgg    1440
cgagccgcag ccattgcctt ttatggtaat cgtgcgagag ggcgcaggga cttcctttgt    1500
cccaaatctg gcggagccga aatctgggag gcgccgccgc acccctcta gcgggcgcgg     1560 gcgaagcggt gcggcgccgg caggaaggaa atgggcgggg agggccttcg tgcgtcgccg    1620
cgccgccgtc cccttctcca tctccagcct cggggctgcc gcaggggac ggctgccttc     1680 ggggggacg gggcagggcg gggttcggct tctggcgtgt gaccggcggc tctagagcct     1740
ctgctaacca tgttcatgcc ttcttctttt tcctacagct cctgggcaac gtgctggttg    1800
ttgtgctgtc tcatcatttt ggcaaagaat tccctgcagg aaattgagcc cgcagcctcc    1860
cgcttcgctc tctgctcctc ctgttcgaca gtcagccgca tcttcttttg cgtcgccagc    1920
cgagccacat cgctcagaca ccgctagcat gaattttctg ctctcttggg tgcactggtc    1980
actggcactg ctgctgtatc tgcaccatgc aaaatggtcc caagcagctc ccatggcaga    2040
gggaggtgga cagaatcatc atgaggttgt caaatttatg gatgtctacc agcggagcta    2100
ctgccaccca attgagacgt tggtagacat ttttcaggaa tatccagacg agattgagta    2160
cattttcaag cctagctgtg tgcccttgat gcgatgcgt ggctgttgca atgatgaggg     2220
actcgagtgt gtccccaccg aggaaagcaa tataaccatg caaatcatgc gaatcaaacc    2280
ccaccagggc cagcatatcg gcgagatgtc tttcttgcaa cataacaaat gcagtgtcg     2340 gccaaagaag gacagggctc gccaggaaaa tccctgtggt ccttgttcag agcgcaggaa    2400
gcatcttttc gtccaggatc cgcagacttg taaatgttca tgcaagaata ccgattctag    2460
gtgtaaggcg aggcaactcg agcttaacga gagaacctgt aggtgtgaca aacctagaag    2520
aagagccaag agggcaccgg tgaaacagac tttgaatttt gaccttctga agttggcagg    2580
agacgttgag tccaaccctg ggcccatggg cagcgaactg gaaaccgcca tggagacttt    2640
gataaatgtt ttccacgcgc atagcggcaa agaaggggac aagtacaagc tgtcaaaaaa    2700
ggagctgaaa gaactgctgc agaccgaatt gagcggcttc ctggacgctc agaaagatgt    2760
cgatgccgtc gacaaagtga tgaaagagct tgacgagaac ggtgacggtg aagtcgattt    2820
tcaggaatat gtggtgctgg tggccgccct tactgtagca tgcaacaatt cttttgggaa    2880
aaattcataa atcgattacg ctcctctact ctttgagaca tcactggcct ataataaatg    2940
ggttaattta tgtaacaaaa ttgccttggc ttgttaactt tattagacat tctgatgttt    3000
gcattgtgta aatactgttg tattggaaaa gcgtgccaag atggattatt gtaattcagt    3060
gtctttttta gtagcgtcac gtgccaaaca ctgttagtca cagagggcat gagacagcct    3120
gtgctggaac agctcagttc atagggctat ggagatgggg agaaggggc gcttctgtca     3180 gagacaagct gtggtctggg aaggccttag cactaaaagc accacaatga gaagcaaccg    3240
ccagaagcag ggcccgcagg cctttgttcc agctgcaaag agaaaggaaa agtggggaa     3300 taagagttgg ggctgcggag ggggtgggga gcattgtgca ggttccgtac ttgaacagaa    3360
agcagggacc aacacaagga aggctcgagc tggcggaata ggttccaatc tgtcgcggcc    3420
gcattaccct gttatcccta atctcgttta actatgactc tcttaaggta gccaaattcc    3480
ggaactataa attgcgttgc gctcactgcc cgctttccag tcgggaaacc tgtcgtgcca    3540
gctgcataaa tgaatcggcc aacgcgcggg gagaggcggt ttgcgtattg ggcgcgcttc    3600
```

| cgcttcctcg ctcactgact cgctgcgctc ggtcgttcgg ctgcggcgag cggtatcagc | 3660 |
| tcactcaaag gcggtaatac ggttatccac agaatcaggg gataacgcag gaaagaacat | 3720 |
| gtgagcaaaa ggccagcaaa aggccaggaa ccgtaaaaag gccgcgttgc tggcgttttt | 3780 |
| ccataggctc cgcccccctg acgagcatca caaaaatcga cgctcaagtc agaggtggcg | 3840 |
| aaacccgaca ggactataaa gataccaggc gtttccccct ggaagctccc tcgtgcgctc | 3900 |
| tcctgttccg accctgccgc ttaccggata cctgtccgcc tttctccctt cgggaagcgt | 3960 |
| ggcgctttct catagctcac gctgtaggta tctcagttcg gtgtaggtcg ttcgctccaa | 4020 |
| gctgggctgt gtgcacgaac cccccgttca gcccgaccgc tgcgccttat ccggtaacta | 4080 |
| tcgtcttgag tccaacccgg taagacacga cttatcgcca ctggcagcag ccactggtaa | 4140 |
| caggattagc agagcgaggt atgtaggcgg tgctacagag ttcttgaagt ggtggcctaa | 4200 |
| ctacggctac actagaagaa cagtatttgg tatctgcgct ctgctgaagc cagttacctt | 4260 |
| cggaaaaaga gttggtagct cttgatccgg caaacaaacc accgctggta gcggtggttt | 4320 |
| ttttgtttgc aagcagcaga ttacgcgcag aaaaaaagga tctcaagaag atcctttgat | 4380 |
| cttttctacg gggtctgacg ctcagtggaa cgaaaactca cgttaaggga ttttggtcat | 4440 |
| gagattatca aaaaggatct tcacctagat ccttttaaat taaaaatgaa gttttaaatc | 4500 |
| aatctaaagt atatatgagt aaacttggtc tgacatgcgc atctgacgct cagtggaacg | 4560 |
| aaaactcact taagggattt tggtcatgct ctcagaagac tcgtcaaga aggcgataga | 4620 |
| aggcgatgcg ctgcgaatcg ggagcggcga taccgtaaag cacgaggaag cggtcagccc | 4680 |
| attcgccgcc aagctcttca gcaatatcac gggtagccaa cgctatgtcc tgatagcggt | 4740 |
| ccgccacacc cagccggcca cagtcgatga atccagaaaa gcggccattt tccaccatga | 4800 |
| tattcggcaa gcaggcatcg ccatgggtca cgacgagatc ctcgccgtcg gcatgcgcg | 4860 |
| ccttgagcct ggcgaacagt tcggctggcg cgagcccctg atgctcttcg tccagatcat | 4920 |
| cctgatcgac aagaccggct tccatccgag tacgtgctcg ctcgatgcga tgtttcgctt | 4980 |
| ggtggtcgaa tgggcaggta gccggatcaa gcgtatgcag ccgccgcatt gcatcagcca | 5040 |
| tgatggatac tttctcggca ggagcaaggt gagatgacag gagatcctgc cccggcactt | 5100 |
| cgcccaatag cagccagtcc cttcccgctt cagtgacaac gtcgagcaca gctgcgcaag | 5160 |
| gaacgcccgt cgtggccagc cacgatagcc gcgctgcctc gtcctgcagt tcattcaggg | 5220 |
| caccggacag gtcggtcttg acaaaaagaa ccgggcgccc ctgcgctgac agccggaaca | 5280 |
| cggcggcatc agagcagccg attgtctgtt gtgcccagtc atagccgaat agcctctcca | 5340 |
| cccaagcggc cggagaacct gcgtgcaatc catcttgttc aatcatgcga acgatcctc | 5400 |
| attcatttat cagggttatt gtctcatgag cggatacata tttgaatgta tttaggctga | 5460 |
| gcatctatgt cgggtgcgga gaaagaggta atgaaatggc aggcgccttt ttcgttagat | 5520 |
| atgtagtaag tatcttaata tacagcttta tctgtttttt aagatactta ctactttct | 5580 |
| tagtggaaac tattagtggc tgttaattaa gctagtacta cccaagattt gacagaatgc | 5640 |
| atcgtttgca ttcgaa | 5656 |

<210> SEQ ID NO 16
<211> LENGTH: 5638
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 16
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaataggg actttccatt     300
gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc     540 tccccacccc caattttgta tttatttatt ttttaattat tttgtgcagc gatggggggcg    600 ggggggggggg gggcgcgcgc caggcggggc ggggcggggc gagggcgggg gcggggcgag    660
gcggagaggt gcggcggcag ccaatcagag cggcgcgctc cgaaagtttc cttttatggc    720
gaggcggcgg cggcggcggc cctataaaaa gcgaagcgcg cggcgggcgg gagtcgctgc    780
gttgccttcg ccccgtgccc cgctccgcgc cgcctcgcgc cgcccgcccc ggctctgact    840
gaccgcgtta ctcccacagg tgagcgggcg ggacggccct tctcctccgg gctgtaatta    900
gcgcttggtt taatgacggc tcgtttcttt tctgtggctg cgtgaaagcc ttaaagggct    960
ccgggagggc cctttgtgcg ggggggagcg gctcggggg tgcgtgcgtg tgtgtgtgcg    1020
tggggagcgc cgcgtgcggc ccgcgctgcc cggcggctgt gagcgctgcg ggcgcggcgc    1080
ggggctttgt gcgctccgcg tgtgcgcgag gggagcgcgg ccggggggcgg tgccccgcgg    1140 tgcggggggg ctgcgagggg aacaaaggct gcgtgcgggg tgtgtgcgtg gggggtgag    1200 cagggggtgt gggcgcggcg gtcgggctgt aaccccccc tgcacccccc tccccgagtt    1260
gctgagcacg gcccggcttc gggtgcgggg ctccgtgcgg ggcgtggcgc ggggctcgcc    1320
gtgccgggcg ggggtggcg gcaggtgggg gtgccgggcg gggcggggcc gcctcgggcc    1380
ggggagggct cggggaggg gcgcggcggc cccggagcgc cggcggctgt cgaggcgcgg    1440
cgagccgcag ccattgcctt ttatggtaat cgtgcgagag ggcgcaggga cttcctttgt    1500
cccaaatctg gcgagccga aatctgggag gcgccgccgc accccctcta gcgggcgcgg    1560
gcgaagcggt gcggcgccgg caggaaggaa atgggcgggg agggccttcg tgcgtcgccg    1620
cgccgccgtc cccttctcca tctccagcct cggggctgcc gcaggggac ggctgccttc    1680 ggggggggacg gggcagggcg gggttcggct tctggcgtgt gaccggcggc tctagagcct    1740
ctgctaacca tgttcatgcc ttcttctttt tcctacagct cctgggcaac gtgctggttg    1800
ttgtgctgtc tcatcatttt ggcaaagaat tccctgcagg aaattgagcc cgcagcctcc    1860
cgcttcgctc tctgctcctc ctgttcgaca gtcagccgca tcttcttttg cgtcgccagc    1920
cgagccacat cgctcagaca ccgctagcat gggcagcgaa ctggaaaccg ccatggagac    1980
tttgataaat gttttccacg cgcatagcgg caaagaaggg gacaagtaca agctgtcaaa    2040
aaaggagctg aaagaactgc tgcagaccga attgagcgg ttcctggacg ctcagaaaga    2100
tgtcgatgcc gtcgacaaag tgatgaaaga gcttgacgag aacggtgacg gtgaagtcga    2160
ttttcaggaa tatgtggtgc tggtggccgc ccttactgta gcatgcaaca atttcttttg    2220
ggaaaattca ggaagcggag ctactaactt cagcctgctg aagcaggctg agacgtgga    2280
```

```
ggagaaccct ggacctatga attttctgct ctcttgggtg cactggtcac tggcactgct    2340
gctgtatctg caccatgcaa aatggtccca agcagctccc atggcagagg gaggtggaca    2400
gaatcatcat gaggttgtca aatttatgga tgtctaccag cggagctact gccacccaat    2460
tgagacgttg gtagacattt ttcaggaata tccagacgag attgagtaca ttttcaagcc    2520
tagctgtgtg cccttgatgc gatgcggtgg ctgttgcaat gatgagggac tcgagtgtgt    2580
ccccaccgag gaaagcaata taaccatgca aatcatgcga atcaaacccc accagggcca    2640
gcatatcggc gagatgtctt tcttgcaaca taacaaatgc gagtgtcggc caaagaagga    2700
cagggctcgc caggaaaatc cctgtggtcc ttgttcagag cgcaggaagc atcttttcgt    2760
ccaggatccg cagacttgta aatgttcatg caagaatacc gattctaggt gtaaggcgag    2820
gcaactcgag cttaacgaga gaacctgtag gtgtgacaaa cctagaagat aaatcgatta    2880
cgctcctcta ctctttgaga catcactggc ctataataaa tgggttaatt tatgtaacaa    2940
aattgccttg gcttgttaac tttattagac attctgatgt ttgcattgtg taaatactgt    3000
tgtattggaa aagcgtgcca agatggatta ttgtaattca gtgtctttttt tagtagcgtc    3060 acgtgccaaa cactgttagt cacagagggc atgagacagc ctgtgctgga acagctcagt    3120
tcatagggct atggagatgg ggagaaaggg gcgcttctgt cagagacaag ctgtggtctg    3180
ggaaggcctt agcactaaaa gcaccacaat gagaagcaac cgccagaagc agggcccgca    3240
ggcctttgtt ccagctgcaa agagaaagga aaaagtgggg aataagagtt ggggctgcgg    3300
agggggtggg gagcattgtg caggttccgt acttgaacag aaagcaggga ccaacacaag    3360
gaaggctcga gctggcggaa taggttccaa tctgtcgcgg ccgcattacc ctgttatccc    3420
taatctcgtt taactatgac tctcttaagg tagccaaatt ccggaactat aaattgcgtt    3480
gcgctcactg cccgctttcc agtcgggaaa cctgtcgtgc cagctgcata atgaatcgg    3540 ccaacgcgcg gggagaggcg gtttgcgtat gggcgcgct tccgcttcct cgctcactga    3600
ctcgctgcgc tcggtcgttc ggctgcggcg agcggtatca gctcactcaa aggcggtaat    3660
acggttatcc acagaatcag gggataacgc aggaaagaac atgtgagcaa aaggccagca    3720
aaaggccagg aaccgtaaaa aggccgcgtt gctggcgttt ttccataggc tccgcccccc    3780
tgacgagcat cacaaaaatc gacgctcaag tcagaggtgg cgaaacccga caggactata    3840
aagataccag gcgtttcccc ctggaagctc cctcgtgcgc tctcctgttc cgaccctgcc    3900
gcttaccgga tacctgtccg cctttctccc ttcgggaagc gtggcgcttt ctcatagctc    3960
acgctgtagg tatctcagtt cggtgtaggt cgttcgctcc aagctgggct gtgtgcacga    4020
accccccgtt cagcccgacc gctgcgcctt atccggtaac tatcgtcttg agtccaaccc    4080
ggtaagacac gacttatcgc cactggcagc agccactggt aacaggatta gcagagcgag    4140
gtatgtaggc ggtgctacag agttcttgaa gtggtggcct aactacggct acactagaag    4200
aacagtattt ggtatctgcg ctctgctgaa gccagttacc ttcggaaaaa gagttggtag    4260
ctcttgatcc ggcaaacaaa ccaccgctgg tagcggtggt ttttttgttt gcaagcagca    4320
gattacgcgc agaaaaaaag gatctcaaga agatcctttg atcttttcta cggggtctga    4380
cgctcagtgg aacgaaaact cacgttaagg gattttggtc atgagattat caaaaaggat    4440
cttcacctag atccttttaa attaaaaatg aagttttaaa tcaatctaaa gtatatatga    4500
gtaaacttgg tctgacatgc gcatctgacg ctcagtggaa cgaaaactca cgttaaggga    4560
ttttggtcat gcctcagaag aactcgtcaa gaaggcgata aaggcgatg cgctgcgaat    4620 cgggagcggc gataccgtaa agcacgagga agcggtcagc ccattcgccg ccaagctctt    4680
```

-continued

```
cagcaatatc acgggtagcc aacgctatgt cctgatagcg gtccgccaca cccagccggc    4740
cacagtcgat gaatccagaa aagcggccat tttccaccat gatattcggc aagcaggcat    4800
cgccatgggt cacgacgaga tcctcgccgt cgggcatgcg cgccttgagc ctggcgaaca    4860
gttcggctgg cgcgagcccc tgatgctctt cgtccagatc atcctgatcg acaagaccgg    4920
cttccatccg agtacgtgct cgctcgatgc gatgtttcgc ttggtggtcg aatgggcagg    4980
tagccggatc aagcgtatgc agccgccgca ttgcatcagc catgatggat actttctcgg    5040
caggagcaag gtgagatgac aggagatcct gccccggcac ttcgcccaat agcagccagt    5100
cccttcccgc ttcagtgaca acgtcgagca cagctgcgca aggaacgccc gtcgtggcca    5160
gccacgatag ccgcgctgcc tcgtcctgca gttcattcag ggcaccggac aggtcggtct    5220
tgacaaaaag aaccgggcgc ccctgcgctg acagccggaa cacggcggca tcagagcagc    5280
cgattgtctg ttgtgcccag tcatagccga atagcctctc cacccaagcg gccggagaac    5340
ctgcgtgcaa tccatcttgt tcaatcatgc gaaacgatcc tcattcattt atcagggtta    5400
ttgtctcatg agcggataca tatttgaatg tatttaggct gagcatctat gtcgggtgcg    5460
gagaaagagg taatgaaatg gcaggcgcct ttttcgttag atatgtagta agtatcttaa    5520
tatacagctt tatctgtttt ttaagatact tactactttt cttagtggaa actattagtg    5580
gctgttaatt aagctagtac tacccaagat ttgacagaat gcatcgtttg cattcgaa     5638
```

<210> SEQ ID NO 17  
<211> LENGTH: 5638  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 17

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaataggg actttccatt     300
gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc     540 tccccacccc caattttgta tttatttatt ttttaattat tttgtgcagc gatggggcg     600 ggggggggg gggcgcgcgc caggcggggc gggcgggc gaggggcggg gcggggcgag     660
gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcgggcg ggacggccct tctcctccgg gctgtaatta     900
gcgcttggtt taatgacggc tcgtttcttt tctgtggctg cgtgaaagcc ttaaagggct     960 ccggagggc cctttgtgcg ggggggagcg gctcgggggg tgcgtgcgtg tgtgtgtgcg    1020
```

```
tggggagcgc cgcgtgcggc ccgcgctgcc cggcggctgt gagcgctgcg ggcgcggcgc    1080
gggctttgt gcgctccgcg tgtgcgcgag gggagcgcgg ccgggggcgg tgccccgcgg     1140
tgcggggggg ctgcgagggg aacaaaggct gcgtgcgggg tgtgtgcgtg gggggtgag     1200
caggggtgt gggcgcggcg gtcggctgt aaccccccc tgcacccccc tccccgagtt       1260
gctgagcacg gcccggcttc gggtgcgggg ctccgtgcgg ggcgtggcgc ggggctcgcc    1320
gtgccgggcg ggggtggcg gcaggtgggg gtgccgggcg gggcggggcc gcctcgggcc    1380
ggggagggct cggggaggg gcgcggcggc cccggagcgc cggcggctgt cgaggcgcgg     1440
cgagccgcag ccattgcctt ttatggtaat cgtgcgagag ggcgcaggga cttcctttgt   1500
cccaaatctg gcggagccga aatctgggag gcgccgccgc accccctcta gcgggcgcgg   1560
gcgaagcggt gcggcgccgg caggaaggaa atgggcgggg agggccttcg tgcgtcgccg   1620
cgccgccgtc cccttctcca tctccagcct cggggctgcc gcaggggac ggctgccttc    1680
ggggggacg gggcagggcg gggttcggct tctggcgtgt gaccggcggc tctagagcct    1740
ctgctaacca tgttcatgcc ttcttctttt tcctacagct cctgggcaac gtgctggttg   1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcat gaattttctg ctctcttggg tgcactggtc   1980
actggcactg ctgctgtatc tgcaccatgc aaaatggtcc caagcagctc ccatggcaga   2040
gggaggtgga cagaatcatc atgaggttgt caaatttatg gatgtctacc agcggagcta   2100
ctgccaccca attgagacgt tggtagacat ttttcaggaa tatccagacg agattgagta   2160
cattttcaag cctagctgtg tgcccttgat gcgatgcggt ggctgttgca atgatgaggg   2220
actcgagtgt gtccccaccg aggaaagcaa tataaccatg caaatcatgc gaatcaaacc   2280
ccaccagggc cagcatatcg gcgagatgtc tttcttgcaa cataacaaat gcgagtgtcg   2340
gccaaagaag gacagggctc gccaggaaaa tccctgtggt ccttgttcag agcgcaggaa   2400
gcatcttttc gtccaggatc cgcagacttg taaatgttca tgcaagaata ccgattctag   2460
gtgtaaggcg aggcaactcg agcttaacga gagaacctgt aggtgtgaca aacctagaag   2520
aggaagcgga gctactaact tcagcctgct gaagcaggct ggagacgtgg aggagaaccc   2580
tggacctatg ggcagcgaac tggaaaccgc catggagact tgataaatg ttttccacgc    2640
gcatagcggc aaagaagggg acaagtacaa gctgtcaaaa aaggagctga agaactgct    2700
gcagaccgaa ttgagcggct tcctggacgc tcagaaagat gtcgatgccg tcgacaaagt   2760
gatgaaagag cttgacgaga acggtgacgg tgaagtcgat tttcaggaat atgtggtgct   2820
ggtgccgcc cttactgtag catgcaacaa tttctttgg gaaaattcat aaatcgatta     2880
cgctcctcta ctcttgaga catcactggc ctataataaa tgggttaatt tatgtaacaa    2940
aattgccttg gcttgttaac tttattagac attctgatgt ttgcattgtg taaatactgt   3000
tgtattggaa aagcgtgcca agatggatta ttgtaattca gtgtcttttt tagtagcgtc   3060
acgtgccaaa cactgttagt cacagagggc atgagacagc ctgtgctgga acagctcagt   3120
tcatagggct atggagatgg ggagaaaggg gcgcttctgt cagagacaag ctgtggtctg   3180
ggaaggcctt agcactaaaa gcaccacaat gagaagcaac cgccagaagc agggcccgca   3240
ggcctttgtt ccagctgcaa agagaaagga aaaagtgggg aataagagtt ggggctgcgg   3300
aggggtggg gagcattgtg caggttccgt acttgaacag aaagcaggga ccaacacaag    3360
gaaggctcga gctggcggaa taggttccaa tctgtcgcgg ccgcattacc ctgttatccc   3420
```

```
taatctcgtt taactatgac tctcttaagg tagccaaatt ccggaactat aaattgcgtt    3480
gcgctcactg cccgctttcc agtcgggaaa cctgtcgtgc cagctgcata atgaatcgg     3540 ccaacgcgcg gggagaggcg gtttgcgtat tgggcgcgct tccgcttcct cgctcactga    3600
ctcgctgcgc tcggtcgttc ggctgcggcg agcggtatca gctcactcaa aggcggtaat    3660
acggttatcc acagaatcag gggataacgc aggaaagaac atgtgagcaa aaggccagca    3720
aaaggccagg aaccgtaaaa aggccgcgtt gctggcgttt ttccataggc tccgcccccc    3780
tgacgagcat cacaaaaatc gacgctcaag tcagaggtgg cgaaacccga caggactata    3840
aagataccag gcgtttcccc ctggaagctc cctcgtgcgc tctcctgttc cgaccctgcc    3900
gcttaccgga tacctgtccg cctttctccc ttcgggaagc gtggcgcttt ctcatagctc    3960
acgctgtagg tatctcagtt cggtgtaggt cgttcgctcc aagctgggct gtgtgcacga    4020
accccccgtt cagcccgacc gctgcgcctt atccggtaac tatcgtcttg agtccaaccc    4080
ggtaagacac gacttatcgc cactggcagc agccactggt aacaggatta gcagagcgag    4140
gtatgtaggc ggtgctacag agttcttgaa gtggtggcct aactacggct acactagaag    4200
aacagtattt ggtatctgcg ctctgctgaa gccagttacc ttcggaaaaa gagttggtag    4260
ctcttgatcc ggcaaacaaa ccaccgctgg tagcggtggt ttttttgttt gcaagcagca    4320
gattacgcgc agaaaaaaag gatctcaaga agatcctttg atcttttcta cggggtctga    4380
cgctcagtgg aacgaaaact cacgttaagg gattttggtc atgagattat caaaaaggat    4440
cttcacctag atccttttaa attaaaaatg aagttttaaa tcaatctaaa gtatatatga    4500
gtaaacttgg tctgacatgc gcatctgacg ctcagtggaa cgaaaactca cgttaaggga    4560
ttttggtcat gcctcagaag aactcgtcaa gaaggcgata gaaggcgatg cgctgcgaat    4620
cgggagcggc gataccgtaa agcacgagga agcggtcagc ccattcgccg ccaagctctt    4680
cagcaatatc acgggtagcc aacgctatgt cctgatagcg gtccgccaca cccagccggc    4740
cacagtcgat gaatccagaa aagcggccat tttccaccat gatattcggc aagcaggcat    4800
cgccatgggt cacgacgaga tcctcgccgt cgggcatgcg cgccttgagc ctggcgaaca    4860
gttcggctgg cgcgagcccc tgatgctctt cgtccagatc atcctgatcg acaagaccgg    4920
cttccatccg agtacgtgct cgctcgatgc gatgtttcgc ttggtggtcg aatgggcagg    4980
tagccggatc aagcgtatgc agccgccgca ttgcatcagc catgatggat actttctcgg    5040
caggagcaag gtgagatgac aggagatcct gccccggcac ttcgcccaat agcagccagt    5100
cccttcccgc ttcagtgaca acgtcgagca cagctgcgca aggaacgccc gtcgtggcca    5160
gccacgatag ccgcgctgcc tcgtcctgca gttcattcag gcaccggac aggtcggtct    5220 tgacaaaaag aaccgggcgc ccctgcgctg acagccggaa cacggcggca tcagagcagc    5280
cgattgtctg ttgtgcccag tcatagccga atagcctctc cacccaagcg gccggagaac    5340
ctgcgtgcaa tccatcttgt tcaatcatgc gaaacgatcc tcattcattt atcagggtta    5400
ttgtctcatg agcggataca tatttgaatg tatttaggct gagcatctat gtcgggtgcg    5460
gagaaagagg taatgaaatg gcaggcgcct ttttcgttag atatgtagta agtatcttaa    5520
tatacagctt tatctgtttt ttaagatact tactactttt cttagtggaa actattagtg    5580
gctgttaatt aagctagtac tacccaagat ttgacagaat gcatcgtttg cattcgaa     5638
```

<210> SEQ ID NO 18
<211> LENGTH: 5665
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgacccc      240
gcccattgac gtcaataatg acgtatgttc ccatagtaac gccaataggg actttccatt     300
gacgtcaatg ggtggactat ttacggtaaa ctgcccactt ggcagtacat caagtgtatc     360
atatgccaag tacgcccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctccccccc      540
tccccacccc caattttgta tttatttatt ttttaattat tttgtgcagc gatggggcg      600
gggggggggg gggcgcgcgc caggcggggc ggggcggggc gaggggcggg gcggggcgag     660
gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
gaccgcgtta ctcccacagg tgagcgggcg ggacggccct tctcctccgg gctgtaatta     900
gcgcttggtt taatgacggc tcgtttcttt tctgtggctg cgtgaaagcc ttaaagggct     960
ccgggagggc cctttgtgcg ggggggagcg gctcggggg tgcgtgcgtg tgtgtgtgcg    1020
tggggagcgc cgcgtgcggc ccgcgctgcc cggcggctgt gagcgctgcg ggcgcggcgc    1080
ggggctttgt gcgctccgcg tgtgcgcgag gggagcgcgg ccggggcgg tgccccgcgg    1140
tgcggggggg ctgcgagggg aacaaaggct gcgtgcgggg tgtgtgcgtg ggggggtgag    1200
cagggggtgt gggcgcggcg tcgggctgt aacccccccc tgcaccccccc tccccgagtt   1260
gctgagcacg gcccggcttc gggtgcgggg ctccgtgcgg ggcgtggcgc ggggctcgcc    1320
gtgccgggcg ggggtggcg gcaggtgggg gtgccgggcg gggcggggcc gcctcgggcc    1380
ggggagggct cggggagggt gcgcggcggc cccggagcgc cggcggctgt cgaggcgcgg    1440
cgagccgcag ccattgcctt ttatggtaat cgtgcgagag ggcgcaggga cttcctttgt    1500
cccaaatctg gcggagccga atctgggag gcgccgccgc accccctcta gcgggcgcgg    1560
gcgaagcggt gcggcgccgg caggaaggaa atgggcgggg agggccttcg tgcgtcgccg    1620
cgccgccgtc cccttctcca tctccagcct cggggctgcc gcaggggac ggctgccttc    1680
ggggggacg gggcagggcg gggttcggct tctggcgtgt gaccggcggc tctagagcct    1740
ctgctaacca tgttcatgcc ttcttctttt cctacagct cctgggcaac gtgctggttg    1800
ttgtgctgtc tcatcatttt ggcaaagaat tccctgcagg aaattgagcc cgcagcctcc    1860
cgcttcgctc tctgctcctc ctgttcgaca gtcagccgca tcttcttttg cgtcgccagc    1920
cgagccacat cgctcagaca ccgctagcat gggcagcgaa ctggaaaccg ccatggagac    1980
tttgataaat gttttccacg cgcatagcgg caaagaaggg gacaagtaca agctgtcaaa    2040
aaaggagctg aaagaactgc tgcagaccga attgagcggc ttcctggacg ctcagaaaga    2100
tgtcgatgcc gtcgacaaag tgatgaaaga gcttgacgag aacggtgacg gtgaagtcga    2160
```

```
ttttcaggaa tatgtggtgc tggtggccgc ccttactgta gcatgcaaca atttcttttg    2220
ggaaaattca cgtgcaaagc gtgcaccggt gaaacaggga agcggagcta ctaacttcag    2280
cctgctgaag caggctggag acgtggagga gaaccctgga cctatgaatt ttctgctctc    2340
ttgggtgcac tggtcactgg cactgctgct gtatctgcac catgcaaaat ggtcccaagc    2400
agctcccatg gcagagggag gtggacagaa tcatcatgag gttgtcaaat ttatggatgt    2460
ctaccagcgg agctactgcc acccaattga gacgttggta gacattttc aggaatatcc     2520 agacgagatt gagtacattt tcaagcctag ctgtgtgccc ttgatgcgat gcggtggctg    2580
ttgcaatgat gagggactcg agtgtgtccc caccgaggaa agcaatataa ccatgcaaat    2640
catgcgaatc aaaccccacc agggccagca tatcggcgag atgtctttct tgcaacataa    2700
caaatgcgag tgtcggccaa agaaggacag ggctcgccag gaaaatccct gtggtccttg    2760
ttcagagcgc aggaagcatc ttttcgtcca ggatccgcag acttgtaaat gttcatgcaa    2820
gaataccgat tctaggtgta aggcgaggca actcgagctt aacgagagaa cctgtaggtg    2880
tgacaaacct agaagataaa tcgattacgc tcctctactc tttgagacat cactggccta    2940
taataaatgg gttaatttat gtaacaaaat tgccttggct tgttaacttt attagacatt    3000
ctgatgtttg cattgtgtaa atactgttgt attggaaaag cgtgccaaga tggattattg    3060
taattcagtg tcttttttag tagcgtcacg tgccaaacac tgttagtcac agagggcatg    3120
agacagcctg tgctggaaca gctcagttca tagggctatg gagatgggga gaaaggggcg    3180
cttctgtcag agacaagctg tggtctggga aggccttagc actaaaagca ccacaatgag    3240
aagcaaccgc cagaagcagg gcccgcaggc ctttgttcca gctgcaaaga gaaaggaaaa    3300
agtggggaat aagagttggg gctgcggagg gggtggggag cattgtgcag gttccgtact    3360
tgaacagaaa gcagggacca acacaaggaa ggctcgagct ggcggaatag gttccaatct    3420
gtcgcggccg cattaccctg ttatccctaa tctcgtttaa ctatgactct cttaaggtag    3480
ccaaattccg gaactataaa ttgcgttgcg ctcactgccc gctttccagt cgggaaacct    3540
gtcgtgccag ctgcataaat gaatcggcca acgcgcgggg agaggcggtt tgcgtattgg    3600
gcgcgcttcc gcttcctcgc tcactgactc gctgcgctcg tcgttcggc tgcggcgagc      3660 ggtatcagct cactcaaagg cggtaatacg gttatccaca gaatcagggg ataacgcagg    3720
aaagaacatg tgagcaaaag gccagcaaaa ggccaggaac cgtaaaaagg ccgcgttgct    3780
ggcgtttttc cataggctcc gcccccctga cgagcatcac aaaaatcgac gctcaagtca    3840
gaggtggcga aacccgacag gactataaag ataccaggcg tttccccctg gaagctccct    3900
cgtgcgctct cctgttccga cctgccgct taccggatac ctgtccgcct ttctcccttc      3960
gggaagcgtg gcgctttctc atagctcacg ctgtaggtat ctcagttcgg tgtaggtcgt    4020
tcgctccaag ctgggctgtg tgcacgaacc ccccgttcag cccgaccgct gcgccttatc    4080
cggtaactat cgtcttgagt ccaacccggt aagacacgac ttatcgccac tggcagcagc    4140
cactggtaac aggattagca gagcgaggta tgtaggcggt gctacagagt tcttgaagtg    4200
gtggcctaac tacggctaca ctagaagaac agtatttggt atctgcgctc tgctgaagcc    4260
agttaccttc ggaaaaagag ttggtagctc ttgatccggc aaacaaacca ccgctggtag    4320
cggtggtttt tttgtttgca agcagcagat tacgcgcaga aaaaaggat ctcaagaaga     4380 tcctttgatc ttttctacgg ggtctgacgc tcagtggaac gaaaactcac gttaagggat    4440
tttggtcatg agattatcaa aaaggatctt cacctagatc cttttaaatt aaaaatgaag    4500
```

```
ttttaaatca atctaaagta tatatgagta aacttggtct gacatgcgca tctgacgctc    4560
agtggaacga aaactcacgt taagggattt tggtcatgcc tcagaagaac tcgtcaagaa    4620
ggcgatagaa ggcgatgcgc tgcgaatcgg gagcggcgat accgtaaagc acgaggaagc    4680
ggtcagccca ttcgccgcca agctcttcag caatatcacg ggtagccaac gctatgtcct    4740
gatagcggtc cgccacaccc agccggccac agtcgatgaa tccagaaaag cggccatttt    4800
ccaccatgat attcggcaag caggcatcgc catgggtcac gacgagatcc tcgccgtcgg    4860
gcatgcgcgc cttgagcctg gcgaacagtt cggctggcgc gagcccctga tgctcttcgt    4920
ccagatcatc ctgatcgaca agaccggctt ccatccgagt acgtgctcgc tcgatgcgat    4980
gtttcgcttg gtggtcgaat gggcaggtag ccggatcaag cgtatgcagc cgccgcattg    5040
catcagccat gatggatact ttctcggcag gagcaaggtg agatgacagg agatcctgcc    5100
ccggcacttc gcccaatagc agccagtccc ttcccgcttc agtgacaacg tcgagcacag    5160
ctgcgcaagg aacgcccgtc gtggccagcc acgatagccg cgctgcctcg tcctgcagtt    5220
cattcagggc accggacagg tcggtcttga caaaaagaac cgggcgcccc tgcgctgaca    5280
gccggaacac ggcggcatca gagcagccga ttgtctgttg tgcccagtca tagccgaata    5340
gcctctccac ccaagcggcc ggagaacctg cgtgcaatcc atcttgttca atcatgcgaa    5400
acgatcctca ttcatttatc agggttattg tctcatgagc ggatacatat ttgaatgtat    5460
ttaggctgag catctatgtc gggtgcggag aaagaggtaa tgaaatggca ggcgccttt     5520 tcgttagata tgtagtaagt atcttaatat acagctttat ctgttttta agatacttac     5580 tactttctt agtggaaact attagtggct gttaattaag ctagtactac ccaagatttg    5640
acagaatgca tcgtttgcat tcgaa                                          5665
```

<210> SEQ ID NO 19
<211> LENGTH: 5356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
agttccgcgt tacataactt acggtaaatg gcccgcctgg ctgaccgccc aacgaccccc     240
gcccattgac gtcaataatg acgtatgttc ccatagtaac gccaatagg actttccatt      300 gacgtcaatg ggtggactat ttacggtaaa ctgcccactt ggcagtacat caagtgtatc     360
atatgccaag tacgccccct attgacgtca atgacggtaa atggcccgcc tggcattatg     420
cccagtacat gaccttatgg gactttccta cttggcagta catctacgta ttagtcatcg     480
ctattaccat gggtcgaggt gagccccacg ttctgcttca ctctccccat ctcccccccc     540
tccccacccc caattttgta tttatttatt ttttaattat tttgtgcagc gatggggcg      600 ggggggggggg gggcgcgcgc caggcggggc ggggcgggg gaggggcggg gcggggcgag     660
gcggagaggt gcggcggcag ccaatcagag cggcgcgctc cgaaagtttc cttttatggc     720
gaggcggcgg cggcggcggc cctataaaaa gcgaagcgcg cggcgggcgg gagtcgctgc     780
gttgccttcg ccccgtgccc cgctccgcgc cgcctcgcgc cgcccgcccc ggctctgact     840
```

| | |
|---|---|
| gaccgcgtta ctcccacagg tgagcgggcg ggacggccct tctcctccgg gctgtaatta | 900 |
| gcgcttggtt taatgacggc tcgtttcttt tctgtggctg cgtgaaagcc ttaaagggct | 960 |
| ccgggagggc cctttgtgcg ggggggagcg gctcggggg tgcgtgcgtg tgtgtgtgcg | 1020 |
| tggggagcgc cgcgtgcggc ccgcgctgcc cggcggctgt gagcgctgcg ggcgcggcgc | 1080 |
| ggggctttgt gcgctccgcg tgtgcgcgag gggagcgcgg ccggggggcgg tgccccgcgg | 1140 |
| tgcggggggg ctgcgagggg aacaaaggct gcgtgcgggg tgtgtgcgtg ggggggtgag | 1200 |
| caggggggtgt gggcgcggcg gtcgggctgt aaccccccc tgcaccccc tccccgagtt | 1260 |
| gctgagcacg gcccggcttc gggtgcgggg ctccgtgcgg ggcgtggcgc ggggctcgcc | 1320 |
| gtgccgggcg gggggtggcg gcaggtgggg gtgccgggcg gggcggggcc gcctcgggcc | 1380 |
| ggggagggct cggggagggg gcgcggcggc cccggagcgc cggcggctgt cgaggcgcgg | 1440 |
| cgagccgcag ccattgcctt ttatggtaat cgtgcgagag ggcgcaggga cttcctttgt | 1500 |
| cccaaatctg gcggagccga aatctgggag gcgccgccgc accccctcta gcgggcgcgg | 1560 |
| gcgaagcggt gcggcgccgg caggaaggaa atgggcgggg agggccttcg tgcgtcgccg | 1620 |
| cgccgccgtc cccttctcca tctccagcct cggggctgcc gcaggggac ggctgccttc | 1680 |
| gggggggacg gggcagggcg gggttcggct tctggcgtgt gaccggcggc tctagagcct | 1740 |
| ctgctaacca tgttcatgcc ttcttctttt tcctacagct cctgggcaac gtgctggttg | 1800 |
| ttgtgctgtc tcatcatttt ggcaaagaat tccctgcagg aaattgagcc cgcagcctcc | 1860 |
| cgcttcgctc tctgctcctc ctgttcgaca gtcagccgca tcttcttttg cgtcgccagc | 1920 |
| cgagccacat cgctcagaca ccgctagcgc caccatgggc agcgaactgg aaaccgccat | 1980 |
| ggagactttg ataaatgttt tccacgcgca tagcggcaaa aaggggggaca agtacaagct | 2040 |
| gtcaaaaaag gagctgaaag aactgctgca gaccgaattg agcggcttcc tggacgctca | 2100 |
| gaaagatgtc gatgccgtcg acaaagtgat gaaagagctt gacgagaacg gtgacggtga | 2160 |
| agtcgatttt caggaatatg tggtgctggt ggccgcccctt actgtagcat gcaacaattt | 2220 |
| cttttgggaa aattcaagag ccaagagggc accggtgaaa cagactttga attttgacct | 2280 |
| tctgaagttg gcaggagacg ttgagtccaa ccctgggccc atgaatgcca aggtcgttgt | 2340 |
| ggtgcttgta cttgtgctga ctgctctgtg tctgagcgac ggaaaaccag tctccctcag | 2400 |
| ctacaggtgc ccatgccgat tcttcgaatc tcatgtggcc cggccaatg tgaagcactt | 2460 |
| gaaaatcctg aatacaccca actgcgcgtt gcagatcgtg gcccgcctga aaataataa | 2520 |
| taggcaggta tgtatcgatc caaagcttaa gtggatccag gagtatctgg aaaaggctct | 2580 |
| caataaataa atcgattacg ctcctctact ctttgagaca tcactggcct ataataaatg | 2640 |
| ggttaattta tgtaacaaaa ttgccttggc ttgttaactt tattagacat tctgatgttt | 2700 |
| gcattgtgta aatactgttg tattggaaaa gcgtgccaag atggattatt gtaattcagt | 2760 |
| gtcttttta gtagcgtcac gtgccaaaca ctgttagtca cagagggcat gagacagcct | 2820 |
| gtgctggaac agctcagttc atagggctat ggagatgggg agaaaggggc gcttctgtca | 2880 |
| gagacaagct gtggtctggg aaggccttag cactaaaagc accacaatga gaagcaaccg | 2940 |
| ccagaagcag ggcccgcagg cctttgttcc agctgcaaag agaaaggaaa aagtggggaa | 3000 |
| taagagttgg ggctgcggag ggggtgggga gcattgtgca ggttccgtac ttgaacagaa | 3060 |
| agcagggacc aacacaagga aggctcgagc tggcggaata ggttccaatc tgtcgcggcc | 3120 |
| gcattaccct gttatcccta atctcgttta actatgactc tcttaaggta gccaaattcc | 3180 |

```
ggaactataa attgcgttgc gctcactgcc cgctttccag tcgggaaacc tgtcgtgcca    3240
gctgcataaa tgaatcggcc aacgcgcggg gagaggcggt ttgcgtattg ggcgcgcttc    3300
cgcttcctcg ctcactgact cgctgcgctc ggtcgttcgg ctgcggcgag cggtatcagc    3360
tcactcaaag gcggtaatac ggttatccac agaatcaggg gataacgcag gaaagaacat    3420
gtgagcaaaa ggccagcaaa aggccaggaa ccgtaaaaag gccgcgttgc tggcgttttt    3480
ccataggctc cgcccccctg acgagcatca caaaaatcga cgctcaagtc agaggtggcg    3540
aaacccgaca ggactataaa gataccaggc gtttccccct ggaagctccc tcgtgcgctc    3600
tcctgttccg accctgccgc ttaccggata cctgtccgcc tttctccctt cgggaagcgt    3660
ggcgctttct catagctcac gctgtaggta tctcagttcg gtgtaggtcg ttcgctccaa    3720
gctgggctgt gtgcacgaac cccccgttca gcccgaccgc tgcgccttat ccggtaacta    3780
tcgtcttgag tccaacccgg taagacacga cttatcgcca ctggcagcag ccactggtaa    3840
caggattagc agagcgaggt atgtaggcgg tgctacagag ttcttgaagt ggtggcctaa    3900
ctacggctac actagaagaa cagtatttgg tatctgcgct ctgctgaagc cagttacctt    3960
cggaaaaaga gttggtagct cttgatccgg caaacaaacc accgctggta gcggtggttt    4020
ttttgtttgc aagcagcaga ttacgcgcag aaaaaaagga tctcaagaag atcctttgat    4080
cttttctacg gggtctgacg ctcagtggaa cgaaaactca cgttaaggga ttttggtcat    4140
gagattatca aaaaggatct tcacctagat ccttttaaat taaaaatgaa gttttaaatc    4200
aatctaaagt atatatgagt aaacttggtc tgacatgcgc atctgacgct cagtggaacg    4260
aaaactcacg ttaagggatt ttggtcatgc ctcagaagaa ctcgtcaaga aggcgataga    4320
aggcgatgcg ctgcgaatcg ggagcggcga taccgtaaag cacgaggaag cggtcagccc    4380
attcgccgcc aagctcttca gcaatatcac gggtagccaa cgctatgtcc tgatagcggt    4440
ccgccacacc cagccggcca cagtcgatga atccagaaaa gcggccattt tccaccatga    4500
tattcggcaa gcaggcatcg ccatgggtca cgacgagatc ctcgccgtcg gcatgcgcg    4560 ccttgagcct ggcgaacagt tcggctggcg cgagcccctg atgctcttcg tccagatcat    4620
cctgatcgac aagaccggct tccatccgag tacgtgctcg ctcgatgcga tgtttcgctt    4680
ggtggtcgaa tgggcaggta gccggatcaa gcgtatgcag ccgccgcatt gcatcagcca    4740
tgatggatac tttctcggca ggagcaaggt gagatgacag gagatcctgc cccggcactt    4800
cgcccaatag cagccagtcc cttcccgctt cagtgacaac gtcgagcaca gctgcgcaag    4860
gaacgcccgt cgtggccagc cacgatagcc gcgctgcctc gtcctgcagt tcattcaggg    4920
caccggacag gtcggtcttg acaaaaagaa ccgggcgccc ctgcgctgac agccggaaca    4980
cggcggcatc agagcagccg attgtctgtt gtgcccagtc atagccgaat agcctctcca    5040
cccaagcggc cggagaacct gcgtgcaatc catcttgttc aatcatgcga aacgatcctc    5100
attcatttat cagggttatt gtctcatgag cggatacata tttgaatgta tttaggctga    5160
gcatctatgt cgggtgcgga aaagaggta atgaaatggc aggcgccttt ttcgttagat    5220
atgtagtaag tatcttaata tacagcttta tctgtttttt aagatactta ctacttttct    5280
tagtggaaac tattagtggc tgttaattaa gctagtacta cccaagattt gacagaatgc    5340
atcgtttgca ttcgaa                                                   5356
```

<210> SEQ ID NO 20
<211> LENGTH: 5356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

| | | | | | |
|---|---|---|---|---|---|
| ctagcgccac | catgaatgcc | aaggtcgttg | tggtgcttgt | acttgtgctg | actgctctgt | 60 |
| gtctgagcga | cggaaaacca | gtctccctca | gctacaggtg | cccatgccga | ttcttcgaat | 120 |
| ctcatgtggc | ccgggccaat | gtgaagcact | tgaaaatcct | gaatacaccc | aactgcgcgt | 180 |
| tgcagatcgt | ggcccgcctg | aaaaataata | ataggcaggt | atgtatcgat | ccaaagctta | 240 |
| agtggatcca | ggagtatctg | gaaaaggctc | tcaataaaag | agccaagagg | gcaccggtga | 300 |
| aacagacttt | gaattttgac | cttctgaagt | tggcaggaga | cgttgagtcc | aaccctgggc | 360 |
| ccatgggcag | cgaactggaa | accgccatgg | agactttgat | aaatgttttc | cacgcgcata | 420 |
| gcggcaaaga | aggggacaag | tacaagctgt | caaaaaagga | gctgaaagaa | ctgctgcaga | 480 |
| ccgaattgag | cggcttcctg | gacgctcaga | agatgtcga | tgccgtcgac | aaagtgatga | 540 |
| aagagcttga | cgagaacggt | gacggtgaag | tcgattttca | ggaatatgtg | gtgctggtgg | 600 |
| ccgcccttac | tgtagcatgc | aacaatttct | tttgggaaaa | ttcataaatc | gattacgctc | 660 |
| ctctactctt | tgagacatca | ctggcctata | ataaatgggt | taatttatgt | aacaaaattg | 720 |
| ccttggcttg | ttaactttat | tagacattct | gatgtttgca | ttgtgtaaat | actgttgtat | 780 |
| tggaaaagcg | tgccaagatg | gattattgta | attcagtgtc | tttttttagta | gcgtcacgtg | 840 |
| ccaaacactg | ttagtcacag | agggcatgag | acagcctgtg | ctggaacagc | tcagttcata | 900 |
| gggctatgga | gatggggaga | aagggcgct | tctgtcagag | acaagctgtg | gtctgggaag | 960 |
| gccttagcac | taaaagcacc | acaatgagaa | gcaaccgcca | gaagcagggc | ccgcaggcct | 1020 |
| ttgttccagc | tgcaaagaga | aaggaaaaag | tggggaataa | gagttgggc | tgcggagggg | 1080 |
| gtggggagca | ttgtgcaggt | tccgtacttg | aacagaaagc | agggaccaac | acaaggaagg | 1140 |
| ctcgagctgg | cggaataggt | tccaatctgt | cgcggccgca | ttaccctgtt | atccctaatc | 1200 |
| tcgtttaact | atgactctct | taaggtagcc | aaattccgga | actataaatt | gcgttgcgct | 1260 |
| cactgcccgc | tttccagtcg | ggaaacctgt | cgtgccagct | gcataaatga | atcggccaac | 1320 |
| gcgcggggag | aggcggtttg | cgtattgggc | gcgcttccgc | ttcctcgctc | actgactcgc | 1380 |
| tgcgctcggt | cgttcggctg | cggcgagcgg | tatcagctca | ctcaaaggcg | gtaatacggt | 1440 |
| tatccacaga | atcaggggat | aacgcaggaa | agaacatgtg | agcaaaaggc | cagcaaaagg | 1500 |
| ccaggaaccg | taaaaaggcc | gcgttgctgg | cgttttttcca | taggctccgc | ccccctgacg | 1560 |
| agcatcacaa | aaatcgacgc | tcaagtcaga | ggtggcgaaa | cccgacagga | ctataaagat | 1620 |
| accaggcgtt | tccccctgga | agctccctcg | tgcgctctcc | tgttccgacc | ctgccgctta | 1680 |
| ccggatacct | gtccgccttt | ctcccttcgg | gaagcgtggc | gctttctcat | agctcacgct | 1740 |
| gtaggtatct | cagttcggtg | taggtcgttc | gctccaagct | gggctgtgtg | cacgaacccc | 1800 |
| ccgttcagcc | cgaccgctgc | gccttatccg | gtaactatcg | tcttgagtcc | aacccggtaa | 1860 |
| gacacgactt | atcgccactg | gcagcagcca | ctggtaacag | gattagcaga | gcgaggtatg | 1920 |
| taggcggtgc | tacagagttc | ttgaagtggt | ggcctaacta | cggctacact | agaagaacag | 1980 |
| tatttggtat | ctgcgctctg | ctgaagccag | ttaccttcgg | aaaaagagtt | ggtagctctt | 2040 |
| gatccggcaa | acaaaccacc | gctggtagcg | gtggtttttt | tgtttgcaag | cagcagatta | 2100 |
| cgcgcagaaa | aaaaggatct | caagaagatc | ctttgatctt | ttctacgggg | tctgacgctc | 2160 |

```
agtggaacga aaactcacgt taagggattt tggtcatgag attatcaaaa aggatcttca    2220
cctagatcct tttaaattaa aaatgaagtt ttaaatcaat ctaaagtata tatgagtaaa    2280
cttggtctga catgcgcatc tgacgctcag tggaacgaaa actcacgtta agggattttg    2340
gtcatgcctc agaagaactc gtcaagaagg cgatagaagg cgatgcgctg cgaatcggga    2400
gcggcgatac cgtaaagcac gaggaagcgg tcagcccatt cgccgccaag ctcttcagca    2460
atatcacggg tagccaacgc tatgtcctga tagcggtccg ccacacccag ccggccacag    2520
tcgatgaatc cagaaaagcg gccattttcc accatgatat tcggcaagca ggcatcgcca    2580
tgggtcacga cgagatcctc gccgtcgggc atgcgcgcct tgagcctggc gaacagttcg    2640
gctggcgcga gcccctgatg ctcttcgtcc agatcatcct gatcgacaag accggcttcc    2700
atccgagtac gtgctcgctc gatgcgatgt ttcgcttggt ggtcgaatgg gcaggtagcc    2760
ggatcaagcg tatgcagccg ccgcattgca tcagccatga tggatacttt ctcggcagga    2820
gcaaggtgag atgacaggag atcctgcccc ggcacttcgc ccaatagcag ccagtccctt    2880
cccgcttcag tgacaacgtc gagcacagct gcgcaaggaa cgcccgtcgt ggccagccac    2940
gatagccgcg ctgcctcgtc ctgcagttca ttcagggcac cggacaggtc ggtcttgaca    3000
aaaagaaccg ggcgccctg cgctgacagc cggaacacgg cggcatcaga gcagccgatt    3060
gtctgttgtg cccagtcata gccgaatagc ctctccaccc aagcggccgg agaacctgcg    3120
tgcaatccat cttgttcaat catgcgaaac gatcctcatt catttatcag gttattgtc    3180 tcatgagcgg atacatattt gaatgtattt aggctgagca tctatgtcgg gtgcggagaa    3240
agaggtaatg aaatggcagg cgcctttttc gttagatatg tagtaagtat cttaatatac    3300
agctttatct gttttttaag atacttacta cttttcttag tggaaactat tagtggctgt    3360
taattaagct agtactaccc aagatttgac agaatgcatc gtttgcattc gaataactat    3420
aacggtccta aggtagcgac gtacgaaccg ttgggcgcgc ctggggatag cgatcgctgc    3480
tggcgcggtc cgctatgagg tctctgatag accacagacg cgtcgacatt gattattgac    3540
tagttattaa tagtaatcaa ttacggggtc attagttcat agcccatata tggagttccg    3600
cgttacataa cttacggtaa atggcccgcc tggctgaccg cccaacgacc cccgcccatt    3660
gacgtcaata atgacgtatg ttcccatagt aacgccaata gggactttcc attgacgtca    3720
atgggtggac tatttacggt aaactgccca cttggcagta catcaagtgt atcatatgcc    3780
aagtacgccc cctattgacg tcaatgacgg taaatggccc gcctggcatt atgcccagta    3840
catgacctta tgggactttc ctacttggca gtacatctac gtattagtca tcgctattac    3900
catgggtcga ggtgagcccc acgttctgct tcactctccc catctccccc cctccccac    3960 ccccaatttt gtatttattt atttttaat tattttgtgc agcgatgggg gcggggggg    4020 ggggggcgcg cgccaggcgg ggcggggcgg ggcgagggc ggggcgggc gaggcggaga    4080 ggtgcggcgg cagccaatca gagcggcgcg ctccgaaagt ttccttttat ggcgaggcgg    4140
cggcggcggc ggccctataa aaagcgaagc gcgcggcggg cggagtcgc tgcgttgcct    4200 tcgccccgtg ccccgctccg cgccgcctcg cgccgcccgc cccggctctg actgaccgcg    4260
ttactcccac aggtgagcgg gcgggacggc ccttctcctc cgggctgtaa ttagcgcttg    4320
gtttaatgac ggctcgtttc ttttctgtgg ctgcgtgaaa gccttaaagg ctccgggag    4380 ggccctttgt gcgggggga gcggctcggg gggtgcgtgc gtgtgtgtgt gcgtgggag    4440 cgccgcgtgc ggcccgcgct gcccggcggc tgtgagcgct gcgggcgcgg cgcggggctt    4500
tgtgcgctcc gcgtgtgcgc gaggggagcg cggccgggg cggtgccccg cggtgcgggg    4560
```

```
gggctgcgag gggaacaaag gctgcgtgcg gggtgtgtgc gtgggggggt gagcagggggg    4620 tgtgggcgcg gcggtcgggc tgtaaccccc ccctgcaccc ccctccccga gttgctgagc     4680
acggcccggc ttcgggtgcg gggctccgtg cggggcgtgg cgcgggctc gccgtgccgg      4740 gcgggggtg gcggcaggtg ggggtgccgg gcggggcggg gccgcctcgg gccggggagg      4800
gctcggggga ggggcgcggc ggccccggag cgccggcggc tgtcgaggcg cggcgagccg     4860
cagccattgc ctttatggt aatcgtgcga gagggcgcag ggacttcctt tgtcccaaat     4920
ctggcggagc cgaaatctgg gaggcgccgc cgcacccccct ctagcgggcg cgggcgaagc    4980
ggtgcggcgc cggcaggaag gaaatgggcg gggagggcct tcgtgcgtcg ccgcgccgcc    5040
gtccccttct ccatctccag cctcggggct gccgcagggg gacggctgcc ttcgggggg    5100 acggggcagg gcggggttcg gcttctggcg tgtgaccggc ggctctagag cctctgctaa   5160
ccatgttcat gccttcttct ttttcctaca gctcctgggc aacgtgctgg ttgttgtgct   5220
gtctcatcat tttggcaaag aattcccctgc aggaaattga gcccgcagcc tcccgcttcg   5280
ctctctgctc ctcctgttcg acagtcagcc gcatcttctt ttgcgtcgcc agccgagcca   5340
catcgctcag acaccg                                                    5356

<210> SEQ ID NO 21
<211> LENGTH: 5647
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
ctagcgccac catgaatgcc aaggtcgttg tggtgcttgt acttgtgctg actgctctgt      60
gtctgagcga cggaaaacca gtctccctca gctacaggtg cccatgccga ttcttcgaat     120
ctcatgtggc ccgggccaat gtgaagcact tgaaaatcct gaatacaccc aactgcgcgt     180
tgcagatcgt ggcccgcctg aaaaataata ataggcaggt atgtatcgat ccaaagctta     240
agtggatcca ggagtatctg gaaaaggctc tcaataaaag agccaagagg gcaccggtga     300
aacagacttt gaattttgac cttctgaagt tggcaggaga cgttgagtcc aaccctgggc     360
ccatgaattt tctgctctct tgggtgcact ggtcactggc actgctgctg tatctgcacc     420
atgcaaaatg gtcccaagca gctcccatgg cagagggagg tggacagaat catcatgagg     480
ttgtcaaatt tatggatgtc taccagcgga gctactgcca cccaattgag acgttggtag     540
acatttttca ggaatatcca gacgagattg agtacatttt caagcctagc tgtgtgccct     600
tgatgcgatg cggtggctgt tgcaatgatg agggactcga gtgtgtcccc accgaggaaa     660
gcaatataac catgcaaatc atgcgaatca acccccacca gggccagcat atcggcgaga     720
tgtctttctt gcaacataac aaatgcgagt gtcggccaaa gaaggacagg gctcgccagg     780
aaaatccctg tggtccttgt tcagagcgca ggaagcatct tttcgtccag gatccgcaga     840
cttgtaaatg ttcatgcaag aataccgatt ctaggtgtaa ggcgaggcaa ctcgagctta     900
acgagagaac ctgtaggtgt gacaaaccta agataaaat cgattacgct cctctactct    960
ttgagacatc actggcctat aataaatggg ttaatttatg taacaaaatt gccttggctt   1020
gttaacttta ttagcattc tgatgttgc attgtgtaaa tactgttgta ttggaaaagc   1080
gtgccaagat ggattattgt aattcagtgt cttttttagt agcgtcacgt gccaaacact   1140
```

```
gttagtcaca gagggcatga gacagcctgt gctggaacag ctcagttcat agggctatgg   1200
agatggggag aaaggggcgc ttctgtcaga gacaagctgt ggtctgggaa ggccttagca   1260
ctaaaagcac cacaatgaga agcaaccgcc agaagcaggg cccgcaggcc tttgttccag   1320
ctgcaaagaa aaaggaaaaa gtggggaata agagttgggg ctgcggaggg ggtggggagc   1380
attgtgcagg ttccgtactt gaacagaaag cagggaccaa cacaaggaag gctcgagctg   1440
gcggaatagg ttccaatctg tcgcggccgc attaccctgt tatccctaat ctcgtttaac   1500
tatgactctc ttaaggtagc caaattccgg aactataaat tgcgttgcgc tcactgcccg   1560
ctttccagtc gggaaacctg tcgtgccagc tgcataaatg aatcggccaa cgcgcgggga   1620
gaggcggttt gcgtattggg cgcgcttccg cttcctcgct cactgactcg ctgcgctcgg   1680
tcgttcggct gcggcgagcg gtatcagctc actcaaaggc ggtaatacgg ttatccacag   1740
aatcagggga taacgcagga agaacatgt gagcaaaagg ccagcaaaag gccaggaacc   1800
gtaaaaaggc cgcgttgctg gcgttttttcc ataggctccg ccccccctgac gagcatcaca   1860 aaaatcgacg ctcaagtcag aggtggcgaa acccgacagg actataaaga taccaggcgt   1920
ttccccctgg aagctccctc gtgcgctctc ctgttccgac cctgccgctt accggatacc   1980
tgtccgcctt tctcccttcg ggaagcgtgg cgctttctca tagctcacgc tgtaggtatc   2040
tcagttcggt gtaggtcgtt cgctccaagc tgggctgtgt gcacgaaccc cccgttcagc   2100
ccgaccgctg cgccttatcc ggtaactatc gtcttgagtc caacccggta agacacgact   2160
tatcgccact ggcagcagcc actggtaaca ggattagcag agcgaggtat gtaggcggtg   2220
ctacagagtt cttgaagtgg tggcctaact acggctacac tagaagaaca gtatttggta   2280
tctgcgctct gctgaagcca gttaccttcg gaaaagagt tggtagctct tgatccggca   2340
aacaaaccac cgctggtagc ggtggttttt tgtttgcaa gcagcagatt acgcgcagaa   2400
aaaaaggatc tcaagaagat cctttgatct tttctacggg gtctgacgct cagtggaacg   2460
aaaactcacg ttaagggatt ttggtcatga gattatcaaa aaggatcttc acctagatcc   2520
ttttaaatta aaaatgaagt tttaaatcaa tctaaagtat atatgagtaa acttggtctg   2580
acatgcgcat ctgacgctca gtggaacgaa aactcacgtt aagggatttt ggtcatgcct   2640
cagaagaact cgtcaagaag gcgatagaag gcgatgcgct gcgaatcggg agcggcgata   2700
ccgtaaagca cgaggaagcg gtcagcccat tcgccgccaa gctcttcagc aatatcacgg   2760
gtagccaacg ctatgtcctg atagcggtcc gccacaccca gccggccaca gtcgatgaat   2820
ccagaaaagc ggccattttc caccatgata ttcggcaagc aggcatcgcc atgggtcacg   2880
acgagatcct cgccgtcggg catgcgcgcc ttgagcctgg cgaacagttc ggctggcgcg   2940
agcccctgat gctcttcgtc cagatcatcc tgatcgacaa gaccggcttc catccgagta   3000
cgtgctcgct cgatgcgatg tttcgcttgg tggtcgaatg ggcaggtagc cggatcaagc   3060
gtatgcagcc gccgcattgc atcagccatg atggatactt tctcggcagg agcaaggtga   3120
gatgacagga gatcctgccc cggcacttcg cccaatagca gccagtccct tcccgcttca   3180
gtgacaacgt cgagcacagc tgcgcaagga acgcccgtcg tggccagcca cgatagccgc   3240
gctgcctcgt cctgcagttc attcagggca ccggacaggc ggtcttgac aaaaagaacc   3300 gggcgcccct gcgctgacag ccggaacacg gcggcatcag agcagccgat tgtctgttgt   3360
gcccagtcat agccgaatag cctctccacc caagcggccg gagaacctgc gtgcaatcca   3420
tcttgttcaa tcatgcgaaa cgatcctcat tcatttatca gggttattgt ctcatgagcg   3480
gatacatatt tgaatgtatt taggctgagc atctatgtcg ggtgcggaga aagaggtaat   3540
```

```
gaaatggcag gcgcctttt  cgttagatat gtagtaagta tcttaatata cagctttatc    3600
tgttttttaa gatacttact acttttctta gtggaaacta ttagtggctg ttaattaagc    3660
tagtactacc caagatttga cagaatgcat cgtttgcatt cgaataacta taacggtcct    3720
aaggtagcga cgtacgaacc gttgggcgcg cctggggata gcgatcgctg ctggcgcggt    3780
ccgctatgag gtctctgata gaccacagac gcgtcgacat tgattattga ctagttatta    3840
atagtaatca attacggggt cattagttca tagcccatat atggagttcc gcgttacata    3900
acttacggta aatggcccgc ctggctgacc gcccaacgac ccccgcccat tgacgtcaat    3960
aatgacgtat gttcccatag taacgccaat agggactttc cattgacgtc aatgggtgga    4020
ctatttacgg taaactgccc acttggcagt acatcaagtg tatcatatgc caagtacgcc    4080
ccctattgac gtcaatgacg gtaaatggcc cgcctggcat tatgcccagt acatgacctt    4140
atgggacttt cctacttggc agtacatcta cgtattagtc atcgctatta ccatgggtcg    4200
aggtgagccc cacgttctgc ttcactctcc ccatctcccc cccctcccca ccccaatttt    4260
tgtatttatt tattttttaa ttattttgtg cagcgatggg ggcgggggg ggggggcgc     4320 gcgccaggcg gggcggggcg gggcgagggg cgggcgggg cgaggcggag aggtgcggcg     4380
gcagccaatc agagcggcgc gctccgaaag tttccttttta tggcgaggcg gcggcggcgg   4440
cggccctata aaagcgaag cgcgcggcgg gcgggagtcg ctgcgttgcc ttcgccccgt     4500
gccccgctcc gcgccgcctc gcgccgcccg ccccggctct gactgaccgc gttactccca    4560
caggtgagcg ggcgggacgg cccttctcct ccgggctgta attagcgctt ggtttaatga    4620
cggctcgttt cttttctgtg gctgcgtgaa agccttaaag ggctccggga gggcccttg     4680 tgcggggggg agcggctcgg ggggtgcgtg cgtgtgtgtg tgcgtgggga gcgccgcgtg    4740
cggcccgcgc tgcccggcgg ctgtgagcgc tgcgggcgcg gcgcggggct tgtgcgctc     4800 cgcgtgtgcg cgaggggagc gcggccgggg gcggtgcccc gcggtgcggg ggggctgcga    4860
ggggaacaaa ggctgcgtgc ggggtgtgtg cgtgggggg tgagcagggg gtgtgggcgc     4920
ggcggtcggg ctgtaacccc ccctgcacc cccctccccg agttgctgag cacggcccgg     4980
cttcgggtgc ggggctccgt gcgggcgtg gcgcggggct cgccgtgccg ggcggggggt     5040
ggcggcaggt gggggtgccg ggcggggcgg ggccgcctcg ggccggggag ggctcggggg    5100 aggggcgcg cggccccgga gcgccggcgg ctgtcgaggc gcggcgagcc gcagccattg     5160
ccttttatgg taatcgtgcg agagggcgca gggacttcct ttgtcccaaa tctggcggag    5220
ccgaaatctg ggaggcgccg ccgcacccc tctagcgggc gcgggcgaag cggtgcggcg     5280
ccggcaggaa ggaaatgggc ggggagggcc ttcgtgcgtc gccgcgccgc cgtcccttc     5340 tccatctcca gcctcgggc tgccgcaggg ggacggctgc cttcgggggg gacggggcag    5400
ggcggggttc ggcttctggc gtgtgaccgg cggctctaga gcctctgcta accatgttca    5460
tgccttcttc ttttcctac agctcctggg caacgtgctg gttgttgtgc tgtctcatca    5520
ttttggcaaa gaattccctg caggaaattg agcccgcagc ctcccgcttc gctctctgct    5580
cctcctgttc gacagtcagc cgcatcttct tttgcgtcgc cagccgagcc acatcgctca    5640
gacaccg                                                              5647
```

<210> SEQ ID NO 22
<211> LENGTH: 5647
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 22

| | | | | | |
|---|---|---|---|---|---|
| taactataac | ggtcctaagg | tagcgacgta | cgaaccgttg | ggcgcgcctg | gggatagcga | 60 |
| tcgctgctgg | cgcggtccgc | tatgaggtct | ctgatagacc | acagacgcgt | cgacattgat | 120 |
| tattgactag | ttattaatag | taatcaatta | cggggtcatt | agttcatagc | ccatatatgg | 180 |
| agttccgcgt | tacataactt | acggtaaatg | gcccgcctgg | ctgaccgccc | aacgaccccc | 240 |
| gcccattgac | gtcaataatg | acgtatgttc | ccatagtaac | gccaataggg | actttccatt | 300 |
| gacgtcaatg | ggtggactat | ttacggtaaa | ctgcccactt | ggcagtacat | caagtgtatc | 360 |
| atatgccaag | tacgccccct | attgacgtca | atgacggtaa | atggcccgcc | tggcattatg | 420 |
| cccagtacat | gaccttatgg | gactttccta | cttggcagta | catctacgta | ttagtcatcg | 480 |
| ctattaccat | gggtcgaggt | gagccccacg | ttctgcttca | ctctccccat | ctcccccccc | 540 |
| tccccacccc | caattttgta | tttatttatt | ttttaattat | tttgtgcagc | gatggggggcg | 600 |
| ggggggggggg | gggcgcgcgc | caggcggggc | ggggcggggc | gagggcgggg | cggggcgag | 660 |
| gcggagaggt | gcggcggcag | ccaatcagag | cggcgcgctc | cgaaagtttc | cttttatggc | 720 |
| gaggcggcgg | cggcggcggc | cctataaaaa | gcgaagcgcg | cggcgggcgg | gagtcgctgc | 780 |
| gttgccttcg | ccccgtgccc | cgctccgcgc | cgcctcgcgc | cgcccgcccc | ggctctgact | 840 |
| gaccgcgtta | ctcccacagg | tgagcgggcg | ggacggccct | tctcctccgg | gctgtaatta | 900 |
| gcgcttggtt | taatgacggc | tcgtttcttt | tctgtggctg | cgtgaaagcc | ttaaagggct | 960 |
| ccgggagggc | cctttgtgcg | gggggagcg | gctcgggggg | tgcgtgcgtg | tgtgtgtgcg | 1020 |
| tggggagcgc | cgcgtgcggc | ccgcgctgcc | cggcggctgt | gagcgctgcg | ggcgcggcgc | 1080 |
| ggggctttgt | gcgctccgcg | tgtgcgcgag | gggagcgcgg | ccggggcgg | tgccccgcgg | 1140 |
| tgcggggggg | ctgcgagggg | aacaaaggct | gcgtgcgggg | tgtgtgcgtg | ggggggtgag | 1200 |
| caggggggtgt | gggcgcggcg | gtcgggctgt | aaccccccccc | tgcaccccccc | tccccgagtt | 1260 |
| gctgagcacg | gcccggcttc | gggtgcgggg | ctccgtgcgg | ggcgtggcgc | ggggctcgcc | 1320 |
| gtgccgggcg | ggggggtggcg | gcaggtgggg | gtgccgggcg | gggcggggcc | gcctcgggcc | 1380 |
| ggggagggct | cggggggaggg | gcgcggcggc | cccggagcgc | cggcggctgt | cgaggcgcgg | 1440 |
| cgagccgcag | ccattgcctt | ttatggtaat | cgtgcgagag | ggcgcaggga | cttcctttgt | 1500 |
| cccaaatctg | gcggagccga | aatctgggag | gcgccgccgc | accccctcta | gcgggcgcgg | 1560 |
| gcgaagcggt | gcggcgccgg | caggaaggaa | atgggcgggg | agggccttcg | tgcgtcgccg | 1620 |
| cgccgccgtc | cccttctcca | tctccagcct | cggggctgcc | gcaggggggac | ggctgccttc | 1680 |
| gggggggacg | gggcagggcg | gggttcggct | tctggcgtgt | gaccggcggc | tctagagcct | 1740 |
| ctgctaacca | tgttcatgcc | ttcttctttt | cctacagct | cctgggcaac | gtgctggttg | 1800 |
| ttgtgctgtc | tcatcatttt | ggcaaagaat | tccctgcagg | aaattgagcc | cgcagcctcc | 1860 |
| cgcttcgctc | tctgctcctc | ctgttcgaca | gtcagccgca | tcttcttttg | cgtcgccagc | 1920 |
| cgagccacat | cgctcagaca | ccgctagcgc | caccatgaat | tttctgctct | cttgggtgca | 1980 |
| ctggtcactg | gcactgctgc | tgtatctgca | ccatgcaaaa | tggtcccaag | cagctcccat | 2040 |
| ggcagaggga | ggtggacaga | atcatcatga | ggttgtcaaa | tttatggatg | tctaccagcg | 2100 |
| gagctactgc | cacccaattg | agacgttggt | agacattttt | caggaatatc | cagacgagat | 2160 |
| tgagtacatt | ttcaagccta | gctgtgtgcc | cttgatgcga | tgcggtggct | gttgcaatga | 2220 |

```
tgagggactc gagtgtgtcc ccaccgagga agcaatata accatgcaaa tcatgcgaat    2280
caaaccccac cagggccagc atatcggcga gatgtctttc ttgcaacata acaaatgcga    2340
gtgtcggcca aagaaggaca gggctcgcca ggaaaatccc tgtggtcctt gttcagagcg    2400
caggaagcat cttttcgtcc aggatccgca gacttgtaaa tgttcatgca agaataccga    2460
ttctaggtgt aaggcgaggc aactcgagct taacgagaga acctgtaggt gtgacaaacc    2520
tagaagaaga gccaagaggg caccggtgaa acagactttg aattttgacc ttctgaagtt    2580
ggcaggagac gttgagtcca accctgggcc catgaatgcc aaggtcgttg tggtgcttgt    2640
acttgtgctg actgctctgt gtctgagcga cggaaaacca gtctccctca gctacaggtg    2700
cccatgccga ttcttcgaat ctcatgtggc ccgggccaat gtgaagcact tgaaaatcct    2760
gaatacaccc aactgcgcgt tgcagatcgt ggcccgcctg aaaaataata ataggcaggt    2820
atgtatcgat ccaaagctta agtggatcca ggagtatctg gaaaaggctc tcaataaata    2880
aatcgattac gctcctctac tctttgagac atcactggcc tataataaat gggttaattt    2940
atgtaacaaa attgccttgg cttgttaact ttattagaca ttctgatgtt tgcattgtgt    3000
aaatactgtt gtattggaaa agcgtgccaa gatggattat tgtaattcag tgtctttttt    3060
agtagcgtca cgtgccaaac actgttagtc acagagggca tgagacagcc tgtgctggaa    3120
cagctcagtt catagggcta tggagatggg gagaaagggg cgcttctgtc agagacaagc    3180
tgtggtctgg gaaggcctta gcactaaaag caccacaatg agaagcaacc gccagaagca    3240
gggcccgcag gcctttgttc cagctgcaaa gagaaaggaa aaagtgggga ataagagttg    3300
gggctgcgga gggggtgggg agcattgtgc aggttccgta cttgaacaga aagcagggac    3360
caacacaagg aaggctcgag ctggcggaat aggttccaat ctgtcgcggc cgcattaccc    3420
tgttatccct aatctcgttt aactatgact ctcttaaggt agccaaattc cggaactata    3480
aattgcgttg cgctcactgc ccgctttcca gtcgggaaac ctgtcgtgcc agctgcataa    3540
atgaatcggc caacgcgcgg ggagaggcgg tttgcgtatt gggcgcgctt ccgcttcctc    3600
gctcactgac tcgctgcgct cggtcgttcg gctgcggcga gcggtatcag ctcactcaaa    3660
ggcggtaata cggttatcca cagaatcagg ggataacgca ggaaagaaca tgtgagcaaa    3720
aggccagcaa aaggccagga accgtaaaaa ggccgcgttg ctggcgtttt tccataggct    3780
ccgcccccct gacgagcatc acaaaaatcg acgctcaagt cagaggtggc gaaacccgac    3840
aggactataa agataccagg cgtttccccc tggaagctcc ctcgtgcgct ctcctgttcc    3900
gaccctgccg cttaccggat acctgtccgc ctttctccct tcgggaagcg tggcgctttc    3960
tcatagctca cgctgtaggt atctcagttc ggtgtaggtc gttcgctcca agctgggctg    4020
tgtgcacgaa ccccccgttc agcccgaccg ctgcgcctta tccggtaact atcgtcttga    4080
gtccaacccg gtaagacacg acttatcgcc actggcagca gccactggta acaggattag    4140
cagagcgagg tatgtaggcg gtgctacaga gttcttgaag tggtggccta actacggcta    4200
cactagaaga acagtatttg gtatctgcgc tctgctgaag ccagttacct tcggaaaaag    4260
agttggtagc tcttgatccg gcaaacaaac caccgctggt agcggtggtt ttttgtttg    4320 caagcagcag attacgcgca gaaaaaaagg atctcaagaa gatcctttga tcttttctac    4380
ggggtctgac gctcagtgga acgaaaactc acgttaaggg attttggtca tgagattatc    4440
aaaaaggatc ttcacctaga tccttttaaa ttaaaaatga agttttaaat caatctaaag    4500
tatatatgag taaacttggt ctgacatgcg catctgacgc tcagtggaac gaaaactcac    4560
```

| | |
|---|---|
| gttaagggat tttggtcatg cctcagaaga actcgtcaag aaggcgatag aaggcgatgc | 4620 |
| gctgcgaatc gggagcggcg ataccgtaaa gcacgaggaa gcggtcagcc cattcgccgc | 4680 |
| caagctcttc agcaatatca cgggtagcca acgctatgtc ctgatagcgg tccgccacac | 4740 |
| ccagccggcc acagtcgatg aatccagaaa agcggccatt ttccaccatg atattcggca | 4800 |
| agcaggcatc gccatgggtc acgacgagat cctcgccgtc gggcatgcgc gccttgagcc | 4860 |
| tggcgaacag ttcggctggc gcgagcccct gatgctcttc gtccagatca tcctgatcga | 4920 |
| caagaccggc ttccatccga gtacgtgctc gctcgatgcg atgtttcgct tggtggtcga | 4980 |
| atgggcaggt agccggatca agcgtatgca gccgccgcat tgcatcagcc atgatggata | 5040 |
| cttttctcggc aggagcaagg tgagatgaca ggagatcctg ccccggcact cgcccaata | 5100 |
| gcagccagtc ccttcccgct tcagtgacaa cgtcgagcac agctgcgcaa ggaacgcccg | 5160 |
| tcgtggccag ccacgatagc cgcgctgcct cgtcctgcag ttcattcagg gcaccggaca | 5220 |
| ggtcggtctt gacaaaaaga accgggcgcc cctgcgctga cagccggaac acggcggcat | 5280 |
| cagagcagcc gattgtctgt tgtgcccagt catagccgaa tagcctctcc acccaagcgg | 5340 |
| ccggagaacc tgcgtgcaat ccatcttgtt caatcatgcg aaacgatcct cattcattta | 5400 |
| tcagggttat tgtctcatga gcggatacat atttgaatgt atttaggctg agcatctatg | 5460 |
| tcgggtgcgg agaaagaggt aatgaaatgg caggcgcctt tttcgttaga tatgtagtaa | 5520 |
| gtatcttaat atacagcttt atctgttttt taagatactt actactttc ttagtggaaa | 5580 |
| ctattagtgg ctgttaatta agctagtact acccaagatt tgacagaatg catcgtttgc | 5640 |
| attcgaa | 5647 |

<210> SEQ ID NO 23
<211> LENGTH: 5338
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 23

| | |
|---|---|
| taactataac ggtcctaagg tagcgacgta cgaaccgttg ggcgcgcctg gggatagcga | 60 |
| tcgctgctgg cgcggtccgc tatgaggtct ctgatagacc acagacgcgt cgacattgat | 120 |
| tattgactag ttattaatag taatcaatta cggggtcatt agttcatagc ccatatatgg | 180 |
| agttccgcgt tacataactt acggtaaatg gcccgcctgg ctgaccgccc aacgaccccc | 240 |
| gcccattgac gtcaataatg acgtatgttc ccatagtaac gccaataggg actttccatt | 300 |
| gacgtcaatg ggtggactat ttacggtaaa ctgcccactt ggcagtacat caagtgtatc | 360 |
| atatgccaag tacgccccct attgacgtca atgacggtaa atggcccgcc tggcattatg | 420 |
| cccagtacat gaccttatgg gactttccta cttggcagta catctacgta ttagtcatcg | 480 |
| ctattaccat gggtcgaggt gagccccacg ttctgcttca ctctccccat ctcccccccc | 540 |
| tccccacccc caattttgta tttatttatt ttttaattat tttgtgcagc gatggggcg | 600 |
| gggggggggg gggcgcgcgc caggcggggc gggcgggc gaggggcggg gcggggcgag | 660 |
| gcggagaggt gcggcggcag ccaatcagag cggcgcgctc cgaaagtttc cttttatggc | 720 |
| gaggcggcg cggcggcggc cctataaaaa gcgaagcgcg cggcgggcgg gagtcgctgc | 780 |
| gttgccttcg ccccgtgccc cgctccgcgc cgcctcgcgc cgcccgcccc ggctctgact | 840 |
| gaccgcgtta ctcccacagg tgagcgggcg ggacggccct tctcctccgg gctgtaatta | 900 |

```
gcgcttggtt taatgacggc tcgtttcttt tctgtggctg cgtgaaagcc ttaaagggct    960
ccgggagggc cctttgtgcg gggggagcg gctcggggg tgcgtgcgtg tgtgtgtgcg    1020
tgggagcgc cgcgtgcggc ccgcgctgcc cggcggctgt gagcgctgcg ggcgcggcgc    1080
ggggctttgt gcgctccgcg tgtgcgcgag gggagcgcgg ccggggcgg tgccccgcgg    1140
tgcgggggg ctgcgagggg aacaaaggct gcgtgcgggg tgtgtgcgtg gggggtgag    1200
caggggtgt gggcgcggcg gtcgggctgt aaccccccc tgcacccccc tccccgagtt    1260
gctgagcacg gcccggcttc gggtgcgggg ctccgtgcgg ggcgtggcgc ggggctcgcc    1320
gtgccgggcg ggggtggcg gcaggtgggg gtgccgggcg gggcgggcc gcctcgggcc    1380
ggggagggct cggggagggg gcgcggcggc cccggagcgc cggcggctgt cgaggcgcgg    1440
cgagccgcag ccattgcctt ttatggtaat cgtgcgagag ggcgcaggga cttcctttgt    1500
cccaaatctg gcggagccga aatctgggag gcgccgccgc accccctcta gcgggcgcgg    1560
gcgaagcggt gcgcgccgg caggaaggaa atgggcgggg agggccttcg tgcgtcgccg    1620
cgccgccgtc cccttctcca tctccagcct cggggctgcc gcaggggac ggctgccttc    1680
gggggggacg gggcagggcg gggttcggct tctggcgtgt gaccggcggc tctagagcct    1740
ctgctaacca tgttcatgcc ttcttctttt tcctacagct cctgggcaac gtgctggttg    1800
ttgtgctgtc tcatcatttt ggcaaagaat tccctgcagg aaattgagcc cgcagcctcc    1860
cgcttcgctc tctgctcctc ctgttcgaca gtcagccgca tcttcttttg cgtcgccagc    1920
cgagccacat cgctcagaca ccgctagcgc caccatgggc agcgaactgg aaaccgccat    1980
ggagactttg ataaatgttt tccacgcgca tagcggcaaa aaggggaca agtacaagct    2040
gtcaaaaaag gagctgaaag aactgctgca gaccgaattg agcggcttcc tggacgctca    2100
gaaagatgtc gatgccgtcg acaaagtgat gaaagagctt gacgagaacg gtgacggtga    2160
agtcgatttt caggaatatg tggtgctggt ggccgcccct actgtagcat gcaacaattt    2220
cttttgggaa aattcaggaa gcggagctac taacttcagc ctgctgaagc aggctggaga    2280
cgtggaggag aaccctggac ctatgaatgc caaggtcgtt gtggtgcttg tacttgtgct    2340
gactgctctg tgtctgagcg acggaaaacc agtctccctc agctacaggt gcccatgccg    2400
attcttcgaa tctcatgtgg cccgggccaa tgtgaagcac ttgaaaatcc tgaatacacc    2460
caactgcgcg ttgcagatcg tggcccgcct gaaaaataat aataggcagg tatgtatcga    2520
tccaaagctt aagtggatcc aggagtatct ggaaaaggct ctcaataaat aaatcgatta    2580
cgctcctcta ctctttgaga catcactggc ctataataaa tgggttaatt tatgtaacaa    2640
aattgccttg gcttgttaac tttattagac attctgatgt ttgcattgtg taaatactgt    2700
tgtattggaa aagcgtgcca agatggatta ttgtaattca gtgtctttt tagtagcgtc    2760
acgtgccaaa cactgttagt cacagagggc atgagacagc ctgtgctgga acagctcagt    2820
tcatagggct atggagatgg ggagaaaggg gcgcttctgt cagagacaag ctgtggtctg    2880
ggaaggcctt agcactaaaa gcaccacaat gagaagcaac cgccagaagc agggcccgca    2940
ggcctttgtt ccagctgcaa agagaaagga aaaagtgggg aataagagtt ggggctgcgg    3000
agggggtggg gagcattgtg caggttccgt acttgaacag aaagcaggga ccaacacaag    3060
gaaggctcga gctggcgaa taggttccaa tctgtcgcgg ccgcattacc ctgttatccc    3120
taatctcgtt taactatgac tctcttaagg tagccaaatt ccggaactat aaattgcgtt    3180
gcgctcactg cccgctttcc agtcgggaaa cctgtcgtgc cagctgcata aatgaatcgg    3240
```

```
ccaacgcgcg gggagaggcg gtttgcgtat tgggcgcgct tccgcttcct cgctcactga    3300
ctcgctgcgc tcggtcgttc ggctgcggcg agcggtatca gctcactcaa aggcggtaat    3360
acggttatcc acagaatcag gggataacgc aggaaagaac atgtgagcaa aaggccagca    3420
aaaggccagg aaccgtaaaa aggccgcgtt gctggcgttt ttccataggc tccgcccccc    3480
tgacgagcat cacaaaaatc gacgctcaag tcagaggtgg cgaaacccga caggactata    3540
aagataccag gcgtttcccc ctggaagctc cctcgtgcgc tctcctgttc cgaccctgcc    3600
gcttaccgga tacctgtccg cctttctccc ttcgggaagc gtggcgcttt ctcatagctc    3660
acgctgtagg tatctcagtt cggtgtaggt cgttcgctcc aagctgggct gtgtgcacga    3720
accccccgtt cagcccgacc gctgcgcctt atccggtaac tatcgtcttg agtccaaccc    3780
ggtaagacac gacttatcgc cactggcagc agccactggt aacaggatta gcagagcgag    3840
gtatgtaggc ggtgctacag agttcttgaa gtggtggcct aactacggct acactagaag    3900
aacagtattt ggtatctgcg ctctgctgaa gccagttacc ttcggaaaaa gagttggtag    3960
ctcttgatcc ggcaaacaaa ccaccgctgg tagcggtggt ttttttgttt gcaagcagca    4020
gattacgcgc agaaaaaaag gatctcaaga agatcctttg atcttttcta cggggtctga    4080
cgctcagtgg aacgaaaact cacgttaagg gattttggtc atgagattat caaaaaggat    4140
cttcacctag atccttttaa attaaaaatg aagttttaaa tcaatctaaa gtatatatga    4200
gtaaacttgg tctgacatgc gcatctgacg ctcagtggaa cgaaaactca cgttaaggga    4260
ttttggtcat gcctcagaag aactcgtcaa gaaggcgata gaaggcgatg cgctgcgaat    4320
cgggagcggc gataccgtaa agcacgagga agcggtcagc ccattcgccg ccaagctctt    4380
cagcaatatc acgggtagcc aacgctatgt cctgatagcg gtccgccaca cccagccggc    4440
cacagtcgat gaatccagaa aagcggccat tttccaccat gatattcggc aagcaggcat    4500
cgccatgggt cacgacgaga tcctcgccgt cgggcatgcg cgccttgagc ctggcgaaca    4560
gttcggctgg cgcgagcccc tgatgctctt cgtccagatc atcctgatcg acaagaccgg    4620
cttccatccg agtacgtgct cgctcgatgc gatgtttcgc ttggtggtcg aatgggcagg    4680
tagccggatc aagcgtatgc agccgccgca ttgcatcagc catgatggat actttctcgg    4740
caggagcaag gtgagatgac aggagatcct gccccggcac ttcgcccaat agcagccagt    4800
cccttcccgc ttcagtgaca acgtcgagca gctgcgca aggaacgccc gtcgtggcca    4860
gccacgatag ccgcgctgcc tcgtcctgca gttcattcag ggcaccggac aggtcggtct    4920
tgacaaaaag aaccgggcgc ccctgcgctg acagccggaa cacggcggca tcagagcagc    4980
cgattgtctg ttgtgcccag tcatagccga atagcctctc cacccaagcg gccggagaac    5040
ctgcgtgcaa tccatcttgt tcaatcatgc gaaacgatcc tcattcattt atcagggtta    5100
ttgtctcatg agcggataca tatttgaatg tatttaggct gagcatctat gtcgggtgcg    5160
gagaaagagg taatgaaatg gcaggcgcct ttttcgttag atatgtagta agtatcttaa    5220
tatacagctt tatctgtttt ttaagatact tactactttt cttagtggaa actattagtg    5280
gctgttaatt aagctagtac tacccaagat ttgacagaat gcatcgtttg cattcgaa    5338
```

<210> SEQ ID NO 24
<211> LENGTH: 5338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
taactataac ggtcctaagg tagcgacgta cgaaccgttg ggcgcgcctg gggatagcga        60
tcgctgctgg cgcggtccgc tatgaggtct ctgatagacc acagacgcgt cgacattgat       120
tattgactag ttattaatag taatcaatta cggggtcatt agttcatagc ccatatatgg       180
agttccgcgt tacataactt acggtaaatg gcccgcctgg ctgaccgccc aacgacccccc      240
gcccattgac gtcaataatg acgtatgttc ccatagtaac gccaatagggg actttccatt      300
gacgtcaatg ggtggactat ttacggtaaa ctgcccactt ggcagtacat caagtgtatc      360
atatgccaag tacgccccct attgacgtca atgacggtaa atggcccgcc tggcattatg      420
cccagtacat gaccttatgg gactttccta cttggcagta catctacgta ttagtcatcg      480
ctattaccat gggtcgaggt gagccccacg ttctgcttca ctctccccat ctcccccccc      540
tccccacccc caatttttgta tttatttatt ttttaattat tttgtgcagc gatgggggcg      600
ggggggggggg gggcgcgcgc caggcggggc ggggcggggc gaggggcggg gcggggcgag      660
gcggagaggt gcggcggcag ccaatcagag cggcgcgctc cgaaagtttc cttttatggc      720
gaggcggcgg cggcggcggc cctataaaaa gcgaagcgcg cggcgggcgg gagtcgctgc      780
gttgccttcg ccccgtgccc cgctccgcgc cgcctcgcgc cgcccgcccc ggctctgact      840
gaccgcgtta ctcccacagg tgagcgggcg ggacggccct tctcctccgg gctgtaatta      900
gcgcttggtt taatgacggc tcgtttcttt tctgtggctg cgtgaaagcc ttaaagggct      960
ccgggagggc cctttgtgcg ggggggagcg gctcgggggg tgcgtgcgtg tgtgtgtgcg     1020
tggggagcgc cgcgtgcggc ccgcgctgcc cggcggctgt gagcgctgcg ggcgcggcgc     1080
ggggctttgt gcgctccgcg tgtgcgcgag gggagcgcgg ccggggggcgg tgccccgcgg     1140
tgcggggggg ctgcgagggg aacaaaggct gcgtgcgggg tgtgtgcgtg gggggtgag      1200
cagggggtgt gggcgcggcg gtcgggctgt aaccccccccc tgcaccccccc tccccgagtt    1260
gctgagcacg gcccggcttc gggtgcgggg ctccgtgcgg ggcgtggcgc ggggctcgcc     1320
gtgccgggcg gggggtggcg gcaggtgggg gtgccgggcg gggcggggcc gcctcgggcc     1380
ggggagggct cggggggaggg gcgcggcggc cccggagcgc cggcggctgt cgaggcgcgg     1440
cgagccgcag ccattgcctt ttatggtaat cgtgcgagag ggcgcaggga cttcctttgt     1500
cccaaatctg gcgagccga atctgggag gcgccgccgc accccctcta gcgggcgcgg      1560
gcgaagcggt gcggcgccgg caggaaggaa atgggcgggg agggccttcg tgcgtcgccg     1620
cgccgccgtc ccttctcca tctccagcct cggggctgcc gcaggggac ggctgccttc       1680
gggggggacg gggcagggcg gggttcggct tctggcgtgt gaccggcggc tctagagcct    1740
ctgctaacca tgttcatgcc ttcttctttt tcctacagct cctgggcaac gtgctggttg     1800
ttgtgctgtc tcatcatttt ggcaaagaat ccctgcagg aaattgagcc cgcagcctcc      1860
cgcttcgctc tctgctcctc ctgttcgaca gtcagccgca tcttcttttg cgtcgccagc     1920
cgagccacat cgctcagaca ccgctagcgc caccatgaat gccaaggtcg ttgtggtgct     1980
tgtacttgtg ctgactgctc tgtgtctgag cgacggaaaa ccagtctccc tcagctacag     2040
gtgcccatgc cgattcttcg aatctcatgt ggcccgggcc aatgtgaagc acttgaaaat     2100
cctgaataca cccaactgcg cgttgcagat cgtggcccgc ctgaaaaata taataaggca     2160
ggtatgtatc gatccaaagc ttaagtggat ccaggagtat ctggaaaagg ctctcaataa    2220
aggaagcgga gctactaact tcagcctgct gaagcaggct ggagacgtgg aggagaaccc    2280
```

```
tggacctatg ggcagcgaac tggaaaccgc catggagact ttgataaatg tttttccacgc    2340
gcatagcggc aaagaagggg acaagtacaa gctgtcaaaa aaggagctga aagaactgct    2400
gcagaccgaa ttgagcggct tcctggacgc tcagaaagat gtcgatgccg tcgacaaagt    2460
gatgaaagag cttgacgaga acggtgacgg tgaagtcgat tttcaggaat atgtggtgct    2520
ggtggccgcc cttactgtag catgcaacaa tttcttttgg gaaaattcat aaatcgatta    2580
cgctcctcta ctctttgaga catcactggc ctataataaa tgggttaatt tatgtaacaa    2640
aattgccttg gcttgttaac tttattagac attctgatgt ttgcattgtg taaatactgt    2700
tgtattggaa aagcgtgcca agatggatta ttgtaattca gtgtcttttt tagtagcgtc    2760
acgtgccaaa cactgttagt cacagagggc atgagacagc ctgtgctgga acagctcagt    2820
tcatagggct atggagatgg ggagaaaggg gcgcttctgt cagagacaag ctgtggtctg    2880
ggaaggcctt agcactaaaa gcaccacaat gagaagcaac cgccagaagc agggcccgca    2940
ggcctttgtt ccagctgcaa agagaaagga aaaagtgggg aataagagtt ggggctgcgg    3000
aggggtggg gagcattgtg caggttccgt acttgaacag aaagcaggga ccaacacaag    3060
gaaggctcga gctggcggaa taggttccaa tctgtcgcgg ccgcattacc ctgttatccc    3120
taatctcgtt taactatgac tctcttaagg tagccaaatt ccggaactat aaattgcgtt    3180
gcgctcactg cccgctttcc agtcgggaaa cctgtcgtgc cagctgcata atgaatcgg    3240
ccaacgcgcg gggagaggcg gtttgcgtat gggcgcgct ccgcttcct cgctcactga    3300
ctcgctgcgc tcggtcgttc ggctgcggcg agcggtatca gctcactcaa aggcggtaat    3360
acggttatcc acagaatcag gggataacgc aggaaagaac atgtgagcaa aaggccagca    3420
aaaggccagg aaccgtaaaa aggccgcgtt gctggcgttt ttccataggc tccgcccccc    3480
tgacgagcat cacaaaaatc gacgctcaag tcagaggtgg cgaaacccga caggactata    3540
aagataccag gcgtttcccc ctggaagctc cctcgtgcgc tctcctgttc cgaccctgcc    3600
gcttaccgga tacctgtccg cctttctccc ttcgggaagc gtggcgcttt ctcatagctc    3660
acgctgtagg tatctcagtt cggtgtaggt cgttcgctcc aagctgggct gtgtgcacga    3720
accccccgtt cagcccgacc gctgcgcctt atccggtaac tatcgtcttg agtccaaccc    3780
ggtaagacac gacttatcgc cactggcagc agccactggt aacaggatta gcagagcgag    3840
gtatgtaggc ggtgctacag agttcttgaa gtggtggcct aactacggct acactagaag    3900
aacagtattt ggtatctgcg ctctgctgaa gccagttacc ttcggaaaaa gagttggtag    3960
ctcttgatcc ggcaaacaaa ccaccgctgg tagcggtggt ttttttgttt gcaagcagca    4020
gattacgcgc agaaaaaaag gatctcaaga agatcctttg atcttttcta cggggtctga    4080
cgctcagtgg aacgaaaact cacgttaagg gattttggtc atgagattat caaaaaggat    4140
cttcacctag atccttttaa attaaaaatg aagttttaaa tcaatctaaa gtatatatga    4200
gtaaacttgg tctgacatgc gcatctgacg ctcagtggaa cgaaaactca cgttaaggga    4260
ttttggtcat gcctcagaag aactcgtcaa gaaggcgata gaaggcgatg cgctgcgaat    4320
cgggagcggc gataccgtaa agcacgagga agcggtcagc ccattcgccg ccaagctctt    4380
cagcaatatc acgggtagcc aacgctatgt cctgatagcg gtccgccaca cccagccggc    4440
cacagtcgat gaatccagaa aagcggccat tttccaccat gatattcggc aagcaggcat    4500
cgccatgggt cacgacgaga tcctcgccgt cgggcatgcg cgccttgagc ctggcgaaca    4560
gttcggctgg cgcgagcccc tgatgctctt cgtccagatc atcctgatcg acaagaccgg    4620
cttccatccg agtacgtgct cgctcgatgc gatgtttcgc ttggtggtcg aatgggcagg    4680
```

```
tagccggatc aagcgtatgc agccgccgca ttgcatcagc catgatggat actttctcgg    4740
caggagcaag gtgagatgac aggagatcct gccccggcac ttcgcccaat agcagccagt    4800
cccttcccgc ttcagtgaca acgtcgagca cagctgcgca aggaacgccc gtcgtggcca    4860
gccacgatag ccgcgctgcc tcgtcctgca gttcattcag gcaccggac aggtcggtct      4920 tgacaaaaag aaccgggcgc ccctgcgctg acagccggaa cacggcggca tcagagcagc    4980
cgattgtctg ttgtgcccag tcatagccga atagcctctc cacccaagcg gccggagaac    5040
ctgcgtgcaa tccatcttgt tcaatcatgc gaaacgatcc tcattcattt atcagggtta    5100
ttgtctcatg agcggataca tatttgaatg tatttaggct gagcatctat gtcgggtgcg    5160
gagaaagagg taatgaaatg gcaggcgcct ttttcgttag atatgtagta agtatcttaa    5220
tatacagctt tatctgtttt ttaagatact tactactttt cttagtggaa actattagtg    5280
gctgttaatt aagctagtac tacccaagat ttgacagaat gcatcgtttg cattcgaa      5338
```

<210> SEQ ID NO 25
<211> LENGTH: 5629
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
ctagcgccac catgaatgcc aaggtcgttg tggtgcttgt acttgtgctg actgctctgt      60
gtctgagcga cggaaaacca gtctccctca gctacaggtg cccatgccga ttcttcgaat     120
ctcatgtggc ccgggccaat gtgaagcact tgaaaatcct gaatacaccc aactgcgcgt     180
tgcagatcgt ggcccgcctg aaaaataata ataggcaggt atgtatcgat ccaaagctta     240
agtggatcca ggagtatctg gaaaaggctc tcaataaagg aagcggagct actaacttca     300
gcctgctgaa gcaggctgga gacgtggagg agaaccctgg acctatgaat tttctgctct     360
cttgggtgca ctggtcactg gcactgctgc tgtatctgca ccatgcaaaa tggtcccaag     420
cagctcccat ggcagaggga ggtggacaga atcatcatga ggttgtcaaa tttatggatg     480
tctaccagcg gagctactgc cacccaattg agacgttggt agacattttt caggaatatc     540
cagacgagat tgagtacatt ttcaagccta gctgtgtgcc cttgatgcga tgcggtggct     600
gttgcaatga tgagggactc gagtgtgtcc ccaccgagga agcaatata accatgcaaa      660 tcatgcgaat caaaccccac cagggccagc atatcggcga gatgtctttc ttgcaacata    720
acaaatgcga gtgtcggcca aagaaggaca gggctcgcca ggaaaatccc tgtggtcctt    780
gttcagagcg caggaagcat cttttcgtcc aggatccgca gacttgtaaa tgttcatgca    840
agaataccga ttctaggtgt aaggcgaggc aactcgagct taacgagaga acctgtaggt    900
gtgacaaacc tagaagataa atcgattacg ctcctctact ctttgagaca tcactggcct    960
ataataaatg ggttaattta tgtaacaaaa ttgccttggc ttgttaactt tattagacat   1020
tctgatgttt gcattgtgta aatactgttg tattggaaaa gcgtgccaag atggattatt   1080
gtaattcagt gtctttttta gtagcgtcac gtgccaaaca ctgttagtca cagagggcat   1140
gagacagcct gtgctggaac agctcagttc atagggctat ggagatgggg agaaaggggc   1200
gcttctgtca gagacaagct gtggtctggg aaggccttag cactaaaagc accacaatga   1260
gaagcaaccg ccagaagcag ggcccgcagg cctttgttcc agctgcaaag agaaaggaaa   1320
```

```
aagtggggaa taagagttgg ggctgcggag ggggtgggga gcattgtgca ggttccgtac    1380
ttgaacagaa agcagggacc aacacaagga aggctcgagc tggcggaata ggttccaatc    1440
tgtcgcggcc gcattaccct gttatccta atctcgttta actatgactc tcttaaggta     1500
gccaaattcc ggaactataa attgcgttgc gctcactgcc cgcttccag tcgggaaacc     1560 tgtcgtgcca gctgcataaa tgaatcggcc aacgcgcggg gagaggcggt ttgcgtattg    1620
ggcgcgcttc cgcttcctcg ctcactgact cgctgcgctc ggtcgttcgg ctgcggcgag    1680
cggtatcagc tcactcaaag gcggtaatac ggttatccac agaatcaggg gataacgcag    1740
gaaagaacat gtgagcaaaa ggccagcaaa aggccaggaa ccgtaaaaag gccgcgttgc    1800
tggcgttttt ccataggctc cgcccccctg acgagcatca caaaaatcga cgctcaagtc    1860
agaggtggcg aaacccgaca ggactataaa gataccaggc gtttccccct ggaagctccc    1920
tcgtgcgctc tcctgttccg accctgccgc ttaccggata cctgtccgcc tttctccctt    1980
cgggaagcgt ggcgctttct catagctcac gctgtaggta tctcagttcg gtgtaggtcg    2040
ttcgctccaa gctgggctgt gtgcacgaac cccccgttca gcccgaccgc tgcgccttat    2100
ccggtaacta tcgtcttgag tccaacccgg taagacacga cttatcgcca ctggcagcag    2160
ccactggtaa caggattagc agagcgaggt atgtaggcgg tgctacagag ttcttgaagt    2220
ggtggcctaa ctacggctac actagaagaa cagtatttgg tatctgcgct ctgctgaagc    2280
cagttacctt cggaaaaaga gttggtagct cttgatccgg caaacaaacc accgctggta    2340
gcggtggttt ttttgtttgc aagcagcaga ttacgcgcag aaaaaaagga tctcaagaag    2400
atcctttgat cttttctacg gggtctgacg ctcagtggaa cgaaaactca cgttaaggga    2460
ttttggtcat gagattatca aaaaggatct tcacctagat ccttttaaat taaaaatgaa    2520
gttttaaatc aatctaaagt atatatgagt aaacttggtc tgacatgcgc atctgacgct    2580
cagtggaacg aaaactcacg ttaagggatt ttggtcatgc ctcagaagaa ctcgtcaaga    2640
aggcgataga aggcgatgcg ctgcgaatcg ggagcggcga taccgtaaag cacgaggaag    2700
cggtcagccc attcgccgcc aagctcttca gcaatatcac gggtagccaa cgctatgtcc    2760
tgatagcggt ccgccacacc cagccggcca cagtcgatga atccagaaaa gcggccattt    2820
tccaccatga tattcggcaa gcaggcatcg ccatgggtca cgacgagatc ctcgccgtcg    2880
ggcatgcgcg ccttgagcct ggcgaacagt tcggctggcg cgagccctg atgtcttcg      2940 tccagatcat cctgatcgac aagaccggct tccatccgag tacgtgctcg ctcgatgcga    3000
tgtttcgctt ggtggtcgaa tgggcaggta gccggatcaa gcgtatgcag ccgccgcatt    3060
gcatcagcca tgatggatac tttctcggca ggagcaaggt gagatgacag gagatcctgc    3120
cccggcactt cgcccaatag cagccagtcc cttcccgctt cagtgacaac gtcgagcaca    3180
gctgcgcaag gaacgcccgt cgtggccagc cacgatagcc gcgctgcctc gtcctgcagt    3240
tcattcaggg caccggacag gtcggtcttg acaaaaagaa ccgggcgccc ctgcgctgac    3300
agccggaaca cggcggcatc agagcagccg attgtctgtt gtgcccagtc atagccgaat    3360
agcctctcca cccaagcggc cggagaacct gcgtgcaatc catcttgttc aatcatgcga    3420
aacgatcctc attcatttat cagggttatt gtctcatgag cggatacata tttgaatgta    3480
tttaggctga gcatctatgt cgggtgcgga gaaagaggta atgaaatggc aggcgccttt    3540
ttcgttagat atgtagtaag tatcttaata tacagcttta tctgtttttt aagtacttta    3600
ctacttttct tagtggaaac tattagtggc tgttaattaa gctagtacta cccaagattt    3660
gacagaatgc atcgtttgca ttcgaataac tataacggtc ctaaggtagc gacgtacgaa    3720
```

```
ccgttgggcg cgcctgggga tagcgatcgc tgctggcgcg gtccgctatg aggtctctga    3780
tagaccacag acgcgtcgac attgattatt gactagttat taatagtaat caattacggg    3840
gtcattagtt catagcccat atatggagtt ccgcgttaca taacttacgg taaatggccc    3900
gcctggctga ccgcccaacg accccgccc attgacgtca ataatgacgt atgttcccat     3960
agtaacgcca atagggactt tccattgacg tcaatgggtg gactatttac ggtaaactgc    4020
ccacttggca gtacatcaag tgtatcatat gccaagtacg cccctattg acgtcaatga     4080 cggtaaatgg cccgcctggc attatgccca gtacatgacc ttatgggact ttcctacttg    4140
gcagtacatc tacgtattag tcatcgctat taccatgggt cgaggtgagc ccacgttct     4200 gcttcactct ccccatctcc cccctccc caccccaat tttgtattta tttattttt       4260 aattattttg tgcagcgatg ggggcgggg gggggggggc gcgcgccagg cggggcgggg     4320
cggggcgagg ggcggggcgg ggcgaggcgg agaggtgcgg cggcagccaa tcagagcggc    4380
gcgctccgaa agtttccttt tatggcgagg cggcggcggc ggcggcccta taaaaagcga    4440
agcgcgcggc gggcgggagt cgctgcgttg ccttcgcccc gtgccccgct ccgcgccgcc    4500
tcgcgccgcc cgcccggct ctgactgacc gcgttactcc cacaggtgag cgggcgggac     4560
ggcccttctc ctccgggctg taattagcgc ttggtttaat gacggctcgt ttcttttctg    4620
tggctgcgtg aaagccttaa agggctccgg gagggcccctt tgtgcggggg ggagcggctc   4680 gggggggtgcg tgcgtgtgtg tgtgcgtggg gagcgccgcg tgcggcccgc gctgccggc    4740 ggctgtgagc gctgcgggcg cggcgcgggg ctttgtgcgc tccgcgtgtg cgcgagggga    4800
gcgcggccgg gggcggtgcc ccgcggtgcg ggggggctgc gagggaaca aaggctgcgt     4860 gcggggtgtg tgcgtggggg ggtgagcagg gggtgtgggc gcggcggtcg ggctgtaacc    4920
cccccctgca cccccctccc cgagttgctg agcacggccc ggcttcgggt gcggggctcc    4980
gtgcggggcg tggcgcgggg ctcgccgtgc cgggcggggg gtggcggcag gtgggggtgc    5040
cgggcggggc ggggccgcct cgggccgggg agggctcggg ggaggggcgc ggcggccccg    5100
gagcgccggc ggctgtcgag gcgcggcgag ccgcagccat tgccttttat ggtaatcgtg    5160
cgagagggcg cagggacttc ctttgtccca aatctggcgg agccgaaatc tgggaggcgc    5220
cgccgcaccc cctctagcgg gcgcggggcga agcggtgcgg cgccggcagg aaggaaatgg    5280
gcggggaggg ccttcgtgcg tcgccgcgcc gccgtcccct tctccatctc cagcctcggg    5340
gctgccgcag ggggacggct gccttcgggg gggacggggc agggcggggt tcggcttctg    5400
gcgtgtgacc ggcggctcta gagcctctgc taaccatgtt catgccttct tcttttttcct   5460 acagctcctg ggcaacgtgc tggttgttgt gctgtctcat catttggca agaattccc       5520 tgcaggaaat tgagcccgca gcctcccgct tcgctctctg ctcctcctgt tcgacagtca    5580
gccgcatctt ctttgcgtc gccagccgag ccacatcgct cagacaccg                 5629
```

<210> SEQ ID NO 26
<211> LENGTH: 5629
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26

```
ctagcgccac catgaatttt ctgctctctt gggtgcactg gtcactggca ctgctgctgt    60
```

```
atctgcacca tgcaaaatgg tcccaagcag ctcccatggc agagggaggt ggacagaatc    120
atcatgaggt tgtcaaattt atggatgtct accagcggag ctactgccac ccaattgaga    180
cgttggtaga cattttttcag gaatatccag acgagattga gtacatttttc aagcctagct    240 gtgtgcccctt gatgcgatgc ggtggctgtt gcaatgatga gggactcgag tgtgtcccca    300
ccgaggaaag caatataacc atgcaaatca tgcgaatcaa accccaccag ggccagcata    360
tcggcgagat gtcttttcttg caacataaca aatgcgagtg tcggccaaag aaggacaggg    420
ctcgccagga aaatccctgt ggtccttgtt cagagcgcag gaagcatctt ttcgtccagg    480
atccgcagac ttgtaaatgt tcatgcaaga ataccgattc taggtgtaag gcgaggcaac    540
tcgagcttaa cgagagaacc tgtaggtgtg acaaacctag aagaggaagc ggagctacta    600
acttcagcct gctgaagcag gctggagacg tggaggagaa ccctggacct atgaatgcca    660
aggtcgttgt ggtgcttgta cttgtgctga ctgctctgtg tctgagcgac ggaaaaccag    720 tctcccctcag ctacaggtgc ccatgccgat tcttcgaatc tcatgtggcc cgggccaatg    780
tgaagcactt gaaaatcctg aatacaccca actgcgcgtt gcagatcgtg gcccgcctga    840
aaaataataa taggcaggta tgtatcgatc caaagcttaa gtggatccag gagtatctgg    900
aaaaggctct caataaataa atcgattacg ctcctctact ctttgagaca tcactggcct    960
ataataaatg ggttaattta tgtaacaaaa ttgccttggc ttgttaactt tattagacat   1020
tctgatgttt gcattgtgta aatactgttg tattggaaaa gcgtgccaag atggattat    1080 gtaattcagt gtctttttta gtagcgtcac gtgccaaaca ctgttagtca cagagggcat   1140
gagacagcct gtgctggaac agctcagttc atagggctat ggagatgggg agaaaggggc   1200
gcttctgtca gagacaagct gtggtctggg aaggcttag cactaaaagc accacaatga   1260
gaagcaaccg ccagaagcag ggcccgcagg cctttgttcc agctgcaaag agaaaggaaa   1320
aagtggggaa taagagttgg ggctgcggag ggggtgggga gcattgtgca ggttccgtac   1380
ttgaacagaa agcagggacc aacacaagga aggctcgagc tggcggaata ggttccaatc   1440
tgtcgcggcc gcattaccct gttatcccta atctcgtttta actatgactc tcttaaggta   1500
gccaaattcc ggaactataa attgcgttgc gctcactgcc cgcttttcag tcgggaaacc   1560
tgtcgtgcca gctgcataaa tgaatcggcc aacgcgcggg gagaggcggt ttgcgtattg   1620
ggcgcgcttc cgcttcctcg ctcactgact cgctgcgctc ggtcgttcgg ctgcggcgag   1680
cggtatcagc tcactcaaag gcggtaatac ggttatccac agaatcaggg gataacgcag   1740
gaaagaacat gtgagcaaaa ggccagcaaa aggccaggaa ccgtaaaaag gccgcgttgc   1800
tggcgttttt ccataggctc cgcccccctg acgagcatca caaaaatcga cgctcaagtc   1860
agaggtggcg aaacccgaca ggactataaa gataccaggc gtttcccccct ggaagctccc   1920 tcgtgcgctc tcctgttccg accctgccgc ttaccggata cctgtccgcc tttctccctt   1980
cgggaagcgt ggcgctttct catagctcac gctgtaggta tctcagttcg gtgtaggtcg   2040
ttcgctccaa gctgggctgt gtgcacgaac cccccgttca gcccgaccgc tgcgccttat   2100
ccggtaacta tcgtcttgag tccaacccgg taagacacga cttatcgcca ctggcagcag   2160
ccactggtaa caggattagc agagcgaggt atgtaggcgg tgctacagag ttcttgaagt   2220
ggtggcctaa ctacggctac actagaagaa cagtatttgg tatctgcgct ctgctgaagc   2280
cagttacctt cggaaaaaga gttggtagct cttgatccgg caaacaaacc accgctggta   2340
gcggtggttt ttttgtttgc aagcagcaga ttacgcgcag aaaaaaagga tctcaagaag   2400
atcctttgat cttttctacg gggtctgacg ctcagtggaa cgaaaactca cgttaaggga   2460
```

```
ttttggtcat gagattatca aaaaggatct tcacctagat ccttttaaat taaaaatgaa    2520
gttttaaatc aatctaaagt atatatgagt aaacttggtc tgacatgcgc atctgacgct    2580
cagtggaacg aaaactcacg ttaagggatt ttggtcatgc ctcagaagaa ctcgtcaaga    2640
aggcgataga aggcgatgcg ctgcgaatcg ggagcggcga taccgtaaag cacgaggaag    2700
cggtcagccc attcgccgcc aagctcttca gcaatatcac gggtagccaa cgctatgtcc    2760
tgatagcggt ccgccacacc cagccggcca cagtcgatga atccagaaaa gcggccattt    2820
tccaccatga tattcggcaa gcaggcatcg ccatgggtca cgacgagatc ctcgccgtcg    2880
ggcatgcgcg ccttgagcct ggcgaacagt tcggctggcg cgagcccctg atgctcttcg    2940
tccagatcat cctgatcgac aagaccggct tccatccgag tacgtgctcg ctcgatgcga    3000
tgtttcgctt ggtggtcgaa tgggcaggta gccggatcaa gcgtatgcag ccgccgcatt    3060
gcatcagcca tgatggatac tttctcggca ggagcaaggt gagatgacag gagatcctgc    3120
cccggcactt cgcccaatag cagccagtcc cttcccgctt cagtgacaac gtcgagcaca    3180
gctgcgcaag gaacgcccgt cgtggccagc cacgatagcc gcgctgcctc gtcctgcagt    3240
tcattcaggg caccggacag gtcggtcttg acaaaaagaa ccgggcgccc ctgcgctgac    3300
agccggaaca cggcggcatc agagcagccg attgtctgtt gtgcccagtc atagccgaat    3360
agcctctcca cccaagcggc cggagaacct gcgtgcaatc catcttgttc aatcatgcga    3420
aacgatcctc attcatttat cagggttatt gtctcatgag cggatacata tttgaatgta    3480
tttaggctga gcatctatgt cgggtgcgga gaaagaggta atgaaatggc aggcgccttt    3540
ttcgttagat atgtagtaag tatcttaata tacagcttta tctgtttttt aagatactta    3600
ctacttttct tagtggaaac tattagtggc tgttaattaa gctagtacta cccaagattt    3660
gacagaatgc atcgtttgca ttcgaataac tataacggtc taaggtagc gacgtacgaa    3720 ccgttgggcg cgcctgggga tagcgatcgc tgctggcgcg gtccgctatg aggtctctga    3780
tagaccacag acgcgtcgac attgattatt gactagttat taatagtaat caattacggg    3840
gtcattagtt catagcccat atatggagtt ccgcgttaca taacttacgg taaatggccc    3900
gcctggctga ccgcccaacg accccgccc attgacgtca ataatgacgt atgttcccat    3960
agtaacgcca atagggactt tccattgacg tcaatgggtg gactatttac ggtaaactgc    4020
ccacttggca gtacatcaag tgtatcatat gccaagtacg ccccctattg acgtcaatga    4080
cggtaaatgg cccgcctggc attatgccca gtacatgacc ttatgggact ttcctacttg    4140
gcagtacatc tacgtattag tcatcgctat taccatgggt cgaggtgagc ccacgttct    4200 gcttcactct ccccatctcc ccccctccc caccccaat tttgtattta tttattttt    4260 aattattttg tgcagcgatg ggggcggggg ggggggggc gcgcgccagg cggggcgggg    4320
cggggcgagg ggcggggcgg ggcgaggcgg agaggtgcgg cggcagccaa tcagagcggc    4380
gcgctccgaa agtttccttt tatgcgagg cggcggcgg ggcggcccta taaaaagcga    4440
agcgcgcggc gggcgggagt cgctgcgttg ccttcgcccc gtgccccgct ccgcgccgcc    4500
tcgcgccgcc cgccccggct ctgactgacc gcgttactcc cacaggtgag cgggcgggac    4560
ggcccttctc ctccgggctg taattagcgc ttggtttaat gacggctcgt ttcttttctg    4620
tggctgcgtg aaagccttaa agggctccgg gagggccctt tgtgcggggg ggagcggctc    4680 gggggtgcg tgcgtgtgtg tgtgcgtggg gagcgccgcg tgcggcccgc gctgcccggc    4740
ggctgtgagc gctgcgggcg cggcgcgggg ctttgtgcgc tccgcgtgtg cgcgagggga    4800
```

| | |
|---|---|
| gcgcggccgg gggcggtgcc ccgcggtgcg gggggctgc gaggggaaca aaggctgcgt | 4860 |
| gcggggtgtg tgcgtggggg ggtgagcagg gggtgtgggc gcggcggtcg ggctgtaacc | 4920 |
| cccccctgca cccccctccc cgagttgctg agcacggccc ggcttcgggt gcggggctcc | 4980 |
| gtgcggggcg tggcgcgggg ctcgccgtgc cgggcgggg gtggcggcag gtgggggtgc | 5040 |
| cgggcgggc ggggccgcct cgggccgggg agggctcggg ggaggggcgc ggcggccccg | 5100 |
| gagcgccggc ggctgtcgag gcgcggcgag ccgcagccat tgcctttat ggtaatcgtg | 5160 |
| cgagagggcg cagggacttc ctttgtccca aatctggcgg agccgaaatc tgggaggcgc | 5220 |
| cgccgcaccc cctctagcgg gcgcgggcga agcggtgcgg cgccggcagg aaggaaatgg | 5280 |
| gcggggaggg ccttcgtgcg tcgccgcgcc gccgtcccct tctccatctc cagcctcggg | 5340 |
| gctgccgcag ggggacggct gccttcgggg gggacggggc agggcggggt tcggcttctg | 5400 |
| gcgtgtgacc ggcggctcta gagcctctgc taaccatgtt catgccttct tcttttttcct | 5460 |
| acagctcctg gcaacgtgc tggttgttgt gctgtctcat cattttggca aagaattccc | 5520 |
| tgcaggaaat tgagcccgca gcctcccgct tcgctctctg ctcctcctgt tcgacagtca | 5580 |
| gccgcatctt cttttgcgtc gccagccgag ccacatcgct cagacaccg | 5629 |

<210> SEQ ID NO 27
<211> LENGTH: 5365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

| | |
|---|---|
| taactataac ggtcctaagg tagcgacgta cgaaccgttg ggcgcgcctg gggatagcga | 60 |
| tcgctgctgg cgcggtccgc tatgaggtct ctgatagacc acagacgcgt cgacattgat | 120 |
| tattgactag ttattaatag taatcaatta cggggtcatt agttcatagc ccatatatgg | 180 |
| agttccgcgt tacataactt acggtaaatg gcccgcctgg ctgaccgccc aacgacccccc | 240 |
| gcccattgac gtcaataatg acgtatgttc ccatagtaac gccaataggg actttccatt | 300 |
| gacgtcaatg ggtggactat ttacggtaaa ctgcccactt ggcagtacat caagtgtatc | 360 |
| atatgccaag tacgccccct attgacgtca atgacggtaa atggcccgcc tggcattatg | 420 |
| cccagtacat gaccttatgg gactttccta cttggcagta catctacgta ttagtcatcg | 480 |
| ctattaccat gggtcgaggt gagccccacg ttctgcttca ctctccccat ctcccccccc | 540 |
| tccccacccc caattttgta tttatttatt ttttaattat tttgtgcagc gatggggggcg | 600 |
| gggggggggg gggcgcgcgc caggcggggc ggggcggggc gaggggcggg gcggggcgag | 660 |
| gcggagaggt gcggcggcag ccaatcagag cggcgcgctc cgaaagtttc cttttatggc | 720 |
| gaggcggcgg cggcggcggc cctataaaaa gcgaagcgcg cggcgggcgg gagtcgctgc | 780 |
| gttgccttcg ccccgtgccc cgctccgcgc cgcctcgcgc cgcccgcccc ggctctgact | 840 |
| gaccgcgtta ctcccacagg tgagcgggcg ggacggccct tctcctccgg gctgtaatta | 900 |
| gcgcttggtt taatgacggc tcgtttcttt tctgtggctg cgtgaaagcc ttaaagggct | 960 |
| ccgggagggc cctttgtgcg gggggagcg gctcgggggg tgcgtgcgtg tgtgtgtgcg | 1020 |
| tggggagcgc cgcgtgcgcg ccgcgctgcc cggcggctgt gagcgctgcg ggcgcggcgc | 1080 |
| ggggctttgt gcgctccgcg tgtgcgcgag gggagcgcgg ccggggggcgg tgccccgcgg | 1140 |
| tgcggggggg ctgcgagggg aacaaaggct gcgtgcgggg tgtgtgcgtg gggggtgag | 1200 |

-continued

```
caggggggtgt gggcgcggcg gtcgggctgt aacccccccc tgcaccccccc tcccgagtt    1260
gctgagcacg gcccggcttc gggtgcgggg ctccgtgcgg ggcgtggcgc ggggctcgcc    1320
gtgccgggcg gggggtggcg gcaggtgggg gtgccgggcg gggcggggcc gcctcgggcc    1380
ggggagggct cggggagggg cgcggcggc cccggagcgc cggcggctgt cgaggcgcgg     1440
cgagccgcag ccattgcctt ttatggtaat cgtgcgagag ggcgcaggga cttcctttgt    1500
cccaaatctg gcggagccga aatctgggag gcgccgccgc accccctcta gcgggcgcgg    1560
gcgaagcggt gcggcgccgg caggaaggaa atgggcgggg agggccttcg tgcgtcgccg    1620
cgccgccgtc cccttctcca tctccagcct cggggctgcc gcaggggac ggctgccttc     1680
ggggggggacg gggcagggcg gggttcggct tctggcgtgt gaccggcggc tctagagcct   1740
ctgctaacca tgttcatgcc ttcttctttt tcctacagct cctgggcaac gtgctggttg    1800
ttgtgctgtc tcatcatttt ggcaaagaat tccctgcagg aaattgagcc cgcagcctcc   1860
cgcttcgctc tctgctcctc ctgttcgaca gtcagccgca tcttcttttg cgtcgccagc   1920
cgagccacat cgctcagaca ccgctagcgc caccatgggc agcgaactgg aaaccgccat   1980
ggagactttg ataaatgttt tccacgcgca tagcggcaaa gaagggggaca agtacaagct   2040
gtcaaaaaag gagctgaaag aactgctgca gaccgaattg agcggcttcc tggacgctca   2100
gaaagatgtc gatgccgtcg acaaagtgat gaaagagctt gacgagaacg gtgacggtga   2160
agtcgatttt caggaatatg tggtgctggt ggccgcccct actgtagcat gcaacaattt   2220
cttttgggaa aattcacgtg caaagcgtgc accggtgaaa cagggaagcg gagctactaa   2280
cttcagcctg ctgaagcagg ctggagacgt ggaggagaac cctggaccta tgaatgccaa   2340
ggtcgttgtg gtgcttgtac ttgtgctgac tgctctgtgt ctgagcgacg gaaaaccagt   2400
ctccctcagc tacaggtgcc catgccgatt cttcgaatct catgtggccc gggccaatgt   2460
gaagcacttg aaaatcctga atacacccaa ctgcgcgttg cagatcgtgg cccgcctgaa   2520
aaataataat aggcaggtat gtatcgatcc aaagcttaag tggatccagg agtatctgga   2580
aaaggctctc aataaataaa tcgattacgc tcctctactc tttgagacat cactggccta   2640
taataaatgg gttaatttat gtaacaaaat tgccttggct tgttaacttt attagacatt   2700
ctgatgtttg cattgtgtaa atactgttgt attggaaaag cgtgccaaga tggattattg   2760
taattcagtg tcttttttag tagcgtcacg tgccaaacac tgttagtcac agagggcatg   2820
agacagcctg tgctggaaca gctcagttca tagggctatg gagatgggga gaaagggggcg   2880
cttctgtcag agacaagctg tggtctggga aggccttagc actaaaagca ccacaatgag   2940
aagcaaccgc cagaagcagg gcccgcaggc ctttgttcca gctgcaaaga gaaaggaaaa   3000
agtggggaat aagagttggg gctgcggagg gggtggggag cattgtgcag gttccgtact   3060
tgaacagaaa gcagggacca acacaaggaa ggctcgagct ggcggaatag gttccaatct   3120
gtcgcggccg cattaccctg ttatccctaa tctcgtttaa ctatgactct cttaaggtag   3180
ccaaattccg gaactataaa ttgcgttgcg ctcactgccc gctttccagt cgggaaacct   3240
gtcgtgccag ctgcataaat gaatcggcca acgcgcgggg agaggcggtt tgcgtattgg   3300
gcgcgcttcc gcttcctcgc tcactgactc gctgcgctcg tcgttcggc tgcggcgagc    3360
ggtatcagct cactcaaagg cggtaatacg ttatccaca gaatcagggg ataacgcagg    3420
aaagaacatg tgagcaaaag gccagcaaaa ggccaggaac cgtaaaaagg ccgcgttgct   3480
ggcgtttttc cataggctcc gcccccctga cgagcatcac aaaaatcgac gctcaagtca   3540
```

```
gaggtggcga aacccgacag gactataaag ataccaggcg tttcccctg gaagctccct    3600
cgtgcgctct cctgttccga ccctgccgct taccggatac ctgtccgcct ttctcccttc    3660
gggaagcgtg gcgctttctc atagctcacg ctgtaggtat ctcagttcgg tgtaggtcgt    3720
tcgctccaag ctgggctgtg tgcacgaacc ccccgttcag cccgaccgct gcgccttatc    3780
cggtaactat cgtcttgagt ccaacccggt aagacacgac ttatcgccac tggcagcagc    3840
cactggtaac aggattagca gagcgaggta tgtaggcgt gctacagagt tcttgaagtg    3900
gtggcctaac tacggctaca ctagaagaac agtatttggt atctgcgctc tgctgaagcc    3960
agttaccttc ggaaaaagag ttggtagctc ttgatccggc aaacaaacca ccgctggtag    4020
cggtggtttt tttgtttgca agcagcagat tacgcgcaga aaaaaggat ctcaagaaga    4080
tcctttgatc ttttctacgg ggtctgacgc tcagtggaac gaaaactcac gttaagggat    4140
tttggtcatg agattatcaa aaaggatctt cacctagatc ctttaaatt aaaaatgaag    4200
ttttaaatca atctaaagta tatatgagta aacttggtct gacatgcgca tctgacgctc    4260
agtggaacga aaactcacgt taagggattt tggtcatgcc tcagaagaac tcgtcaagaa    4320
ggcgatagaa ggcgatgcgc tgcgaatcgg gagcggcgat accgtaaagc acgaggaagc    4380
ggtcagccca ttcgccgcca agctcttcag caatatcacg ggtagccaac gctatgtcct    4440
gatagcggtc cgccacaccc agccggccac agtcgatgaa tccagaaaag cggccatttt    4500
ccaccatgat attcggcaag caggcatcgc catgggtcac gacgagatcc tcgccgtcgg    4560
gcatgcgcgc cttgagcctg gcgaacagtt cggctggcgc gagcccctga tgctcttcgt    4620
ccagatcatc ctgatcgaca agaccggctt ccatccgagt acgtgctcgc tcgatgcgat    4680
gtttcgcttg gtggtcgaat gggcaggtag ccggatcaag cgtatgcagc cgccgcattg    4740
catcagccat gatggatact ttctcggcag gagcaaggtg agatgacagg agatcctgcc    4800
ccggcacttc gcccaatagc agccagtccc ttcccgcttc agtgacaacg tcgagcacag    4860
ctgcgcaagg aacgcccgtc gtggccagcc acgatagccg cgctgcctcg tcctgcagtt    4920
cattcagggc accggacagg tcggtcttga caaaaagaac cgggcgcccc tgcgctgaca    4980
gccggaacac ggcggcatca gagcagccga ttgtctgttg tgcccagtca tagccgaata    5040
gcctctccac ccaagcggcc ggagaacctg cgtgcaatcc atcttgttca atcatgcgaa    5100
acgatcctca ttcatttatc agggttattg tctcatgagc ggatacatat ttgaatgtat    5160
ttaggctgag catctatgtc gggtgcggag aaagaggtaa tgaaatggca ggcgcctttt    5220
tcgttagata tgtagtaagt atcttaatat acagctttat ctgttttta agatacttac    5280
tactttcttt agtggaaact attagtggct gttaattaag ctagtactac ccaagatttg    5340
acagaatgca tcgtttgcat tcgaa                                          5365
```

<210> SEQ ID NO 28
<211> LENGTH: 5365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
ctagcgccac catgaatgcc aaggtcgttg tggtgcttgt acttgtgctg actgctctgt      60
gtctgagcga cggaaaacca gtctcccctca gctacaggtg cccatgccga ttcttcgaat    120
ctcatgtggc ccgggccaat gtgaagcact tgaaaatcct gaatacaccc aactgcgcgt    180
```

```
tgcagatcgt ggcccgcctg aaaaataata ataggcaggt atgtatcgat ccaaagctta     240
agtggatcca ggagtatctg aaaaggctc tcaataaacg tgcaaagcgt gcaccggtga      300
aacagggaag cggagctact aacttcagcc tgctgaagca ggctggagac gtggaggaga     360
accctggacc tatgggcagc gaactggaaa ccgccatgga gactttgata aatgttttcc    420
acgcgcatag cggcaaagaa ggggacaagt acaagctgtc aaaaaaggag ctgaaagaac   480
tgctgcagac cgaattgagc ggcttcctgg acgtcagaa agatgtcgat gccgtcgaca     540
aagtgatgaa agagcttgac gagaacggtg acggtgaagt cgattttcag gaatatgtgg   600
tgctggtggc cgcccttact gtagcatgca acaatttctt ttgggaaaat tcataaatcg   660
attacgctcc tctactcttt gagacatcac tggcctataa taaatgggtt aatttatgta    720
acaaaattgc cttggcttgt taactttatt agacattctg atgtttgcat tgtgtaaata    780
ctgttgtatt ggaaaagcgt gccaagatgg attattgtaa ttcagtgtct tttttagtag    840
cgtcacgtgc caaacactgt tagtcacaga gggcatgaga cagcctgtgc tggaacagct   900
cagttcatag ggctatggag atggggagaa aggggcgctt ctgtcagaga caagctgtgg  960
tctgggaagg cctagcact aaaagcacca caatgagaag caaccgccag aagcagggcc    1020
cgcaggcctt tgttccagct gcaaagagaa aggaaaaagt ggggaataag agttggggct   1080
gcggaggggg tggggagcat tgtgcaggtt ccgtacttga acagaaagca gggaccaaca   1140
caaggaaggc tcgagctggc ggaataggtt ccaatctgtc gcggccgcat taccctgtta   1200
tccctaatct cgtttaacta tgactctctt aaggtagcca aattccggaa ctataaattg   1260
cgttgcgctc actgcccgct ttccagtcgg gaaacctgtc gtgccagctg cataaatgaa   1320
tcggccaacg cgcggggaga ggcggtttgc gtattgggcg cgcttccgct tcctcgctca   1380
ctgactcgct gcgctcggtc gttcggctgc ggcgagcggt atcagctcac tcaaaggcgg   1440
taatacggtt atccacagaa tcaggggata acgcaggaaa gaacatgtga gcaaaaggcc   1500
agcaaaaggc caggaaccgt aaaaaggccg cgttgctggc gttttccat aggctccgcc    1560 cccctgacga gcatcacaaa aatcgacgct caagtcagag gtggcgaaac ccgacaggac   1620
tataaagata ccaggcgttt ccccctggaa gctccctcgt gcgctctcct gttccgaccc   1680
tgccgcttac cggatacctg tccgcctttc tcccttcggg aagcgtggcg ctttctcata   1740
gctcacgctg taggtatctc agttcggtgt aggtcgttcg ctccaagctg ggctgtgtgc   1800
acgaaccccc cgttcagccc gaccgctgcg ccttatccgg taactatcgt cttgagtcca   1860
acccggtaag acacgactta tcgccactgg cagcagccac tggtaacagg attagcagag   1920
cgaggtatgt aggcggtgct acagagttct tgaagtggtg gcctaactac ggctacacta   1980
gaagaacagt atttggtatc tgcgctctgc tgaagccagt taccttcgga aaaagagttg   2040
gtagctcttg atccggcaaa caaaccaccg ctggtagcgg tggtttttttt gtttgcaagc   2100 agcagattac gcgcagaaaa aaaggatctc aagaagatcc tttgatcttt tctacggggt    2160
ctgacgctca gtggaacgaa aactcacgtt aagggatttt ggtcatgaga ttatcaaaaa   2220
ggatcttcac ctagatcctt ttaaattaaa aatgaagttt taaatcaatc taaagtatat   2280
atgagtaaac ttggtctgac atgcgcatct gacgctcagt ggaacgaaaa ctcacgttaa   2340
gggattttgg tcatgcctca gaagaactcg tcaagaaggc gatagaaggc gatgcgctgc   2400
gaatcgggag cggcgatacc gtaaagcacg aggaagcggt cagcccattc gccgccaagc   2460
tcttcagcaa tatcacgggt agccaacgct atgtcctgat agcggtccgc cacacccagc   2520
```

```
cggccacagt cgatgaatcc agaaaagcgg ccattttcca ccatgatatt cggcaagcag    2580
gcatcgccat gggtcacgac gagatcctcg ccgtcgggca tgcgcgcctt gagcctggcg    2640
aacagttcgg ctggcgcgag cccctgatgc tcttcgtcca gatcatcctg atcgacaaga    2700
ccggcttcca tccgagtacg tgctcgctcg atgcgatgtt tcgcttggtg gtcgaatggg    2760
caggtagccg gatcaagcgt atgcagccgc cgcattgcat cagccatgat ggatactttc    2820
tcggcaggag caaggtgaga tgacaggaga tcctgccccg gcacttcgcc caatagcagc    2880
cagtcccttc ccgcttcagt gacaacgtcg agcacagctg cgcaaggaac gcccgtcgtg    2940
gccagccacg atagccgcgc tgcctcgtcc tgcagttcat tcagggcacc ggacaggtcg    3000
gtcttgacaa aaagaaccgg gcgcccctgc gctgacagcc ggaacacggc ggcatcagag    3060
cagccgattg tctgttgtgc ccagtcatag ccgaatagcc tctccaccca gcggccgga    3120 gaacctgcgt gcaatccatc ttgttcaatc atgcgaaacg atcctcattc atttatcagg    3180
gttattgtct catgagcgga tacatatttg aatgtattta ggctgagcat ctatgtcggg    3240
tgcggagaaa gaggtaatga aatggcaggc gcctttttcg ttagatatgt agtaagtatc    3300
ttaatataca gctttatctg ttttttaaga tacttactac ttttcttagt ggaaactatt    3360
agtggctgtt aattaagcta gtactaccca agatttgaca gaatgcatcg tttgcattcg    3420
aataactata acgtcctaa ggtagcgacg tacgaaccgt tgggcgcgcc tggggatagc    3480
gatcgctgct ggcgcggtcc gctatgaggt ctctgataga ccacagacgc gtcgacattg    3540
attattgact agttattaat agtaatcaat tacggggtca ttagttcata gcccatatat    3600
ggagttccgc gttacataac ttacggtaaa tggcccgcct ggctgaccgc caacgaccc    3660 ccgcccattg acgtcaataa tgacgtatgt tcccatagta acgccaatag ggactttcca    3720
ttgacgtcaa tgggtggact atttacggta aactgcccac ttggcagtac atcaagtgta    3780
tcatatgcca agtacgcccc ctattgacgt caatgacggt aaatggcccg cctggcatta    3840
tgcccagtac atgaccttat gggactttcc tacttggcag tacatctacg tattagtcat    3900
cgctattacc atgggtcgag gtgagcccca cgttctgctt cactctcccc atctccccc    3960 cctccccacc cccaattttg tatttattta tttttttaatt attttgtgca gcgatggggg    4020 cgggggggg ggggcgcgc gccaggcggg gcggggcggg gcgagggcg gggcggggcg    4080 aggcggagag gtgcggcggc agccaatcag agcggcgcgc tccgaaagtt tccttttatg    4140
gcgaggcggc ggcggcggcg gccctataaa aagcgaagcg cgcggcgggc gggagtcgct    4200
gcgttgcctt cgccccgtgc cccgctccgc gccgcctcgc gccgcccgcc ccggctctga    4260
ctgaccgcgt tactcccaca ggtgagcggg cgggacggcc cttctcctcc gggctgtaat    4320
tagcgcttgg tttaatgacg gctcgttct tttctgtggc tgcgtgaaag ccttaaaggg    4380
ctccgggagg gccctttgtg cggggggag cggctcgggg ggtgcgtgcg tgtgtgtgtg    4440
cgtggggagc gccgcgtgcg gcccgcgctg cccggcggct gtgagcgctg cgggcgcggc    4500
gcggggcttt gtgcgctccg cgtgtgcgcg agggagcgc ggccggggc ggtgccccgc    4560 ggtgcggggg ggctgcgagg ggaacaaagg ctgcgtgcgg ggtgtgtgcg tggggggtg    4620 agcagggggt gtgggcgcgg cggtcgggct gtaaccccc cctgcacccc cctccccgag    4680
ttgctgagca cggcccggct tcgggtgcgg ggctccgtgc gggggcgtggc gcggggctcg    4740 ccgtgccggg cgggggtgg cggcaggtgg gggtgccggg cggggcgggg ccgcctcggg    4800
ccggggaggg ctcgggggag gggcgcgcg gccccggagc gccggcggct gtcgaggcgc    4860
ggcgagccgc agccattgcc ttttatggta atcgtgcgag agggcgcagg gacttccttt    4920
```

```
gtcccaaatc tggcggagcc gaaatctggg aggcgccgcc gcaccccctc tagcgggcgc    4980
gggcgaagcg gtgcggcgcc ggcaggaagg aaatgggcgg ggagggcctt cgtgcgtcgc    5040
cgcgccgccg tccccttctc catctccagc ctcggggctg ccgcaggggg acggctgcct    5100
tcggggggga cggggcaggg cggggttcgg cttctggcgt gtgaccggcg gctctagagc    5160
ctctgctaac catgttcatg ccttcttctt tttcctacag ctcctgggca acgtgctggt    5220
tgttgtgctg tctcatcatt ttggcaaaga attccctgca ggaaattgag cccgcagcct    5280
cccgcttcgc tctctgctcc tctgttcga cagtcagccg catcttcttt gcgtcgcca     5340 gccgagccac atcgctcaga caccg                                         5365
```

<210> SEQ ID NO 29
<211> LENGTH: 5656
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
ctagcgccac catgaatgcc aaggtcgttg tggtgcttgt acttgtgctg actgctctgt      60
gtctgagcga cggaaaacca gtctccctca gctacaggtg cccatgccga ttcttcgaat     120
ctcatgtggc ccgggccaat gtgaagcact tgaaaatcct gaatacaccc aactgcgcgt     180
tgcagatcgt ggcccgcctg aaaaataata taggcaggt atgtatcgat ccaaagctta      240
agtggatcca ggagtatctg gaaaaggctc tcaataaacg tgcaaagcgt gcaccggtga     300
aacagggaag cggagctact aacttcagcc tgctgaagca ggctggagac gtggaggaga     360
accctggacc tatgaatttt ctgctctctt gggtgcactg gtcactggca ctgctgctgt     420
atctgcacca tgcaaaatgg tcccaagcag ctcccatggc agagggaggt ggacagaatc     480
atcatgaggt tgtcaaattt atggatgtct accagcggag ctactgccac ccaattgaga     540
cgttggtaga catttttcag gaatatccaa acgagattga gtacattttc aagcctagct     600
gtgtgccctt gatgcgatgc ggtggctgtt gcaatgatga gggactcgag tgtgtcccca     660
ccgaggaaag caatataacc atgcaaatca tgcgaatcaa accccaccag ggccagcata     720
tcggcgagat gtctttcttg caacataaca atgcgagtgt cggccaaaag aaggacaggg     780
ctcgccagga aaatccctgt ggtccttgtt cagagcgcag gaagcatctt ttcgtccagg     840
atccgcagac ttgtaaatgt tcatgcaaga ataccgattc taggtgtaag gcgaggcaac     900
tcgagcttaa cgagagaacc tgtaggtgtg acaaacctag aagataaatc gattacgctc     960
ctctactctt tgagacatca ctggcctata ataaatgggt taatttatgt aacaaaattg    1020
ccttggcttg ttaactttat tagacattct gatgtttgca ttgtgtaaat actgttgtat    1080
tggaaaagcg tgccaagatg gattattgta attcagtgtc ttttttagta gcgtcacgtg    1140
ccaaacactg ttagtcacag agggcatgag acagcctgtg ctggaacagc tcagttcata    1200
gggctatgga gatggggaga aaggggcgct tctgtcagag acaagctgtg gtctgggaag    1260
gccttagcac taaaagcacc acaatgagaa gcaccgccaa gagcagggc ccgcaggcct     1320 ttgttccagc tgcaaagaga aggaaaaag tggggaataa gagttggggc tgcggagggg     1380
gtggggagca ttgtgcaggt tccgtacttg aacagaaagc agggaccaac acaaggaagg    1440
ctcgagctgg cggaataggt tccaatctgt cgcggccgca ttaccctgtt atccctaatc    1500
```

```
tcgtttaact atgactctct taaggtagcc aaattccgga actataaatt gcgttgcgct    1560
cactgcccgc tttccagtcg ggaaacctgt cgtgccagct gcataaatga atcggccaac    1620
gcgcggggag aggcggtttg cgtattgggc gcgcttccgc ttcctcgctc actgactcgc    1680
tgcgctcggt cgttcggctg cggcgagcgg tatcagctca ctcaaaggcg gtaatacggt    1740
tatccacaga atcaggggat aacgcaggaa agaacatgtg agcaaaaggc cagcaaaagg    1800
ccaggaaccg taaaaaggcc gcgttgctgg cgtttttcca taggctccgc ccccctgacg    1860
agcatcacaa aaatcgacgc tcaagtcaga ggtggcgaaa cccgacagga ctataaagat    1920
accaggcgtt tccccctgga agctccctcg tgcgctctcc tgttccgacc ctgccgctta    1980
ccggatacct gtccgccttt ctcccttcgg gaagcgtggc gctttctcat agctcacgct    2040
gtaggtatct cagttcggtg taggtcgttc gctccaagct gggctgtgtg cacgaacccc    2100
ccgttcagcc cgaccgctgc gccttatccg gtaactatcg tcttgagtcc aacccggtaa    2160
gacacgactt atcgccactg gcagcagcca ctggtaacag gattagcaga gcgaggtatg    2220
taggcggtgc tacagagttc ttgaagtggt ggcctaacta cggctacact agaagaacag    2280
tatttggtat ctgcgctctg ctgaagccag ttaccttcgg aaaaagagtt ggtagctctt    2340
gatccggcaa acaaaccacc gctggtagcg gtggtttttt tgtttgcaag cagcagatta    2400
cgcgcagaaa aaaaggatct caagaagatc ctttgatctt ttctacgggg tctgacgctc    2460
agtggaacga aaactcacgt taagggattt tggtcatgag attatcaaaa aggatcttca    2520
cctagatcct tttaaattaa aaatgaagtt ttaaatcaat ctaaagtata tatgagtaaa    2580
cttggtctga catgcgcatc tgacgctcag tggaacgaaa actcacgtta agggattttg    2640
gtcatgcctc agaagaactc gtcaagaagg cgatagaagg cgatgcgctg cgaatcggga    2700
gcggcgatac cgtaaagcac gaggaagcgg tcagcccatt cgccgccaag ctcttcagca    2760
atatcacggg tagccaacgc tatgtcctga tagcggtccg ccacacccag ccggccacag    2820
tcgatgaatc cagaaaagcg gccatttttcc accatgatat tcggcaagca ggcatcgcca    2880
tgggtcacga cgagatcctc gccgtcgggc atgcgcgcct tgagcctggc gaacagttcg    2940
gctggcgcga gcccctgatg ctcttcgtcc agatcatcct gatcgacaag accggcttcc    3000
atccgagtac gtgctcgctc gatgcgatgt ttcgcttggt ggtcgaatgg gcaggtagcc    3060
ggatcaagcg tatgcagccg ccgcattgca tcagccatga tggatacttt ctcggcagga    3120
gcaaggtgag atgacaggag atcctgcccc ggcacttcgc ccaatagcag ccagtccctt    3180
cccgcttcag tgacaacgtc gagcacagct gcgcaaggaa cgcccgtcgt ggccagccac    3240
gatagccgcg ctgcctcgtc ctgcagttca ttcagggcac cggacaggtc ggtcttgaca    3300
aaaagaaccg ggcgcccctg cgctgacagc cggaacacgg cggcatcaga gcagccgatt    3360
gtctgttgtg cccagtcata gccgaatagc ctctccaccc aagcggccgg agaacctgcg    3420
tgcaatccat cttgttcaat catgcgaaac gatcctcatt catttatcag gttattgtc    3480
tcatgagcgg atacatattt gaatgtattt aggctgagca tctatgtcgg gtgcggagaa    3540
agaggtaatg aaatggcagg cgccttttc gttagatatg tagtaagtat cttaatatac    3600
agctttatct gttttttaag atacttacta cttttcttag tggaaactat tagtggctgt    3660
taattaagct agtactaccc aagatttgac agaatgcatc gtttgcattc gaataactat    3720
aacggtccta aggtagcgac gtacgaaccg ttgggcgcgc tgggggatag cgatcgctgc    3780
tggcgcggtc cgctatgagg tctctgatag accacagacg cgtcgacatt gattattgac    3840
tagttattaa tagtaatcaa ttacggggtc attagttcat agcccatata tggagttccg    3900
```

```
cgttacataa cttacggtaa atggcccgcc tggctgaccg cccaacgacc cccgcccatt    3960
gacgtcaata atgacgtatg ttcccatagt aacgccaata gggactttcc attgacgtca    4020
atgggtggac tatttacggt aaactgccca cttggcagta catcaagtgt atcatatgcc    4080
aagtacgccc cctattgacg tcaatgacgg taaatggccc gcctggcatt atgcccagta    4140
catgacctta tgggactttc ctacttggca gtacatctac gtattagtca tcgctattac    4200
catgggtcga ggtgagcccc acgttctgct tcactctccc catctccccc cctccccac     4260 ccccaatttt gtatttattt attttttaat tattttgtgc agcgatgggg gcggggggg     4320 gggggcgcg cgccaggcgg ggcggggcgg ggcgagggc ggggcgggc gaggcggaga       4380 ggtgcggcgg cagccaatca gagcggcgcg ctccgaaagt ttcctttat ggcgaggcgg     4440 cggcggcggc ggcctataa aaagcgaagc gcgcggcggg cggagtcgc tgcgttgcct     4500 tcgcccgtg ccccgctccg cgccgcctcg cgccgcccgc cccggctctg actgaccgcg    4560
ttactcccac aggtgagcgg gcgggacggc ccttctcctc cgggctgtaa ttagcgcttg    4620
gtttaatgac ggctcgtttc ttttctgtgg ctgcgtgaaa gccttaaagg gctccgggag    4680 ggcccttgt gcggggggga gcggctcggg gggtgcgtgc gtgtgtgtgt gcgtggggag    4740
cgccgcgtgc ggcccgcgct gcccggcggc tgtgagcgct gcgggcgcgg cgcggggctt   4800
tgtgcgctcc gcgtgtgcgc gaggggagcg cggccggggg cggtgcccg cggtgcgggg    4860 gggctgcgag gggaacaaag gctgcgtgcg gggtgtgtgc gtgggggggt gagcagggg    4920 tgtgggcgcg gcgtcgggc tgtaaccccc ccctgcaccc ccctccccga gttgctgagc   4980
acggcccggc ttcgggtgcg gggctccgtg cggggcgtgg cgcggggctc gccgtgccgg   5040 gcgggggtg gcggcaggtg ggggtgccgg gcggggcggg gccgcctcgg gccggggagg   5100
gctcggggga ggggcgcggc ggccccggag cgccggcggc tgtcgaggcg cggcgagccg   5160
cagccattgc cttttatggt aatcgtgcga gagggcgcag ggacttcctt tgtcccaaat   5220
ctggcggagc cgaaatctgg gaggcgccgc cgcaccccct ctagcgggcg cgggcgaagc   5280
ggtgcggcgc cggcaggaag gaaatgggcg gggagggcct tcgtgcgtcg ccgcgccgcc   5340
gtccccttct ccatctccag cctcggggct gccgcagggg gacggctgcc ttcggggggg   5400
acggggcagg gcggggttcg gcttctggcg tgtgaccggc ggctctagag cctctgctaa   5460
ccatgttcat gccttcttct ttttcctaca gctcctgggc aacgtgctgg ttgttgtgct   5520
gtctcatcat tttggcaaag aattccctgc aggaaattga gcccgcagcc tcccgcttcg   5580
ctctctgctc ctcctgttcg acagtcagcc gcatcttctt ttgcgtcgcc agccgagcca   5640
catcgctcag acaccg                                                   5656
```

<210> SEQ ID NO 30
<211> LENGTH: 5656
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
taactataac ggtcctaagg tagcgacgta cgaaccgttg ggcgcgcctg gggatagcga      60
tcgctgctgg cgcggtccgc tatgaggtct ctgatagacc acagacgcgt cgacattgat     120
tattgactag ttattaatag taatcaatta cggggtcatt agttcatagc ccatatatgg     180
```

```
agttccgcgt tacataactt acggtaaatg gcccgcctgg ctgaccgccc aacgaccccc      240
gcccattgac gtcaataatg acgtatgttc ccatagtaac gccaataggg actttccatt      300
gacgtcaatg ggtggactat ttacggtaaa ctgcccactt ggcagtacat caagtgtatc      360
atatgccaag tacgccccct attgacgtca atgacggtaa atggcccgcc tggcattatg      420
cccagtacat gaccttatgg gactttccta cttggcagta catctacgta ttagtcatcg      480
ctattaccat gggtcgaggt gagccccacg ttctgcttca ctctccccat ctcccccccc      540
tccccacccc caattttgta tttatttatt ttttaattat tttgtgcagc gatggggcg       600 gggggggggg gggcgcgcgc caggcggggc ggggcgggc gaggcgggg gcgggcgag         660 gcggagaggt gcggcggcag ccaatcagag cggcgcgctc cgaaagtttc cttttatggc      720
gaggcggcgg cggcggcggc cctataaaaa gcgaagcgcg cggcgggcgg gagtcgctgc      780
gttgccttcg ccccgtgccc cgctccgcgc cgcctcgcgc cgcccgcccc ggctctgact      840
gaccgcgtta ctcccacagg tgagcgggcg gacggccct tctcctccgg gctgtaatta      900
gcgcttggtt taatgacggc tcgtttcttt tctgtggctg cgtgaaagcc ttaaagggct     960
ccgggagggc cctttgtgcg ggggggagcg gctcgggggg tgcgtgcgtg tgtgtgtgcg     1020
tggggagcgc cgcgtgcggc ccgcgctgcc cggcggctgt gagcgctgcg ggcgcggcgc     1080
ggggctttgt gcgctccgcg tgtgcgcgag gggagcgcgg ccgggggcgg tgccccgcgg     1140
tgcggggggg ctgcgagggg aacaaaggct gcgtgcgggg tgtgtgcgtg ggggggtgag     1200 caggggtgt gggcgcggcg gtcgggctgt aaccccccc tgcacccccc tccccgagtt      1260
gctgagcacg gccggcttc gggtgcgggg ctccgtgcgg ggcgtggcgc ggggctcgcc      1320
gtgccgggcg ggggtggcg gcaggtgggg gtgccgggcg gggcggggcc gcctcgggcc      1380
ggggagggct cggggaggg gcgcggcggc cccggagcgc cggcggctgt cgaggcgcgg     1440
cgagccgcag ccattgcctt ttatggtaat cgtgcgagag ggcgcaggga cttcctttgt     1500
cccaaatctg gcgagccga aatctgggag gcgccgccgc accccctcta gcgggcgcgg     1560
gcgaagcggt gcggcgccgg caggaaggaa atgggcgggg agggccttcg tgcgtcgccg     1620
cgccgccgtc cccttctcca tctccagcct cggggctgcc gcaggggac ggctgccttc      1680 ggggggacg gggcagggcg gggttcggct tctggcgtgt gaccggcggc tctagagcct     1740
ctgctaacca tgttcatgcc ttcttctttt tcctacagct cctgggcaac gtgctggttg     1800
ttgtgctgtc tcatcatttt ggcaaagaat tccctgcagg aaattgagcc cgcagcctcc     1860
cgcttcgctc tctgctcctc ctgttcgaca gtcagccgca tcttcttttg cgtcgccagc     1920
cgagccacat cgctcagaca ccgctagcgc caccatgaat tttctgctct cttgggtgca      1980
ctggtcactg gcactgctgc tgtatctgca ccatgcaaaa tggtcccaag cagctcccat     2040
ggcagaggga ggtggacaga atcatcatga ggttgtcaaa tttatggatg tctaccagcg     2100
gagctactgc cacccaattg agacgttggt agacattttt caggaatatc agacgagat      2160 tgagtacatt ttcaagccta gctgtgtgcc cttgatgcga tgcggtggct gttgcaatga     2220
tgagggactc gagtgtgtcc ccaccgagga aagcaatata accatgcaaa tcatgcgaat     2280
caaaccccac cagggccagc atatcggcga gatgtctttc ttgcaacata caaatgcga      2340 gtgtcggcca aagaaggaca gggctcgcca ggaaaatccc tgtggtcctt gttcagagcg     2400
caggaagcat cttttcgtcc aggatccgca gacttgtaaa tgttcatgca agaataccga     2460
ttctaggtgt aaggcgaggc aactcgagct taacgagaga acctgtaggt gtgacaaacc     2520
tagaagacgt gcaaagcgtg caccggtgaa acagggaagc ggagctacta acttcagcct     2580
```

```
gctgaagcag gctggagacg tggaggagaa ccctggacct atgaatgcca aggtcgttgt   2640
ggtgcttgta cttgtgctga ctgctctgtg tctgagcgac ggaaaaccag tctccctcag   2700
ctacaggtgc ccatgccgat tcttcgaatc tcatgtggcc cgggccaatg tgaagcactt   2760
gaaaatcctg aatacaccca actgcgcgtt gcagatcgtg gcccgcctga aaataataa    2820 taggcaggta tgtatcgatc caaagcttaa gtggatccag gagtatctgg aaaaggctct   2880
caataaataa atcgattacg ctcctctact ctttgagaca tcactggcct ataataaatg   2940
ggttaattta tgtaacaaaa ttgccttggc ttgttaactt tattagacat tctgatgttt   3000
gcattgtgta aatactgttg tattggaaaa gcgtgccaag atggattatt gtaattcagt   3060 gtcttttta gtagcgtcac gtgccaaaca ctgttagtca cagagggcat gagacagcct    3120
gtgctggaac agctcagttc atagggctat ggagatgggg agaaaggggc gcttctgtca   3180
gagacaagct gtggtctggg aaggccttag cactaaaagc accacaatga gaagcaaccg   3240
ccagaagcag ggcccgcagg cctttgttcc agctgcaaag agaaaggaaa aagtggggaa   3300
taagagttgg ggctgcggag ggggtgggga gcattgtgca ggttccgtac ttgaacagaa   3360
agcagggacc aacacaagga aggctcgagc tggcggaata ggttccaatc tgtcgcggcc   3420
gcattaccct gttatcccta atctcgttta actatgactc tcttaaggta gccaaattcc   3480
ggaactataa attgcgttgc gctcactgcc cgctttccag tcgggaaacc tgtcgtgcca   3540
gctgcataaa tgaatcggcc aacgcgcggg gagaggcggt ttgcgtattg ggcgcgcttc   3600
cgcttcctcg ctcactgact cgctgcgctc ggtcgttcgg ctgcggcgag cggtatcagc   3660
tcactcaaag gcggtaatac ggttatccac agaatcaggg gataacgcag gaaagaacat   3720
gtgagcaaaa ggccagcaaa aggccaggaa ccgtaaaaag gccgcgttgc tggcgttttt   3780
ccataggctc cgcccccctg acgagcatca caaaaatcga cgctcaagtc agaggtggcg   3840
aaacccgaca ggactataaa gataccaggc gtttccccct ggaagctccc tcgtgcgctc   3900
tcctgttccg accctgccgc ttaccggata cctgtccgcc tttctccctt cgggaagcgt   3960
ggcgctttct catagctcac gctgtaggta tctcagttcg gtgtaggtcg ttcgctccaa   4020
gctgggctgt gtgcacgaac cccccgttca gcccgaccgc tgcgccttat ccggtaacta   4080
tcgtcttgag tccaacccgg taagacacga cttatcgcca ctggcagcag ccactggtaa   4140
caggattagc agagcgaggt atgtaggcgg tgctacagag ttcttgaagt ggtggcctaa   4200
ctacggctac actagaagaa cagtatttgg tatctgcgct ctgctgaagc cagttacctt   4260
cggaaaaaga gttggtagct cttgatccgg caaacaaacc accgctggta gcggtggttt   4320
ttttgtttgc aagcagcaga ttacgcgcag aaaaaaagga tctcaagaag atcctttgat   4380
cttttctacg gggtctgacg ctcagtggaa cgaaaactca cgttaaggga ttttggtcat   4440
gagattatca aaaaggatct tcacctagat ccttttaaat taaaaatgaa gttttaaatc   4500
aatctaaagt atatatgagt aaacttggtc tgacatgcgc atctgacgct cagtggaacg   4560
aaaactcacg ttaagggatt tggtcatgc ctcagaagaa ctcgtcaaga aggcgataga    4620
aggcgatgcg ctgcgaatcg ggagcggcga taccgtaaag cacgaggaag cggtcagccc   4680
attcgccgcc aagctcttca gcaatatcac gggtagccaa cgctatgtcc tgatagcggt   4740
ccgccacacc cagccggcca cagtcgatga atccagaaaa gcggccattt ccaccatga    4800 tattcggcaa gcaggcatcg ccatgggtca cgacgagatc ctcgccgtcg gcatgcgcg    4860 ccttgagcct ggcgaacagt tcggctggcg cgagcccctg atgctcttcg tccagatcat   4920
```

```
cctgatcgac aagaccggct tccatccgag tacgtgctcg ctcgatgcga tgtttcgctt    4980
ggtggtcgaa tgggcaggta gccggatcaa gcgtatgcag ccgccgcatt gcatcagcca    5040
tgatggatac tttctcggca ggagcaaggt gagatgacag gagatcctgc cccggcactt    5100
cgcccaatag cagccagtcc cttcccgctt cagtgacaac gtcgagcaca gctgcgcaag    5160
gaacgcccgt cgtggccagc cacgatagcc gcgctgcctc gtcctgcagt tcattcaggg    5220
caccggacag gtcggtcttg acaaaaagaa ccgggcgccc ctgcgctgac agccggaaca    5280
cggcggcatc agagcagccg attgtctgtt gtgcccagtc atagccgaat agcctctcca    5340
cccaagcggc cggagaacct gcgtgcaatc catcttgttc aatcatgcga aacgatcctc    5400
attcatttat cagggttatt gtctcatgag cggatacata tttgaatgta tttaggctga    5460
gcatctatgt cgggtgcgga gaaagaggta atgaaatggc aggcgccttt ttcgttagat    5520
atgtagtaag tatcttaata tacagcttta tctgtttttt aagatactta ctacttttct    5580
tagtggaaac tattagtggc tgttaattaa gctagtacta cccaagattt gacagaatgc    5640
atcgtttgca ttcgaa                                                   5656
```

<210> SEQ ID NO 31
<211> LENGTH: 5671
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

```
ctagcgccac catgaatttt ctgctctctt gggtgcactg gtcactggca ctgctgctgt      60
atctgcacca tgcaaaatgg tcccaagcag ctcccatggc agagggaggt ggacagaatc     120
atcatgaggt tgtcaaattt atggatgtct accagcggag ctactgccac ccaattgaga     180
cgttggtaga cattttcag gaatatccag acgagattga gtacattttc aagcctagct     240
gtgtgccctt gatgcgatgc ggtggctgtt gcaatgatga gggactcgag tgtgtcccca     300
ccgaggaaag caatataacc atgcaaatca tgcgaatcaa accccaccag ggccagcata     360
tcggcgagat gtcttcttg caacataaca aatgcgagtg tcggccaaag aaggacaggg     420
ctcgccagga aaatccctgt ggtccttgtt cagagcgcag gaagcatctt ttcgtccagg     480
atccgcagac ttgtaaatgt tcatgcaaga ataccgattc taggtgtaag gcgaggcaac     540
tcgagcttaa cgagagaacc tgtaggtgtg acaaacctag aagacgtgca aagcgtgcac     600
cggtgaaaca gggaagcgga gctactaact tcagcctgct gaagcaggct ggagacgtgg     660
aggagaaccc tggacctatg ggcagcgaac tggaaccgc catggagact ttgataaatg     720
ttttccacgc gcatagcggc aaagaagggg acaagtacaa gctgtcaaaa aaggagctga     780
aagaactgct gcagaccgaa ttgagcggct tcctggacgc tcagaaagat gtcgatgccg     840
tcgacaaagt gatgaaagag cttgacgaga acggtgacgg tgaagtcgat tttcaggaat     900
atgtggtgct ggtggccgcc cttactgtag catgcaacaa tttcttttgg gaaaattcat     960
aaatcgatta cgctcctcta ctctttgaga catcactggc ctataataaa tgggttaatt    1020
tatgtaacaa aattgccttg gcttgttaac tttattagac attctgatgt ttgcattgtg    1080
taaatactgt tgtattggaa aagcgtgcca agatggatta ttgtaattca gtgtctttt    1140 tagtagcgtc acgtgccaaa cactgttagt cacagagggc atgagacagc ctgtgctgga    1200
acagctcagt tcataggggct atggagatgg ggagaaaggg gcgcttctgt cagagacaag    1260
```

```
ctgtggtctg ggaaggcctt agcactaaaa gcaccacaat gagaagcaac cgccagaagc   1320
agggcccgca ggcctttgtt ccagctgcaa agagaaagga aaaagtgggg aataagagtt   1380
ggggctgcgg aggggtggg gagcattgtg caggttccgt acttgaacag aaagcaggga   1440
ccaacacaag gaaggctcga gctggcgaaa taggttccaa tctgtcgcgg ccgcattacc   1500
ctgttatccc taatctcgtt taactatgac tctcttaagg tagccaaatt ccggaactat   1560
aaattgcgtt gcgctcactg cccgctttcc agtcggaaaa cctgtcgtgc cagctgcata   1620
aatgaatcgg ccaacgcgcg gggagaggcg gtttgcgtat tgggcgcgct ccgcttcct    1680 cgctcactga ctcgctgcgc tcggtcgttc ggctgcggcg agcggtatca gctcactcaa   1740
aggcggtaat acggttatcc acagaatcag gggataacgc aggaaagaac atgtgagcaa   1800
aaggccagca aaaggccagg aaccgtaaaa aggccgcgtt gctggcgttt ttccataggc   1860 tccgccccc tgacgagcat cacaaaaatc gacgctcaag tcagaggtgg cgaaacccga    1920
caggactata aagataccag gcgtttcccc ctggaagctc cctcgtgcgc tctcctgttc   1980
cgaccctgcc gcttaccgga tacctgtccg cctttctccc ttcgggaagc gtggcgcttt   2040
ctcatagctc acgctgtagg tatctcagtt cggtgtaggt cgttcgctcc aagctgggct   2100
gtgtgcacga acccccgtt cagcccgacc gctgcgcctt atccggtaac tatcgtcttg    2160
agtccaaccc ggtaagacac gacttatcgc cactggcagc agccactggt aacaggatta   2220
gcagagcgag gtatgtaggc ggtgctacag agttcttgaa gtggtggcct aactacggct   2280
acactagaag aacagtattt ggtatctgcg ctctgctgaa gccagttacc ttcggaaaaa   2340
gagttggtag ctcttgatcc ggcaaacaaa ccaccgctgg tagcggtggt ttttttgttt   2400
gcaagcagca gattacgcgc agaaaaaaag gatctcaaga agatcctttg atcttttcta   2460
cggggtctga cgctcagtgg aacgaaaact cacgttaagg gattttggtc atgagattat   2520
caaaaaggat cttcacctag atccttttaa attaaaaatg aagttttaaa tcaatctaaa   2580
gtatatatga gtaaacttgg tctgacatgc gcatctgacg ctcagtggaa cgaaaactca   2640
cgttaaggga ttttggtcat gcctcagaag aactcgtcaa gaaggcgata gaaggcgatg   2700
cgctgcgaat cgggagcggc gataccgtaa agcacgagga gcggtcagc ccattcgccg    2760 ccaagctctt cagcaatatc acgggtagcc aacgctatgt cctgatagcg gtccgccaca   2820
cccagccggc cacagtcgat gaatccagaa aagcggccat tttccaccat gatattcggc   2880
aagcaggcat cgccatgggt cacgacgaga tcctcgccgt cgggcatgcg cgccttgagc   2940
ctggcgaaca gttcggctgg cgcgagcccc tgatgctctt cgtccagatc atcctgatcg   3000
acaagaccgg cttccatccg agtacgtgct cgctcgatgc gatgtttcgc ttggtggtcg   3060
aatgggcagg tagccggatc aagcgtatgc agccgccgca ttgcatcagc catgatggat   3120
actttctcgg caggagcaag gtgagatgac aggagatcct gccccggcac ttcgcccaat   3180
agcagccagt cccttcccgc ttcagtgaca acgtcgagca cagctgcgca aggaacgccc   3240
gtcgtggcca gccacgatag ccgcgctgcc tcgtcctgca gttcattcag ggcaccggac   3300
aggtcggtct tgacaaaaag aaccgggcgc ccctgcgctg acagccggaa cacggcggca   3360
tcagagcagc cgattgtctg ttgtgcccag tcatagccga atagcctctc cacccaagcg   3420
gccggagaac ctgcgtgcaa tccatcttgt tcaatcatgc gaaacgatcc tcattcattt   3480
atcagggtta ttgtctcatg agcggataca tatttgaatg tatttaggct gagcatctat   3540
gtcgggtgcg gagaaagagg taatgaaatg gcaggcgcct ttttcgttag atatgtagta   3600
```

| | |
|---|---|
| agtatcttaa tatacagctt tatctgtttt ttaagatact tactactttt cttagtggaa | 3660 |
| actattagtg gctgttaatt aagctagtac tacccaagat ttgacagaat gcatcgtttg | 3720 |
| cattcgaata actataacgg tcctaaggta gcgacgtacg aaccgttggg cgcgcctggg | 3780 |
| gatagcgatc gctgctggcg cggtccgcta tgaggtctct gatagaccac agacgcgtcg | 3840 |
| acattgatta ttgactagtt attaatagta atcaattacg gggtcattag ttcatagccc | 3900 |
| atatatggag ttccgcgtta cataacttac ggtaaatggc ccgcctggct gaccgcccaa | 3960 |
| cgaccccgc ccattgacgt caataatgac gtatgttccc atagtaacgc caatagggac | 4020 |
| tttccattga cgtcaatggg tggactattt acggtaaact gcccacttgg cagtacatca | 4080 |
| agtgtatcat atgccaagta cgccccctat tgacgtcaat gacggtaaat ggcccgcctg | 4140 |
| gcattatgcc cagtacatga ccttatggga ctttcctact tggcagtaca tctacgtatt | 4200 |
| agtcatcgct attaccatgg gtcgaggtga gccccacgtt ctgcttcact ctccccatct | 4260 |
| cccccccctc cccaccccca attttgtatt tatttatttt ttaattattt tgtgcagcga | 4320 |
| tgggggcggg ggggggggg gcgcgcgcca ggcggggcgg ggcggggcga ggggcggggc | 4380 |
| ggggcgaggc ggagaggtgc ggcggcagcc aatcagagcg gcgcgctccg aaagtttcct | 4440 |
| tttatggcga ggcggcggcg gcggcggccc tataaaaagc gaagcgcgcg gcgggcggga | 4500 |
| gtcgctgcgt tgccttcgcc ccgtgccccg ctccgcgccg cctcgcgccg cccgccccgg | 4560 |
| ctctgactga ccgcgttact cccacaggtg agcgggcggg acggcccttc tcctccgggc | 4620 |
| tgtaattagc gcttggttta atgacggctc gtttcttttc tgtggctgcg tgaaagcctt | 4680 |
| aaagggctcc gggagggccc tttgtgcggg gggagcggc tcgggggtg cgtgcgtgtg | 4740 |
| tgtgtgcgtg gggagcgccg cgtgcggccc gcgctgcccg gcggctgtga gcgctgcggg | 4800 |
| cgcggcgcgg ggctttgtgc gctccgcgtg tgcgcgaggg gagcgcggcc ggggcggtg | 4860 |
| ccccgcggtg cggggggct gcgagggaa caaaggctgc gtgcggggtg tgtgcgtggg | 4920 |
| ggggtgagca ggggtgtgg gcgcggcggt cgggctgtaa cccccccctg caccccctc | 4980 |
| cccgagttgc tgagcacggc ccggcttcgg gtgcggggct ccgtgcgggg cgtggcgcgg | 5040 |
| ggctcgccgt gccgggcggg gggtggcggc aggtgggggt gccgggcggg gcggggccgc | 5100 |
| ctcgggccgg ggagggctcg ggggaggggc gcggcggccc cggagcgccg gcggctgtcg | 5160 |
| aggcgcggcg agccgcagcc attgcctttt atggtaatcg tgcgagaggg cgcagggact | 5220 |
| tcctttgtcc caaatctggc ggagccgaaa tctgggaggc gccgccgcac cccctctagc | 5280 |
| gggcgcgggc gaagcggtgc ggcgccggca ggaaggaaat gggcggggag ggccttcgtg | 5340 |
| cgtcgccgcg ccgccgtccc cttctccatc tccagcctcg gggctgccgc aggggacgg | 5400 |
| ctgccttcgg gggggacggg gcagggcggg gttcggcttc tggcgtgtga ccggcggctc | 5460 |
| tagagcctct gctaaccatg ttcatgcctt cttctttttc ctacagctcc tgggcaacgt | 5520 |
| gctggttgtt gtgctgtctc atcatttttgg caaagaattc cctgcaggaa attgagcccg | 5580 |
| cagcctcccg cttcgctctc tgctcctcct gttcgacagt cagccgcatc ttcttttgcg | 5640 |
| tcgccagccg agccacatcg ctcagacacc g | 5671 |

<210> SEQ ID NO 32
<211> LENGTH: 4
<212> TYPE: PRT
<213> ORGANISM: Unknown
<220> FEATURE:
<221> NAME/KEY: source
<223> OTHER INFORMATION: /note="Description of Unknown:
    Furinlink1 linker"

<400> SEQUENCE: 32

Arg Ala Lys Arg
1

<210> SEQ ID NO 33
<211> LENGTH: 12
<212> TYPE: DNA
<213> ORGANISM: Unknown
<220> FEATURE:
<221> NAME/KEY: source
<223> OTHER INFORMATION: /note="Description of Unknown:
      Furinlink1 linker"

<400> SEQUENCE: 33
cgtgcaaagc gt                                                             12

<210> SEQ ID NO 34
<211> LENGTH: 28
<212> TYPE: PRT
<213> ORGANISM: Unknown
<220> FEATURE:
<221> NAME/KEY: source
<223> OTHER INFORMATION: /note="Description of Unknown:
      fmdv linker"

<400> SEQUENCE: 34

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 35
<211> LENGTH: 84
<212> TYPE: DNA
<213> ORGANISM: Unknown
<220> FEATURE:
<221> NAME/KEY: source
<223> OTHER INFORMATION: /note="Description of Unknown:
fmdv linker"

<400> SEQUENCE: 35
agagccaaga gggcaccggt gaaacagact ttgaattttg accttctgaa gttggcagga 60
gacgttgagt ccaaccctgg gccc 84

<210> SEQ ID NO 36
<211> LENGTH: 19
<212> TYPE: PRT
<213> ORGANISM: Unknown
<220> FEATURE:
<221> NAME/KEY: source
<223> OTHER INFORMATION: /note="Description of Unknown:
p2a linker"

<400> SEQUENCE: 36

Ala Thr Asn Phe Ser Leu Leu Lys Gln Ala Gly Asp Val Glu Glu Asn
1 5 10 15

Pro Gly Pro

<210> SEQ ID NO 37
<211> LENGTH: 57
<212> TYPE: DNA
<213> ORGANISM: Unknown
<220> FEATURE:
<221> NAME/KEY: source
<223> OTHER INFORMATION: /note="Description of Unknown:

p2a linker"

<400> SEQUENCE: 37
gctactaact tcagcctgct gaagcaggct ggagacgtgg aggagaaccc tggacct        57

<210> SEQ ID NO 38
<211> LENGTH: 22
<212> TYPE: PRT
<213> ORGANISM: Unknown
<220> FEATURE:
<221> NAME/KEY: source
<223> OTHER INFORMATION: /note="Description of Unknown:
      GSG-p2a linker"

<400> SEQUENCE: 38

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 39
<211> LENGTH: 66
<212> TYPE: DNA
<213> ORGANISM: Unknown
<220> FEATURE:
<221> NAME/KEY: source
<223> OTHER INFORMATION: /note="Description of Unknown:
      GSG-p2a linker"

<400> SEQUENCE: 39
ggaagcggag ctactaactt cagcctgctg aagcaggctg agacgtgga ggagaaccct      60 ggacct                                                               66

<210> SEQ ID NO 40
<211> LENGTH: 31
<212> TYPE: PRT
<213> ORGANISM: Unknown
<220> FEATURE:
<221> NAME/KEY: source
<223> OTHER INFORMATION: /note="Description of Unknown:
      fp2a linker"

<400> SEQUENCE: 40

Arg Ala Lys Arg Ala Pro Val Lys Gln Gly Ser Gly Ala Thr Asn Phe
1               5                   10                  15

Ser Leu Leu Lys Gln Ala Gly Asp Val Glu Glu Asn Pro Gly Pro
            20                  25                  30

<210> SEQ ID NO 41
<211> LENGTH: 93
<212> TYPE: DNA
<213> ORGANISM: Unknown
<220> FEATURE:
<221> NAME/KEY: source
<223> OTHER INFORMATION: /note="Description of Unknown:
      fp2a linker"

<400> SEQUENCE: 41
cgtgcaaagc gtgcaccggt gaaacaggga agcggagcta ctaacttcag cctgctgaag    60
caggctggag acgtggagga gaaccctgga cct                                 93

<210> SEQ ID NO 42
<211> LENGTH: 5
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 42

Ala Pro Val Lys Gln
1               5

<210> SEQ ID NO 43
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Pro Val Lys Gln
1               5

<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Val Pro Val Lys Gln
1               5

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ile Pro Val Lys Gln
1               5

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Met Pro Val Lys Gln
1               5

<210> SEQ ID NO 47
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 47

Ala Pro Ile Lys Gln
1               5

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Pro Ile Lys Gln
1               5

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Val Pro Ile Lys Gln
1               5

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ile Pro Ile Lys Gln
1               5

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Met Pro Ile Lys Gln
1               5

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Pro Ala Lys Gln
```

```
1               5
```

```
<210> SEQ ID NO 53
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Pro Ala Lys Gln
1               5

<210> SEQ ID NO 54
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Val Pro Ala Lys Gln
1               5

<210> SEQ ID NO 55
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ile Pro Ala Lys Gln
1               5

<210> SEQ ID NO 56
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Met Pro Ala Lys Gln
1               5

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ala Pro Val Arg Gln
1               5

<210> SEQ ID NO 58
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Pro Val Arg Gln
1               5

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Val Pro Val Arg Gln
1               5

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ile Pro Val Arg Gln
1               5

<210> SEQ ID NO 61
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Met Pro Val Arg Gln
1               5

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Pro Ile Arg Gln
1               5

<210> SEQ ID NO 63
<211> LENGTH: 5
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 63

Gly Pro Ile Arg Gln
1               5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Val Pro Ile Arg Gln
1               5

<210> SEQ ID NO 65
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ile Pro Ile Arg Gln
1               5

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Met Pro Ile Arg Gln
1               5

<210> SEQ ID NO 67
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Pro Ala Arg Gln
1               5

<210> SEQ ID NO 68
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 68

Gly Pro Ala Arg Gln
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Val Pro Ala Arg Gln
1               5

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ile Pro Ala Arg Gln
1               5

<210> SEQ ID NO 71
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Met Pro Ala Arg Gln
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ala Pro Val Lys Asn
1               5

<210> SEQ ID NO 73
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Pro Val Lys Asn
1               5
```

```
<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Val Pro Val Lys Asn
1               5

<210> SEQ ID NO 75
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ile Pro Val Lys Asn
1               5

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Met Pro Val Lys Asn
1               5

<210> SEQ ID NO 77
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ala Pro Ile Lys Asn
1               5

<210> SEQ ID NO 78
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Pro Ile Lys Asn
1               5

<210> SEQ ID NO 79
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Val Pro Ile Lys Asn
1               5

<210> SEQ ID NO 80
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Ile Pro Ile Lys Asn
1               5

<210> SEQ ID NO 81
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Met Pro Ile Lys Asn
1               5

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Ala Pro Ala Lys Asn
1               5

<210> SEQ ID NO 83
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gly Pro Ala Lys Asn
1               5

<210> SEQ ID NO 84
<211> LENGTH: 5
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 84

Val Pro Ala Lys Asn
1               5

<210> SEQ ID NO 85
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Ile Pro Ala Lys Asn
1               5

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Met Pro Ala Lys Asn
1               5

<210> SEQ ID NO 87
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ala Pro Val Arg Asn
1               5

<210> SEQ ID NO 88
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Pro Val Arg Asn
1               5

<210> SEQ ID NO 89
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

```
Val Pro Val Arg Asn
1               5

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ile Pro Val Arg Asn
1               5

<210> SEQ ID NO 91
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Met Pro Val Arg Asn
1               5

<210> SEQ ID NO 92
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ala Pro Ile Arg Asn
1               5

<210> SEQ ID NO 93
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Pro Ile Arg Asn
1               5

<210> SEQ ID NO 94
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Val Pro Ile Arg Asn
1               5
```

```
<210> SEQ ID NO 95
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ile Pro Ile Arg Asn
1               5

<210> SEQ ID NO 96
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Met Pro Ile Arg Asn
1               5

<210> SEQ ID NO 97
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ala Pro Ala Arg Asn
1               5

<210> SEQ ID NO 98
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Pro Ala Arg Asn
1               5

<210> SEQ ID NO 99
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Val Pro Ala Arg Asn
1               5

<210> SEQ ID NO 100
<211> LENGTH: 5
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Ile Pro Ala Arg Asn
1               5

<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Met Pro Ala Arg Asn
1               5

<210> SEQ ID NO 102
<211> LENGTH: 89
<212> TYPE: PRT
<213> ORGANISM: Homo sapiens

<400> SEQUENCE: 102

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 103
<211> LENGTH: 267
<212> TYPE: DNA
<213> ORGANISM: Homo sapiens

<400> SEQUENCE: 103
atgaatgcca aggtcgttgt ggtgcttgta cttgtgctga ctgctctgtg tctgagcgac    60
ggaaaaccag tctccctcag ctacaggtgc ccatgccgat tcttcgaatc tcatgtggcc   120
cgggccaatg tgaagcactt gaaaatcctg aatacaccca actgcgcgtt gcagatcgtg   180
gcccgcctga aaataataa taggcaggta tgtatagatc caaagcttaa gtggatccag   240
gagtatctgg aaaaggctct caataaa                                       267

<210> SEQ ID NO 104
<211> LENGTH: 94
<212> TYPE: PRT
<213> ORGANISM: Homo sapiens

<400> SEQUENCE: 104

Met Gly Ser Glu Leu Glu Thr Ala Met Glu Thr Leu Ile Asn Val Phe
```

```
                1               5                    10                   15
His Ala His Ser Gly Lys Glu Gly Asp Lys Tyr Lys Leu Ser Lys Lys
                    20                   25                   30

Glu Leu Lys Glu Leu Leu Gln Thr Glu Leu Ser Gly Phe Leu Asp Ala
                    35                   40                   45

Gln Lys Asp Val Asp Ala Val Asp Lys Val Met Lys Glu Leu Asp Glu
            50                   55                   60

Asn Gly Asp Gly Glu Val Asp Phe Gln Glu Tyr Val Val Leu Val Ala
65                   70                   75                   80

Ala Leu Thr Val Ala Cys Asn Asn Phe Phe Trp Glu Asn Ser
                    85                   90

<210> SEQ ID NO 105
<211> LENGTH: 282
<212> TYPE: DNA
<213> ORGANISM: Homo sapiens

<400> SEQUENCE: 105
atgggcagcg aactggaaac cgccatggag actttgataa atgttttcca cgcgcatagc      60
ggcaaagaag gggacaagta caagctgtca aaaaaggagc tgaaagaact gctgcagacc     120
gaattgagcg gcttcctgga cgctcagaaa gatgtcgatg ccgtcgacaa agtgatgaaa     180
gagcttgacg agaacggtga cggtgaagtc gatttcagg  aatatgtggt gctggtggcc     240
gcccttactg tagcatgcaa caatttcttt tgggaaaatt ca                        282

<210> SEQ ID NO 106
<211> LENGTH: 191
<212> TYPE: PRT
<213> ORGANISM: Homo sapiens

<400> SEQUENCE: 106

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                    20                  25                  30

Gly Gly Gln Asn His His Glu Val Val Lys Phe Met Asp Val Tyr Gln
                    35                  40                  45

Arg Ser Tyr Cys His Pro Ile Glu Thr Leu Val Asp Ile Phe Gln Glu
            50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                    85                  90                  95

Thr Glu Glu Ser Asn Ile Thr Met Gln Ile Met Arg Ile Lys Pro His
                    100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                    165                 170                 175

Leu Glu Leu Asn Glu Arg Thr Cys Arg Cys Asp Lys Pro Arg Arg
                    180                 185                 190
```

<210> SEQ ID NO 107
<211> LENGTH: 573
<212> TYPE: DNA
<213> ORGANISM: Homo sapiens

<400> SEQUENCE: 107

| | | | | | | |
|---|---|---|---|---|---|---|
| atgaattttc | tgctctcttg | ggtgcactgg | tcactggcac | tgctgctgta | tctgcaccat | 60 |
| gcaaaatggt | cccaagcagc | tcccatggca | gagggaggtg | acagaatca | tcatgaggtt | 120 |
| gtcaaattta | tggatgtcta | ccagcggagc | tactgccacc | caattgagac | gttggtagac | 180 |
| attttcagg | aatatccaga | cgagattgag | tacattttca | agcctagctg | tgtgcccttg | 240 |
| atgcgatgcg | gtggctgttg | caatgatgag | ggactcgagt | gtgtccccac | cgaggaaagc | 300 |
| aatataacca | tgcaaatcat | gcgaatcaaa | ccccaccagg | gccagcatat | cggcgagatg | 360 |
| tctttcttgc | aacataacaa | atgcgagtgt | cggccaaaga | aggacagggc | tcgccaggaa | 420 |
| aatccctgtg | gtccttgttc | agagcgcagg | aagcatcttt | tcgtccagga | tccgcagact | 480 |
| tgtaaatgtt | catgcaagaa | taccgattct | aggtgtaagg | cgaggcaact | cgagcttaac | 540 |
| gagagaacct | gtaggtgtga | caaacctaga | aga | | | 573 |

<210> SEQ ID NO 108
<211> LENGTH: 6034
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 108

| | | | | | | |
|---|---|---|---|---|---|---|
| taactataac | ggtcctaagg | tagcgacgta | cgaaccgttg | ggcgcgcctg | gggatagcga | 60 |
| tcgctgctgg | cgcggtccgc | tatgaggtct | ctgatagacc | acagacgcgt | cgacattgat | 120 |
| tattgactag | ttattaatag | taatcaatta | cggggtcatt | agttcatagc | ccatatatgg | 180 |
| agttccgcgt | tacataactt | acggtaaatg | gcccgcctgg | ctgaccgccc | aacgacccc | 240 |
| gcccattgac | gtcaataatg | acgtatgttc | ccatagtaac | gccaataggg | actttccatt | 300 |
| gacgtcaatg | ggtggagtat | ttacggtaaa | ctgcccactt | ggcagtacat | caagtgtatc | 360 |
| atatgccaag | tacgccccct | attgacgtca | atgacggtaa | atggcccgcc | tggcattatg | 420 |
| cccagtacat | gaccttatgg | gactttccta | cttggcagta | catctacgta | ttagtcatcg | 480 |
| ctattaccat | ggtcgaggtg | agccccacgt | tctgcttcac | tctccccatc | tcccccccct | 540 |
| ccccacccc | aattttgtat | ttatttattt | tttaattatt | ttgtgcagcg | atggggggcgg | 600 |
| ggggggggg | gggcgcgcg | ccaggcgggg | cgggcgggg | cgaggggcgg | ggcgggcga | 660 |
| ggcggagagg | tgcggcggca | gccaatcaga | gcggcgcgct | ccgaaagttt | ccttttatgg | 720 |
| cgaggcggcg | gcggcggcgg | ccctataaaa | agcgaagcgc | gcggcgggcg | ggagtcgctg | 780 |
| cgcgctgcct | tcgccccgtg | ccccgctccg | ccgccgcctc | gcgccgcccg | ccccggctct | 840 |
| gactgaccgc | gttactccca | caggtgagcg | ggcgggacgg | cccttctcct | ccgggctgta | 900 |
| attagcgctt | ggtttaatga | cggcttgttt | cttttctgtg | gctgcgtgaa | agccttgagg | 960 |
| ggctccggga | gggccctttg | tgcggggga | gcggctcggg | ggtgcgtgc | gtgtgtgtgt | 1020 |
| gcgtggggag | cgccgcgtgc | ggctccgcgc | tgcccggcgg | ctgtgagcgc | tgcgggcgcg | 1080 |
| gcgcggggct | ttgtgcgctc | cgcagtgtgc | gcgaggggag | cgcggccggg | ggcggtgccc | 1140 |
| cgcggtgcgg | gggggctgc | gaggggaaca | aaggctgcgt | gcggggtgtg | tgcgtggggg | 1200 |

```
ggtgagcagg gggtgtgggc gcgtcggtcg ggctgcaacc ccccctgcac cccccteccc    1260 gagttgctga gcacggcccg gcttcgggtg cggggctccg tacggggcgt ggcgcggggc    1320
tcgccgtgcc gggcggggg  tggcggcagg tgggggtgcc gggcggggcg gggccgcctc    1380 gggccggggga gggctcgggg gagggcgcg  gcggcccccg gagcgccggc ggctgtcgag    1440
gcgcggcgag ccgcagccat tgccttttat ggtaatcgtg cgagagggcg cagggacttc    1500
ctttgtccca aatctgtgcg gagccgaaat ctgggaggcg ccgccgcacc ccctctagcg    1560 ggcgcgggc  gaagcggtgc ggcgccggca ggaaggaaat gggcggggag ggccttcgtg    1620
cgtcgccgcg ccgccgtccc cttctccctc tccagcctcg gggctgtccg cgggggggacg    1680 gctgccttcg gggggacgg  ggcagggcgg ggttcggctt ctggcgtgtg accggcggct    1740
ctagagcctc tgctaaccat gttcatgcct tcttcttttt cctacagctc ctgggcaacg    1800
tgctggttat tgtgctgtct catcattttg gcaaagaatt ccctgcagga aattgagccc    1860
gcagcctccc gcttcgctct ctgctcctcc tgttcgacag tcagccgcat cttcttttgc    1920
gtcgccagcc gagccacatc gctcagacac cgctagcatg ggcagcgaac tggaaaccgc    1980
catggagact ttgataaatg ttttccacgc gcatagcggc aaagaagggg acaagtacaa    2040
gctgtcaaaa aaggagctga agaactgct  gcagaccgaa ttgagcggct tcctggacgc    2100
tcagaaagat gtcgatgccg tcgacaaagt gatgaaagag cttgacgaga cggtgacgg     2160 tgaagtcgat tttcaggaat atgtggtgct ggtggccgcc cttactgtag catgcaacaa    2220
tttcttttgg gaaaattcac gtgcaaagcg tgcaccggtg aaacagggaa gcggagctac    2280
taacttcagc ctgctgaagc aggctggaga cgtggaggag aaccctggac ctatgaatgc    2340
caaggtcgtt gtggtgcttg tacttgtgct gactgctctg tgtctgagcg acggaaaacc    2400 agtctcccte agctacaggt gcccatgccg attcttcgaa tctcatgtgg cccgggccaa    2460
tgtgaagcac ttgaaaatcc tgaatacacc caactgcgcg ttgcagatcg tggcccgcct    2520
gaaaaataat aataggcagg tatgtataga tccaaagctt aagtggatcc aggagtatct    2580
ggaaaaggct ctcaataaac gtgcaaagcg tgcaccggtg aaacagggaa gcggagctac    2640
taacttcagc ctgctgaagc aggctggaga cgtggaggag aaccctggac ctatgaattt    2700
tctgctctct tgggtgcact ggtcactggc actgctgctg tatctgcacc atgcaaaatg    2760
gtcccaagca gctcccatgg cagagggagg tggacagaat catcatgagg ttgtcaaatt    2820
tatggatgtc taccagcgga gctactgcca cccaattgag acgttggtag acattttca    2880 ggaatatcca gacgagattg agtacatttt caagcctagc tgtgtgccct tgatgcgatg    2940
cggtggctgt tgcaatgatg agggactcga gtgtgtcccc accgaggaaa gcaatataac    3000
catgcaaatc atgcgaatca aaccccacca gggccagcat atcggcgaga tgtctttctt    3060
gcaacataac aaaatgcgag tcggccaaa  gaaggacagg gctcgccagg aaaatccctg    3120
tggtccttgt tcagagcgca ggaagcatct tttcgtccag gatccgcaga cttgtaaatg    3180
ttcatgcaag aataccgatt ctaggtgtaa ggcgaggcaa ctcgagctta acgagagaac    3240
ctgtaggtgt gacaaaccta gaagataaat cgattacgct cctctactct ttgagacatc    3300
actggcctat aataaatggg ttaatttatg taacaaaatt gccttggctt gttaacttta    3360
ttagacattc tgatgtttgc attgtgtaaa tactgttgta ttggaaaagc gtgccaagat    3420
ggattattgt aattcagtgt cttttttagt agcgtcacgt gccaaacact gttagtcaca    3480
gagggcatga gacagcctgt gctggaacag ctcagttcat agggctatgg agatggggag    3540
```

```
aaagggggcgc ttctgtcaga gacaagctgt ggtctgggaa ggccttagca ctaaaagcac    3600
cacaatgaga agcaaccgcc agaagcaggg cccgcaggcc tttgttccag ctgcaaagag    3660
aaaggaaaaa gtgggaata agagttgggg ctgcggaggg ggtggggagc attgtgcagg    3720
ttccgtactt gaacagaaag cagggaccaa cacaaggaag gctcgagctg gcggaatagg    3780
ttccaatctg tcgcggccgc attaccctgt tatccctaat ctcgtttaac tatgactctc    3840
ttaaggtagc caaattccgg aactataaat tgcgttgcgc tcactgcccg ctttccagtc    3900
gggaaacctg tcgtgccagc tgcataaatg aatcggccaa cgcgcgggga gaggcggttt    3960
gcgtattggg cgcgcttccg cttcctcgct cactgactcg ctgcgctcgg tcgttcggct    4020
gcggcgagcg gtatcagctc actcaaaggc ggtaatacgg ttatccacag aatcagggga    4080
taacgcagga aagaacatgt gagcaaaagg ccagcaaaag gccaggaacc gtaaaaaggc    4140
cgcgttgctg gcgtttttcc ataggctccg ccccctgac gagcatcaca aaaatcgacg    4200
ctcaagtcag aggtggcgaa acccgacagg actataaaga taccaggcgt ttccccctgg    4260
aagctccctc gtgcgctctc ctgttccgac cctgccgctt accggatacc tgtccgcctt    4320
tctcccttcg ggaagcgtgg cgctttctca tagctcacgc tgtaggtatc tcagttcggt    4380
gtaggtcgtt cgctccaagc tgggctgtgt gcacgaaccc ccgttcagc ccgaccgctg    4440
cgccttatcc ggtaactatc gtcttgagtc aacccggta agacacgact tatcgccact    4500
ggcagcagcc actggtaaca ggattagcag agcgaggtat gtaggcggtg ctacagagtt    4560
cttgaagtgg tggcctaact acggctacac tagaagaaca gtatttggta tctgcgctct    4620
gctgaagcca gttaccttcg gaaaaagagt tggtagctct tgatccggca acaaaccac    4680
cgctggtagc ggtggttttt ttgtttgcaa gcagcagatt acgcgcagaa aaaaaggatc    4740
tcaagaagat cctttgatct tttctacggg gtctgacgct cagtggaacg aaaactcacg    4800
ttaagggatt ttggtcatga gattatcaaa aaggatcttc acctagatcc ttttaaatta    4860
aaaatgaagt tttaaatcaa tctaaagtat atatgagtaa acttggtctg acatgcgcat    4920
ctgacgctca gtggaacgaa aactcacgtt aagggatttt ggtcatgcct cagaagaact    4980
cgtcaagaag gcgatagaag gcgatgcgct gcgaatcggg agcggcgata ccgtaaagca    5040
cgaggaagcg gtcagcccat tcgccgccaa gctcttcagc aatatcacgg gtagccaacg    5100
ctatgtcctg atagcggtcc gccacaccca gccggccaca gtcgatgaat ccagaaaagc    5160
ggccattttc caccatgata ttcggcaagc aggcatcgcc atgggtcacg acgagatcct    5220
cgccgtcggg catgcgcgcc ttgagcctgg cgaacagttc ggctggcgcg agccctgat    5280
gctcttcgtc cagatcatcc tgatcgacaa gaccggcttc catccgagta cgtgctcgct    5340
cgatgcgatg tttcgcttgg tggtcgaatg ggcaggtagc cggatcaagc gtatgcagcc    5400
gccgcattgc atcagccatg atggatactt tctcggcagg agcaaggtga gatgacagga    5460
gatcctgccc cggcacttcg cccaatagca gccagtccct tcccgcttca gtgacaacgt    5520
cgagcacagc tgcgcaagga acgcccgtcg tggccagcca cgatagccgc gctgcctcgt    5580
cctgcagttc attcagggca ccggacaggt cggtcttgac aaaaagaacc gggcgcccct    5640
gcgctgacag ccggaacacg gcggcatcag agcagccgat tgtctgttgt gcccagtcat    5700
agccgaatag cctctccacc caagcggccg gagaacctgc gtgcaatcca tcttgttcaa    5760
tcatgcgaaa cgatcctcat tcatttatca gggttattgt ctcatgagcg atacatatt    5820
tgaatgtatt taggctgagc atctatgtcg ggtgcggaga aagaggtaat gaaatggcag    5880
gcgccttttt cgttagatat gtagtaagta tcttaatata cagctttatc tgttttttaa    5940
```

```
gatacttact actttctta gtggaaacta ttagtggctg ttaattaagc tagtactacc    6000
caagatttga cagaatgcat cgtttgcatt cgaa                               6034
```

<210> SEQ ID NO 109
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 0-15
      "Gly Ser" repeating units wherein some positions may be absent"

<400> SEQUENCE: 109

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 110
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 0-15
      "Ser Gly" repeating units wherein some positions may be absent"

<400> SEQUENCE: 110

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
            20                  25                  30

<210> SEQ ID NO 111
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(45)
<223> OTHER INFORMATION: /note="This sequence may encompass 0-15
      "Gly Ser Gly" repeating units wherein some positions may be
      absent"

<400> SEQUENCE: 111

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly Gly Ser
            20                  25                  30

Gly Gly Ser Gly Gly Ser Gly Gly Ser Gly Gly Ser Gly
        35                  40                  45

-continued

```
<210> SEQ ID NO 112
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(45)
<223> OTHER INFORMATION: /note="This sequence may encompass 0-15
      "Ser Gly Ser" repeating units wherein some positions may be
      absent"

<400> SEQUENCE: 112

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser
            35                  40                  45

<210> SEQ ID NO 113
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-15
      "Gly Ser" repeating units wherein some positions may be absent"

<400> SEQUENCE: 113

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 114
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-15
      "Ser Gly" repeating units wherein some positions may be absent"

<400> SEQUENCE: 114

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
            20                  25                  30

<210> SEQ ID NO 115
<211> LENGTH: 45
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"
<220> FEATURE:
<221> NAME/KEY: MISC_FEATURE
<222> LOCATION: (1)..(45)
<223> OTHER INFORMATION: /note="This sequence may encompass 1-15
      "Gly Ser Gly" repeating units wherein some positions may be
      absent"

<400> SEQUENCE: 115

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly Gly Ser
            20                  25                  30

Gly Gly Ser Gly Gly Ser Gly Gly Ser Gly Gly Ser Gly
        35                  40                  45

<210> SEQ ID NO 116
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(45)
<223> OTHER INFORMATION: /note="This sequence may encompass 1-15
      "Ser Gly Ser" repeating units wherein some positions may be
      absent"

<400> SEQUENCE: 116

Ser Gly Ser Ser Gly Ser Ser Gly Ser Ser Gly Ser Ser Gly Ser Ser
1               5                   10                  15

Gly Ser Ser Gly Ser Ser Gly Ser Ser Gly Ser Ser Gly Ser Ser Gly
            20                  25                  30

Ser Ser Gly Ser Ser Gly Ser Ser Gly Ser Ser Gly Ser
        35                  40                  45

<210> SEQ ID NO 117
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: MISC_FEATURE
<222> LOCATION: (2)..(2)
<223> OTHER INFORMATION: /note="Variant residue given in the sequence
      has no preference with respect to that in the annotations for
      variant position"
<220> FEATURE:
<221> NAME/KEY: MOD_RES
<222> LOCATION: (4)..(4)
<223> OTHER INFORMATION: Any amino acid

<400> SEQUENCE: 117

Asp Val Glu Xaa Asn Pro Gly Pro
1               5

<210> SEQ ID NO 118
<211> LENGTH: 4

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Ser Gly Ser Gly
1

<210> SEQ ID NO 119
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ala Pro Val Lys Gln Gly Ser Gly
1               5

<210> SEQ ID NO 120
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Gly Gly Gly Ser
1               5

<210> SEQ ID NO 121
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (1)..(10)
<223> OTHER INFORMATION: /note="This sequence may encompass 2-5
      "Xaa Pro" repeating units wherein some positions may be absent"

<400> SEQUENCE: 121
```

```
Xaa Pro Xaa Pro Xaa Pro Xaa Pro Xaa Pro
1               5                   10
```

<210> SEQ ID NO 122
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MISC_FEATURE
<222> LOCATION: (2)..(26)
<223> OTHER INFORMATION: /note="This region may encompass 2-5 "Glu Ala Ala Ala Lys" repeating units wherein some positions may be absent"

<400> SEQUENCE: 122

```
Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Ala
            20                  25
```

<210> SEQ ID NO 123
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: 2A tail"

<400> SEQUENCE: 123

```
Arg Ala Lys Arg Ala Pro Val Lys Gln Gly Ser Gly Ala Thr Asn Phe
1               5                   10                  15
Ser Leu Leu Lys Gln Ala Gly Asp Val Glu Glu Asn Pro Gly
            20                  25                  30
```

<210> SEQ ID NO 124
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: S100A1 with 2A tail"

<400> SEQUENCE: 124

```
Met Gly Ser Glu Leu Glu Thr Ala Met Glu Thr Leu Ile Asn Val Phe
1               5                   10                  15
His Ala His Ser Gly Lys Glu Gly Asp Lys Tyr Lys Leu Ser Lys Lys
            20                  25                  30
Glu Leu Lys Glu Leu Leu Gln Thr Glu Leu Ser Gly Phe Leu Asp Ala
        35                  40                  45
Gln Lys Asp Val Asp Ala Val Asp Lys Val Met Lys Glu Leu Asp Glu
    50                  55                  60
Asn Gly Asp Gly Glu Val Asp Phe Gln Glu Tyr Val Val Leu Val Ala
65                  70                  75                  80
Ala Leu Thr Val Ala Cys Asn Asn Phe Phe Trp Glu Asn Ser Arg Ala
                85                  90                  95
Lys Arg Ala Pro Val Lys Gln Gly Ser Gly Ala Thr Asn Phe Ser Leu
            100                 105                 110
Leu Lys Gln Ala Gly Asp Val Glu Glu Asn Pro Gly
```

<210> SEQ ID NO 125
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
atgggcagcg aactggaaac cgccatggag actttgataa atgttttcca cgcgcatagc      60
ggcaaagaag gggacaagta caagctgtca aaaaaggagc tgaaagaact gctgcagacc     120
gaattgagcg gcttcctgga cgctcagaaa gatgtcgatg ccgtcgacaa agtgatgaaa     180
gagcttgacg agaacggtga cggtgaagtc gattttcagg aatatgtggt gctggtggcc     240
gcccttactg tagcatgcaa caatttcttt tgggaaaatt cacgtgcaaa gcgtgcaccg     300
gtgaaacagg gaagcggagc tactaacttc agcctgctga gcaggctgg agacgtggag      360
gagaaccctg ga                                                         372
```

<210> SEQ ID NO 126
<211> LENGTH: 165
<212> TYPE: PRT
<213> ORGANISM: Homo sapiens

<400> SEQUENCE: 126

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165
```

<210> SEQ ID NO 127
<211> LENGTH: 495
<212> TYPE: DNA
<213> ORGANISM: Homo sapiens

<400> SEQUENCE: 127

```
gctcccatgg cagagggagg tggacagaat catcatgagg ttgtcaaatt tatggatgtc      60
```

-continued

```
taccagcgga gctactgcca cccaattgag acgttggtag acattttca ggaatatcca      120 gacgagattg agtacatttt caagcctagc tgtgtgccct tgatgcgatg cggtggctgt      180
tgcaatgatg agggactcga gtgtgtcccc accgaggaaa gcaatataac catgcaaatc      240
atgcgaatca aacccacca gggccagcat atcggcgaga tgtctttctt gcaacataac       300
aaatgcgagt gtcggccaaa gaaggacagg gctcgccagg aaaatccctg tggtccttgt      360
tcagagcgca ggaagcatct tttcgtccag gatccgcaga cttgtaaatg ttcatgcaag      420
aataccgatt ctaggtgtaa ggcgaggcaa ctcgagctta acgagagaac ctgtaggtgt      480
gacaaaccta gaaga                                                      495
```

What is claimed is:

1. A polynucleotide that encodes a polypeptide that comprises a S100 calcium binding protein (S100) polypeptide that comprises the sequence of SEQ ID NO: 104, a stromal cell derived factor (SDF) polypeptide that comprises the sequence of SEQ ID NO: 102, and a vascular endothelial growth factor (VEGF) polypeptide that comprises the sequence of SEQ ID NO: 106, wherein said S100 polypeptide, said SDF polypeptide, and said VEGF polypeptide are separated from each other by one or more in vivo cleavable linkers.

2. The polynucleotide of claim 1, wherein said one or more in vivo cleavable linkers comprises a 2A peptide that mediates a ribosome skipping translational effect.

3. The polynucleotide of claim 1, wherein said one or more in vivo cleavable linkers are selected from the group consisting of a furin linker, a fp2a linker, a p2a linker, a GSG-p2a linker, a fmdv linker, and any combination thereof.

4. The polynucleotide of claim 3, wherein said one or more in vivo cleavable linkers further comprise a sequence selected from the group consisting of APVKQ (SEQ ID NO: 42), GPVKQ (SEQ ID NO: 43), VPVKQ (SEQ ID NO: 44), IPVKQ (SEQ ID NO: 45), MPVKQ (SEQ ID NO: 46), APIKQ (SEQ ID NO: 47), GPIKQ (SEQ ID NO: 48), VPIKQ (SEQ ID NO: 49), IPIKQ (SEQ ID NO: 50), MPIKQ (SEQ ID NO: 51), APAKQ (SEQ ID NO: 52), GPAKQ (SEQ ID NO: 53), VPAKQ (SEQ ID NO: 54), IPAKQ (SEQ ID NO: 55), MPAKQ (SEQ ID NO: 56), APVRQ (SEQ ID NO: 57), GPVRQ (SEQ ID NO: 58), VPVRQ (SEQ ID NO: 59), IPVRQ (SEQ ID NO: 60), MPVRQ (SEQ ID NO: 61), APIRQ (SEQ ID NO: 62), GPIRQ (SEQ ID NO: 63), VPIRQ (SEQ ID NO: 64), IPIRQ (SEQ ID NO: 65), MPIRQ (SEQ ID NO: 66), APARQ (SEQ ID NO: 67), GPRAQ (SEQ ID NO: 68), VPARQ (SEQ ID NO: 69), IPARQ (SEQ ID NO: 70), MPARQ (SEQ ID NO: 71), APVKN (SEQ ID NO: 72), GPVKN (SEQ ID NO: 73), VPVKN (SEQ ID NO: 74), IPVKN (SEQ ID NO: 75), MPVKN (SEQ ID NO: 76), APIKN (SEQ ID NO: 77), GPIKN (SEQ ID NO: 78), VPIKN (SEQ ID NO: 79), IPIKN (SEQ ID NO: 80), MPIKN (SEQ ID NO: 81), APAKN (SEQ ID NO: 82), GPAKN (SEQ ID NO: 83), VPAKN (SEQ ID NO: 84), IPAKN (SEQ ID NO: 85), IVIPAKN (SEQ ID NO: 86), APVRN (SEQ ID NO: 87), GPVRN (SEQ ID NO: 88), VPVRN (SEQ ID NO: 89), IPVRN (SEQ ID NO: 90), IVIPVRN (SEQ ID NO: 91), APIRN (SEQ ID NO: 92), GPIRN (SEQ ID NO: 93), VPIRN (SEQ ID NO: 94), IPIRN (SEQ ID NO: 95), MPIRN (SEQ ID NO: 96), APARN (SEQ ID NO: 97), GPARN (SEQ ID NO: 98), VPARN (SEQ ID NO: 99), IPARN (SEQ ID NO: 100) or MPARN (SEQ ID NO: 101).

5. The polynucleotide of claim 1, wherein said one or more in vivo cleavable linkers comprise a sequence as shown in SEQ ID NO: 32, SEQ ID NO: 34, SEQ ID NO: 36, SEQ ID NO: 38, or SEQ ID NO: 40.

6. A cell comprising the polynucleotide of claim 1.

7. An expression vector comprising the polynucleotide of claim 1, wherein said polynucleotide is operably linked to a promoter.

8. The expression vector of claim 7, wherein said promoter is a constitutive promoter, a tissue specific promoter, or an inducible promoter.

9. The expression vector of claim 8, wherein said inducible promoter is a small molecule ligand-inducible two polypeptide ecdysone receptor-based gene switch.

10. The expression vector of claim 8, wherein said promoter is a cardiac promoter.

11. A pharmaceutical composition comprising: the polynucleotide of claim 1 and a pharmaceutically acceptable excipient.

12. A method comprising: contacting at least one cardiac cell with the polynucleotide of claim 1.

13. The method of claim 12, wherein said cardiac cell is a myocardial cell.

14. A polynucleotide that encodes a polypeptide that comprises a S100 calcium-binding protein (S100) polypeptide, a stromal cell derived factor (SDF) polypeptide, and a vascular endothelial growth factor (VEGF) polypeptide, wherein said polynucleotide comprises the sequence of SEQ ID NO: 108.

* * * * *